US011684665B2

(12) United States Patent
Roos et al.

(10) Patent No.: US 11,684,665 B2
(45) Date of Patent: Jun. 27, 2023

(54) METHOD FOR PRODUCING RNA MOLECULE COMPOSITIONS

(71) Applicant: CureVac SE, Tübingen (DE)

(72) Inventors: Tilmann Roos, Kusterdingen (DE); Martin Kunze, Rottenburg (DE); Benyamin Yazdan Panah, Tübingen (DE); Salih Yilmaz, Biberach an der Riss (DE); Markus Conzelmann, Tübingen (DE)

(73) Assignee: CureVac SE, Tübingen (DE)

( * ) Notice: Subject to any disclaimer, the term of this patent is extended or adjusted under 35 U.S.C. 154(b) by 1013 days.

(21) Appl. No.: 16/063,999

(22) PCT Filed: Dec. 22, 2016

(86) PCT No.: PCT/EP2016/082487

§ 371 (c)(1),
(2) Date: Jun. 19, 2018

(87) PCT Pub. No.: WO2017/109134

PCT Pub. Date: Jun. 29, 2017

(65) Prior Publication Data

US 2019/0083602 A1 Mar. 21, 2019

(30) Foreign Application Priority Data

Dec. 22, 2015 (WO) ................ PCT/EP2015/081000

(51) Int. Cl.

| | |
|---|---|
| ***A61K 39/12*** | (2006.01) |
| ***C12Q 1/68*** | (2018.01) |
| ***C07K 14/005*** | (2006.01) |
| ***C12Q 1/6844*** | (2018.01) |
| ***A61P 21/00*** | (2006.01) |
| ***A61P 31/00*** | (2006.01) |
| ***A61P 39/00*** | (2006.01) |
| ***C12N 15/10*** | (2006.01) |
| ***C40B 40/02*** | (2006.01) |
| ***C40B 40/08*** | (2006.01) |
| *A61K 39/00* | (2006.01) |
| *A61K 38/00* | (2006.01) |
| *C40B 10/00* | (2006.01) |

(52) U.S. Cl.

CPC .............. *A61K 39/12* (2013.01); *A61P 21/00* (2018.01); *A61P 31/00* (2018.01); *A61P 39/00* (2018.01); *C07K 14/005* (2013.01); *C12N 15/1024* (2013.01); *C12Q 1/6844* (2013.01); *C40B 40/02* (2013.01); *C40B 40/08* (2013.01); *A61K 38/00* (2013.01); *A61K 2039/53* (2013.01); *A61K 2039/70* (2013.01); *C12N 2760/16111* (2013.01); *C12N 2760/16122* (2013.01); *C12N 2760/16134* (2013.01); *C12N 2760/16222* (2013.01); *C12N 2760/16234* (2013.01); *C40B 10/00* (2013.01); *Y02A 50/30* (2018.01)

(58) Field of Classification Search

CPC ...... C12Q 1/6844; C40B 40/08; A61K 39/12; A61K 2039/53; A61P 21/00

See application file for complete search history.

(56) References Cited

U.S. PATENT DOCUMENTS

| | | | |
|---|---|---|---|
| 2005/0032730 | A1 | 2/2005 | von der Mülbe et al. |
| 2005/0059624 | A1 | 3/2005 | Hoerr et al. |
| 2005/0250723 | A1 | 11/2005 | Hoerr et al. |
| 2006/0188490 | A1 | 8/2006 | Hoerr et al. |
| 2008/0025944 | A1 | 1/2008 | Hoerr et al. |
| 2008/0267873 | A1 | 10/2008 | Hoerr et al. |
| 2009/0324584 | A1 | 12/2009 | Hoerr et al. |
| 2010/0048883 | A1 | 2/2010 | Ketterer et al. |
| 2010/0189729 | A1 | 7/2010 | Hoerr et al. |
| 2010/0203076 | A1 | 8/2010 | Fotin-Mleczek et al. |
| 2010/0291156 | A1 | 11/2010 | Barner et al. |
| 2010/0305196 | A1 | 12/2010 | Probst et al. |
| 2011/0053829 | A1 | 3/2011 | Baumhof et al. |
| 2011/0250225 | A1 | 10/2011 | Fotin-Mleczek et al. |
| 2012/0021043 | A1 | 1/2012 | Kramps et al. |
| 2012/0258046 | A1 | 10/2012 | Mutzke |
| 2013/0129754 | A1 | 5/2013 | Thess et al. |
| 2013/0142818 | A1 | 6/2013 | Baumhof et al. |

(Continued)

FOREIGN PATENT DOCUMENTS

| | | |
|---|---|---|
| EP | 1083232 | 2/2005 |
| WO | WO 2010/037408 | 4/2010 |

(Continued)

OTHER PUBLICATIONS

Spiess et al., "Bispecific antibodies with natural architecture produced by co-culture of bacteria expressing two distinct half-antibodies", *Nat. Biotechnol.*, 31(8):753-758, 2013.
"In vitro Transcription T7 Kit (for siRNA Synthesis)", TaKaRa, China, No. 6140. Machine translation appended.
Murgha et al., "Combined in vitro transcription and reverse transcription to amplify and label complex synthetic oligonucleotide probe libraries", *Biotechniques*, 58(6):301-307, 2015.

(Continued)

*Primary Examiner* — Antonio Galisteo Gonzalez
(74) *Attorney, Agent, or Firm* — Parker Highlander PLLC

(57) ABSTRACT

The invention relates to a method for producing a ribonucleic acid (RNA) molecule composition comprising n different RNA molecule species, the method comprising a step of RNA in vitro transcription of a mixture of m different deoxyribonucleic acid (DNA) molecule species in a single reaction vessel in parallel, i.e. simultaneously, and a step of obtaining the RNA molecule composition. Also provided is the RNA composition provided by the inventive method and a pharmaceutical composition comprising the same as well as a pharmaceutical container. Moreover, the invention provides the RNA composition and the pharmaceutical composition for use as medicament.

25 Claims, 15 Drawing Sheets

Specification includes a Sequence Listing.

(56) References Cited

U.S. PATENT DOCUMENTS

| | | | |
|---|---|---|---|
| 2013/0259879 | A1 | 10/2013 | Baumhof et al. |
| 2013/0280283 | A1 | 10/2013 | Lorenz et al. |
| 2013/0295043 | A1 | 11/2013 | Kallen et al. |
| 2013/0336998 | A1 | 12/2013 | Kallen et al. |
| 2015/0037326 | A1 | 2/2015 | Butler-Ransohoff et al. |
| 2015/0050302 | A1 | 2/2015 | Thess |
| 2015/0057340 | A1 | 2/2015 | Thess et al. |
| 2015/0093413 | A1 | 4/2015 | Thess et al. |
| 2015/0118183 | A1 | 4/2015 | Baumhof |
| 2015/0118264 | A1 | 4/2015 | Baumhof et al. |
| 2015/0165006 | A1 | 6/2015 | Thess et al. |
| 2015/0184195 | A1 | 7/2015 | Thess et al. |
| 2015/0218554 | A1 | 8/2015 | Thess |
| 2015/0306249 | A1 | 10/2015 | Baumhof et al. |
| 2015/0320847 | A1 | 11/2015 | Thess et al. |
| 2016/0130345 | A1 | 5/2016 | Fotin-Mleczek et al. |
| 2016/0166668 | A1 | 6/2016 | Kallen et al. |
| 2016/0166678 | A1 | 6/2016 | Kallen et al. |
| 2016/0166710 | A1 | 6/2016 | Baumhof |
| 2016/0166711 | A1 | 6/2016 | Schnee et al. |
| 2016/0168207 | A1 | 6/2016 | Kramps et al. |
| 2016/0168227 | A1 | 6/2016 | Kallen et al. |
| 2016/0235864 | A1 | 8/2016 | Schlake et al. |
| 2016/0304883 | A1 | 10/2016 | Grund et al. |
| 2016/0304938 | A1 | 10/2016 | Wochner |
| 2016/0326575 | A1 | 11/2016 | von der Mülbe |
| 2016/0331844 | A1 | 11/2016 | Fotin-Mleczek et al. |
| 2016/0367651 | A1 | 12/2016 | Shiku et al. |
| 2017/0014496 | A1 | 1/2017 | Fotin-Mleczek et al. |
| 2017/0029847 | A1 | 2/2017 | Thess |
| 2017/0114378 | A1 | 4/2017 | Wochner et al. |
| 2017/0252430 | A1 | 9/2017 | Fotin-Mleczek et al. |
| 2017/0326225 | A1 | 11/2017 | Rauch et al. |
| 2018/0044687 | A1 | 2/2018 | Thess et al. |
| 2018/0125952 | A1 | 5/2018 | Fotin-Mleczek et al. |
| 2018/0126003 | A1 | 5/2018 | Hoerr |
| 2018/0142275 | A1 | 5/2018 | Roos et al. |
| 2018/0147146 | A1 | 5/2018 | Eber et al. |
| 2018/0148727 | A1 | 5/2018 | Grund et al. |
| 2018/0201967 | A1 | 7/2018 | Eber et al. |
| 2018/0208957 | A1 | 7/2018 | Roos et al. |
| 2018/0214537 | A1 | 8/2018 | Mutzke et al. |
| 2018/0237786 | A1 | 8/2018 | Schlake et al. |
| 2018/0237817 | A1 | 8/2018 | Roos et al. |
| 2018/0243219 | A1 | 8/2018 | Ketterer et al. |
| 2018/0296663 | A1 | 10/2018 | Hipp et al. |
| 2018/0298372 | A1 | 10/2018 | Funkner et al. |
| 2018/0312545 | A1 | 11/2018 | Baumhof et al. |
| 2018/0371392 | A1 | 12/2018 | Mayer et al. |
| 2019/0010485 | A1 | 1/2019 | Yazdan Panah et al. |
| 2019/0017100 | A1 | 1/2019 | Wochner et al. |
| 2019/0024096 | A1 | 1/2019 | Schmid et al. |
| 2019/0040378 | A1 | 2/2019 | Fotin-Mleczek et al. |
| 2019/0049414 | A1 | 2/2019 | Wochner et al. |
| 2019/0083602 | A1 | 3/2019 | Roos et al. |
| 2019/0100784 | A1 | 4/2019 | Eber et al. |
| 2019/0125857 | A1 | 5/2019 | Rauch et al. |
| 2019/0133950 | A1 | 5/2019 | Eber et al. |
| 2019/0160164 | A1 | 5/2019 | Rauch et al. |
| 2019/0177714 | A1 | 6/2019 | Kunze et al. |
| 2019/0185859 | A1 | 6/2019 | Fotin-Mleczek et al. |
| 2019/0194760 | A1 | 6/2019 | Koch et al. |
| 2019/0225971 | A1 | 7/2019 | Williams |
| 2019/0241633 | A1 | 8/2019 | Fotin-Mleczek et al. |
| 2019/0249219 | A1 | 8/2019 | Reichert et al. |
| 2019/0336608 | A1 | 11/2019 | Baumhof et al. |
| 2019/0336611 | A1 | 11/2019 | Baumhof et al. |
| 2019/0343933 | A1 | 11/2019 | Horscroft et al. |
| 2019/0343942 | A1 | 11/2019 | Fotin-Mleczek et al. |
| 2019/0351044 | A1 | 11/2019 | Jasny et al. |
| 2019/0351047 | A1 | 11/2019 | Jasny et al. |
| 2019/0351048 | A1 | 11/2019 | Rauch |
| 2019/0381180 | A1 | 12/2019 | Baumhof et al. |
| 2020/0023076 | A1 | 1/2020 | Fotin-Mleczek et al. |
| 2020/0085852 | A1 | 3/2020 | Fotin-Mleczek |
| 2020/0085944 | A1 | 3/2020 | Heidenreich et al. |
| 2020/0149026 | A1 | 5/2020 | Horscroft et al. |
| 2020/0163878 | A1 | 5/2020 | Baumhof et al. |
| 2020/0179526 | A1 | 6/2020 | Baumhof et al. |
| 2020/0318097 | A1 | 10/2020 | Funkner et al. |
| 2020/0392572 | A1 | 12/2020 | Yazdan Panah et al. |
| 2021/0030864 | A1 | 2/2021 | Petsch et al. |
| 2021/0069315 | A1 | 3/2021 | Baumhof et al. |
| 2021/0162037 | A1 | 6/2021 | Jasny et al. |
| 2021/0170017 | A1 | 6/2021 | Lutz et al. |
| 2021/0180106 | A1 | 6/2021 | Wochner et al. |
| 2021/0205434 | A1 | 7/2021 | Petsch et al. |
| 2021/0260178 | A1 | 8/2021 | Jasny et al. |
| 2021/0261897 | A1 | 8/2021 | Yazdan Panah et al. |
| 2021/0361761 | A1 | 11/2021 | Lutz et al. |

FOREIGN PATENT DOCUMENTS

| | | |
|---|---|---|
| WO | WO 2015-024669 | 2/2015 |
| WO | WO 2015/050158 | 4/2015 |
| WO | WO 2015/135558 | 9/2015 |
| WO | WO 2018/172556 | 9/2018 |
| WO | WO 2018/211038 | 11/2018 |
| WO | WO 2019/077001 | 4/2019 |
| WO | WO 2019/092153 | 5/2019 |
| WO | WO 2020/123300 | 6/2020 |
| WO | WO 2020/127959 | 6/2020 |
| WO | WO 2020/128031 | 6/2020 |
| WO | WO 2020/161342 | 8/2020 |
| WO | WO 2021/156267 | 8/2021 |

OTHER PUBLICATIONS

Office Communication issued in corresponding Singaporean Application No. 11201804398X, dated Jan. 14, 2020.

Bennett et al., "Rapid simultaneous detection of enterovirus and parechovirus RNAs in clinical samples by one-step real-time reverse transcription-PCR assay," *Journal of Clinical Microbiology*, 49(7):2620-2624, 2011.

Hu et al., "Simultaneously typing nine serotypes of enteroviruses associated with hand, foot, and mouth disease by a GeXP analyzer-based multiplex reverse transcription-PCR assay," *Journal of Clinical Microbiology*, 50(2):288-293, 2012.

Kramps et al., "Messenger RNA-based vaccines: progress, challenges, applications," *Wiley Interdisciplinary Reviews: RNA*, 4:737-749, 2013.

Li et al., "The development of a GeXP-based multiplex reverse transcription-PCR assay for simultaneous detection of sixteen human respiratory virus types/subtypes," *BMC Infectious Diseases*, 12(1):1-8, 2012.

Pascolo, "Vaccination with messenger RNA," *Methods in Molecular Medicine*, pp. 23-20, 2006.

PCT International Preliminary Report on Patentability issued in International Application No. PCT/EP2016/082487, dated Feb. 14, 2018.

PCT International Search Report and Written Opinion issued in International Application No. PCT/EP2016/082487, dated Mar. 13, 2017.

Petsch et al., "Protective efficacy of in vitro synthesized, specific mRNA vaccines against influenza A virus infection," *Nature Biotechnology*, 30(12):1210-1216, 2012.

Tavernier et al., "mRNA as gene therapeutic: How to control protein expression," *Journal of Controlled Release*, 150(3):238-247, 2011.

Ulmber et al., "Vaccines 'on demand': science fiction or a future reality," *Expert Opinion on Drug Discovery*, 10(2):101-106, 2015.

Fukuda et al., "In vitro evolution of single-chain antibodies using mRNA display," *Nucleic Acids Research*, 34:e127, 2006.

Kajitani and Ishihama, "Determination of the promoter strength in the mixed transcription system: promoters of lactose, tryptophan and ribosomal protein L10 operons from *Escherichia coli*," *Nucleic Acids Research*, 11:671-686, 1983.

Kajitani and Ishihama, "Promoter Selectivity of *Escherichia coli* RNA Polymerase," *Journal of Biological Chemistry*, 259:1951-1957, 1984.

(56) References Cited

OTHER PUBLICATIONS

Langert et al., "Functional Characteristics of the rrnD Promoters of *Escherichia coli*," *Journal of Biological Chemistry*, 266:21608-21615, 1991.
Nomura et al., "Promoter selectivity of *Escherichia coli* RNA polymerase: alteration by fMet-tRNAf Met," *Nucleic Acids Research*, 14:6857-6870, 1986.
Opposition against European Patent No. 3319622, by BioNTech RNA Pharmaceuticals GmbH, dated Nov. 12, 2020.
Shimada et al., "The Whole Set of Constitutive Promoters Recognized by RNA Polymerase RpoD Holoenzyme of *Escherichia coli*," *PLoS ONE*, 9:e90447, 2014.
Wilson and Geiduschek, "A Template-Selective Inhibitor of In Vitro Transcription," *Proc. Nat. Acad. Sei. USA*, 62:514-520, 1969.
Brown et al., "Sequences of three promoters for the bacteriophage SP6 Rna polymerase" *Nuc. Acids Res.*, 14:3521-3526, 1986.
GenBank: CY112249.1, Apr. 3, 2012.
GenBank: DQ458992.1, Apr. 2, 2006.
GenBank: EF541402.1, May 1, 2008.
GenBank: FN401574.1, Aug. 13, 2009.
Komura et al., "High-throughput evaluation of T7 promoter variants using biased randomization and DNA barcoding" *PLOS One*, pp. 1-16, 2018.
Kudla et al., "High Guanine and Cytosine Content Increases mRNA Levels in Mammalian Cells" *PLoS Biology*, vol. 4, 2006.
Nam et al., "Transcription Initiation Site Selection and Abortive Initiation Cycling of Phage SP6 RNA Polymerase" *J. Biol. Chem.* 263: 18123-18127, 1988.
Okayama et al., "A cDNA Cloning Vector That Permits Expression of cDNA Inserts in Mammalian Cells" *Mol. Cell Biol.*, vol. 3:280-289 1983.
Opposition against EP 3 319 622 submission of BioNTech dated Aug. 5, 2022.
Opposition against EP 3 319 622 submission of BioNTech dated Sep. 13, 2022.
Patentee submission in EP 3 319 622 Apr. 1, 2022.
Patentee submission in EP 3 319 622 Aug. 5, 2022.
Sambrook, "Molecular cloning: a laboratory manual" Cold Spring Harbor Laboratory Press, Ed. 3rd, 2001.
Stump et al., "SP6 RNA polymerase efficiently synthesizes RNA from short double-stranded DNA templates " *Nuc. Acids Res.*, 21:5480-5484, 1993.
Wladyka et al., "Efficient co-expression of a recombinant staphopain A and its inhibitor staphostatin A in *Escherichia coli*" *Biochem. J.*, vol. 385:181-187, 2005.

| | | | | | | | | | | | | | | |
|---|---|---|---|---|---|---|---|---|---|---|---|---|---|---|
| SEQ ID NO 27 | 100.00 | 82.31 | 82.36 | 82.00 | 81.95 | 81.81 | 82.01 | 81.37 | 81.97 | 82.13 | 82.09 | 81.41 | 80.78 | 80.76 |
| SEQ ID NO 17 | 82.31 | 100.00 | 99.87 | 98.13 | 98.26 | 92.16 | 93.02 | 88.51 | 88.43 | 88.73 | 88.71 | 84.41 | 84.49 | 84.59 |
| SEQ ID NO 26 | 82.36 | 99.87 | 100.00 | 98.26 | 98.13 | 92.16 | 93.04 | 88.59 | 88.45 | 88.76 | 88.73 | 84.46 | 84.49 | 84.64 |
| SEQ ID NO 16 | 82.00 | 98.13 | 98.26 | 100.00 | 99.87 | 92.64 | 92.51 | 88.61 | 88.20 | 88.86 | 88.81 | 84.31 | 84.23 | 84.62 |
| SEQ ID NO 28 | 81.95 | 98.26 | 98.13 | 99.87 | 100.00 | 92.64 | 92.48 | 88.54 | 88.17 | 88.83 | 88.78 | 84.26 | 84.23 | 84.56 |
| SEQ ID NO 15 | 81.81 | 92.16 | 92.16 | 92.64 | 92.64 | 100.00 | 93.50 | 89.64 | 88.93 | 88.95 | 88.90 | 83.38 | 83.30 | 84.02 |
| SEQ ID NO 21 | 82.01 | 93.02 | 93.04 | 92.51 | 92.48 | 93.50 | 100.00 | 88.91 | 88.47 | 88.62 | 88.60 | 83.30 | 83.71 | 83.55 |
| SEQ ID NO 24 | 81.37 | 88.51 | 88.59 | 88.61 | 88.54 | 89.64 | 88.91 | 100.00 | 91.24 | 90.91 | 90.86 | 83.49 | 83.21 | 83.13 |
| SEQ ID NO 10 | 81.97 | 88.43 | 88.45 | 88.20 | 88.17 | 88.93 | 88.47 | 91.24 | 100.00 | 95.09 | 95.08 | 83.75 | 83.39 | 84.08 |
| SEQ ID NO 18 | 82.13 | 88.73 | 88.76 | 88.86 | 88.83 | 88.95 | 88.62 | 90.91 | 95.09 | 100.00 | 99.95 | 84.21 | 83.31 | 84.31 |
| SEQ ID NO 19 | 82.09 | 88.71 | 88.73 | 88.81 | 88.78 | 88.90 | 88.60 | 90.86 | 95.08 | 99.95 | 100.00 | 84.08 | 83.31 | 84.26 |
| SEQ ID NO 25 | 81.41 | 84.41 | 84.46 | 84.31 | 84.26 | 83.38 | 83.30 | 83.49 | 83.75 | 84.21 | 84.08 | 100.00 | 85.81 | 85.49 |
| SEQ ID NO 22 | 80.78 | 84.49 | 84.49 | 84.23 | 84.23 | 83.30 | 83.71 | 83.21 | 83.39 | 83.31 | 83.31 | 85.81 | 100.00 | 93.53 |
| SEQ ID NO 23 | 80.76 | 84.59 | 84.64 | 84.62 | 84.56 | 84.02 | 83.55 | 83.13 | 84.08 | 84.31 | 84.26 | 85.49 | 93.53 | 100.00 |

Figure 1 (continued)
B

| | | | | | | | | | | | | | | |
|---|---|---|---|---|---|---|---|---|---|---|---|---|---|---|
| SEQ ID NO 13 | 100.00 | 56.63 | 56.63 | 57.05 | 57.05 | 56.51 | 57.35 | 56.57 | 56.75 | 56.97 | 57.02 | 55.88 | 54.68 | 54.21 |
| SEQ ID NO 02 | 56.63 | 100.00 | 99.74 | 96.14 | 96.40 | 84.80 | 84.54 | 76.44 | 75.63 | 77.09 | 76.99 | 66.63 | 66.37 | 67.37 |
| SEQ ID NO 14 | 56.63 | 99.74 | 100.00 | 96.40 | 96.14 | 84.80 | 84.49 | 76.29 | 75.58 | 77.04 | 76.94 | 66.53 | 66.37 | 67.27 |
| SEQ ID NO 03 | 57.05 | 96.14 | 96.40 | 100.00 | 99.74 | 83.81 | 85.59 | 76.23 | 76.05 | 76.78 | 76.73 | 66.68 | 66.90 | 67.27 |
| SEQ ID NO 12 | 57.05 | 96.40 | 96.14 | 99.74 | 100.00 | 83.81 | 85.64 | 76.39 | 76.10 | 76.83 | 76.78 | 66.79 | 66.90 | 67.37 |
| SEQ ID NO 01 | 56.51 | 84.80 | 84.80 | 83.81 | 83.81 | 100.00 | 86.58 | 78.56 | 77.16 | 77.21 | 77.11 | 64.83 | 64.77 | 65.99 |
| SEQ ID NO 07 | 57.35 | 84.54 | 84.49 | 85.59 | 85.64 | 86.58 | 100.00 | 77.04 | 76.27 | 76.58 | 76.53 | 64.72 | 65.73 | 65.46 |
| SEQ ID NO 10 | 56.57 | 76.44 | 76.29 | 76.23 | 76.39 | 78.56 | 77.04 | 100.00 | 81.77 | 81.19 | 81.08 | 65.37 | 64.60 | 64.76 |
| SEQ ID NO 06 | 56.75 | 75.63 | 75.58 | 76.05 | 76.10 | 77.16 | 76.27 | 81.77 | 100.00 | 89.85 | 89.86 | 65.05 | 65.14 | 66.31 |
| SEQ ID NO 04 | 56.97 | 77.09 | 77.04 | 76.78 | 76.83 | 77.21 | 76.58 | 81.19 | 89.85 | 100.00 | 99.90 | 65.83 | 65.14 | 66.68 |
| SEQ ID NO 05 | 57.02 | 76.99 | 76.94 | 76.73 | 76.78 | 77.11 | 76.53 | 81.08 | 89.86 | 99.90 | 100.00 | 65.68 | 65.14 | 66.58 |
| SEQ ID NO 11 | 55.88 | 66.63 | 66.53 | 66.68 | 66.79 | 64.83 | 64.72 | 65.37 | 65.05 | 65.83 | 65.68 | 100.00 | 68.15 | 68.01 |
| SEQ ID NO 08 | 54.68 | 66.37 | 66.37 | 66.90 | 66.90 | 64.77 | 65.73 | 64.60 | 65.14 | 65.14 | 65.14 | 68.15 | 100.00 | 86.22 |
| SEQ ID NO 09 | 54.21 | 67.37 | 67.27 | 67.27 | 67.37 | 65.99 | 65.46 | 64.76 | 66.31 | 66.68 | 66.58 | 68.01 | 86.22 | 100.00 |

A

B

A

B

SEQUENCE LISTING

<160> NUMBER OF SEQ ID NOS: 28

<210> SEQ ID NO 1
<211> LENGTH: 1915
<212> TYPE: RNA
<213> ORGANISM: Artificial sequence
<220> FEATURE:
<223> OTHER INFORMATION: GC optimized HA mRNA

<400> SEQUENCE: 1

```
gggagaaagc uuaccaugaa ggccaaccug cucgugcugc ugugcgcccu cgcggccgcc     60
gacgccgaca ccaucugcau cggcuaccac gccaacaaca gcaccgacac ggucgacacc    120
gugcuggaga agaacgugac cgucacccac uccgugaacc ugcucgagga cagccacaac    180
gggaagcugu gccggcugaa gggcaucgcg ccccuccagc uggggaagug caacaucgcc    240
ggcuggcugc ucgggaaccc ggagugcgac ccccugcugc ccgugcgcuc cuggagcuac    300
aucgucgaga cgcccaacuc cgagaacggc aucugcuacc cgggcgacuu caucgacuac    360
gaggagcucc gggagcagcu gagcuccgug agcuccuucg agcgcuucga gaucuucccc    420
aaggagagcu ccuggcccaa ccacaacacc aacgggguga ccgccgccug cagccacgag    480
ggcaagucca gcuucuaccg gaaccugcuc uggcugaccg agaaggaggg guccuacccc    540
aagcugaaga acagcuacgu caacaagaag ggcaaggagg ugcucgugcu gugggggauc    600
caccacccgc ccaacuccaa ggagcagcag aaccuguacc agaacgagaa cgcguacguc    660
agcgugguga cguccaacua caaccgccgg uucacccccg agaucgccga gcgccccaag    720
guccgggacc aggccggccg caugaacuac uacuggaccc uccugaagcc gggcgacacc    780
aucaucuucg aggccaacgg gaaccugauc gccccgaugu acgcguucgc ccucagccgg    840
ggcuucggga gcggcaucau cacguccaac gccagcaugc acgagugcaa caccaagugc    900
cagaccccccc ugggcgccau caacuccagc cugcccuacc agaacaucca cccggugacc    960
aucggggagu gccccaagua cgugcgcucc gccaagcucc ggaugguc ac gggccugcgc   1020
aacaacccca gcauccaguc ccgggggcug uucggcgcga ucgccggguu caucgagggc   1080
ggcuggaccg ggaugaucga cggcugguac ggguaccacc accagaacga gcagggcagc   1140
ggguacgccg ccgaccagaa guccacccag aacgccauca acggcaucac caacaaggug   1200
aacacgguga ucgagaagau gaacauccag uucaccgcgg ucggcaagga guucaacaag   1260
cucgagaagc gcauggagaa ccugaacaag aagguggacg acggguuccu ggacaucugg   1320
accuacaacg ccgagcuccu ggugcugcuc gagaacgagc ggacccugga cuuccacgac   1380
agcaacguca agaaccugua cgagaaggug aagucccagc ucaagaacaa cgccaaggag   1440
aucggcaacg ggugcuucga guucuaccac aagugcgaca acgagugcau ggagagcguc   1500
cgcaacggca cguacgacua ccccaaguac uccgaggaga gcaagcugaa ccgggagaag   1560
guggacgggg ugaagcugga guccaugggc aucuaccaga uccucgccau cuacagcacc   1620
gucgccucca gccuggugcu gcuggugucc cucggcgcga ucagcuucug gaugugcagc   1680
aacggguccc ugcagugccg caucugcauc ugaccacuag uuauaagacu gacuagcccg   1740
augggccucc caacgggccc uccuccccuc cuugcaccga gauuaauaaa aaaaaaaaaa   1800
aaaaaaaaaa aaaaaaaaaa aaaaaaaaaa aaaaaaaaaa aaaaaaaaaa augcaucccc   1860
cccccccccc cccccccccc cccccccaaa ggcucuuuuc agagccacca gaauu        1915
```

<210> SEQ ID NO 2
<211> LENGTH: 1918

```
<212> TYPE: RNA
<213> ORGANISM: Artificial sequence
<220> FEATURE:
<223> OTHER INFORMATION: GC optimized HA mRNA

<400> SEQUENCE: 2

gggagaaagc uuaccaugaa ggccauccug gugguccucc uguacaccuu cgccaccgcg     60

aacgccgaca cgcugugcau cggcuaccac gccaacaaca gcaccgacac cguggacacc    120

gugcucgaga agaacgucac ggugacccac uccgugaacc ugcuggagga caagcacaac    180

gggaagcucu gcaagcugcg gggcgucgcc ccgcugcacc ucgggaagug caacaucgcc    240

ggcuggaucc uggggaaccc ggagugcgag agccugucca ccgcgagcuc cuggagcuac    300

aucguggaga ccuccagcuc cgacaacggc acgugcuacc ccggcgacuu caucgacuac    360

gaggagcucc gcgagcagcu gagcuccgug agcuccuucg agcgguucga gaucuucccc    420

aagaccagcu ccuggcccaa ccacgacagc aacaaggggg ucaccgccgc cugcccgcac    480

gccggcgcga aguccuucua caagaaccug aucuggcucg ugaagaaggg gaacagcuac    540

cccaagcugu ccaagagcua caucaacgac aagggcaagg aggugcuggu ccucuggggg    600

auccaccacc ccagcaccuc cgccgaccag cagagccugu accagaacgc cgacgccuac    660

guguucgugg gcuccagccg cuacuccaag aaguucaagc ccgagaucgc cauccggccg    720

aagguccgcg accaggaggg ccggaugaac uacuacugga cgcuggugga gcccggggac    780

aagaucaccu ucgaggcgac cggcaaccuc gugguccccc gcuacgccuu cgccauggag    840

cggaacgccg ggagcggcau caucaucucc gacacccccg ugcacgacug caacacgacc    900

ugccagaccc cgaagggcgc caucaacacc agccugcccu uccagaacau ccaccccauc    960

acgaucggga agugccccaa guacgugaag uccaccaagc ugcgccucgc gaccggccug   1020

cggaacgucc cgagcaucca gucccgcggg cuguucggcg ccaucgccgg guucaucgag   1080

ggcggcugga ccgggauggu ggacggcugg uacggguacc accaccagaa cgagcagggc   1140

agcggguacg ccgccgaccu caaguccacg cagaacgcga ucgacgagau caccaacaag   1200

gugaacagcg ucaucgagaa gaugaacacc caguucaccg ccgugggcaa ggaguucaac   1260

caccuggaga agcggaucga gaaccugaac aagaaggucg acgacggcuu ccucgacauc   1320

uggacguaca acgccgagcu gcuggugcuc cuggagaacg agcgcacccu ggacuaccac   1380

gacuccaacg ugaagaaccu cuacgagaag guccggagcc agcugaagaa caacgccaag   1440

gagaucggga acggcugcuu cgaguucuac cacaagugcg acaacaccug cauggagucc   1500

gugaagaacg ggaccuacga cuaccccaag uacagcgagg aggccaagcu gaaccgcgag   1560

gagaucgacg gcgugaagcu cgaguccacg cggaucuacc agauccuggc gaucuacagc   1620

accgucgcca gcucccuggu gcucgugguc agccuggggg ccaucuccuu cuggaugugc   1680

agcaacggcu cccugcagug ccgcaucugc aucugaccac uaguuauaag acugacuagc   1740

ccgaugggcc ucccaacggg cccuccuccc cuccuugcac cgagauuaau aaaaaaaaaa   1800

aaaaaaaaaa aaaaaaaaaa aaaaaaaaaa aaaaaaaaaa aaaaaaaaaa aaaaugcauc   1860

cccccccccc cccccccccc cccccccccc aaaggcucuu uucagagcca ccagaauu     1918


<210> SEQ ID NO 3
<211> LENGTH: 1918
<212> TYPE: RNA
<213> ORGANISM: Artificial sequence
<220> FEATURE:
<223> OTHER INFORMATION: GC optimized HA mRNA
```

-continued

<400> SEQUENCE: 3
gggagaaagc uuaccaugaa ggccauccug gugguccucc uguacaccuu cgccaccgcg 60
aacgccgaca cgcugugcau cggcuaccac gccaacaaca gcaccgacac cguggacacc 120
gugcucgaga agaacgucac ggugacccac uccgugaacc ugcuggagga caagcacaac 180
gggaagcucu gcaagcugcg gggcgucgcc ccgcugcacc ucgggaagug caacaucgcc 240
ggcuggaucc uggggaaccc ggagugcgag agccugucca ccgcgagcuc cuggagcuac 300
aucguggaga cccccuccag cgacaacggc acgugcuacc ccggcgacuu caucgacuac 360
gaggagcucc gcgagcagcu guccagcgug uccagcuucg agcgguucga gaucuucccc 420
aagaccucca gcuggccgaa ccacgacucc gacaaggggg ucaccgccgc cugcccccac 480
gccggcgcga agagcuucua caagaaccug aucuggcucg ugaagaaggg gaacuccuac 540
cccaagcuga gcaaguccua caucaacgac aagggcaagg aggugcuggu ccucuggggg 600
auccaccacc ccagcaccag cgccgaccag caguccugu accagaacgc cgacgccuac 660
guguucgugg gcagcucccg cuacagcaag acguucaagc cggagaucgc cauccggccc 720
aagguccgcg accgggaggg ccgcaugaac uacuacugga cccuggugga gcccggggac 780
aagaucaccu ucgaggcgac cggcaaccuc gugguccccc gguacgccuu cgccauggag 840
cgcaacgccg gguccggcau caucaucagc gacacgccgg ugcacgacug caacaccacc 900
ugccagaccc ccaagggcgc caucaacacg ucccugcccu uccagaacau ccaccccauc 960
accaucggga agugcccgaa guacgugaag agcaccaagc ugcggcucgc gaccggccug 1020
cgcaacaucc ccuccaucca gagccggggg cuguucggcg ccaucgccgg guucaucgag 1080
ggcggcugga cggggauggu cgacggcugg uacggguacc accaccagaa cgagcagggc 1140
agcggguacg ccgccgaccu caaguccacg cagaacgcga ucgacgagau caccaacaag 1200
gugaacagcg ucaucgagaa gaugaacacc caguucaccg ccgugggcaa ggaguucaac 1260
caccuggaga agcggaucga gaaccugaac aagaaggucg acgacggcuu ccucgacauc 1320
uggacguaca acgccgagcu gcuggugcuc cuggagaacg agcgcacccu ggacuaccac 1380
gacuccaacg ugaagaaccu cuacgagaag guccggagcc agcugaagaa caacgccaag 1440
gagaucggga acggcugcuu cgaguucuac cacaagugcg acaacaccug cauggagucc 1500
gugaagaacg ggaccuacga cuaccccaag uacagcgagg aggccaagcu gaaccgcgag 1560
gagaucgacg gcgugaagcu cgaguccacg cggaucuacc agauccuggc gaucuacagc 1620
accgucgcca gcucccuggu gcucguggug agccuggggg ccaucuccuu cuggaugugc 1680
agcaacggcu cccugcagug ccgcaucugc aucugaccac uaguuauaag acugacuagc 1740
ccgaugggcc ucccaacggg cccuccuccc cuccuugcac cgagauuaau aaaaaaaaaa 1800
aaaaaaaaaa aaaaaaaaaa aaaaaaaaaa aaaaaaaaaa aaaaaaaaaa aaaaugcauc 1860
cccccccccc cccccccccc cccccccccc aaaggcucuu uucagagcca ccagaauu 1918

<210> SEQ ID NO 4
<211> LENGTH: 1912
<212> TYPE: RNA
<213> ORGANISM: Artificial sequence
<220> FEATURE:
<223> OTHER INFORMATION: GC optimized HA mRNA

<400> SEQUENCE: 4
gggagaaagc uuaccaugga gaagaucgug cugcucuucg ccaucgucag ccuggugaag 60
uccgaccaga ucugcaucgg cuaccacgcc aacaacagca ccgagcaggu ggacaccauc 120

-continued auggagaaga acgucacggu gacccacgcg caggacaucc uggagaagac ccacaacggg 180
aagcucugcg accuggacgg cgugaagccc cugauccucc gggacugcuc cgucgccggg 240
uggcugcugg gcaacccgau gugcgacgag uucaucaacg ugcccgagug gagcuacauc 300
guggagaagg ccaaccccgu caacgaccuc ugcuaccccg gggacuucaa cgacuacgag 360
gagcugaagc accugcucuc ccgcaucaac cacuucgaga agauccagau caucccgaag 420
agcuccugga gcucccacga ggccagccug ggcgugucca gcgccugccc cuaccagggc 480
aaguccagcu ucuuccggaa cgugguc ugg cugaucaaga agaacuccac cuaccccacg 540
aucaagcgca gcuacaacaa caccaaccag gaggaccucc uggugcugug ggggauccac 600
caccccaacg acgcggccga gcagaccaag cucuaccaga acccgaccac guacaucucc 660
gugggcacca gcacccugaa ccagcggcug gucccccgca ucgccacccg guccaaggug 720
aacgggcaga gcggccgcau ggaguucuuc uggacgaucc ucaagcccaa cgacgccauc 780
aacuucgaga gcaacgggaa cuucaucgcg cccgaguacg ccuacaagau cgugaagaag 840
ggcgacucca ccaucaugaa gagcgagcug gaguacggca acugcaacac caagugccag 900
accccgaugg gggccaucaa cuccagcaug cccuuccaca acauccaccc ccugacgauc 960
ggcgagugcc ccaaguacgu caaguccaac cggcucgugc uggccaccgg gcugcgcaac 1020
agcccgcagc gggagacccg cggccucuuc ggcgccaucg cgggguucau cgagggcggg 1080
uggcagggca ugguggacgg gugguacggc uaccaccacu ccaacgagca gggcagcggg 1140
uacgccgccg acaaggaguc cacccagaag gccaucgacg gcgucacgaa caaggugaac 1200
agcaucaucg acaagaugaa cacccaguuc gaggccgugg ggcgggaguu caacaaccug 1260
gagcgccgga ucgagaaccu gaacaagaag auggaggacg gcuuccucga cgucuggacc 1320
uacaacgcgg agcugcuggu gcucauggag aacgagcgca cccuggacuu ccacgacucc 1380
aacgucaaga accuguacga caaggugcgg cuccagcugc gcgacaacgc caaggagcug 1440
gggaacggcu gcuucgaguu cuaccacaag ugcgacaacg agugcaugga gagcgugcgg 1500
aacggcacgu acgacuaccc ccaguacucc gaggaggccc gccucaagcg ggaggagauc 1560
agcgggguca agcuggaguc caucggcauc uaccagaucc ugagcaucua cuccaccgug 1620
gccagcuccc ucgcccuggc gaucauggug gccgggcuga gccucuggau gugcagcaac 1680
ggcucccugc agugccgcau cugcaucuga ggacuaguua uaagacugac uagcccgaug 1740
ggccucccaa cgggcccucc uccccuccuu gcaccgagau uaauaaaaaa aaaaaaaaaa 1800
aaaaaaaaaa aaaaaaaaaa aaaaaaaaaa aaaaaaaaaa aaaaaaaaug cauccccccc 1860
cccccccccc cccccccccc ccccaaaggc ucuuuucaga gccaccagaa uu 1912

<210> SEQ ID NO 5
<211> LENGTH: 1924
<212> TYPE: RNA
<213> ORGANISM: Artificial sequence
<220> FEATURE:
<223> OTHER INFORMATION: GC optimized HA mRNA

<400> SEQUENCE: 5
gggagaaagc uuaccaugga gaagaucgug cugcucuucg ccaucgucag ccuggugaag 60
uccgaccaga ucugcaucgg cuaccacgcc aacaacagca ccgagcaggu ggacaccauc 120
auggagaaga acgucacggu gacccacgcg caggacaucc uggagaagac ccacaacggg 180
aagcucugcg accuggacgg cgugaagccc cugauccucc gggacugcuc cgucgccggg 240

-continued uggcugcugg gcaacccgau gugcgacgag uucaucaacg ugcccgagug gagcuacauc 300
guggagaagg ccaaccccgu caacgaccuc ugcuaccccg ggacuucaa cgacuacgag 360 gagcugaagc accugcucuc ccgcaucaac cacuucgaga agauccagau caucccgaag 420
agcuccugga gcucccacga ggccagccug ggcgugucca gcgccugccc cuaccagggc 480
aaguccagcu ucuuccggaa cgugggucugg cugaucaaga agaacuccac cuaccccacg 540
aucaagcgca gcuacaacaa caccaaccag gaggaccucc uggugcugug ggggauccac 600
caccccaacg acgcggccga gcagaccaag cucuaccaga acccgaccac guacaucucc 660
gugggcacca gcacccugaa ccagcggcug gucccccgca ucgccacccg guccaaggug 720
aacgggcaga gcggccgcau ggaguucuuc uggacgaucc ucaagcccaa cgacgccauc 780
aacuucgaga gcaacgggaa cuucaucgcg cccgaguacg ccuacaagau cgugaagaag 840
ggcgacucca ccaucaugaa gagcgagcug gaguacggca acugcaacac caagugccag 900
accccgaugg gggccaucaa cuccagcaug cccuuccaca acauccaccc ccugacgauc 960
ggcgagugcc ccaaguacgu caaguccaac cggcucgugc uggccaccgg gcugcgcaac 1020
agcccgcagc gggagcggcg ccggaagaag cgcggccucu ucggcgccau cgcgggguuc 1080
aucgagggcg ggugggcaggg cauggugggac ggguggguacg gcuaccacca cuccaacgag 1140
cagggcagcg gguacgccgc cgacaaggag uccacccaga aggccaucga cggcgucacg 1200 aacaaggu ga acagcaucau cgacaagaug aacacccagu ucgaggccgu ggggcgggag 1260
uucaacaacc uggagcgccg gaucgagaac cugaacaaga agauggagga cggcuuccuc 1320
gacgucugga ccuacaacgc ggagcugcug gugcucaugg agaacgagcg cacccuggac 1380
uuccacgacu ccaacgucaa gaaccuguac gacaaggugc ggcuccagcu gcgcgacaac 1440
gccaaggagc uggggaacgg cugcuucgag uucuaccaca agugcgacaa cgagugcaug 1500
gagagcgugc ggaacggcac guacgacuac ccccaguacu ccgaggaggc ccgccucaag 1560
cgggaggaga ucagcggggu caagcuggag uccaucggca ucuaccagau ccugagcauc 1620
uacuccaccg uggccagcuc ccucgcccug gcgaucaugg uggccgggcu gagccucugg 1680
augugcagca acggcucccu gcagugccgc aucugcaucu gaggacuagu uauaagacug 1740
acuagcccga ugggccuccc aacgggcccu ccucccuccc uugcaccgag auuaauaaaa 1800
aaaaaaaaaa aaaaaaaaaa aaaaaaaaaa aaaaaaaaaa aaaaaaaaaa aaaaaaaaaa 1860 ugcaucccccc cccccccccc cccccccccc ccccccaaag gcucuuuuca gagccaccag 1920
aauu 1924

<210> SEQ ID NO 6
<211> LENGTH: 1924
<212> TYPE: RNA
<213> ORGANISM: Artificial sequence
<220> FEATURE:
<223> OTHER INFORMATION: GC optimized HA mRNA

<400> SEQUENCE: 6
gggagaaagc uuaccaugga gaagaucaug cugcuccugg ccaucgugag ccuggucaag 60
uccgaccaga ucugcaucgg cuaccacgcc aacaacagca ccgagcaggu ggacaccauc 120
auggagaaga acgugacggu cacccacgcg caggacaucc ucgagaagac ccacaacggg 180
aagcugugcg accuggacgg cgugaagccc cucauccugc gggacugcuc cguggccggg 240
uggcugcucg gcaacccgau gugcgacgag uuccugaacg uccccgagug gagcuacauc 300
guggagaaga ucaaccccgc caacgaccug ugcuaccccg ggaacuucaa cgacuacgag 360
gagcucaagc accugcuguc ccgcaucaac cacuucgaga agauccagau caucccgaag 420
agcuccugga gcgaccacga ggccuccagc ggcgugucca gcgccugccc cuaccagggc 480
cgguccagcu ucuuccgcaa cgucguguggg cucaucaaga aggacaacgc guaccccacc 540
aucaagcggu ccuacaacaa cacgaaccag gaggaccugc uggugcucug ggggauccac 600
caccccaacg acgccgccga gcagacccgc cuguaccaga acccgaccac cuacaucagc 660
gucggcacgu ccacccugaa ccagcggcuc gugcccaaga ucgccacccg cagcaaggug 720
aacgggcagu ccggccggau ggaguucuuc uggaccaucc ugaagcccaa cgacgcgauc 780
aacuucgaga gcaacgggaa cuucaucgcc cccgagaacg ccuacaagau cgucaagaag 840
ggcgacagca cgaucaugaa guccgagcug gaguacggca acugcaacac caagugccag 900
accccgaucg gggccaucaa cagcuccaug cccuuccaca acauccaccc ccucaccauc 960
ggcgagugcc ccaaguacgu gaagagcaac cgccuggugc uggccacggg gcuccggaac 1020
uccccgcagg gcgagcgccg gcgcaagaag cggggccugu ucggggcgau cgccggcuuc 1080
aucgagggcg gguggcaggg gauggucgac ggcugguacg gcuaccacca cagcaacgag 1140
caggggucgg gcuacgccgc cgacaaggag agcacccaga aggccaucga cggggugacc 1200
aacaagguga acuccaucau cgacaagaug aacacccagu ucgaggcggu cggccgcgag 1260
uucaacaacc uggagcggcg caucgagaac cucaacaaga agauggagga cggguuccug 1320 gacguguggga cguacaacgc cgagcugcuc gugcugaugg agaacgagcg gacccuggac 1380
uuccacgaca gcaacgucaa gaaccucuac gacaaggugc gccugcagcu gcgggacaac 1440
gccaaggagc ucggcaacgg cugcuucgag uucuaccacc gcugcgacaa cgagugcaug 1500
gaguccgucc ggaacgggac cuacgacuac ccccaguaca gcgaggaggc ccggcugaag 1560
cgcgaggaga ucuccggcgu gaagcuggag agcaucggga ccuaccagau ccucuccauc 1620
uacagcacgg uggccuccag ccuggcgcug gccaucaugg ucgccggccu cucccugugg 1680
augugcagca acgggagccu gcagugccgg aucugcaucu gaccacuagu uauaagacug 1740
acuagcccga ugggccuccc aacgggcccu ccucccccucc uugcaccgag auuaauaaaa 1800
aaaaaaaaaa aaaaaaaaaa aaaaaaaaaa aaaaaaaaaa aaaaaaaaaa aaaaaaaaaa 1860 ugcaucccccc cccccccccc cccccccccc cccccccaaag gcucuuuuca gagccaccag 1920
aauu 1924

<210> SEQ ID NO 7
<211> LENGTH: 1915
<212> TYPE: RNA
<213> ORGANISM: Artificial sequence
<220> FEATURE:
<223> OTHER INFORMATION: GC optimized HA mRNA

<400> SEQUENCE: 7
gggagaaagc uuaccaugaa ggugaagcug cucguccugc ugugcaccuu caccgccacg 60
uacgccgaca ccaucugcau cggcuaccac gcgaacaaca gcaccgacac cguggacacg 120
gugcucgaga agaacgucac cgugacccac uccgugaacc ugcuggagaa cagccacaac 180
gggaagcucu gccugcugaa gggcaucgcc ccccuccagc uggggaacug cuccgucgcc 240
ggcuggaucc uggggaaccc ggagugcgag cuccugauca gcaaggaguc cuggagcuac 300
aucguggaga agcccaaccc cgagaacggc accugcuacc ccggccacuu cgccgacuac 360
gaggagcugc gggagcagcu cuccagcgug uccagcuucg agcgcuucga gaucuucccg 420

-continued aaggagucca gcuggcccaa ccacacgguc accggggugu ccgccagcug cucccacaac 480
ggcgagagcu ccuucuaccg gaaccugcug uggcucaccg ggaagaacgg ccuguacccc 540
aaccugagca aguccuacgc gaacaacaag gagaaggagg ugcucguccu gugggggcgug 600 caccacccgc cgaacaucgg gaaccagaag gcccuguacc acaccgagaa cgccuacgug 660
agcgucguga gcucccacua cagccgcaag uucacgcccg agaucgccaa gcggcccaag 720
gugcgcgacc aggagggccg gaucaacuac uacuggaccc uccuggagcc cggggacacc 780
aucaucuucg aggcgaacgg caaccugauc gccccgcgcu acgccuucgc ccucucccgg 840
ggguucggca gcggcaucau caacuccaac gccccgaugg acaagugcga cgcgaagugc 900 cagaccccccc agggggccau caacagcucc cugcccuucc agaacgucca cccggugacg 960
aucggcgagu gccccaagua cgugcgcagc gccaagcugc ggauggucac cgggcuccgc 1020 aacaucccccu ccauccagag ccggggccug uucggggcca ucgccggcuu caucgagggc 1080 gggguggaccg gcauggugga cggguggguac ggcuaccacc accagaacga gcaggggucc 1140
ggcuacgcgg ccgaccagaa gagcacccag aacgccauca acggcaucac gaacaaggug 1200
aacuccguca ucgagaagau gaacacccag uucaccgccg uggggaagga guucaacaag 1260
cuggagcgcc ggauggagaa ccucaacaag aaggucgacg acggcuucau cgacaucugg 1320
accuacaacg ccgagcugcu ggugcuccug gagaacgagc gcacgcugga cuuccacgac 1380
agcaacguga agaaccucua cgagaagguc aaguccccagc ugaagaacaa cgcgaaggag 1440
aucgggaacg gcugcuucga guucuaccac aagugcaacg acgagugcau ggagagcgug 1500
aagaacggga ccuacgacua ccccaaguac uccgaggaga gcaagcugaa ccgggagaag 1560
aucgacggcg ugaagcucga guccaugggc gucuaccaga uccuggccau cuacagcacc 1620
guggccagcu cccuggugcu ccuggucagc cugggggcca ucuccuucug gaugugcagc 1680
aacggcuccc ugcagugccg caucugcauc ugaggacuag uuauaagacu gacuagcccg 1740
augggccucc caacgggccc uccuccccuc cuugcaccga gauuaauaaa aaaaaaaaaa 1800
aaaaaaaaaa aaaaaaaaaa aaaaaaaaaa aaaaaaaaaa aaaaaaaaaa augcaucccc 1860
cccccccccc cccccccccc cccccccaaa ggcucuuuuc agagccacca gaauu 1915

<210> SEQ ID NO 8
<211> LENGTH: 1918
<212> TYPE: RNA
<213> ORGANISM: Artificial sequence
<220> FEATURE:
<223> OTHER INFORMATION: GC optimized HA mRNA

<400> SEQUENCE: 8
gggagaaagc uuaccaugaa gaccaucauc gcccugagcu acauccucug ccugguguuc 60
gcccagaagc ugcccggcaa cgacaacucc accgcgacgc ucugccuggg gcaccacgcc 120
gucccgaacg gcaccaucgu gaagaccauc accaacgacc agaucgaggu gacgaacgcc 180
accgagcugg uccagagcuc cagcaccggg gagaucugcg acuccccccca ccagauccuc 240 gacggcgaga acugcacccu gaucgacgcc cugcucgggg acccccagug cgacggcuuc 300
cagaacaaga agugggaccu guucguggag cggagcaagg ccuacuccaa cugcuacccc 360
uacgacgugc cggacuacgc gagccugcgc ucccucgucg ccagcuccgg cacgcuggag 420
uucaacaacg agagcuucaa cuggaccggg gugacccaga acggcaccuc cagcuccugc 480 auccgggggga gcaacaacuc cuucuucagc cgccugaacu ggcucacgca ccugaaguuc 540
aaguaccccg cccugaacgu gaccaugccc aacaacgaga aguucgacaa gcucuacauc 600
uggggcgucc accaccccgg gaccgacaac gaccagaucu ucccguacgc ccaggcgucc 660
ggccggauca ccgugagcac gaagcgcagc cagcagaccg ugaucccaa caucggcucc 720 cggccccgcg uccggaacau ccccagccgc aucuccaucu acuggaccau cgugaagccg 780
ggggacaucc ugcugaucaa cagcaccggc aaccucaucg ccccgcgggg guacuucaag 840
auccgcuccg gcaagagcuc caucaugcgg agcgacgccc ccaucggcaa gugcaacucc 900
gagugcauca cgcccaacgg gagcaucccg aacgacaagc ccuuccagaa cgugaaccgc 960
aucaccuacg gcgccugccc ccgguacguc aagcagaaca cccugaagcu ggccaccggg 1020
augcgcaacg ugcccgagaa gcagacgcgg ggcaucuucg ggcgaucgc cggcuucauc 1080 gagaacggcu gggaggggau gguggacggc ugguacgggu uccgccacca gaacuccgag 1140
ggcaucgggc aggccgccga ccucaagagc acccaggccg cgaucgacca gaucaacggc 1200
aagcugaacc ggcugaucgg caagaccaac gagaaguucc accagaucga gaaggaguuc 1260
uccgaggucg aggggcgcau ccaggaccuc gagaaguacg uggaggacac caagaucgac 1320
cuguggagcu acaacgccga gcugcucgug gcccuggaga accagcacac gaucgaccug 1380
accgacuccg agaugaacaa gcucuucgag aagaccaaga agcagcugcg ggagaacgcc 1440
gaggacaugg gcaacgggug cuucaagauc uaccacaagu gcgacaacgc cugcaucggc 1500
agcauccgca acgggaccua cgaccacgac gucuaccggg acgaggcgcu gaacaaccgg 1560
uuccagauca agggcgugga gcucaagucc ggcuacaagg acuggauccu guggaucagc 1620
uucgccaucu ccugcuuccu gcucugcgug gcccugcugg gguucaucau gugggccugc 1680
cagaagggca acauccgcug caacaucugc aucugaggac uaguuauaag acugacuagc 1740
ccgaugggcc ucccaacggg cccuccuccc cuccuugcac cgagauuaau aaaaaaaaaa 1800
aaaaaaaaaa aaaaaaaaaa aaaaaaaaaa aaaaaaaaaa aaaaaaaaaa aaaaugcauc 1860
cccccccccc cccccccccc cccccccccc aaaggcucuu uucagagcca ccagaauu 1918

<210> SEQ ID NO 9
<211> LENGTH: 1918
<212> TYPE: RNA
<213> ORGANISM: Artificial sequence
<220> FEATURE:
<223> OTHER INFORMATION: GC optimized HA mRNA

<400> SEQUENCE: 9
gggagaaagc uuaccaugaa gaccaucauc gcccugagcu acaucuucug ccucgcccug 60
ggccaggacc ugcccgggaa cgacaacucc accgcgacgc ucugccuggg ccaccacgcc 120
gugccgaacg ggacccuggu caagaccauc accgacgacc agaucgaggu gacgaacgcc 180
accgagcucg ugcagagcuc cagcaccggc aagaucugca acaacCCCCa ccggauccug 240
gacgggaucg acugcacccu gaucgacgcc cuccugggcg acccccacug cgacgucuuc 300
cagaacgaga cgugggaccu guucguggag cgcuccaagg ccuucagcaa cugcuacccc 360
uacgacgugc cggacuacgc gucccuccgg agccuggucg ccuccagcgg cacccuggag 420
uucaucaccg aggguucac cuggacgggc gugacccaga acgggggcuc caacgccugc 480
aagcgcgggc ccggcagcgg cuucuucucc cggcucaacu ggcugaccaa gagcgggucc 540
accuaccccg ugcugaacgu cacgaugccc aacaacgaca acuucgacaa gcucuacauc 600
uggggcgugc accacccgag caccaaccag gagcagaccu cccuguacgu gcaggccagc 660
gggcgcguca ccguguccac gcggcgcagc cagcagacca ucauccccaa caucgagagc 720

-continued

```
cggcccuggg ugcgcggcca guccagccgg aucuccaucu acuggaccau cgucaagccc    780
ggcgacgugc uggugaucaa cagcaacggg aaccucaucg cgccgcgcgg cuacuucaag    840
augcggaccg ggaaguccag caucaugcgc uccgacgccc ccaucgacac gugcaucagc    900
gagugcauca cccccaacgg cuccaucccc aacgacaagc cguuccagaa cgucaacaag    960
aucaccuacg ggccugcccc caaguacgug aagcagaaca cccugaagcu ggccacgggc   1020
augcggaacg ugcccgagaa gcagacccgc ggccucuucg ggccaucgc gggcuucauc   1080 gagaacgggu gggagggcau gaucgacggg ugguacggcu uccggcacca gaacagcgag   1140
ggcaccgggc aggccgccga ccugaagucc acccaggccg ccaucgacca gaucaacggc   1200
aaggucaacc gcaucaucga gaagacgaac gagaaguucc accagaucga gaaggaguuc   1260
agcgaggugg aggggcggau ccaggaccug gagaaguacg uggaggacac caagaucgac   1320
cucugguccu acaacgcgga gcugcugguc gcccucgaga accagcacac caucgaccug   1380
accgacagcg agaugaacaa gcuguucgag aagacgcgcc ggcagcuccg cgagaacgcc   1440
gaggacaugg gcaacgggug cuucaagauc uaccacaagu gcgacaacgc cugcaucgag   1500
uccauccgga gcggcaccua cgaccacgac guguaccggg acgaggcccu gaacaaccgc   1560
uuccagauca agggcgucga gcugaagucc ggguacaagg acuggauccu cuggaucagc   1620
uucgcgaucu ccugcuuccu gcugugcgug gugcuccugg gcuucaucau gugggccugc   1680 cagcgggga acauccgcug caacaucugc aucugaggac uaguuauaag acugacuagc   1740
ccgaugggcc ucccaacggg cccuccuccc cuccuugcac cgagauuaau aaaaaaaaaa   1800
aaaaaaaaaa aaaaaaaaaa aaaaaaaaaa aaaaaaaaaa aaaaaaaaaa aaaaugcauc   1860
cccccccccc cccccccccc cccccccccc aaaggcucuu uucagagcca ccagaauu     1918

<210> SEQ ID NO 10
<211> LENGTH: 1906
<212> TYPE: RNA
<213> ORGANISM: Artificial sequence
<220> FEATURE:
<223> OTHER INFORMATION: GC optimized HA mRNA

<400> SEQUENCE: 10
gggagaaagc uuaccauggc caucaucuac cugauccucc uguucaccgc cgugcggggc     60
gaccagaucu gcaucgggua ccacgcgaac aacagcaccg agaaggucga cacgauccug    120
gagcgcaacg ugaccgugac ccacgccaag gacauccucg agaagaccca caacggcaag    180
cugugcaagc ugaacgggau cccgccgcuc gagcugggcg acugcuccau cgccgggugg    240
cugcucggca accccgagug cgaccggcug cugagcgucc ccgagugguc cuacaucaug    300
gagaaggaga acccccgcga cggccucugc uacccgggga gcuucaacga cuacgaggag    360
cugaagcacc ugcucuccag cgugaagcac uucgagaagg ugaagauccu gcccaaggac    420
cgguggacgc agcacaccac caccggcggg ucccgcgccu gcgccgucag cggcaacccc    480
uccuucuucc ggaacauggu guggcugacg gagaagggga gcaacuaccc cguggcgaag    540
ggcuccuaca acaacaccag cggcgagcag augcucauca ucuggggcgu ccaccacccg    600
aacgacgaga ccgagcagcg cacccuguac cagaacgugg ggacguacgu guccgucggg    660
accagcaccc ugaacaagcg guccaccccc gagaucgcca cgcgccccaa ggugaacggc    720
cagggcgggc ggauggaguu cagcuggacc cuccuggaca ugugggacac caucaacuuc    780
gaguccaccg gcaaccugau cgcccccgag uacggguuca agaucagcaa gcgcggcucc    840
agcgggauca ugaagacgga gggcacccuc gagaacugcg agaccaagug ccagaccccg    900
```

cugggcgcca ucaacacgac ccugcccuuc cacaacgugc acccccucac caucggggag 960
ugccccaagu acgucaagag cgagaagcug gugcuggcga ccggccuccg gaacgugccg 1020
cagaucgagu cccgcgggcu guucggcgcc aucgccgggu ucaucgaggg cggcuggcag 1080 gggaugggucg acggcuggua cggguaccac cacagcaacg accagggcuc cggguacgcc 1140
gccgacaagg agagcacgca gaaggcguuc gacggcauca ccaacaaggu gaacuccgug 1200
aucgagaaga ugaacaccca guucgaggcc gucggcaagg aguucagcaa ccuggagcgg 1260
cgccucgaga accugaacaa gaagauggag gacggguucc uggacgugug gaccuacaac 1320
gccgagcucc uggugcugau ggagaacgag cggacgcucg acuuccacga cuccaacguc 1380
aagaaccugu acgacaaggu gcgcaugcag cugcgggaca acgucaagga gcucggcaac 1440
gggugcuucg aguucuacca caagugcgac gacgagugca ugaacagcgu gaagaacggc 1500
accuacgacu accccaagua cgaggaggag uccaagcuga accgcaacga gaucaagggc 1560
gugaagcuga gcuccauggg ggucuaccag auccucgcca ucuacgccac cguggcgggc 1620
agccuguccc uggccaucau gauggccggg aucagcuucu ggaugugcuc caacggcagc 1680
cugcagugcc ggaucugcau cugaggacua guuauaagac ugacuagccc gaugggccuc 1740
ccaacgggcc cuccuccccu ccuugcaccg agauuaauaa aaaaaaaaaa aaaaaaaaaa 1800
aaaaaaaaaa aaaaaaaaaa aaaaaaaaaa aaaaaaaaaa aaugcauccc cccccccccc 1860
cccccccccc cccccccaa aggcucuuuu cagagccacc agaauu 1906

<210> SEQ ID NO 11
<211> LENGTH: 1909
<212> TYPE: RNA
<213> ORGANISM: Artificial sequence
<220> FEATURE:
<223> OTHER INFORMATION: GC optimized HA mRNA

<400> SEQUENCE: 11
gggagaaagc uuaccaugaa cacccagauc cugguguucg cccucgucgc cgugauccac 60
accaacgcgg acaagaucug ccugggccac cacgccguga gcaacgggac gaaggucaac 120
acccugaccg agcggggcgu ggaggugguc aacgccaccg agacggugga gcgcaccaac 180
auccccaaga ucugcuccaa ggggaagcgg accguggacc ucggccagug cgggcugcug 240
ggcaccauca cgggccagcc gcagugcgac caguuccucg aguucagcgc cgaccugauc 300
aucgagcgcc gggacgggaa cgacgucugc uaccccggca aguucgugaa cggggaggcc 360
cugcgccaga ucccuccggaa guccggcggg aucaacaagg agaccauggg cuucaccuac 420
agcggcaucc gcaccaacgg gacgaccucc gcgugccggc gcagcggcuc cagcuucuac 480
gccgagauga aguggcugcu guccgacacc gacaacgccg ccuuccccca gaugaccaag 540
agcuacaaga acacgcggcg cgagcccgcg cucaucgugu gggggaucca ccacuccggc 600
agcaccaccg agcagaccaa gcuguacggc uccgggaaca agcugguccac ggugggcagc 660 uccaaguacc agcagagcuu cgugccgucc cccgagaccc ggccccaggu caacgggcag 720
agcggccgca ucgacuucca cuggcucauc cuggacucca acgacaccgu gaccuucagc 780
uucaacgggg ccuucaucgc ccccgaccgg gccagcuucc ugaagggcaa guccaugggc 840
auccagagcg acgugcaggu cgacgccaac ugcgaggggg agugcuacca cuccggcggg 900
acgaucacca gcucccuccc guuccagaac aucaacagcc gcgcgguggg caagugcccc 960
cgguacguga agcaggaguc ccugcugcuc gccaccggga ugaagaacgu ccccgagcug 1020

-continued agcaagaagc gccggaagcg cggccuguuc ggcgccaucg ccggguucau cgagaacggc 1080
ugggaggggc ucguggacgg cugguacggg uuccggcacc agaacgccca gggcgagggc 1140
accgcggccg acuacaaguc cacgcagagc gccaucgacc agaucaccgg gaagcugaac 1200
cgccugaucg agaagaccaa ccagcaguuc gagcucaucg acaacgaguu caccgaggug 1260
gagaagcaga ucggcaacgu caucaacugg acgcgggacu ccaucaccga ggugugggagc 1320 uacaacgccg agcugcuggu cgccauggag aaccagcaca ccaucgaccu cgcggacucc 1380
gagaugaaca agcuguacga gcgggugcgc aagcagcugc gggagaacgc cgaggaggac 1440
gggaccggcu gcuucgagau cuuccacaag ugcgacgacg acugcauggc cagcauccgc 1500
aacaacacgu acgaccacuc caaguaccgg gaggaggcca ugcagaaccg cauccagauc 1560
gaccccguga agcucagcgg cggguacaag gacgucaucc ugugguucuc cuucggcgcc 1620
agcugcuucc ugcuccuggc gaucgccaug ggcuggugu ucaucugcgu gaagaacggc 1680
aacaugcggu gcaccaucug caucugacca cuaguuauaa gacugacuag cccgaugggc 1740
cucccaacgg gcccuccucc ccuccuugca ccgagauuaa uaaaaaaaaa aaaaaaaaaa 1800
aaaaaaaaaa aaaaaaaaaa aaaaaaaaaa aaaaaaaaaa aaaaaugcau cccccccccc 1860
cccccccccc cccccccccc caaaggcucu uuucagagcc accagaauu 1909

<210> SEQ ID NO 12
<211> LENGTH: 1918
<212> TYPE: RNA
<213> ORGANISM: Artificial sequence
<220> FEATURE:
<223> OTHER INFORMATION: GC optimized HA mRNA

<400> SEQUENCE: 12
gggagaaagc uuaccaugaa ggccauccug gugguccucc uguacaccuu cgccaccgcg 60
aacgccgaca cgcugugcau cggcuaccac gccaacaaca gcaccgacac cguggacacc 120
gugcucgaga agaacgucac ggugacccac uccgugaacc ugcuggagga caagcacaac 180
gggaagcucu gcaagcugcg gggcgucgcc ccgcugcacc ucgggaagug caacaucgcc 240
ggcuggaucc uggggaaccc ggagugcgag agccugucca ccgcgagcuc cuggagcuac 300
aucguggaga ccuccuccag cgacaacggc acgugcuacc ccggcgacuu caucgacuac 360
gaggagcucc gcgagcagcu guccagcgug uccagcuucg agcgguucga gaucuucccc 420
aagaccucca gcuggccgaa ccacgacucc aacaaggggg ucaccgccgc cugcccccac 480
gccggcgcga agagcuucua caagaaccug aucuggcucg ugaagaaggg gaacuccuac 540
cccaagcuga gcaaguccua caucaacgac aagggcaagg aggugcuggu ccucuggggg 600
auccaccacc ccagcaccag cgccgaccag caguccugu accagaacgc cgacgccuac 660
guguucgugg gcagcucccg cuacagcaag aaguucaagc cggagaucgc cauccggccc 720
aagguccgcg accaggaggg ccgcaugaac uacuacugga cccuggugga gcccggggac 780
aagaucaccu ucgaggcgac cggcaaccuc gugguccccc gguacgccuu cgccauggag 840
cgcaacgccg gguccggcau caucaucagc gacacgccgg ugcacgacug caacaccacc 900
ugccagaccc ccaagggcgc caucaacacg ucccugcccu uccagaacau ccaccccauc 960
accaucggga agugcccgaa guacgugaag agcaccaagc ugcggcucgc gaccggccug 1020
cgcaacgucc ccuccaucca gagccggggg cuguucggcg ccaucgccgg guucaucgag 1080
ggcggcugga cggggauggu cgacggcugg uacggguacc accaccagaa cgagcagggc 1140
agcggguacg ccgccgaccu caaguccacg cagaacgcga ucgacgagau caccaacaag 1200
gugaacagcg ucaucgagaa gaugaacacc caguucaccg ccgugggcaa ggaguucaac 1260
caccuggaga agcggaucga gaaccugaac aagaaggucg acgacggcuu ccucgacauc 1320
uggacguaca acgccgagcu gcuggugcuc cuggagaacg agcgcacccu ggacuaccac 1380
gacuccaacg ugaagaaccu cuacgagaag guccggagcc agcugaagaa caacgccaag 1440
gagaucggga acggcugcuu cgaguucuac cacaagugcg acaacaccug cauggagucc 1500
gugaagaacg ggaccuacga cuaccccaag uacagcgagg aggccaagcu gaaccgcgag 1560
gagaucgacg gcgugaagcu cgaguccacg cggaucuacc agauccuggc gaucuacagc 1620
accgucgcca gcucccuggu gcucgugguc agccuggggg ccaucuccuu cuggaugugc 1680
agcaacggcu cccugcagug ccgcaucugc aucugaccac uaguuauaag acugacuagc 1740
ccgaugggcc ucccaacggg cccuccuccc cuccuugcac cgagauuaau aaaaaaaaaa 1800
aaaaaaaaaa aaaaaaaaaa aaaaaaaaaa aaaaaaaaaa aaaaaaaaaa aaaaugcauc 1860
cccccccccc cccccccccc cccccccccc aaaggcucuu uucagagcca ccagaauu 1918

<210> SEQ ID NO 13
<211> LENGTH: 1975
<212> TYPE: RNA
<213> ORGANISM: Artificial sequence
<220> FEATURE:
<223> OTHER INFORMATION: GC optimized HA mRNA

<400> SEQUENCE: 13
gggagaaagc uuaccaugaa ggccaucauc gugcugcuca uggucgugac cagcaacgcc 60
gaccggaucu gcaccggcau cacguccagc aacuccccgc acguggucaa gaccgcgacc 120
cagggggagg ugaacgugac cggcgucauc ccgcugacga ccacccccac caagagccac 180
uucgccaacc ugaaggggac ggagacccgc ggcaagcucu gccccaagug ccugaacugc 240
accgaccugg acguggcccu cgggcggccc aagugcaccg gcaagauccc guccgcccgc 300
gugagcaucc ugcacgaggu ccggcccgug acguccggcu gcuuccccau caugcacgac 360
cgcaccaaga uccggcagcu gcccaaccuc cugcgcgggu acgagcacau ccggcugagc 420
acccacaacg ugaucaacgc cgagaacgcg ccgggcgggc ccuacaagau cggcaccucc 480
gggagcugcc ccaacaucac gaacggcaac ggcuucuucg ccaccauggc cugggccguc 540
cccaagaacg acaagaacaa gaccgcgacc aacccgcuca cgaucgaggu gcccuacauc 600
ugcaccgagg gggaggacca gaucaccgug uggggcuucc acuccgacaa cgagacccag 660
auggccaagc uguacgggga cagcaagccc cagaaguuca cguccagcgc caacggcguc 720
accacccacu acgnguccca gaucggcggg uuccccaacc agaccgagga cggcgggcug 780
ccgcagagcg gccgcaucgu ggucgacuac auggugcaga aguccgggaa gacgggcacc 840
aucaccuacc agcggggcau ccuccugccc cagaaggugu ggugcgccag cgggcgcucc 900
aaggucauca agggcagccu gccccucauc ggggaggccg acugccugca cgagaaguac 960
ggcgggcuga acaagagcaa gcccuacuac accggcgagc acgcgaaggc caucggcaac 1020
ugcccgaucu gggugaagac gccccucaag cuggccaacg ggaccaagua ccggcccccc 1080
gccaagcugc ucaaggagcg cggcuucuuc ggggccaucg cgggcuuccu ggagggcggg 1140
ugggagggca ugaucgccgg guggcacggc uacaccuccc acggggccca cggcguggcc 1200
gucgccgcgg accugaagag cacccaggag gccaucaaca agaucacgaa gaaccucaac 1260
ucccugagcg agcuggaggu gaagaaccuc cagcggcugu ccggcgccau ggacgagcug 1320

-continued cacaacgaga uccucgagcu ggacgagaag gucgacgacc ugcgcgccga caccaucagc 1380
ucccagaucg agcucgccgu gcugcugagc aacgagggga ucaucaacuc cgaggacgag 1440
caccuccugg cgcuggagcg gaagcucaag aagaugcugg gcccgagcgc cguggagauc 1500
gggaacggcu gcuucgagac caagcacaag ugcaaccaga ccugccugga ccgcaucgcc 1560
gccgggaccu ucgacgcggg cgaguucucc cuccccacgu ucgacagccu gaacaucacc 1620
gccgccuccc ugaacgacga cggccuggac aaccacacca uccuccugua cuacagcacc 1680
gccgccucca gccuggcggu cacgcucaug aucgccaucu ucgugguga cauggucucc 1740 cgggacaacg ugagcugcuc caucugccug ugaggacuag uuauaagacu gacuagcccg 1800
augggccucc caacgggccc uccuccccuc cuugcaccga gauuaauaaa aaaaaaaaaa 1860
aaaaaaaaaa aaaaaaaaaa aaaaaaaaaa aaaaaaaaaa aaaaaaaaaa augcaucccc 1920
cccccccccc cccccccccc cccccccaaa ggcucuuuuc agagccacca gaauu 1975

<210> SEQ ID NO 14
<211> LENGTH: 1918
<212> TYPE: RNA
<213> ORGANISM: Artificial sequence
<220> FEATURE:
<223> OTHER INFORMATION: GC optimized HA mRNA

<400> SEQUENCE: 14
gggagaaagc uuaccaugaa ggccauccug guggccuccc uguacaccuu cgccaccgcg 60
aacgccgaca cgcugugcau cggcuaccac gccaacaaca gcaccgacac cguggacacc 120
gugcucgaga agaacgucac ggugacccac uccgugaacc ugcuggagga caagcacaac 180
gggaagcucu gcaagcugcg gggcgucgcc ccgcugcacc ucgggaagug caacaucgcc 240
ggcuggaucc uggggaaccc ggagugcgag agccugucca ccgcgagcuc cuggagcuac 300
aucguggaga cccccagcuc cgacaacggc acgugcuacc ccggcgacuu caucgacuac 360
gaggagcucc gcgagcagcu gagcuccgug agcuccuucg agcgguucga gaucuucccc 420
aagaccagcu ccuggcccaa ccacgacagc gacaaggggg ucaccgccgc cugcccgcac 480
gccggcgcga aguccuucua caagaaccug aucuggcucg ugaagaaggg gaacagcuac 540
cccaagcugu ccaagagcua caucaacgac aagggcaagg aggugcuggu ccucuggggg 600
auccaccacc ccagcaccuc cgccgaccag cagagccugu accagaacgc cgacgccuac 660
guguucgugg gcuccagccg cuacuccaag acguucaagc ccgagaucgc cauccggccg 720
aagguccgcg accgggaggg ccggaugaac uacuacugga cgcuggugga gcccggggac 780
aagaucaccu ucgaggcgac cggcaaccuc gugguccccc gcuacgccuu cgccauggag 840
cggaacgccg ggagcggcau caucaucucc gacacccccg ugcacgacug caacacgacc 900
ugccagaccc cgaagggcgc caucaacacc agccugcccu uccagaacau ccaccccauc 960
acgaucggga agugccccaa guacgugaag uccaccaagc ugcgccucgc gaccggccug 1020
cggaacaucc cgagcaucca gucccgcggg cuguucggcg ccaucgccgg guucaucgag 1080
ggcggcugga ccgggauggu ggacggcugg uacggguacc accaccagaa cgagcagggc 1140
agcggguacg ccgccgaccu caaguccacg cagaacgcga ucgacgagau caccaacaag 1200
gugaacagcg ucaucgagaa gaugaacacc caguucaccg ccgugggcaa ggaguucaac 1260
caccuggaga agcggaucga gaaccugaac aagaaggucg acgacggcuu ccucgacauc 1320
uggacguaca acgccgagcu gcuggugcuc cuggagaacg agcgcacccu ggacuaccac 1380
gacuccaacg ugaagaaccu cuacgagaag guccggagcc agcugaagaa caacgccaag 1440
gagaucggga acggcugcuu cgaguucuac cacaagugcg acaacaccug cauggagucc 1500
gugaagaacg ggaccuacga cuaccccaag uacagcgagg aggccaagcu gaaccgcgag 1560
gagaucgacg gcgugaagcu cgaguccacg cggaucuacc agauccuggc gaucuacagc 1620
accgucgcca gcucccuggu gcucguggu agccuggggg ccaucuccuu cuggaugugc 1680
agcaacggcu cccugcagug ccgcaucugc aucugaccac uaguuauaag acugacuagc 1740
ccgaugggcc ucccaacggg cccuccuccc cuccuugcac cgagauuaau aaaaaaaaaa 1800
aaaaaaaaaa aaaaaaaaaa aaaaaaaaaa aaaaaaaaaa aaaaaaaaaa aaaaugcauc 1860
cccccccccc cccccccccc cccccccccc aaaggcucuu uucagagcca ccagaauu 1918

<210> SEQ ID NO 15
<211> LENGTH: 3952
<212> TYPE: DNA
<213> ORGANISM: Artificial sequence
<220> FEATURE:
<223> OTHER INFORMATION: GC optimized HA construct

<400> SEQUENCE: 15
cagctgcatt aatgaatcgg ccaacgcgcg gggagaggcg gtttgcgtat tgggcgctct 60
tccgcttcct cgctcactga ctcgctgcgc tcggtcgttc ggctgcggcg agcggtatca 120
gctcactcaa aggcggtaat acggttatcc acagaatcag gggataacgc aggaaagaac 180
atgtgagcaa aaggccagca aaaggccagg aaccgtaaaa aggccgcgtt gctggcgttt 240
ttccataggc tccgcccccc tgacgagcat cacaaaaatc gacgctcaag tcagaggtgg 300
cgaaacccga caggactata aagataccag gcgtttcccc ctggaagctc cctcgtgcgc 360
tctcctgttc cgaccctgcc gcttaccgga tacctgtccg cctttctccc ttcgggaagc 420
gtggcgcttt ctcatagctc acgctgtagg tatctcagtt cggtgtaggt cgttcgctcc 480
aagctgggct gtgtgcacga accccccgtt cagcccgacc gctgcgcctt atccggtaac 540
tatcgtcttg agtccaaccc ggtaagacac gacttatcgc cactggcagc agccactggt 600
aacaggatta gcagagcgag gtatgtaggc ggtgctacag agttcttgaa gtggtggcct 660
aactacggct acactagaag aacagtattt ggtatctgcg ctctgctgaa gccagttacc 720
ttcggaaaaa gagttggtag ctcttgatcc ggcaaacaaa ccaccgctgg tagcggtggt 780 tttttgttt gcaagcagca gattacgcgc agaaaaaaag gatctcaaga agatcctttg 840
atcttttcta cggggtctga cgctcagtgg aacgaaaact cacgttaagg gattttggtc 900
atgagattat caaaaaggat cttcacctag atccttttaa attaaaaatg aagttttaaa 960
tcaatctaaa gtatatatga gtaaacttgg tctgacagtt accaatgctt aatcagtgag 1020
gcacctatct cagcgatctg tctatttcgt tcatccatag ttgcctgact ccccgtcgtg 1080
tagataacta cgatacggga gggcttacca tctggcccca gtgctgcaat gataccgcga 1140
gacccacgct caccggctcc agatttatca gcaataaacc agccagccgg aagggccgag 1200
cgcagaagtg gtcctgcaac tttatccgcc tccatccagt ctattaattg ttgccgggaa 1260
gctagagtaa gtagttcgcc agttaatagt ttgcgcaacg ttgttgccat tgctacaggc 1320
atcgtggtgt cacgctcgtc gtttggtatg gcttcattca gctccggttc ccaacgatca 1380
aggcgagtta catgatcccc catgttgtgc aaaaaagcgg ttagctcctt cggtcctccg 1440
atcgttgtca gaagtaagtt ggccgcagtg ttatcactca tggttatggc agcactgcat 1500
aattctctta ctgtcatgcc atccgtaaga tgcttttctg tgactggtga gtactcaacc 1560

-continued

```
aagtcattct gagaatagtg tatgcggcga ccgagttgct cttgcccggc gtcaatacgg   1620
gataataccg cgccacatag cagaacttta aaagtgctca tcattggaaa acgttcttcg   1680
gggcgaaaac tctcaaggat cttaccgctg ttgagatcca gttcgatgta acccactcgt   1740
gcacccaact gatcttcagc atcttttact ttcaccagcg tttctgggtg agcaaaaaca   1800
ggaaggcaaa atgccgcaaa aaagggaata agggcgacac ggaaatgttg aatactcata   1860
ctcttccttt ttcaatatta ttgaagcatt tatcagggtt attgtctcat gagcggatac   1920
atatttgaat gtatttagaa aaataaacaa ataggggttc cgcgcacatt tccccgaaaa   1980
gtgccacctg acgtctaata cgactcacta tagggagaaa gcttaccatg aaggccaacc   2040
tgctcgtgct gctgtgcgcc ctcgcggccg ccgacgccga caccatctgc atcggctacc   2100
acgccaacaa cagcaccgac acggtcgaca ccgtgctgga gaagaacgtg accgtcaccc   2160
actccgtgaa cctgctcgag gacagccaca acgggaagct gtgccggctg aagggcatcg   2220
cgcccctcca gctggggaag tgcaacatcg ccggctggct gctcgggaac ccggagtgcg   2280
acccccctgct gcccgtgcgc tcctggagct acatcgtcga gacgcccaac tccgagaacg   2340
gcatctgcta cccgggcgac ttcatcgact acgaggagct ccgggagcag ctgagctccg   2400
tgagctcctt cgagcgcttc gagatcttcc ccaaggagag ctcctggccc aaccacaaca   2460
ccaacggggt gaccgccgcc tgcagccacg agggcaagtc cagcttctac cggaacctgc   2520
tctggctgac cgagaaggag gggtcctacc ccaagctgaa gaacagctac gtcaacaaga   2580
agggcaagga ggtgctcgtg ctgtggggga tccaccaccc gcccaactcc aaggagcagc   2640
agaacctgta ccagaacgag aacgcgtacg tcagcgtggt gacgtccaac tacaaccgcc   2700
ggttcacccc cgagatcgcc gagcgcccca aggtccggga ccaggccggc cgcatgaact   2760
actactggac cctcctgaag ccgggcgaca ccatcatctt cgaggccaac gggaacctga   2820
tcgccccgat gtacgcgttc gccctcagcc ggggcttcgg gagcggcatc atcacgtcca   2880
acgccagcat gcacgagtgc aacaccaagt gccagacccc cctgggcgcc atcaactcca   2940
gcctgcccta ccagaacatc cacccggtga ccatcgggga gtgccccaag tacgtgcgct   3000
ccgccaagct ccggatggtc acgggcctgc gcaacaaccc cagcatccag tcccgggggc   3060
tgttcggcgc gatcgccggg ttcatcgagg gcggctggac cgggatgatc gacggctggt   3120
acgggtacca ccaccagaac gagcagggca gcgggtacgc cgccgaccag aagtccaccc   3180
agaacgccat caacggcatc accaacaagg tgaacacggt gatcgagaag atgaacatcc   3240
agttcaccgc ggtcggcaag gagttcaaca agctcgagaa gcgcatggag aacctgaaca   3300
agaaggtgga cgacgggttc ctggacatct ggacctacaa cgccgagctc ctggtgctgc   3360
tcgagaacga gcggaccctg gacttccacg acagcaacgt caagaacctg tacgagaagg   3420
tgaagtccca gctcaagaac aacgccaagg agatcggcaa cgggtgcttc gagttctacc   3480
acaagtgcga caacgagtgc atggagagcg tccgcaacgg cacgtacgac taccccaagt   3540
actccgagga gagcaagctg aaccgggaga aggtggacgg ggtgaagctg gagtccatgg   3600
gcatctacca gatcctcgcc atctacagca ccgtcgcctc cagcctggtg ctgctggtgt   3660
ccctcggcgc gatcagcttc tggatgtgca gcaacgggtc cctgcagtgc cgcatctgca   3720
tctgaccact agttataaga ctgactagcc cgatgggcct cccaacgggc cctcctcccc   3780
tccttgcacc gagattaata aaaaaaaaaa aaaaaaaaaa aaaaaaaaaa aaaaaaaaaa   3840
aaaaaaaaaa aaaaaaaaaa aaatgcatcc cccccccccc cccccccccc cccccccccca   3900
aaggctcttt tcagagccac cagaattcgg atactctaga catatgctta ag           3952
```

<210> SEQ ID NO 16
<211> LENGTH: 3955
<212> TYPE: DNA
<213> ORGANISM: Artificial sequence
<220> FEATURE:
<223> OTHER INFORMATION: GC optimized HA construct

<400> SEQUENCE: 16
cagctgcatt aatgaatcgg ccaacgcgcg gggagaggcg gtttgcgtat tgggcgctct 60
tccgcttcct cgctcactga ctcgctgcgc tcggtcgttc ggctgcggcg agcggtatca 120
gctcactcaa aggcggtaat acggttatcc acagaatcag gggataacgc aggaaagaac 180
atgtgagcaa aaggccagca aaaggccagg aaccgtaaaa aggccgcgtt gctggcgttt 240
ttccataggc tccgcccccc tgacgagcat cacaaaaatc gacgctcaag tcagaggtgg 300
cgaaacccga caggactata aagataccag gcgtttcccc ctggaagctc cctcgtgcgc 360
tctcctgttc cgaccctgcc gcttaccgga tacctgtccg cctttctccc ttcgggaagc 420
gtggcgcttt ctcatagctc acgctgtagg tatctcagtt cggtgtaggt cgttcgctcc 480
aagctgggct gtgtgcacga accccccgtt cagcccgacc gctgcgcctt atccggtaac 540
tatcgtcttg agtccaaccc ggtaagacac gacttatcgc cactggcagc agccactggt 600
aacaggatta gcagagcgag gtatgtaggc ggtgctacag agttcttgaa gtggtggcct 660
aactacggct acactagaag aacagtattt ggtatctgcg ctctgctgaa gccagttacc 720
ttcggaaaaa gagttggtag ctcttgatcc ggcaaacaaa ccaccgctgg tagcggtggt 780 tttttgttt gcaagcagca gattacgcgc agaaaaaaag gatctcaaga agatcctttg 840
atcttttcta cggggtctga cgctcagtgg aacgaaaact cacgttaagg gattttggtc 900
atgagattat caaaaaggat cttcacctag atccttttaa attaaaaatg aagttttaaa 960
tcaatctaaa gtatatatga gtaaacttgg tctgacagtt accaatgctt aatcagtgag 1020
gcacctatct cagcgatctg tctatttcgt tcatccatag ttgcctgact ccccgtcgtg 1080
tagataacta cgatacggga gggcttacca tctggcccca gtgctgcaat gataccgcga 1140
gacccacgct caccggctcc agatttatca gcaataaacc agccagccgg aagggccgag 1200
cgcagaagtg gtcctgcaac tttatccgcc tccatccagt ctattaattg ttgccgggaa 1260
gctagagtaa gtagttcgcc agttaatagt ttgcgcaacg ttgttgccat tgctacaggc 1320
atcgtggtgt cacgctcgtc gtttggtatg gcttcattca gctccggttc ccaacgatca 1380
aggcgagtta catgatcccc catgttgtgc aaaaaagcgg ttagctcctt cggtcctccg 1440
atcgttgtca gaagtaagtt ggccgcagtg ttatcactca tggttatggc agcactgcat 1500
aattctctta ctgtcatgcc atccgtaaga tgcttttctg tgactggtga gtactcaacc 1560
aagtcattct gagaatagtg tatgcggcga ccgagttgct cttgcccggc gtcaatacgg 1620
gataataccg cgccacatag cagaacttta aaagtgctca tcattggaaa acgttcttcg 1680
gggcgaaaac tctcaaggat cttaccgctg ttgagatcca gttcgatgta acccactcgt 1740
gcacccaact gatcttcagc atcttttact ttcaccagcg tttctgggtg agcaaaaaca 1800
ggaaggcaaa atgccgcaaa aaagggaata agggcgacac ggaaatgttg aatactcata 1860
ctcttccttt ttcaatatta ttgaagcatt tatcagggtt attgtctcat gagcggatac 1920
atatttgaat gtatttagaa aaataaacaa ataggggttc cgcgcacatt tccccgaaaa 1980
gtgccacctg acgtctaata cgactcacta tagggagaaa gcttaccatg aaggccatcc 2040

-continued tggtggtcct cctgtacacc ttcgccaccg cgaacgccga cacgctgtgc atcggctacc 2100
acgccaacaa cagcaccgac accgtggaca ccgtgctcga gaagaacgtc acggtgaccc 2160
actccgtgaa cctgctggag gacaagcaca acgggaagct ctgcaagctg cggggcgtcg 2220
ccccgctgca cctcgggaag tgcaacatcg ccggctggat cctggggaac ccggagtgcg 2280
agagcctgtc caccgcgagc tcctggagct acatcgtgga gacctccagc tccgacaacg 2340
gcacgtgcta ccccggcgac ttcatcgact acgaggagct ccgcgagcag ctgagctccg 2400
tgagctcctt cgagcggttc gagatcttcc ccaagaccag ctcctggccc aaccacgaca 2460
gcaacaaggg ggtcaccgcc gcctgcccgc acgccggcgc gaagtccttc tacaagaacc 2520
tgatctggct cgtgaagaag gggaacagct accccaagct gtccaagagc tacatcaacg 2580
acaagggcaa ggaggtgctg gtcctctggg ggatccacca ccccagcacc tccgccgacc 2640
agcagagcct gtaccagaac gccgacgcct acgtgttcgt gggctccagc cgctactcca 2700
agaagttcaa gcccgagatc gccatccggc cgaaggtccg cgaccaggag ggccggatga 2760
actactactg gacgctggtg gagcccgggg acaagatcac cttcgaggcg accggcaacc 2820
tcgtggtccc ccgctacgcc ttcgccatgg agcggaacgc cgggagcggc atcatcatct 2880
ccgacacccc cgtgcacgac tgcaacacga cctgccagac ccccgaagggc gccatcaaca 2940 ccagcctgcc cttccagaac atccacccca tcacgatcgg gaagtgcccc aagtacgtga 3000
agtccaccaa gctgcgcctc gcgaccggcc tgcggaacgt cccgagcatc cagtcccgcg 3060
ggctgttcgg cgccatcgcc gggttcatcg agggcggctg gaccgggatg gtggacggct 3120
ggtacgggta ccaccaccag aacgagcagg gcagcgggta cgccgccgac ctcaagtcca 3180
cgcagaacgc gatcgacgag atcaccaaca aggtgaacag cgtcatcgag aagatgaaca 3240
cccagttcac cgccgtgggc aaggagttca accacctgga gaagcggatc gagaacctga 3300
acaagaaggt cgacgacggc ttcctcgaca tctggacgta caacgccgag ctgctggtgc 3360
tcctggagaa cgagcgcacc ctggactacc acgactccaa cgtgaagaac ctctacgaga 3420
aggtccggag ccagctgaag aacaacgcca aggagatcgg gaacggctgc ttcgagttct 3480
accacaagtg cgacaacacc tgcatggagt ccgtgaagaa cgggacctac gactacccca 3540
agtacagcga ggaggccaag ctgaaccgcg aggagatcga cggcgtgaag ctcgagtcca 3600
cgcggatcta ccagatcctg gcgatctaca gcaccgtcgc cagctccctg gtgctcgtgg 3660
tcagcctggg ggccatctcc ttctggatgt gcagcaacgg ctccctgcag tgccgcatct 3720
gcatctgacc actagttata agactgacta gcccgatggg cctcccaacg ggccctcctc 3780
ccctccttgc accgagatta ataaaaaaaa aaaaaaaaaa aaaaaaaaaa aaaaaaaaaa 3840
aaaaaaaaaa aaaaaaaaaa aaaaaatgca tccccccccc cccccccccc cccccccccc 3900
ccaaaggctc ttttcagagc caccagaatt cggatactct agacatatgc ttaag 3955

<210> SEQ ID NO 17
<211> LENGTH: 3955
<212> TYPE: DNA
<213> ORGANISM: Artificial sequence
<220> FEATURE:
<223> OTHER INFORMATION: GC optimized HA construct

<400> SEQUENCE: 17
cagctgcatt aatgaatcgg ccaacgcgcg gggagaggcg gtttgcgtat tgggcgctct 60
tccgcttcct cgctcactga ctcgctgcgc tcggtcgttc ggctgcggcg agcggtatca 120
gctcactcaa aggcggtaat acggttatcc acagaatcag gggataacgc aggaaagaac 180

-continued atgtgagcaa aaggccagca aaaggccagg aaccgtaaaa aggccgcgtt gctggcgttt 240
ttccataggc tccgcccccc tgacgagcat cacaaaaatc gacgctcaag tcagaggtgg 300
cgaaacccga caggactata aagataccag gcgtttcccc ctggaagctc cctcgtgcgc 360
tctcctgttc cgaccctgcc gcttaccgga tacctgtccg cctttctccc ttcgggaagc 420
gtggcgcttt ctcatagctc acgctgtagg tatctcagtt cggtgtaggt cgttcgctcc 480
aagctgggct gtgtgcacga accccccgtt cagcccgacc gctgcgcctt atccggtaac 540
tatcgtcttg agtccaaccc ggtaagacac gacttatcgc cactggcagc agccactggt 600
aacaggatta gcagagcgag gtatgtaggc ggtgctacag agttcttgaa gtggtggcct 660
aactacggct acactagaag aacagtattt ggtatctgcg ctctgctgaa gccagttacc 720
ttcggaaaaa gagttggtag ctcttgatcc ggcaaacaaa ccaccgctgg tagcggtggt 780 tttttgttt gcaagcagca gattacgcgc agaaaaaaag gatctcaaga agatcctttg 840
atcttttcta cggggtctga cgctcagtgg aacgaaaact cacgttaagg gattttggtc 900
atgagattat caaaaaggat cttcacctag atccttttaa attaaaaatg aagttttaaa 960
tcaatctaaa gtatatatga gtaaacttgg tctgacagtt accaatgctt aatcagtgag 1020
gcacctatct cagcgatctg tctatttcgt tcatccatag ttgcctgact ccccgtcgtg 1080
tagataacta cgatacggga gggcttacca tctggcccca gtgctgcaat gataccgcga 1140
gacccacgct caccggctcc agatttatca gcaataaacc agccagccgg aagggccgag 1200
cgcagaagtg gtcctgcaac tttatccgcc tccatccagt ctattaattg ttgccgggaa 1260
gctagagtaa gtagttcgcc agttaatagt ttgcgcaacg ttgttgccat tgctacaggc 1320
atcgtggtgt cacgctcgtc gtttggtatg gcttcattca gctccggttc ccaacgatca 1380
aggcgagtta catgatcccc catgttgtgc aaaaaagcgg ttagctcctt cggtcctccg 1440
atcgttgtca gaagtaagtt ggccgcagtg ttatcactca tggttatggc agcactgcat 1500
aattctctta ctgtcatgcc atccgtaaga tgcttttctg tgactggtga gtactcaacc 1560
aagtcattct gagaatagtg tatgcggcga ccgagttgct cttgcccggc gtcaatacgg 1620
gataataccg cgccacatag cagaacttta aaagtgctca tcattggaaa acgttcttcg 1680
gggcgaaaac tctcaaggat cttaccgctg ttgagatcca gttcgatgta acccactcgt 1740
gcacccaact gatcttcagc atcttttact ttcaccagcg tttctgggtg agcaaaaaca 1800
ggaaggcaaa atgccgcaaa aaagggaata agggcgacac ggaaatgttg aatactcata 1860
ctcttccttt ttcaatatta ttgaagcatt tatcagggtt attgtctcat gagcggatac 1920
atatttgaat gtatttagaa aaataaacaa ataggggttc cgcgcacatt tccccgaaaa 1980
gtgccacctg acgtctaata cgactcacta tagggagaaa gcttaccatg aaggccatcc 2040
tggtggtcct cctgtacacc ttcgccaccg cgaacgccga cacgctgtgc atcggctacc 2100
acgccaacaa cagcaccgac accgtggaca ccgtgctcga gaagaacgtc acggtgaccc 2160
actccgtgaa cctgctggag gacaagcaca acgggaagct ctgcaagctg cggggcgtcg 2220
ccccgctgca cctcgggaag tgcaacatcg ccggctggat cctggggaac ccggagtgcg 2280
agagcctgtc caccgcgagc tcctggagct acatcgtgga gacccccctcc agcgacaacg 2340 gcacgtgcta ccccggcgac ttcatcgact acgaggagct ccgcgagcag ctgtccagcg 2400
tgtccagctt cgagcggttc gagatcttcc ccaagacctc cagctggccg aaccacgact 2460
ccgacaaggg ggtcaccgcc gcctgccccc acgccggcgc gaagagcttc tacaagaacc 2520

-continued tgatctggct cgtgaagaag gggaactcct accccaagct gagcaagtcc tacatcaacg 2580
acaagggcaa ggaggtgctg gtcctctggg ggatccacca ccccagcacc agcgccgacc 2640
agcagtccct gtaccagaac gccgacgcct acgtgttcgt gggcagctcc cgctacagca 2700
agacgttcaa gccggagatc gccatccggc ccaaggtccg cgaccgggag ggccgcatga 2760
actactactg gaccctggtg gagcccgggg acaagatcac cttcgaggcg accggcaacc 2820
tcgtggtccc ccggtacgcc ttcgccatgg agcgcaacgc cgggtccggc atcatcatca 2880
gcgacacgcc ggtgcacgac tgcaacacca cctgccagac ccccaagggc gccatcaaca 2940
cgtccctgcc cttccagaac atccacccca tcaccatcgg gaagtgcccg aagtacgtga 3000
agagcaccaa gctgcggctc gcgaccggcc tgcgcaacat cccctccatc cagagccggg 3060
ggctgttcgg cgccatcgcc gggttcatcg agggcggctg gacggggatg gtcgacggct 3120
ggtacgggta ccaccaccag aacgagcagg gcagcgggta cgccgccgac ctcaagtcca 3180
cgcagaacgc gatcgacgag atcaccaaca aggtgaacag cgtcatcgag aagatgaaca 3240
cccagttcac cgccgtgggc aaggagttca accacctgga gaagcggatc gagaacctga 3300
acaagaaggt cgacgacggc ttcctcgaca tctggacgta caacgccgag ctgctggtgc 3360
tcctggagaa cgagcgcacc ctggactacc acgactccaa cgtgaagaac ctctacgaga 3420
aggtccggag ccagctgaag aacaacgcca aggagatcgg gaacggctgc ttcgagttct 3480
accacaagtg cgacaacacc tgcatggagt ccgtgaagaa cgggacctac gactacccca 3540
agtacagcga ggaggccaag ctgaaccgcg aggagatcga cggcgtgaag ctcgagtcca 3600
cgcggatcta ccagatcctg gcgatctaca gcaccgtcgc cagctccctg gtgctcgtgg 3660
tcagcctggg ggccatctcc ttctggatgt gcagcaacgg ctccctgcag tgccgcatct 3720
gcatctgacc actagttata agactgacta gcccgatggg cctcccaacg ggccctcctc 3780
ccctccttgc accgagatta ataaaaaaaa aaaaaaaaaa aaaaaaaaaa aaaaaaaaaa 3840
aaaaaaaaaa aaaaaaaaaa aaaaaatgca tccccccccc cccccccccc cccccccccc 3900
ccaaaggctc ttttcagagc caccagaatt cggatactct agacatatgc ttaag 3955

<210> SEQ ID NO 18
<211> LENGTH: 3949
<212> TYPE: DNA
<213> ORGANISM: Artificial sequence
<220> FEATURE:
<223> OTHER INFORMATION: GC optimized HA construct

<400> SEQUENCE: 18
cagctgcatt aatgaatcgg ccaacgcgcg gggagaggcg gtttgcgtat tgggcgctct 60
tccgcttcct cgctcactga ctcgctgcgc tcggtcgttc ggctgcggcg agcggtatca 120
gctcactcaa aggcggtaat acggttatcc acagaatcag gggataacgc aggaaagaac 180
atgtgagcaa aaggccagca aaaggccagg aaccgtaaaa aggccgcgtt gctggcgttt 240
ttccataggc tccgcccccc tgacgagcat cacaaaaatc gacgctcaag tcagaggtgg 300
cgaaacccga caggactata aagataccag gcgtttcccc ctggaagctc cctcgtgcgc 360
tctcctgttc cgaccctgcc gcttaccgga tacctgtccg cctttctccc ttcgggaagc 420
gtggcgcttt ctcatagctc acgctgtagg tatctcagtt cggtgtaggt cgttcgctcc 480
aagctgggct gtgtgcacga accccccgtt cagcccgacc gctgcgcctt atccggtaac 540
tatcgtcttg agtccaaccc ggtaagacac gacttatcgc cactggcagc agccactggt 600
aacaggatta gcagagcgag gtatgtaggc ggtgctacag agttcttgaa gtggtggcct 660

-continued

```
aactacggct acactagaag aacagtattt ggtatctgcg ctctgctgaa gccagttacc    720
ttcggaaaaa gagttggtag ctcttgatcc ggcaaacaaa ccaccgctgg tagcggtggt    780
tttttgttt gcaagcagca gattacgcgc agaaaaaaag gatctcaaga agatcctttg     840
atcttttcta cggggtctga cgctcagtgg aacgaaaact cacgttaagg gattttggtc    900
atgagattat caaaaaggat cttcacctag atccttttaa attaaaaatg aagttttaaa    960
tcaatctaaa gtatatatga gtaaacttgg tctgacagtt accaatgctt aatcagtgag   1020
gcacctatct cagcgatctg tctatttcgt tcatccatag ttgcctgact ccccgtcgtg   1080
tagataacta cgatacggga gggcttacca tctggcccca gtgctgcaat gataccgcga   1140
gacccacgct caccggctcc agatttatca gcaataaacc agccagccgg aagggccgag   1200
cgcagaagtg gtcctgcaac tttatccgcc tccatccagt ctattaattg ttgccgggaa   1260
gctagagtaa gtagttcgcc agttaatagt ttgcgcaacg ttgttgccat tgctacaggc   1320
atcgtggtgt cacgctcgtc gtttggtatg gcttcattca gctccggttc ccaacgatca   1380
aggcgagtta catgatcccc catgttgtgc aaaaaagcgg ttagctcctt cggtcctccg   1440
atcgttgtca gaagtaagtt ggccgcagtg ttatcactca tggttatggc agcactgcat   1500
aattctctta ctgtcatgcc atccgtaaga tgcttttctg tgactggtga gtactcaacc   1560
aagtcattct gagaatagtg tatgcggcga ccgagttgct cttgcccggc gtcaatacgg   1620
gataataccg cgccacatag cagaacttta aaagtgctca tcattggaaa acgttcttcg   1680
gggcgaaaac tctcaaggat cttaccgctg ttgagatcca gttcgatgta acccactcgt   1740
gcacccaact gatcttcagc atcttttact ttcaccagcg tttctgggtg agcaaaaaca   1800
ggaaggcaaa atgccgcaaa aaagggaata agggcgacac ggaaatgttg aatactcata   1860
ctcttccttt ttcaatatta ttgaagcatt tatcagggtt attgtctcat gagcggatac   1920
atatttgaat gtatttagaa aaataaacaa ataggggttc cgcgcacatt tccccgaaaa   1980
gtgccacctg acgtctaata cgactcacta tagggagaaa gcttaccatg gagaagatcg   2040
tgctgctctt cgccatcgtc agcctggtga agtccgacca gatctgcatc ggctaccacg   2100
ccaacaacag caccgagcag gtggacacca tcatggagaa gaacgtcacg gtgacccacg   2160
cgcaggacat cctggagaag acccacaacg ggaagctctg cgacctggac ggcgtgaagc   2220
ccctgatcct ccgggactgc tccgtcgccg ggtggctgct gggcaacccg atgtgcgacg   2280
agttcatcaa cgtgcccgag tggagctaca tcgtggagaa ggccaacccc gtcaacgacc   2340
tctgctaccc cggggacttc aacgactacg aggagctgaa gcacctgctc tcccgcatca   2400
accacttcga gaagatccag atcatcccga agagctcctg gagctcccac gaggccagcc   2460
tgggcgtgtc cagcgcctgc ccctaccagg gcaagtccag cttcttccgg aacgtggtct   2520
ggctgatcaa gaagaactcc acctacccca cgatcaagcg cagctacaac aacaccaacc   2580
aggaggacct cctggtgctg tgggggatcc accaccccaa cgacgcggcc gagcagacca   2640
agctctacca gaacccgacc acgtacatct ccgtgggcac cagcaccctg aaccagcggc   2700
tggtcccccg catcgccacc cggtccaagg tgaacgggca gagcggccgc atggagttct   2760
tctggacgat cctcaagccc aacgacgcca tcaacttcga gagcaacggg aacttcatcg   2820
cgcccgagta cgcctacaag atcgtgaaga agggcgactc caccatcatg aagagcgagc   2880
tggagtacgg caactgcaac accaagtgcc agaccccgat gggggccatc aactccagca   2940
tgcccttcca caacatccac cccctgacga tcggcgagtg ccccaagtac gtcaagtcca   3000
```

-continued

```
accggctcgt gctggccacc gggctgcgca acagcccgca gcgggagacc cgcggcctct   3060

tcggcgccat cgcggggttc atcgagggcg ggtggcaggg catggtggac gggtggtacg   3120

gctaccacca ctccaacgag cagggcagcg ggtacgccgc cgacaaggag tccacccaga   3180

aggccatcga cggcgtcacg aacaaggtga acagcatcat cgacaagatg aacacccagt   3240

tcgaggccgt ggggcgggag ttcaacaacc tggagcgccg gatcgagaac ctgaacaaga   3300

agatggagga cggcttcctc gacgtctgga cctacaacgc ggagctgctg gtgctcatgg   3360

agaacgagcg caccctggac ttccacgact ccaacgtcaa gaacctgtac gacaaggtgc   3420

ggctccagct gcgcgacaac gccaaggagc tggggaacgg ctgcttcgag ttctaccaca   3480

agtgcgacaa cgagtgcatg gagagcgtgc ggaacggcac gtacgactac ccccagtact   3540

ccgaggaggc ccgcctcaag cgggaggaga tcagcggggt caagctggag tccatcggca   3600

tctaccagat cctgagcatc tactccaccg tggccagctc cctcgccctg gcgatcatgg   3660

tggccgggct gagcctctgg atgtgcagca acggctccct gcagtgccgc atctgcatct   3720

gaggactagt tataagactg actagcccga tgggcctccc aacgggccct cctcccctcc   3780

ttgcaccgag attaataaaa aaaaaaaaaa aaaaaaaaaa aaaaaaaaaa aaaaaaaaaa   3840

aaaaaaaaaa aaaaaaaaaa tgcatccccc cccccccccc cccccccccc ccccccaaag   3900

gctcttttca gagccaccag aattcggata ctctagacat atgcttaag              3949
```

```
<210> SEQ ID NO 19
<211> LENGTH: 3961
<212> TYPE: DNA
<213> ORGANISM: Artificial sequence
<220> FEATURE:
<223> OTHER INFORMATION: GC optimized HA construct

<400> SEQUENCE: 19
```

```
cagctgcatt aatgaatcgg ccaacgcgcg gggagaggcg gtttgcgtat tgggcgctct     60

tccgcttcct cgctcactga ctcgctgcgc tcggtcgttc ggctgcggcg agcggtatca    120

gctcactcaa aggcggtaat acggttatcc acagaatcag gggataacgc aggaaagaac    180

atgtgagcaa aaggccagca aaaggccagg aaccgtaaaa aggccgcgtt gctggcgttt    240

ttccataggc tccgcccccc tgacgagcat cacaaaaatc gacgctcaag tcagaggtgg    300

cgaaacccga caggactata aagataccag gcgtttcccc ctggaagctc cctcgtgcgc    360

tctcctgttc cgaccctgcc gcttaccgga tacctgtccg cctttctccc ttcgggaagc    420

gtggcgcttt ctcatagctc acgctgtagg tatctcagtt cggtgtaggt cgttcgctcc    480

aagctgggct gtgtgcacga accccccgtt cagcccgacc gctgcgcctt atccggtaac    540

tatcgtcttg agtccaaccc ggtaagacac gacttatcgc cactggcagc agccactggt    600

aacaggatta gcagagcgag gtatgtaggc ggtgctacag agttcttgaa gtggtggcct    660

aactacggct acactagaag aacagtattt ggtatctgcg ctctgctgaa gccagttacc    720

ttcggaaaaa gagttggtag ctcttgatcc ggcaaacaaa ccaccgctgg tagcggtggt    780

tttttgttt gcaagcagca gattacgcgc agaaaaaaag gatctcaaga agatcctttg     840

atcttttcta cggggtctga cgctcagtgg aacgaaaact cacgttaagg gattttggtc    900

atgagattat caaaaaggat cttcacctag atccttttaa attaaaaatg aagttttaaa    960

tcaatctaaa gtatatatga gtaaacttgg tctgacagtt accaatgctt aatcagtgag   1020

gcacctatct cagcgatctg tctatttcgt tcatccatag ttgcctgact ccccgtcgtg   1080

tagataacta cgatacggga gggcttacca tctggcccca gtgctgcaat gataccgcga   1140
```

-continued

```
gacccacgct caccggctcc agatttatca gcaataaacc agccagccgg aagggccgag   1200
cgcagaagtg gtcctgcaac tttatccgcc tccatccagt ctattaattg ttgccgggaa   1260
gctagagtaa gtagttcgcc agttaatagt ttgcgcaacg ttgttgccat tgctacaggc   1320
atcgtggtgt cacgctcgtc gtttggtatg gcttcattca gctccggttc ccaacgatca   1380
aggcgagtta catgatcccc catgttgtgc aaaaaagcgg ttagctcctt cggtcctccg   1440
atcgttgtca gaagtaagtt ggccgcagtg ttatcactca tggttatggc agcactgcat   1500
aattctctta ctgtcatgcc atccgtaaga tgcttttctg tgactggtga gtactcaacc   1560
aagtcattct gagaatagtg tatgcggcga ccgagttgct cttgcccggc gtcaatacgg   1620
gataataccg cgccacatag cagaacttta aaagtgctca tcattggaaa acgttcttcg   1680
gggcgaaaac tctcaaggat cttaccgctg ttgagatcca gttcgatgta acccactcgt   1740
gcacccaact gatcttcagc atcttttact ttcaccagcg tttctgggtg agcaaaaaca   1800
ggaaggcaaa atgccgcaaa aaagggaata agggcgacac ggaaatgttg aatactcata   1860
ctcttccttt ttcaatatta ttgaagcatt tatcagggtt attgtctcat gagcggatac   1920
atatttgaat gtatttagaa aaataaacaa ataggggttc cgcgcacatt tccccgaaaa   1980
gtgccacctg acgtctaata cgactcacta tagggagaaa gcttaccatg gagaagatcg   2040
tgctgctctt cgccatcgtc agcctggtga agtccgacca gatctgcatc ggctaccacg   2100
ccaacaacag caccgagcag gtggacacca tcatggagaa gaacgtcacg gtgacccacg   2160
cgcaggacat cctggagaag acccacaacg ggaagctctg cgacctggac ggcgtgaagc   2220
ccctgatcct ccgggactgc tccgtcgccg ggtggctgct gggcaacccg atgtgcgacg   2280
agttcatcaa cgtgcccgag tggagctaca tcgtggagaa ggccaacccc gtcaacgacc   2340
tctgctaccc cggggacttc aacgactacg aggagctgaa gcacctgctc tcccgcatca   2400
accacttcga gaagatccag atcatcccga agagctcctg gagctcccac gaggccagcc   2460
tgggcgtgtc cagcgcctgc ccctaccagg gcaagtccag cttcttccgg aacgtggtct   2520
ggctgatcaa gaagaactcc acctacccca cgatcaagcg cagctacaac aacaccaacc   2580
aggaggacct cctggtgctg tgggggatcc accaccccaa cgacgcggcc gagcagacca   2640
agctctacca gaacccgacc acgtacatct ccgtgggcac cagcaccctg aaccagcggc   2700
tggtcccccg catcgccacc cggtccaagg tgaacgggca gagcggccgc atggagttct   2760
tctggacgat cctcaagccc aacgacgcca tcaacttcga gagcaacggg aacttcatcg   2820
cgcccgagta cgcctacaag atcgtgaaga agggcgactc caccatcatg aagagcgagc   2880
tggagtacgg caactgcaac accaagtgcc agaccccgat gggggccatc aactccagca   2940
tgcccttcca caacatccac cccctgacga tcggcgagtg ccccaagtac gtcaagtcca   3000
accggctcgt gctggccacc gggctgcgca acagcccgca gcgggagcgg cgccggaaga   3060
agcgcggcct cttcggcgcc atcgcggggt tcatcgaggg cgggtggcag ggcatggtgg   3120
acgggtggta cggctaccac cactccaacg agcagggcag cgggtacgcc gccgacaagg   3180
agtccaccca gaaggccatc gacggcgtca cgaacaaggt gaacagcatc atcgacaaga   3240
tgaacaccca gttcgaggcc gtggggcggg agttcaacaa cctggagcgc cggatcgaga   3300
acctgaacaa gaagatggag gacggcttcc tcgacgtctg gacctacaac gcggagctgc   3360
tggtgctcat ggagaacgag cgcaccctgg acttccacga ctccaacgtc aagaacctgt   3420
acgacaaggt gcggctccag ctgcgcgaca acgccaagga gctggggaac ggctgcttcg   3480
```

-continued

```
agttctacca caagtgcgac aacgagtgca tggagagcgt gcggaacggc acgtacgact   3540

acccccagta ctccgaggag gcccgcctca agcgggagga gatcagcggg gtcaagctgg   3600

agtccatcgg catctaccag atcctgagca tctactccac cgtggccagc tccctcgccc   3660

tggcgatcat ggtggccggg ctgagcctct ggatgtgcag caacggctcc ctgcagtgcc   3720

gcatctgcat ctgaggacta gttataagac tgactagccc gatgggcctc ccaacgggcc   3780

ctcctcccct ccttgcaccg agattaataa aaaaaaaaaa aaaaaaaaaa aaaaaaaaaa   3840

aaaaaaaaaa aaaaaaaaaa aaaaaaaaaa aatgcatccc cccccccccc cccccccccc   3900

cccccccccaa aggctctttt cagagccacc agaattcgga tactctagac atatgcttaa   3960

g                                                                   3961
```

```
<210> SEQ ID NO 20
<211> LENGTH: 3961
<212> TYPE: DNA
<213> ORGANISM: Artificial sequence
<220> FEATURE:
<223> OTHER INFORMATION: GC optimized HA construct

<400> SEQUENCE: 20

cagctgcatt aatgaatcgg ccaacgcgcg gggagaggcg gtttgcgtat tgggcgctct     60

tccgcttcct cgctcactga ctcgctgcgc tcggtcgttc ggctgcggcg agcggtatca    120

gctcactcaa aggcggtaat acggttatcc acagaatcag gggataacgc aggaaagaac    180

atgtgagcaa aaggccagca aaaggccagg aaccgtaaaa aggccgcgtt gctggcgttt    240

ttccataggc tccgcccccc tgacgagcat cacaaaaatc gacgctcaag tcagaggtgg    300

cgaaacccga caggactata aagataccag gcgtttcccc ctggaagctc cctcgtgcgc    360

tctcctgttc cgaccctgcc gcttaccgga tacctgtccg cctttctccc ttcgggaagc    420

gtggcgcttt ctcatagctc acgctgtagg tatctcagtt cggtgtaggt cgttcgctcc    480

aagctgggct gtgtgcacga accccccgtt cagcccgacc gctgcgcctt atccggtaac    540

tatcgtcttg agtccaaccc ggtaagacac gacttatcgc cactggcagc agccactggt    600

aacaggatta gcagagcgag gtatgtaggc ggtgctacag agttcttgaa gtggtggcct    660

aactacggct acactagaag aacagtattt ggtatctgcg ctctgctgaa gccagttacc    720

ttcggaaaaa gagttggtag ctcttgatcc ggcaaacaaa ccaccgctgg tagcggtggt    780

tttttgttt gcaagcagca gattacgcgc agaaaaaaag gatctcaaga agatcctttg    840

atcttttcta cggggtctga cgctcagtgg aacgaaaact cacgttaagg gattttggtc    900

atgagattat caaaaaggat cttcacctag atccttttaa attaaaaatg aagttttaaa    960

tcaatctaaa gtatatatga gtaaacttgg tctgacagtt accaatgctt aatcagtgag   1020

gcacctatct cagcgatctg tctatttcgt tcatccatag ttgcctgact ccccgtcgtg   1080

tagataacta cgatacggga gggcttacca tctggcccca gtgctgcaat gataccgcga   1140

gacccacgct caccggctcc agatttatca gcaataaacc agccagccgg aagggccgag   1200

cgcagaagtg gtcctgcaac tttatccgcc tccatccagt ctattaattg ttgccgggaa   1260

gctagagtaa gtagttcgcc agttaatagt ttgcgcaacg ttgttgccat tgctacaggc   1320

atcgtggtgt cacgctcgtc gtttggtatg gcttcattca gctccggttc ccaacgatca   1380

aggcgagtta catgatcccc catgttgtgc aaaaaagcgg ttagctcctt cggtcctccg   1440

atcgttgtca gaagtaagtt ggccgcagtg ttatcactca tggttatggc agcactgcat   1500

aattctctta ctgtcatgcc atccgtaaga tgcttttctg tgactggtga gtactcaacc   1560
```

-continued

```
aagtcattct gagaatagtg tatgcggcga ccgagttgct cttgcccggc gtcaatacgg   1620
gataataccg cgccacatag cagaacttta aaagtgctca tcattggaaa acgttcttcg   1680
gggcgaaaac tctcaaggat cttaccgctg ttgagatcca gttcgatgta acccactcgt   1740
gcacccaact gatcttcagc atcttttact ttcaccagcg tttctgggtg agcaaaaaca   1800
ggaaggcaaa atgccgcaaa aaagggaata agggcgacac ggaaatgttg aatactcata   1860
ctcttccttt ttcaatatta ttgaagcatt tatcagggtt attgtctcat gagcggatac   1920
atatttgaat gtatttagaa aaataaacaa ataggggttc cgcgcacatt tccccgaaaa   1980
gtgccacctg acgtctaata cgactcacta tagggagaaa gcttaccatg gagaagatca   2040
tgctgctcct ggccatcgtg agcctggtca agtccgacca gatctgcatc ggctaccacg   2100
ccaacaacag caccgagcag gtggacacca tcatggagaa gaacgtgacg gtcacccacg   2160
cgcaggacat cctcgagaag acccacaacg ggaagctgtg cgacctggac ggcgtgaagc   2220
ccctcatcct gcgggactgc tccgtggccg ggtggctgct cggcaacccg atgtgcgacg   2280
agttcctgaa cgtccccgag tggagctaca tcgtggagaa gatcaacccc gccaacgacc   2340
tgtgctaccc cgggaacttc aacgactacg aggagctcaa gcacctgctg tcccgcatca   2400
accacttcga gaagatccag atcatcccga agagctcctg gagcgaccac gaggcctcca   2460
gcggcgtgtc cagcgcctgc ccctaccagg gccggtccag cttcttccgc aacgtcgtgt   2520
ggctcatcaa gaaggacaac gcgtacccca ccatcaagcg gtcctacaac aacacgaacc   2580
aggaggacct gctggtgctc tgggggatcc accaccccaa cgacgccgcc gagcagaccc   2640
gcctgtacca gaacccgacc acctacatca gcgtcggcac gtccaccctg aaccagcggc   2700
tcgtgcccaa gatcgccacc cgcagcaagg tgaacgggca gtccggccgg atggagttct   2760
tctggaccat cctgaagccc aacgacgcga tcaacttcga gagcaacggg aacttcatcg   2820
cccccgagaa cgcctacaag atcgtcaaga agggcgacag cacgatcatg aagtccgagc   2880
tggagtacgg caactgcaac accaagtgcc agaccccgat cggggccatc aacagctcca   2940
tgcccttcca caacatccac cccctcacca tcggcgagtg ccccaagtac gtgaagagca   3000
accgcctggt gctggccacg gggctccgga actccccgca gggcgagcgc cggcgcaaga   3060
agcggggcct gttcggggcg atcgccggct tcatcgaggg cgggtggcag gggatggtcg   3120
acggctggta cggctaccac cacagcaacg agcaggggtc cggctacgcc gccgacaagg   3180
agagcaccca gaaggccatc gacggggtga ccaacaaggt gaactccatc atcgacaaga   3240
tgaacaccca gttcgaggcg gtcggccgcg agttcaacaa cctggagcgg cgcatcgaga   3300
acctcaacaa gaagatggag gacgggttcc tggacgtgtg gacgtacaac gccgagctgc   3360
tcgtgctgat ggagaacgag cggaccctgg acttccacga cagcaacgtc aagaacctct   3420
acgacaaggt gcgcctgcag ctgcgggaca acgccaagga gctcggcaac ggctgcttcg   3480
agttctacca ccgctgcgac aacgagtgca tggagtccgt ccggaacggg acctacgact   3540
acccccagta cagcgaggag gcccggctga agcgcgagga gatctccggc gtgaagctgg   3600
agagcatcgg gacctaccag atcctctcca tctacagcac ggtggcctcc agcctggcgc   3660
tggccatcat ggtcgccggc ctctccctgt ggatgtgcag caacgggagc ctgcagtgcc   3720
ggatctgcat ctgaccacta gttataagac tgactagccc gatgggcctc ccaacgggcc   3780
ctcctcccct ccttgcaccg agattaataa aaaaaaaaaa aaaaaaaaaa aaaaaaaaaa   3840
aaaaaaaaaa aaaaaaaaaa aaaaaaaaaa aatgcatccc cccccccccc cccccccccc   3900
```

cccccccaa aggctctttt cagagccacc agaattcgga tactctagac atatgcttaa 3960
g 3961

<210> SEQ ID NO 21
<211> LENGTH: 3952
<212> TYPE: DNA
<213> ORGANISM: Artificial sequence
<220> FEATURE:
<223> OTHER INFORMATION: GC optimized HA construct

<400> SEQUENCE: 21
cagctgcatt aatgaatcgg ccaacgcgcg gggagaggcg gtttgcgtat tgggcgctct 60
tccgcttcct cgctcactga ctcgctgcgc tcggtcgttc ggctgcggcg agcggtatca 120
gctcactcaa aggcggtaat acggttatcc acagaatcag gggataacgc aggaaagaac 180
atgtgagcaa aaggccagca aaaggccagg aaccgtaaaa aggccgcgtt gctggcgttt 240
ttccataggc tccgcccccc tgacgagcat cacaaaaatc gacgctcaag tcagaggtgg 300
cgaaacccga caggactata aagataccag gcgtttcccc ctggaagctc cctcgtgcgc 360
tctcctgttc cgaccctgcc gcttaccgga tacctgtccg cctttctccc ttcgggaagc 420
gtggcgcttt ctcatagctc acgctgtagg tatctcagtt cggtgtaggt cgttcgctcc 480
aagctgggct gtgtgcacga accccccgtt cagcccgacc gctgcgcctt atccggtaac 540
tatcgtcttg agtccaaccc ggtaagacac gacttatcgc cactggcagc agccactggt 600
aacaggatta gcagagcgag gtatgtaggc ggtgctacag agttcttgaa gtggtggcct 660
aactacggct acactagaag aacagtattt ggtatctgcg ctctgctgaa gccagttacc 720
ttcggaaaaa gagttggtag ctcttgatcc ggcaaacaaa ccaccgctgg tagcggtggt 780 tttttgttt gcaagcagca gattacgcgc agaaaaaaag gatctcaaga agatcctttg 840
atcttttcta cggggtctga cgctcagtgg aacgaaaact cacgttaagg gattttggtc 900
atgagattat caaaaaggat cttcacctag atccttttaa attaaaaatg aagttttaaa 960
tcaatctaaa gtatatatga gtaaacttgg tctgacagtt accaatgctt aatcagtgag 1020
gcacctatct cagcgatctg tctatttcgt tcatccatag ttgcctgact ccccgtcgtg 1080
tagataacta cgatacggga gggcttacca tctggcccca gtgctgcaat gataccgcga 1140
gacccacgct caccggctcc agatttatca gcaataaacc agccagccgg aagggccgag 1200
cgcagaagtg gtcctgcaac tttatccgcc tccatccagt ctattaattg ttgccgggaa 1260
gctagagtaa gtagttcgcc agttaatagt ttgcgcaacg ttgttgccat tgctacaggc 1320
atcgtggtgt cacgctcgtc gtttggtatg gcttcattca gctccggttc ccaacgatca 1380
aggcgagtta catgatcccc catgttgtgc aaaaaagcgg ttagctcctt cggtcctccg 1440
atcgttgtca gaagtaagtt ggccgcagtg ttatcactca tggttatggc agcactgcat 1500
aattctctta ctgtcatgcc atccgtaaga tgcttttctg tgactggtga gtactcaacc 1560
aagtcattct gagaatagtg tatgcggcga ccgagttgct cttgcccggc gtcaatacgg 1620
gataataccg cgccacatag cagaacttta aaagtgctca tcattggaaa acgttcttcg 1680
gggcgaaaac tctcaaggat cttaccgctg ttgagatcca gttcgatgta acccactcgt 1740
gcacccaact gatcttcagc atcttttact ttcaccagcg tttctgggtg agcaaaaaca 1800
ggaaggcaaa atgccgcaaa aaagggaata agggcgacac ggaaatgttg aatactcata 1860
ctcttccttt ttcaatatta ttgaagcatt tatcagggtt attgtctcat gagcggatac 1920
atatttgaat gtatttagaa aaataaacaa ataggggttc cgcgcacatt tccccgaaaa 1980

-continued gtgccacctg acgtctaata cgactcacta tagggagaaa gcttaccatg aaggtgaagc 2040
tgctcgtcct gctgtgcacc ttcaccgcca cgtacgccga caccatctgc atcggctacc 2100
acgcgaacaa cagcaccgac accgtggaca cggtgctcga gaagaacgtc accgtgaccc 2160
actccgtgaa cctgctggag aacagccaca acgggaagct ctgcctgctg aagggcatcg 2220 ccccccctcca gctggggaac tgctccgtcg ccggctggat cctggggaac ccggagtgcg 2280
agctcctgat cagcaaggag tcctggagct acatcgtgga gaagcccaac cccgagaacg 2340
gcacctgcta ccccggccac ttcgccgact acgaggagct gcgggagcag ctctccagcg 2400
tgtccagctt cgagcgcttc gagatcttcc cgaaggagtc cagctggccc aaccacacgg 2460
tcaccggggt gtccgccagc tgctcccaca acggcgagag ctccttctac cggaacctgc 2520
tgtggctcac cgggaagaac ggcctgtacc ccaacctgag caagtcctac gcgaacaaca 2580
aggagaagga ggtgctcgtc ctgtggggcg tgcaccaccc gccgaacatc gggaaccaga 2640
aggccctgta ccacaccgag aacgcctacg tgagcgtcgt gagctcccac tacagccgca 2700
agttcacgcc cgagatcgcc aagcggccca aggtgcgcga ccaggagggc cggatcaact 2760
actactggac cctcctggag cccggggaca ccatcatctt cgaggcgaac ggcaacctga 2820
tcgccccgcg ctacgccttc gccctctccc gggggttcgg cagcggcatc atcaactcca 2880
acgccccgat ggacaagtgc gacgcgaagt gccagacccc ccagggggcc atcaacagct 2940
ccctgccctt ccagaacgtc cacccggtga cgatcggcga gtgccccaag tacgtgcgca 3000
gcgccaagct gcggatggtc accgggctcc gcaacatccc ctccatccag agccggggcc 3060
tgttcggggc catcgccggc ttcatcgagg gcgggtggac cggcatggtg gacgggtggt 3120
acggctacca ccaccagaac gagcaggggt ccggctacgc ggccgaccag aagagcaccc 3180
agaacgccat caacggcatc acgaacaagg tgaactccgt catcgagaag atgaacaccc 3240
agttcaccgc cgtggggaag gagttcaaca agctggagcg ccggatggag aacctcaaca 3300
agaaggtcga cgacggcttc atcgacatct ggacctacaa cgccgagctg ctggtgctcc 3360
tggagaacga gcgcacgctg gacttccacg acagcaacgt gaagaacctc tacgagaagg 3420
tcaagtccca gctgaagaac aacgcgaagg agatcgggaa cggctgcttc gagttctacc 3480
acaagtgcaa cgacgagtgc atggagagcg tgaagaacgg gacctacgac taccccaagt 3540
actccgagga gagcaagctg aaccgggaga agatcgacgg cgtgaagctc gagtccatgg 3600
gcgtctacca gatcctggcc atctacagca ccgtggccag ctccctggtg ctcctggtca 3660
gcctgggggc catctccttc tggatgtgca gcaacggctc cctgcagtgc cgcatctgca 3720
tctgaggact agttataaga ctgactagcc cgatgggcct cccaacgggc cctcctcccc 3780
tccttgcacc gagattaata aaaaaaaaaa aaaaaaaaaa aaaaaaaaaa aaaaaaaaaa 3840
aaaaaaaaaa aaaaaaaaaa aaatgcatcc cccccccccc cccccccccc cccccccccca 3900 aaggctcttt tcagagccac cagaattcgg atactctaga catatgctta ag 3952

<210> SEQ ID NO 22
<211> LENGTH: 3955
<212> TYPE: DNA
<213> ORGANISM: Artificial sequence
<220> FEATURE:
<223> OTHER INFORMATION: GC optimized HA construct

<400> SEQUENCE: 22
cagctgcatt aatgaatcgg ccaacgcgcg gggagaggcg gtttgcgtat tgggcgctct 60

-continued

```
tccgcttcct cgctcactga ctcgctgcgc tcggtcgttc ggctgcggcg agcggtatca    120
gctcactcaa aggcggtaat acggttatcc acagaatcag gggataacgc aggaaagaac    180
atgtgagcaa aaggccagca aaaggccagg aaccgtaaaa aggccgcgtt gctggcgttt    240
ttccataggc tccgcccccc tgacgagcat cacaaaaatc gacgctcaag tcagaggtgg    300
cgaaacccga caggactata aagataccag gcgtttcccc ctggaagctc cctcgtgcgc    360
tctcctgttc cgaccctgcc gcttaccgga tacctgtccg cctttctccc ttcgggaagc    420
gtggcgcttt ctcatagctc acgctgtagg tatctcagtt cggtgtaggt cgttcgctcc    480
aagctgggct gtgtgcacga accccccgtt cagcccgacc gctgcgcctt atccggtaac    540
tatcgtcttg agtccaaccc ggtaagacac gacttatcgc cactggcagc agccactggt    600
aacaggatta gcagagcgag gtatgtaggc ggtgctacag agttcttgaa gtggtggcct    660
aactacggct acactagaag aacagtattt ggtatctgcg ctctgctgaa gccagttacc    720
ttcggaaaaa gagttggtag ctcttgatcc ggcaaacaaa ccaccgctgg tagcggtggt    780
tttttgtttg caagcagcag attacgcgc agaaaaaaag gatctcaaga agatcctttg    840
atcttttcta cggggtctga cgctcagtgg aacgaaaact cacgttaagg gattttggtc    900
atgagattat caaaaaggat cttcacctag atccttttaa attaaaaatg aagttttaaa    960
tcaatctaaa gtatatatga gtaaacttgg tctgacagtt accaatgctt aatcagtgag   1020
gcacctatct cagcgatctg tctatttcgt tcatccatag ttgcctgact ccccgtcgtg   1080
tagataacta cgatacggga gggcttacca tctggcccca gtgctgcaat gataccgcga   1140
gacccacgct caccggctcc agatttatca gcaataaacc agccagccgg aagggccgag   1200
cgcagaagtg gtcctgcaac tttatccgcc tccatccagt ctattaattg ttgccgggaa   1260
gctagagtaa gtagttcgcc agttaatagt ttgcgcaacg ttgttgccat tgctacaggc   1320
atcgtggtgt cacgctcgtc gtttggtatg gcttcattca gctccggttc ccaacgatca   1380
aggcgagtta catgatcccc catgttgtgc aaaaaagcgg ttagctcctt cggtcctccg   1440
atcgttgtca gaagtaagtt ggccgcagtg ttatcactca tggttatggc agcactgcat   1500
aattctctta ctgtcatgcc atccgtaaga tgcttttctg tgactggtga gtactcaacc   1560
aagtcattct gagaatagtg tatgcggcga ccgagttgct cttgcccggc gtcaatacgg   1620
gataataccg cgccacatag cagaacttta aaagtgctca tcattggaaa acgttcttcg   1680
gggcgaaaac tctcaaggat cttaccgctg ttgagatcca gttcgatgta acccactcgt   1740
gcacccaact gatcttcagc atcttttact ttcaccagcg tttctgggtg agcaaaaaca   1800
ggaaggcaaa atgccgcaaa aaagggaata agggcgacac ggaaatgttg aatactcata   1860
ctcttccttt ttcaatatta ttgaagcatt tatcagggtt attgtctcat gagcggatac   1920
atatttgaat gtatttagaa aaataaacaa ataggggttc cgcgcacatt tccccgaaaa   1980
gtgccacctg acgtctaata cgactcacta tagggagaaa gcttaccatg aagaccatca   2040
tcgccctgag ctacatcctc tgcctggtgt tcgcccagaa gctgcccggc aacgacaact   2100
ccaccgcgac gctctgcctg gggcaccacg ccgtcccgaa cggcaccatc gtgaagacca   2160
tcaccaacga ccagatcgag gtgacgaacg ccaccgagct ggtccagagc tccagcaccg   2220
gggagatctg cgactccccc caccagatcc tcgacggcga gaactgcacc ctgatcgacg   2280
ccctgctcgg ggacccccag tgcgacggct tccagaacaa gaagtgggac ctgttcgtgg   2340
agcggagcaa ggcctactcc aactgctacc cctacgacgt gccggactac gcgagcctgc   2400
gctccctcgt cgccagctcc ggcacgctgg agttcaacaa cgagagcttc aactggaccg   2460
```

gggtgaccca gaacggcacc tccagctcct gcatccgggg gagcaacaac tccttcttca 2520
gccgcctgaa ctggctcacg cacctgaagt tcaagtaccc cgccctgaac gtgaccatgc 2580
ccaacaacga gaagttcgac aagctctaca tctggggcgt ccaccacccc gggaccgaca 2640
acgaccagat cttcccgtac gcccaggcgt ccggccggat caccgtgagc acgaagcgca 2700
gccagcagac cgtgatcccc aacatcggct cccggccccg cgtccggaac atccccagcc 2760
gcatctccat ctactggacc atcgtgaagc cgggggacat cctgctgatc aacagcaccg 2820
gcaacctcat cgccccgcgg gggtacttca agatccgctc cggcaagagc tccatcatgc 2880
ggagcgacgc ccccatcggc aagtgcaact ccgagtgcat cacgcccaac gggagcatcc 2940
cgaacgacaa gcccttccag aacgtgaacc gcatcaccta cggcgcctgc cccggtacg 3000 tcaagcagaa caccctgaag ctggccaccg ggatgcgcaa cgtgcccgag aagcagacgc 3060
ggggcatctt cggggcgatc gccggcttca tcgagaacgg ctgggagggg atggtggacg 3120
gctggtacgg gttccgccac cagaactccg agggcatcgg gcaggccgcc gacctcaaga 3180
gcacccaggc cgcgatcgac cagatcaacg gcaagctgaa ccggctgatc ggcaagacca 3240
acgagaagtt ccaccagatc gagaaggagt tctccgaggt cgaggggcgc atccaggacc 3300
tcgagaagta cgtggaggac accaagatcg acctgtggag ctacaacgcc gagctgctcg 3360
tggccctgga gaaccagcac acgatcgacc tgaccgactc cgagatgaac aagctcttcg 3420
agaagaccaa gaagcagctg cgggagaacg ccgaggacat gggcaacggg tgcttcaaga 3480
tctaccacaa gtgcgacaac gcctgcatcg gcagcatccg caacgggacc tacgaccacg 3540
acgtctaccg ggacgaggcg ctgaacaacc ggttccagat caagggcgtg gagctcaagt 3600
ccggctacaa ggactggatc ctgtggatca gcttcgccat ctcctgcttc ctgctctgcg 3660
tggccctgct ggggttcatc atgtgggcct gccagaaggg caacatccgc tgcaacatct 3720
gcatctgagg actagttata agactgacta gcccgatggg cctcccaacg ggccctcctc 3780
ccctccttgc accgagatta ataaaaaaaa aaaaaaaaaa aaaaaaaaaa aaaaaaaaaa 3840
aaaaaaaaaa aaaaaaaaaa aaaaaatgca tccccccccc cccccccccc cccccccccc 3900
ccaaaggctc ttttcagagc caccagaatt cggatactct agacatatgc ttaag 3955

<210> SEQ ID NO 23
<211> LENGTH: 3955
<212> TYPE: DNA
<213> ORGANISM: Artificial sequence
<220> FEATURE:
<223> OTHER INFORMATION: GC optimized HA construct

<400> SEQUENCE: 23
cagctgcatt aatgaatcgg ccaacgcgcg gggagaggcg gtttgcgtat tgggcgctct 60
tccgcttcct cgctcactga ctcgctgcgc tcggtcgttc ggctgcggcg agcggtatca 120
gctcactcaa aggcggtaat acggttatcc acagaatcag gggataacgc aggaaagaac 180
atgtgagcaa aaggccagca aaaggccagg aaccgtaaaa aggccgcgtt gctggcgttt 240
ttccataggc tccgcccccc tgacgagcat cacaaaaatc gacgctcaag tcagaggtgg 300
cgaaacccga caggactata aagataccag gcgtttcccc ctggaagctc cctcgtgcgc 360
tctcctgttc cgaccctgcc gcttaccgga tacctgtccg cctttctccc ttcgggaagc 420
gtggcgcttt ctcatagctc acgctgtagg tatctcagtt cggtgtaggt cgttcgctcc 480
aagctgggct gtgtgcacga accccccgtt cagcccgacc gctgcgcctt atccggtaac 540

-continued

```
tatcgtcttg agtccaaccc ggtaagacac gacttatcgc cactggcagc agccactggt    600
aacaggatta gcagagcgag gtatgtaggc ggtgctacag agttcttgaa gtggtggcct    660
aactacggct acactagaag aacagtattt ggtatctgcg ctctgctgaa gccagttacc    720
ttcggaaaaa gagttggtag ctcttgatcc ggcaaacaaa ccaccgctgg tagcggtggt    780
tttttgttt gcaagcagca gattacgcgc agaaaaaaag gatctcaaga agatcctttg    840
atcttttcta cggggtctga cgctcagtgg aacgaaaact cacgttaagg gattttggtc    900
atgagattat caaaaaggat cttcacctag atccttttaa attaaaaatg aagttttaaa    960
tcaatctaaa gtatatatga gtaaacttgg tctgacagtt accaatgctt aatcagtgag   1020
gcacctatct cagcgatctg tctatttcgt tcatccatag ttgcctgact ccccgtcgtg   1080
tagataacta cgatacggga gggcttacca tctggcccca gtgctgcaat gataccgcga   1140
gacccacgct caccggctcc agatttatca gcaataaacc agccagccgg aagggccgag   1200
cgcagaagtg gtcctgcaac tttatccgcc tccatccagt ctattaattg ttgccgggaa   1260
gctagagtaa gtagttcgcc agttaatagt ttgcgcaacg ttgttgccat tgctacaggc   1320
atcgtggtgt cacgctcgtc gtttggtatg gcttcattca gctccggttc ccaacgatca   1380
aggcgagtta catgatcccc catgttgtgc aaaaaagcgg ttagctcctt cggtcctccg   1440
atcgttgtca gaagtaagtt ggccgcagtg ttatcactca tggttatggc agcactgcat   1500
aattctctta ctgtcatgcc atccgtaaga tgcttttctg tgactggtga gtactcaacc   1560
aagtcattct gagaatagtg tatgcggcga ccgagttgct cttgcccggc gtcaatacgg   1620
gataataccg cgccacatag cagaacttta aaagtgctca tcattggaaa acgttcttcg   1680
gggcgaaaac tctcaaggat cttaccgctg ttgagatcca gttcgatgta acccactcgt   1740
gcacccaact gatcttcagc atcttttact ttcaccagcg tttctgggtg agcaaaaaca   1800
ggaaggcaaa atgccgcaaa aaagggaata agggcgacac ggaaatgttg aatactcata   1860
ctcttccttt ttcaatatta ttgaagcatt tatcagggtt attgtctcat gagcggatac   1920
atatttgaat gtatttagaa aaataaacaa ataggggttc cgcgcacatt tccccgaaaa   1980
gtgccacctg acgtctaata cgactcacta tagggagaaa gcttaccatg aagaccatca   2040
tcgccctgag ctacatcttc tgcctcgccc tgggccagga cctgcccggg aacgacaact   2100
ccaccgcgac gctctgcctg ggccaccacg ccgtgccgaa cgggaccctg gtcaagacca   2160
tcaccgacga ccagatcgag gtgacgaacg ccaccgagct cgtgcagagc tccagcaccg   2220
gcaagatctg caacaacccc caccggatcc tggacgggat cgactgcacc ctgatcgacg   2280
ccctcctggg cgacccccac tgcgacgtct tccagaacga gacgtgggac ctgttcgtgg   2340
agcgctccaa ggccttcagc aactgctacc cctacgacgt gccggactac gcgtccctcc   2400
ggagcctggt cgcctccagc ggcaccctgg agttcatcac cgaggggttc acctggacgg   2460
gcgtgaccca gaacgggggc tccaacgcct gcaagcgcgg gcccggcagc ggcttcttct   2520
cccggctcaa ctggctgacc aagagcgggt ccacctaccc cgtgctgaac gtcacgatgc   2580
ccaacaacga caacttcgac aagctctaca tctggggcgt gcaccacccg agcaccaacc   2640
aggagcagac ctccctgtac gtgcaggcca gcgggcgcgt caccgtgtcc acgcggcgca   2700
gccagcagac catcatcccc aacatcgaga gccggccctg ggtgcgcggc cagtccagcc   2760
ggatctccat ctactggacc atcgtcaagc ccggcgacgt gctggtgatc aacagcaacg   2820
ggaacctcat cgcgccgcgc ggctacttca agatgcggac cgggaagtcc agcatcatgc   2880
gctccgacgc ccccatcgac acgtgcatca gcgagtgcat cacccccaac ggctccatcc   2940
```

```
ccaacgacaa gccgttccag aacgtcaaca agatcaccta cggggcctgc cccaagtacg   3000
tgaagcagaa caccctgaag ctggccacgg gcatgcggaa cgtgcccgag aagcagaccc   3060
gcggcctctt cggggccatc gcgggcttca tcgagaacgg gtgggagggc atgatcgacg   3120
ggtggtacgg cttccggcac cagaacagcg agggcaccgg gcaggccgcc gacctgaagt   3180
ccacccaggc cgccatcgac cagatcaacg gcaaggtcaa ccgcatcatc gagaagacga   3240
acgagaagtt ccaccagatc gagaaggagt tcagcgaggt ggaggggcgg atccaggacc   3300
tggagaagta cgtggaggac accaagatcg acctctggtc ctacaacgcg gagctgctgg   3360
tcgccctcga gaaccagcac accatcgacc tgaccgacag cgagatgaac aagctgttcg   3420
agaagacgcg ccggcagctc cgcgagaacg ccgaggacat gggcaacggg tgcttcaaga   3480
tctaccacaa gtgcgacaac gcctgcatcg agtccatccg gagcggcacc tacgaccacg   3540
acgtgtaccg ggacgaggcc ctgaacaacc gcttccagat caagggcgtc gagctgaagt   3600
ccgggtacaa ggactggatc ctctggatca gcttcgcgat ctcctgcttc ctgctgtgcg   3660
tggtgctcct gggcttcatc atgtgggcct gccagcgggg gaacatccgc tgcaacatct   3720
gcatctgagg actagttata agactgacta gcccgatggg cctcccaacg ggccctcctc   3780
ccctccttgc accgagatta ataaaaaaaa aaaaaaaaaa aaaaaaaaaa aaaaaaaaaa   3840
aaaaaaaaaa aaaaaaaaaa aaaaaatgca tccccccccc cccccccccc cccccccccc   3900
ccaaaggctc ttttcagagc caccagaatt cggatactct agacatatgc ttaag        3955
```

```
<210> SEQ ID NO 24
<211> LENGTH: 3943
<212> TYPE: DNA
<213> ORGANISM: Artificial sequence
<220> FEATURE:
<223> OTHER INFORMATION: GC optimized HA construct

<400> SEQUENCE: 24

cagctgcatt aatgaatcgg ccaacgcgcg gggagaggcg gtttgcgtat tgggcgctct     60
tccgcttcct cgctcactga ctcgctgcgc tcggtcgttc ggctgcggcg agcggtatca    120
gctcactcaa aggcggtaat acggttatcc acagaatcag gggataacgc aggaaagaac    180
atgtgagcaa aaggccagca aaaggccagg aaccgtaaaa aggccgcgtt gctggcgttt    240
ttccataggc tccgcccccc tgacgagcat cacaaaaatc gacgctcaag tcagaggtgg    300
cgaaacccga caggactata aagataccag gcgtttcccc ctggaagctc cctcgtgcgc    360
tctcctgttc cgaccctgcc gcttaccgga tacctgtccg cctttctccc ttcgggaagc    420
gtggcgcttt ctcatagctc acgctgtagg tatctcagtt cggtgtaggt cgttcgctcc    480
aagctgggct gtgtgcacga acccccgtt cagcccgacc gctgcgcctt atccggtaac     540
tatcgtcttg agtccaaccc ggtaagacac gacttatcgc cactggcagc agccactggt    600
aacaggatta gcagagcgag gtatgtaggc ggtgctacag agttcttgaa gtggtggcct    660
aactacggct acactagaag aacagtattt ggtatctgcg ctctgctgaa gccagttacc    720
ttcggaaaaa gagttggtag ctcttgatcc ggcaaacaaa ccaccgctgg tagcggtggt    780
ttttttgttt gcaagcagca gattacgcgc agaaaaaaag gatctcaaga agatcctttg    840
atcttttcta cggggtctga cgctcagtgg aacgaaaact cacgttaagg gattttggtc    900
atgagattat caaaaaggat cttcacctag atccttttaa attaaaaatg aagttttaaa    960
tcaatctaaa gtatatatga gtaaacttgg tctgacagtt accaatgctt aatcagtgag   1020
```

-continued

```
gcacctatct cagcgatctg tctatttcgt tcatccatag ttgcctgact ccccgtcgtg   1080

tagataacta cgatacggga gggcttacca tctggcccca gtgctgcaat gataccgcga   1140

gacccacgct caccggctcc agatttatca gcaataaacc agccagccgg aagggccgag   1200

cgcagaagtg gtcctgcaac tttatccgcc tccatccagt ctattaattg ttgccgggaa   1260

gctagagtaa gtagttcgcc agttaatagt ttgcgcaacg ttgttgccat tgctacaggc   1320

atcgtggtgt cacgctcgtc gtttggtatg gcttcattca gctccggttc ccaacgatca   1380

aggcgagtta catgatcccc catgttgtgc aaaaaagcgg ttagctcctt cggtcctccg   1440

atcgttgtca gaagtaagtt ggccgcagtg ttatcactca tggttatggc agcactgcat   1500

aattctctta ctgtcatgcc atccgtaaga tgcttttctg tgactggtga gtactcaacc   1560

aagtcattct gagaatagtg tatgcggcga ccgagttgct cttgcccggc gtcaatacgg   1620

gataataccg cgccacatag cagaacttta aaagtgctca tcattggaaa acgttcttcg   1680

gggcgaaaac tctcaaggat cttaccgctg ttgagatcca gttcgatgta acccactcgt   1740

gcacccaact gatcttcagc atcttttact ttcaccagcg tttctgggtg agcaaaaaca   1800

ggaaggcaaa atgccgcaaa aaagggaata agggcgacac ggaaatgttg aatactcata   1860

ctcttccttt ttcaatatta ttgaagcatt tatcagggtt attgtctcat gagcggatac   1920

atatttgaat gtatttagaa aaataaacaa ataggggttc cgcgcacatt tccccgaaaa   1980

gtgccacctg acgtctaata cgactcacta tagggagaaa gcttaccatg gccatcatct   2040

acctgatcct cctgttcacc gccgtgcggg gcgaccagat ctgcatcggg taccacgcga   2100

acaacagcac cgagaaggtc gacacgatcc tggagcgcaa cgtgaccgtg acccacgcca   2160

aggacatcct cgagaagacc cacaacggca agctgtgcaa gctgaacggg atcccgccgc   2220

tcgagctggg cgactgctcc atcgccgggt ggctgctcgg caaccccgag tgcgaccggc   2280

tgctgagcgt ccccgagtgg tcctacatca tggagaagga gaacccccgc gacggcctct   2340

gctacccggg gagcttcaac gactacgagg agctgaagca cctgctctcc agcgtgaagc   2400

acttcgagaa ggtgaagatc ctgcccaagg accggtggac gcagcacacc accaccggcg   2460

ggtcccgcgc ctgcgccgtc agcggcaacc cctccttctt ccggaacatg gtgtggctga   2520

cggagaaggg gagcaactac cccgtggcga agggctccta caacaacacc agcggcgagc   2580

agatgctcat catctggggc gtccaccacc cgaacgacga gaccgagcag cgcaccctgt   2640

accagaacgt ggggacgtac gtgtccgtcg ggaccagcac cctgaacaag cggtccaccc   2700

ccgagatcgc cacgcgcccc aaggtgaacg gccagggcgg gcggatggag ttcagctgga   2760

ccctcctgga catgtgggac accatcaact tcgagtccac cggcaacctg atcgcccccg   2820

agtacgggtt caagatcagc aagcgcggct ccagcgggat catgaagacg gagggcaccc   2880

tcgagaactg cgagaccaag tgccagaccc cgctgggcgc catcaacacg accctgccct   2940

tccacaacgt gcacccccctc accatcgggg agtgccccaa gtacgtcaag agcgagaagc   3000

tggtgctggc gaccggcctc cggaacgtgc cgcagatcga gtcccgcggg ctgttcggcg   3060

ccatcgccgg gttcatcgag ggcggctggc aggggatggt cgacggctgg tacgggtacc   3120

accacagcaa cgaccagggc tccgggtacg ccgccgacaa ggagagcacg cagaaggcgt   3180

tcgacggcat caccaacaag gtgaactccg tgatcgagaa gatgaacacc cagttcgagg   3240

ccgtcggcaa ggagttcagc aacctggagc ggcgcctcga gaacctgaac aagaagatgg   3300

aggacgggtt cctggacgtg tggacctaca acgccgagct cctggtgctg atggagaacg   3360

agcggacgct cgacttccac gactccaacg tcaagaacct gtacgacaag gtgcgcatgc   3420
```

```
agctgcggga caacgtcaag gagctcggca acgggtgctt cgagttctac cacaagtgcg    3480

acgacgagtg catgaacagc gtgaagaacg gcacctacga ctaccccaag tacgaggagg    3540

agtccaagct gaaccgcaac gagatcaagg gcgtgaagct gagctccatg ggggtctacc    3600

agatcctcgc catctacgcc accgtggcgg gcagcctgtc cctggccatc atgatggccg    3660

ggatcagctt ctggatgtgc tccaacggca gcctgcagtg ccggatctgc atctgaggac    3720

tagttataag actgactagc ccgatgggcc tcccaacggg ccctcctccc ctccttgcac    3780

cgagattaat aaaaaaaaaa aaaaaaaaaa aaaaaaaaaa aaaaaaaaaa aaaaaaaaaa    3840

aaaaaaaaaa aaaatgcatc cccccccccc cccccccccc cccccccccc aaaggctctt    3900

ttcagagcca ccagaattcg gatactctag acatatgctt aag                     3943
```

<210> SEQ ID NO 25
<211> LENGTH: 3946
<212> TYPE: DNA
<213> ORGANISM: Artificial sequence
<220> FEATURE:
<223> OTHER INFORMATION: GC optimized HA construct

<400> SEQUENCE: 25

```
cagctgcatt aatgaatcgg ccaacgcgcg gggagaggcg gtttgcgtat tgggcgctct      60

tccgcttcct cgctcactga ctcgctgcgc tcggtcgttc ggctgcggcg agcggtatca     120

gctcactcaa aggcggtaat acggttatcc acagaatcag gggataacgc aggaaagaac     180

atgtgagcaa aaggccagca aaaggccagg aaccgtaaaa aggccgcgtt gctggcgttt     240

ttccataggc tccgcccccc tgacgagcat cacaaaaatc gacgctcaag tcagaggtgg     300

cgaaacccga caggactata aagataccag gcgtttcccc ctggaagctc cctcgtgcgc     360

tctcctgttc cgaccctgcc gcttaccgga tacctgtccg cctttctccc ttcgggaagc     420

gtggcgcttt ctcatagctc acgctgtagg tatctcagtt cggtgtaggt cgttcgctcc     480

aagctgggct gtgtgcacga accccccgtt cagcccgacc gctgcgcctt atccggtaac     540

tatcgtcttg agtccaaccc ggtaagacac gacttatcgc cactggcagc agccactggt     600

aacaggatta gcagagcgag gtatgtaggc ggtgctacag agttcttgaa gtggtggcct     660

aactacggct acactagaag aacagtattt ggtatctgcg ctctgctgaa gccagttacc     720

ttcggaaaaa gagttggtag ctcttgatcc ggcaaacaaa ccaccgctgg tagcggtggt     780

ttttttgttt gcaagcagca gattacgcgc agaaaaaaag gatctcaaga agatcctttg     840

atcttttcta cggggtctga cgctcagtgg aacgaaaact cacgttaagg gattttggtc     900

atgagattat caaaaaggat cttcacctag atccttttaa attaaaaatg aagttttaaa     960

tcaatctaaa gtatatatga gtaaacttgg tctgacagtt accaatgctt aatcagtgag    1020

gcacctatct cagcgatctg tctatttcgt tcatccatag ttgcctgact ccccgtcgtg    1080

tagataacta cgatacggga gggcttacca tctggcccca gtgctgcaat gataccgcga    1140

gacccacgct caccggctcc agatttatca gcaataaacc agccagccgg aagggccgag    1200

cgcagaagtg gtcctgcaac tttatccgcc tccatccagt ctattaattg ttgccgggaa    1260

gctagagtaa gtagttcgcc agttaatagt ttgcgcaacg ttgttgccat tgctacaggc    1320

atcgtggtgt cacgctcgtc gtttggtatg gcttcattca gctccggttc ccaacgatca    1380

aggcgagtta catgatcccc catgttgtgc aaaaaagcgg ttagctcctt cggtcctccg    1440

atcgttgtca gaagtaagtt ggccgcagtg ttatcactca tggttatggc agcactgcat    1500
```

-continued

```
aattctctta ctgtcatgcc atccgtaaga tgcttttctg tgactggtga gtactcaacc   1560
aagtcattct gagaatagtg tatgcggcga ccgagttgct cttgcccggc gtcaatacgg   1620
gataataccg cgccacatag cagaacttta aaagtgctca tcattggaaa acgttcttcg   1680
gggcgaaaac tctcaaggat cttaccgctg ttgagatcca gttcgatgta acccactcgt   1740
gcacccaact gatcttcagc atcttttact ttcaccagcg tttctgggtg agcaaaaaca   1800
ggaaggcaaa atgccgcaaa aaagggaata agggcgacac ggaaatgttg aatactcata   1860
ctcttccttt ttcaatatta ttgaagcatt tatcagggtt attgtctcat gagcggatac   1920
atatttgaat gtatttagaa aaataaacaa ataggggttc cgcgcacatt tccccgaaaa   1980
gtgccacctg acgtctaata cgactcacta tagggagaaa gcttaccatg aacacccaga   2040
tcctggtgtt cgccctcgtc gccgtgatcc acaccaacgc ggacaagatc tgcctgggcc   2100
accacgccgt gagcaacggg acgaaggtca acaccctgac cgagcggggc gtggaggtgg   2160
tcaacgccac cgagacggtg gagcgcacca acatccccaa gatctgctcc aaggggaagc   2220
ggaccgtgga cctcggccag tgcgggctgc tgggcaccat cacgggccag ccgcagtgcg   2280
accagttcct cgagttcagc gccgacctga tcatcgagcg ccgggacggg aacgacgtct   2340
gctaccccgg caagttcgtg aacggggagg ccctgcgcca gatcctccgg aagtccggcg   2400
ggatcaacaa ggagaccatg ggcttcacct acagcggcat ccgcaccaac gggacgacct   2460
ccgcgtgccg gcgcagcggc tccagcttct acgccgagat gaagtggctg ctgtccgaca   2520
ccgacaacgc cgccttcccc cagatgacca agagctacaa gaacacgcgg cgcgagcccg   2580
cgctcatcgt gtgggggatc caccactccg gcagcaccac cgagcagacc aagctgtacg   2640
gctccgggaa caagctggtc acggtgggca gctccaagta ccagcagagc ttcgtgccgt   2700
cccccgagac ccggccccag gtcaacgggc agagcggccg catcgacttc cactggctca   2760
tcctggactc caacgacacc gtgaccttca gcttcaacgg ggccttcatc gcccccgacc   2820
gggccagctt cctgaagggc aagtccatgg gcatccagag cgacgtgcag gtcgacgcca   2880
actgcgaggg ggagtgctac cactccggcg ggacgatcac cagctccctc ccgttccaga   2940
acatcaacag ccgcgcggtg ggcaagtgcc cccggtacgt gaagcaggag tccctgctgc   3000
tcgccaccgg gatgaagaac gtccccgagc tgagcaagaa gcgccggaag cgcggcctgt   3060
tcggcgccat cgccgggttc atcgagaacg gctgggaggg gctcgtggac ggctggtacg   3120
ggttccggca ccagaacgcc cagggcgagg gcaccgcggc cgactacaag tccacgcaga   3180
gcgccatcga ccagatcacc gggaagctga accgcctgat cgagaagacc aaccagcagt   3240
tcgagctcat cgacaacgag ttcaccgagg tggagaagca gatcggcaac gtcatcaact   3300
ggacgcggga ctccatcacc gaggtgtgga gctacaacgc cgagctgctg gtcgccatgg   3360
agaaccagca caccatcgac ctcgcggact ccgagatgaa caagctgtac gagcgggtgc   3420
gcaagcagct gcgggagaac gccgaggagg acgggaccgg ctgcttcgag atcttccaca   3480
agtgcgacga cgactgcatg gccagcatcc gcaacaacac gtacgaccac tccaagtacc   3540
gggaggaggc catgcagaac cgcatccaga tcgaccccgt gaagctcagc ggcgggtaca   3600
aggacgtcat cctgtggttc tccttcggcg ccagctgctt cctgctcctg gcgatcgcca   3660
tggggctggt gttcatctgc gtgaagaacg gcaacatgcg gtgcaccatc tgcatctgac   3720
cactagttat aagactgact agcccgatgg gcctcccaac gggccctcct cccctccttg   3780
caccgagatt aataaaaaaa aaaaaaaaaa aaaaaaaaaa aaaaaaaaaa aaaaaaaaaa   3840
aaaaaaaaaa aaaaaaatgc atcccccccc cccccccccc cccccccccc cccaaaggct   3900
```

-continued cttttcagag ccaccagaat tcggatactc tagacatatg cttaag 3946

<210> SEQ ID NO 26
<211> LENGTH: 3955
<212> TYPE: DNA
<213> ORGANISM: Artificial sequence
<220> FEATURE:
<223> OTHER INFORMATION: GC optimized HA construct

<400> SEQUENCE: 26
cagctgcatt aatgaatcgg ccaacgcgcg gggagaggcg gtttgcgtat tgggcgctct 60
tccgcttcct cgctcactga ctcgctgcgc tcggtcgttc ggctgcggcg agcggtatca 120
gctcactcaa aggcggtaat acggttatcc acagaatcag gggataacgc aggaaagaac 180
atgtgagcaa aaggccagca aaaggccagg aaccgtaaaa aggccgcgtt gctggcgttt 240
ttccataggc tccgcccccc tgacgagcat cacaaaaatc gacgctcaag tcagaggtgg 300
cgaaacccga caggactata aagataccag gcgtttcccc ctggaagctc cctcgtgcgc 360
tctcctgttc cgaccctgcc gcttaccgga tacctgtccg cctttctccc ttcgggaagc 420
gtggcgcttt ctcatagctc acgctgtagg tatctcagtt cggtgtaggt cgttcgctcc 480
aagctgggct gtgtgcacga accccccgtt cagcccgacc gctgcgcctt atccggtaac 540
tatcgtcttg agtccaaccc ggtaagacac gacttatcgc cactggcagc agccactggt 600
aacaggatta gcagagcgag gtatgtaggc ggtgctacag agttcttgaa gtggtggcct 660
aactacggct acactagaag aacagtattt ggtatctgcg ctctgctgaa gccagttacc 720
ttcggaaaaa gagttggtag ctcttgatcc ggcaaacaaa ccaccgctgg tagcggtggt 780 tttttgttt gcaagcagca gattacgcgc agaaaaaaag gatctcaaga agatcctttg 840
atcttttcta cggggtctga cgctcagtgg aacgaaaact cacgttaagg gattttggtc 900
atgagattat caaaaaggat cttcacctag atccttttaa attaaaaatg aagttttaaa 960
tcaatctaaa gtatatatga gtaaacttgg tctgacagtt accaatgctt aatcagtgag 1020
gcacctatct cagcgatctg tctatttcgt tcatccatag ttgcctgact ccccgtcgtg 1080
tagataacta cgatacggga gggcttacca tctggcccca gtgctgcaat gataccgcga 1140
gacccacgct caccggctcc agatttatca gcaataaacc agccagccgg aagggccgag 1200
cgcagaagtg gtcctgcaac tttatccgcc tccatccagt ctattaattg ttgccgggaa 1260
gctagagtaa gtagttcgcc agttaatagt ttgcgcaacg ttgttgccat tgctacaggc 1320
atcgtggtgt cacgctcgtc gtttggtatg gcttcattca gctccggttc ccaacgatca 1380
aggcgagtta catgatcccc catgttgtgc aaaaaagcgg ttagctcctt cggtcctccg 1440
atcgttgtca gaagtaagtt ggccgcagtg ttatcactca tggttatggc agcactgcat 1500
aattctctta ctgtcatgcc atccgtaaga tgcttttctg tgactggtga gtactcaacc 1560
aagtcattct gagaatagtg tatgcggcga ccgagttgct cttgcccggc gtcaatacgg 1620
gataataccg cgccacatag cagaacttta aaagtgctca tcattggaaa acgttcttcg 1680
gggcgaaaac tctcaaggat cttaccgctg ttgagatcca gttcgatgta acccactcgt 1740
gcacccaact gatcttcagc atcttttact ttcaccagcg tttctgggtg agcaaaaaca 1800
ggaaggcaaa atgccgcaaa aaagggaata agggcgacac ggaaatgttg aatactcata 1860
ctcttccttt ttcaatatta ttgaagcatt tatcagggtt attgtctcat gagcggatac 1920
atatttgaat gtatttagaa aaataaacaa ataggggttc cgcgcacatt tccccgaaaa 1980

-continued gtgccacctg acgtctaata cgactcacta tagggagaaa gcttaccatg aaggccatcc 2040
tggtggtcct cctgtacacc ttcgccaccg cgaacgccga cacgctgtgc atcggctacc 2100
acgccaacaa cagcaccgac accgtggaca ccgtgctcga gaagaacgtc acggtgaccc 2160
actccgtgaa cctgctggag gacaagcaca acgggaagct ctgcaagctg cggggcgtcg 2220
ccccgctgca cctcgggaag tgcaacatcg ccggctggat cctggggaac ccggagtgcg 2280
agagcctgtc caccgcgagc tcctggagct acatcgtgga gacctcctcc agcgacaacg 2340
gcacgtgcta ccccggcgac ttcatcgact acgaggagct ccgcgagcag ctgtccagcg 2400
tgtccagctt cgagcggttc gagatcttcc ccaagacctc cagctggccg aaccacgact 2460
ccaacaaggg ggtcaccgcc gcctgccccc acgccggcgc gaagagcttc tacaagaacc 2520
tgatctggct cgtgaagaag gggaactcct accccaagct gagcaagtcc tacatcaacg 2580
acaagggcaa ggaggtgctg gtcctctggg ggatccacca ccccagcacc agcgccgacc 2640
agcagtccct gtaccagaac gccgacgcct acgtgttcgt gggcagctcc cgctacagca 2700
agaagttcaa gccggagatc gccatccggc ccaaggtccg cgaccaggag ggccgcatga 2760
actactactg gaccctggtg gagcccgggg acaagatcac cttcgaggcg accggcaacc 2820
tcgtggtccc ccggtacgcc ttcgccatgg agcgcaacgc cgggtccggc atcatcatca 2880
gcgacacgcc ggtgcacgac tgcaacacca cctgccagac ccccaagggc gccatcaaca 2940
cgtccctgcc cttccagaac atccacccca tcaccatcgg gaagtgcccg aagtacgtga 3000
agagcaccaa gctgcggctc gcgaccggcc tgcgcaacgt cccctccatc cagagccggg 3060
ggctgttcgg cgccatcgcc gggttcatcg agggcggctg gacggggatg gtcgacggct 3120
ggtacgggta ccaccaccag aacgagcagg gcagcgggta cgccgccgac ctcaagtcca 3180
cgcagaacgc gatcgacgag atcaccaaca aggtgaacag cgtcatcgag aagatgaaca 3240
cccagttcac cgccgtgggc aaggagttca accacctgga gaagcggatc gagaacctga 3300
acaagaaggt cgacgacggc ttcctcgaca tctggacgta caacgccgag ctgctggtgc 3360
tcctggagaa cgagcgcacc ctggactacc acgactccaa cgtgaagaac ctctacgaga 3420
aggtccggag ccagctgaag aacaacgcca aggagatcgg gaacggctgc ttcgagttct 3480
accacaagtg cgacaacacc tgcatggagt ccgtgaagaa cgggacctac gactacccca 3540
agtacagcga ggaggccaag ctgaaccgcg aggagatcga cggcgtgaag ctcgagtcca 3600
cgcggatcta ccagatcctg gcgatctaca gcaccgtcgc cagctccctg gtgctcgtgg 3660
tcagcctggg ggccatctcc ttctggatgt gcagcaacgg ctccctgcag tgccgcatct 3720
gcatctgacc actagttata agactgacta gcccgatggg cctcccaacg ggccctcctc 3780
ccctccttgc accgagatta ataaaaaaaa aaaaaaaaaa aaaaaaaaaa aaaaaaaaaa 3840
aaaaaaaaaa aaaaaaaaaa aaaaaatgca tccccccccc cccccccccc cccccccccc 3900
ccaaaggctc ttttcagagc caccagaatt cggatactct agacatatgc ttaag 3955

<210> SEQ ID NO 27
<211> LENGTH: 4012
<212> TYPE: DNA
<213> ORGANISM: Artificial sequence
<220> FEATURE:
<223> OTHER INFORMATION: GC optimized HA construct

<400> SEQUENCE: 27
cagctgcatt aatgaatcgg ccaacgcgcg gggagaggcg gtttgcgtat tgggcgctct 60
tccgcttcct cgctcactga ctcgctgcgc tcggtcgttc ggctgcggcg agcggtatca 120

-continued

```
gctcactcaa aggcggtaat acggttatcc acagaatcag gggataacgc aggaaagaac    180
atgtgagcaa aaggccagca aaaggccagg aaccgtaaaa aggccgcgtt gctggcgttt    240
ttccataggc tccgcccccc tgacgagcat cacaaaaatc gacgctcaag tcagaggtgg    300
cgaaacccga caggactata aagataccag gcgtttcccc ctggaagctc cctcgtgcgc    360
tctcctgttc cgaccctgcc gcttaccgga tacctgtccg cctttctccc ttcgggaagc    420
gtggcgcttt ctcatagctc acgctgtagg tatctcagtt cggtgtaggt cgttcgctcc    480
aagctgggct gtgtgcacga accccccgtt cagcccgacc gctgcgcctt atccggtaac    540
tatcgtcttg agtccaaccc ggtaagacac gacttatcgc cactggcagc agccactggt    600
aacaggatta gcagagcgag gtatgtaggc ggtgctacag agttcttgaa gtggtggcct    660
aactacggct acactagaag aacagtattt ggtatctgcg ctctgctgaa gccagttacc    720
ttcggaaaaa gagttggtag ctcttgatcc ggcaaacaaa ccaccgctgg tagcggtggt    780
tttttgttt gcaagcagca gattacgcgc agaaaaaaag gatctcaaga agatcctttg    840
atcttttcta cggggtctga cgctcagtgg aacgaaaact cacgttaagg gattttggtc    900
atgagattat caaaaaggat cttcacctag atccttttaa attaaaaatg aagttttaaa    960
tcaatctaaa gtatatatga gtaaacttgg tctgacagtt accaatgctt aatcagtgag   1020
gcacctatct cagcgatctg tctatttcgt tcatccatag ttgcctgact ccccgtcgtg   1080
tagataacta cgatacggga gggcttacca tctggcccca gtgctgcaat gataccgcga   1140
gacccacgct caccggctcc agatttatca gcaataaacc agccagccgg aagggccgag   1200
cgcagaagtg gtcctgcaac tttatccgcc tccatccagt ctattaattg ttgccgggaa   1260
gctagagtaa gtagttcgcc agttaatagt ttgcgcaacg ttgttgccat tgctacaggc   1320
atcgtggtgt cacgctcgtc gtttggtatg gcttcattca gctccggttc ccaacgatca   1380
aggcgagtta catgatcccc catgttgtgc aaaaaagcgg ttagctcctt cggtcctccg   1440
atcgttgtca gaagtaagtt ggccgcagtg ttatcactca tggttatggc agcactgcat   1500
aattctctta ctgtcatgcc atccgtaaga tgcttttctg tgactggtga gtactcaacc   1560
aagtcattct gagaatagtg tatgcggcga ccgagttgct cttgcccggc gtcaatacgg   1620
gataataccg cgccacatag cagaacttta aaagtgctca tcattggaaa acgttcttcg   1680
gggcgaaaac tctcaaggat cttaccgctg ttgagatcca gttcgatgta acccactcgt   1740
gcacccaact gatcttcagc atcttttact ttcaccagcg tttctgggtg agcaaaaaca   1800
ggaaggcaaa atgccgcaaa aaagggaata agggcgacac ggaaatgttg aatactcata   1860
ctcttccttt ttcaatatta ttgaagcatt tatcagggtt attgtctcat gagcggatac   1920
atatttgaat gtatttagaa aaataaacaa ataggggttc cgcgcacatt tccccgaaaa   1980
gtgccacctg acgtctaata cgactcacta tagggagaaa gcttaccatg aaggccatca   2040
tcgtgctgct catggtcgtg accagcaacg ccgaccggat ctgcaccggc atcacgtcca   2100
gcaactcccc gcacgtggtc aagaccgcga cccaggggga ggtgaacgtg accggcgtca   2160
tcccgctgac gaccaccccc accaagagcc acttcgccaa cctgaagggg acggagaccc   2220
gcggcaagct ctgccccaag tgcctgaact gcaccgacct ggacgtggcc ctcgggcggc   2280
ccaagtgcac cggcaagatc ccgtccgccc gcgtgagcat cctgcacgag gtccggcccg   2340
tgacgtccgg ctgcttcccc atcatgcacg accgcaccaa gatccggcag ctgcccaacc   2400
tcctgcgcgg gtacgagcac atccggctga gcacccacaa cgtgatcaac gccgagaacg   2460
```

```
cgccgggcgg gccctacaag atcggcacct ccgggagctg ccccaacatc acgaacggca   2520
acggcttctt cgccaccatg gcctgggccg tccccaagaa cgacaagaac aagaccgcga   2580
ccaacccgct cacgatcgag gtgccctaca tctgcaccga gggggaggac cagatcaccg   2640
tgtggggctt ccactccgac aacgagaccc agatggccaa gctgtacggg gacagcaagc   2700
cccagaagtt cacgtccagc gccaacggcg tcaccaccca ctacgtgtcc cagatcggcg   2760
ggttccccaa ccagaccgag gacggcgggc tgccgcagag cggccgcatc gtggtcgact   2820
acatggtgca gaagtccggg aagacgggca ccatcaccta ccagcggggc atcctcctgc   2880
cccagaaggt gtggtgcgcc agcgggcgct ccaaggtcat caagggcagc ctgcccctca   2940
tcggggaggc cgactgcctg cacgagaagt acggcgggct gaacaagagc aagccctact   3000
acaccggcga gcacgcgaag gccatcggca actgcccgat ctgggtgaag acgcccctca   3060
agctggccaa cgggaccaag taccggcccc ccgccaagct gctcaaggag cgcggcttct   3120
tcggggccat cgcgggcttc ctggagggcg ggtgggaggg catgatcgcc gggtggcacg   3180
gctacacctc ccacggggcc cacggcgtgg ccgtcgccgc ggacctgaag agcacccagg   3240
aggccatcaa caagatcacg aagaacctca actccctgag cgagctggag gtgaagaacc   3300
tccagcggct gtccggcgcc atggacgagc tgcacaacga gatcctcgag ctggacgaga   3360
aggtcgacga cctgcgcgcc gacaccatca gctcccagat cgagctcgcc gtgctgctga   3420
gcaacgaggg gatcatcaac tccgaggacg agcacctcct ggcgctggag cggaagctca   3480
agaagatgct gggcccgagc gccgtggaga tcgggaacgg ctgcttcgag accaagcaca   3540
agtgcaacca gacctgcctg gaccgcatcg ccgccgggac cttcgacgcg ggcgagttct   3600
ccctccccac gttcgacagc ctgaacatca ccgccgcctc cctgaacgac gacggcctgg   3660
acaaccacac catcctcctg tactacagca ccgccgcctc cagcctggcg gtcacgctca   3720
tgatcgccat cttcgtggtg tacatggtct cccgggacaa cgtgagctgc tccatctgcc   3780
tgtgaggact agttataaga ctgactagcc cgatgggcct cccaacgggc cctcctcccc   3840
tccttgcacc gagattaata aaaaaaaaaa aaaaaaaaaa aaaaaaaaaa aaaaaaaaaa   3900
aaaaaaaaaa aaaaaaaaaa aaatgcatcc cccccccccc cccccccccc cccccccccca   3960
aaggctcttt tcagagccac cagaattcgg atactctaga catatgctta ag           4012
```

<210> SEQ ID NO 28
<211> LENGTH: 3955
<212> TYPE: DNA
<213> ORGANISM: Artificial sequence
<220> FEATURE:
<223> OTHER INFORMATION: GC optimized HA construct

<400> SEQUENCE: 28

```
cagctgcatt aatgaatcgg ccaacgcgcg gggagaggcg gtttgcgtat tgggcgctct     60
tccgcttcct cgctcactga ctcgctgcgc tcggtcgttc ggctgcggcg agcggtatca    120
gctcactcaa aggcggtaat acggttatcc acagaatcag gggataacgc aggaaagaac    180
atgtgagcaa aaggccagca aaaggccagg aaccgtaaaa aggccgcgtt gctggcgttt    240
ttccataggc tccgcccccc tgacgagcat cacaaaaatc gacgctcaag tcagaggtgg    300
cgaaacccga caggactata aagataccag gcgtttcccc ctggaagctc cctcgtgcgc    360
tctcctgttc cgaccctgcc gcttaccgga tacctgtccg cctttctccc ttcgggaagc    420
gtggcgcttt ctcatagctc acgctgtagg tatctcagtt cggtgtaggt cgttcgctcc    480
aagctgggct gtgtgcacga accccccgtt cagcccgacc gctgcgcctt atccggtaac    540
```

-continued

```
tatcgtcttg agtccaaccc ggtaagacac gacttatcgc cactggcagc agccactggt    600
aacaggatta gcagagcgag gtatgtaggc ggtgctacag agttcttgaa gtggtggcct    660
aactacggct acactagaag aacagtattt ggtatctgcg ctctgctgaa gccagttacc    720
ttcggaaaaa gagttggtag ctcttgatcc ggcaaacaaa ccaccgctgg tagcggtggt    780
tttttgttt gcaagcagca gattacgcgc agaaaaaaag gatctcaaga agatcctttg    840
atcttttcta cggggtctga cgctcagtgg aacgaaaact cacgttaagg gattttggtc    900
atgagattat caaaaaggat cttcacctag atccttttaa attaaaaatg aagttttaaa    960
tcaatctaaa gtatatatga gtaaacttgg tctgacagtt accaatgctt aatcagtgag   1020
gcacctatct cagcgatctg tctatttcgt tcatccatag ttgcctgact ccccgtcgtg   1080
tagataacta cgatacggga gggcttacca tctggcccca gtgctgcaat gataccgcga   1140
gacccacgct caccggctcc agatttatca gcaataaacc agccagccgg aagggccgag   1200
cgcagaagtg gtcctgcaac tttatccgcc tccatccagt ctattaattg ttgccgggaa   1260
gctagagtaa gtagttcgcc agttaatagt ttgcgcaacg ttgttgccat tgctacaggc   1320
atcgtggtgt cacgctcgtc gtttggtatg gcttcattca gctccggttc ccaacgatca   1380
aggcgagtta catgatcccc catgttgtgc aaaaaagcgg ttagctcctt cggtcctccg   1440
atcgttgtca gaagtaagtt ggccgcagtg ttatcactca tggttatggc agcactgcat   1500
aattctctta ctgtcatgcc atccgtaaga tgcttttctg tgactggtga gtactcaacc   1560
aagtcattct gagaatagtg tatgcggcga ccgagttgct cttgcccggc gtcaatacgg   1620
gataataccg cgccacatag cagaacttta aaagtgctca tcattggaaa acgttcttcg   1680
gggcgaaaac tctcaaggat cttaccgctg ttgagatcca gttcgatgta acccactcgt   1740
gcacccaact gatcttcagc atcttttact ttcaccagcg tttctgggtg agcaaaaaca   1800
ggaaggcaaa atgccgcaaa aaagggaata agggcgacac ggaaatgttg aatactcata   1860
ctcttccttt ttcaatatta ttgaagcatt tatcagggtt attgtctcat gagcggatac   1920
atatttgaat gtatttagaa aaataaacaa ataggggttc cgcgcacatt tccccgaaaa   1980
gtgccacctg acgtctaata cgactcacta tagggagaaa gcttaccatg aaggccatcc   2040
tggtggtcct cctgtacacc ttcgccaccg cgaacgccga cacgctgtgc atcggctacc   2100
acgccaacaa cagcaccgac accgtggaca ccgtgctcga gaagaacgtc acggtgaccc   2160
actccgtgaa cctgctggag gacaagcaca acgggaagct ctgcaagctg cggggcgtcg   2220
ccccgctgca cctcgggaag tgcaacatcg ccggctggat cctggggaac ccggagtgcg   2280
agagcctgtc caccgcgagc tcctggagct acatcgtgga gacccccagc tccgacaacg   2340
gcacgtgcta ccccggcgac ttcatcgact acgaggagct ccgcgagcag ctgagctccg   2400
tgagctcctt cgagcggttc gagatcttcc ccaagaccag ctcctggccc aaccacgaca   2460
gcgacaaggg ggtcaccgcc gcctgcccgc acgccggcgc gaagtccttc tacaagaacc   2520
tgatctggct cgtgaagaag gggaacagct accccaagct gtccaagagc tacatcaacg   2580
acaagggcaa ggaggtgctg gtcctctggg ggatccacca ccccagcacc tccgccgacc   2640
agcagagcct gtaccagaac gccgacgcct acgtgttcgt gggctccagc cgctactcca   2700
agacgttcaa gcccgagatc gccatccggc cgaaggtccg cgaccgggag ggccggatga   2760
actactactg gacgctggtg gagcccgggg acaagatcac cttcgaggcg accggcaacc   2820
tcgtggtccc ccgctacgcc ttcgccatgg agcggaacgc cgggagcggc atcatcatct   2880
```

-continued

```
ccgacacccc cgtgcacgac tgcaacacga cctgccagac cccgaagggc gccatcaaca   2940
ccagcctgcc cttccagaac atccacccca tcacgatcgg gaagtgcccc aagtacgtga   3000
agtccaccaa gctgcgcctc gcgaccggcc tgcggaacat cccgagcatc cagtcccgcg   3060
ggctgttcgg cgccatcgcc gggttcatcg agggcggctg gaccgggatg gtggacggct   3120
ggtacgggta ccaccaccag aacgagcagg gcagcgggta cgccgccgac ctcaagtcca   3180
cgcagaacgc gatcgacgag atcaccaaca aggtgaacag cgtcatcgag aagatgaaca   3240
cccagttcac cgccgtgggc aaggagttca accacctgga gaagcggatc gagaacctga   3300
acaagaaggt cgacgacggc ttcctcgaca tctggacgta caacgccgag ctgctggtgc   3360
tcctggagaa cgagcgcacc ctggactacc acgactccaa cgtgaagaac ctctacgaga   3420
aggtccggag ccagctgaag aacaacgcca aggagatcgg gaacggctgc ttcgagttct   3480
accacaagtg cgacaacacc tgcatggagt ccgtgaagaa cgggacctac gactacccca   3540
agtacagcga ggaggccaag ctgaaccgcg aggagatcga cggcgtgaag ctcgagtcca   3600
cgcggatcta ccagatcctg gcgatctaca gcaccgtcgc cagctccctg gtgctcgtgg   3660
tcagcctggg ggccatctcc ttctggatgt gcagcaacgg ctccctgcag tgccgcatct   3720
gcatctgacc actagttata agactgacta gcccgatggg cctcccaacg ggccctcctc   3780
ccctccttgc accgagatta ataaaaaaaa aaaaaaaaaa aaaaaaaaaa aaaaaaaaaa   3840
aaaaaaaaaa aaaaaaaaaa aaaaaatgca tccccccccc cccccccccc cccccccccc   3900
ccaaaggctc ttttcagagc caccagaatt cggatactct agacatatgc ttaag        3955
```

METHOD FOR PRODUCING RNA MOLECULE COMPOSITIONS

This application is a national phase application under 35 U.S.C. § 371 of International Application No. PCT/EP2016/082487, filed Dec. 22, 2016, which claims benefit of International Application No. PCT/EP2015/081000, filed Dec. 22, 2015, the entire contents of each of which are hereby incorporated by reference.

SEQUENCE LISTING

The sequence listing disclosed herein is included in a text file having the name "CRVCP0203US.TXT," created on Dec. 3, 2018, having a size of 111101 bytes.

FIELD OF THE INVENTION

The present invention is directed to a method for producing a ribonucleic acid (RNA) molecule composition comprising n different RNA molecule species which are derived from m different deoxyribonucleic acid (DNA) molecule species comprising RNA in vitro transcription of a mixture of m different DNA molecule species in a single reaction vessel, wherein each of the m different DNA molecule species encodes one or more of the n different RNA molecule species thereby generating the n different RNA molecule species, and obtaining the RNA molecule composition comprising n different RNA molecule species, wherein n is an integer of at least 2, and wherein m is an integer of at least 1. The present invention also provides the RNA molecule composition produced by the above method as well as a pharmaceutical composition and pharmaceutical container comprising the RNA molecule composition. In a further aspect, the inventive RNA molecule composition and the pharmaceutical composition are useful as medicament, such as in the treatment or prophylaxis of a disease selected from the group consisting of genetic diseases, allergies, autoimmune diseases, infectious diseases, neoplasms, cancer, and tumor-related diseases, inflammatory diseases, diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system, independently if they are inherited or acquired, and combinations thereof. Also provided is the use of the RNA molecule composition as immunotherapeutic agent, gene-therapeutic agent or as vaccine.

INTRODUCTION

Immunotherapy, gene therapy and (genetic) vaccination belong to the most promising and quickly developing methods of modern medicine. They may provide highly specific and individual treatment options for therapy of a large variety and combination of diseases. Particularly, inherited genetic diseases, but also autoimmune diseases, infectious diseases, cancerous or tumor-related diseases as well as inflammatory diseases may be the subject of such treatment approaches. It is also envisaged to prevent (early) onset of such diseases by these approaches by use of the RNA molecule compositions as medicament.

While DNA is known to be relatively stable and easy to handle, the use of DNA in therapy bears the risk of undesired insertion of the administered DNA fragments into the patient's genome potentially resulting in loss of function of the genes. As a further risk, the undesired generation of anti-DNA antibodies has emerged. Another drawback is the limited expression level of the encoded peptide or protein that can be achieved by DNA administration and its subsequent transcription/translation.

By using RNA molecules instead of DNA molecules for gene therapy or genetic vaccination, the risk of undesired genomic integration and generation of anti-DNA antibodies is minimized or is even prevented completely. For many years it was generally accepted that mRNA is too unstable to be efficiently used for gene therapy purposes. In the last decade, however, several research groups faced this challenge and not only proved the feasibility of mRNA-mediated transfection with surprising results regarding transfection efficiency and duration of protein expression, but were also able to demonstrate major advantages over the use of DNA. One of these advantages is that mRNA does not need to cross the nuclear barrier for its encoded proteins to be expressed (reviewed in Tavernier et al., J Control Release. (2011); 150(3):238-47.

To further develop effective treatment options in the field of gene therapy and genetic vaccination, processes for the recombinant production of RNA molecules in preparative amounts have been recently developed. That process includes the RNA in vitro transcription using phage DNA dependent RNA polymerases (e.g., T7, SP6, T3) in the presence of a suitable DNA template (e.g., a plasmid that harbors the DNA template) and respective nucleotides (see for example Pascolo, Steve. "Vaccination with messenger RNA." *DNA Vaccines*. Humana Press, 2006. 23-40).

Problem in the Art

Current RNA production methods known in the art are only suitable to generate one single specific RNA molecule species encoding one specific therapeutic target wherein said single RNA molecule species has to be produced in one separate production process.

However, for certain medical treatments it is desired to apply a mixture of RNA species (that is more than one RNA molecule species with distinct sequences derived from different DNA templates), hereinafter referred to as RNA molecule composition.

Examples of such treatments may include the application of polyvalent RNA molecule compositions that provide protection against several serotypes or strains of a pathogen (e.g., heamagglutin (HA) from multiple serotypes of Influenza A and B virus); RNA molecule compositions that provide different antigens form a pathogen (e.g., different antigens from Influenza, such as HA, nucleoprotein (NP), neuraminidase (NA) etc.); RNA molecule compositions that provide protection against several isoforms or variants of a cancer antigen (e.g., prostate specific antigen (PSA) in the context of prostate carcinoma); RNA molecule compositions comprising n different RNA molecule species that provide different epitopes of an antigen; RNA molecule compositions comprising n different RNA molecule species that contain a cancer specific and/or patient specific RNA composition of cancer antigens (expressed antigens or mutated antigens); RNA molecule compositions comprising n different RNA molecule species that encode a variety of antibodies (e.g., antibodies that are targeted against different epitopes, e.g. wherein the antibodies are mRNA-coded), or any other therapeutically active RNA molecule compositions comprising n different RNA molecule species (e.g., different isoforms of an enzyme for molecular therapy, different therapeutic proteins for treatment a patient-specific indication, e.g., indication wherein several proteins have to be supplemented). Said applications may also find application in an individual(ized) therapy of a patient.

Examples in the art where RNA molecule compositions comprising n different RNA molecule species have been produced and tested in vivo comprise polyvalent influenza mRNA vaccines (WO2015/024669). However, each single antigen of said RNA vaccine compositions has been produced separately in a separate production process.

The conventional production of a polyvalent vaccine containing several antigens, or an RNA molecule composition in general, is laborious and costly since it requires several runs for DNA template (e.g., plasmid DNA) and RNA production. Therefore, it is desirable to produce such RNA molecule compositions simultaneously in only one production batch. Such a procedure would safe time, labor costs, production costs, and production capacities (e.g., space, equipment) especially in the context of pandemic scenarios or in the context of personalized RNA production. Especially in the context of cGMP (current good manufacturing practice) conform RNA production processes where various productions steps have to be implemented, having only one production pipeline for the inventive RNA molecule compositions comprising n different RNA molecule species would be a major cost and time advantage.

Therefore, a robust process that allows the simultaneous, i.e. in parallel, production of n different RNA species in one production batch would be a major advantage in the art.

SUMMARY OF THE INVENTION

The above mentioned problems in the art are solved by the inventive method for producing a ribonucleic acid (RNA) molecule composition comprising n different RNA molecule species, the method comprising the following steps:

a) RNA in vitro transcription of a mixture of m different deoxyribonucleic acid (DNA) molecule species in a single reaction vessel in parallel, i.e. simultaneously, wherein each of the m different DNA molecule species encodes one or more of the n different RNA molecule species thereby generating the n different RNA molecule species, and
b) obtaining the RNA molecule composition comprising n different RNA molecule species generated in step a), wherein n is an integer of at least 2, and wherein m is an integer of at least 1 or preferably of at least 2.

Preferably, the method further comprises prior to step a) a step of c1) generating the mixture of m different DNA molecule species using bacterial amplification,
c2) generating the mixture of m different DNA molecule species using polymerase chain reaction (PCR),
c3) generating the mixture of m different DNA molecule species using chemical DNA synthesis, and/or
c4) generating the mixture of m different DNA molecule species using enzymatic amplification, for example by rolling circle amplification.

In another preferred embodiment, step c1) comprises a step of d) transforming a bacterial cell culture with at least one single DNA plasmid species of the mixture of m different DNA plasmid species, wherein each DNA plasmid species encodes one or more of the n different RNA molecule species.

In a further preferred embodiment, step c1) comprises a step of d1) transforming m single bacterial cell cultures each with a single DNA plasmid species of the m different DNA plasmid species, wherein the single DNA plasmid species encodes one or more of the n different RNA molecule species, or
d2) transforming a single bacterial cell culture with a mixture of m different DNA plasmid species, wherein each DNA plasmid species encodes one or more of the n different RNA molecule species.

Optionally, the method comprises a step of e) isolating at least one single bacterial cell clone for each DNA plasmid species of the mixture of m different DNA plasmid species and
f) growing each of the at least one single bacterial cell clone isolated in step e) in a separate bacterial cell clone culture.

In another preferred embodiment, the method of the invention further comprises after step d1) the following steps:

e1) isolating at least one single bacterial cell clone of each of the m single bacterial cell cultures transformed in step d1),
f1) growing each of the single bacterial cell clones isolated in step e1) in a separate bacterial cell culture,
g1) optionally determining the identity of the DNA plasmid species of each of the bacterial cell clone cultures grown in step f1),
h1) selecting at least one bacterial cell clone culture for each of the m different DNA plasmid species.

In another preferred embodiment, the method of the invention further comprises after step d2) the following steps:

e2) isolating at least m single bacterial cell clones, and
f2) growing each of the at least m single bacterial cell clones isolated in step e2) in a separate bacterial cell clone culture,
g2) determining the identity of the DNA plasmid species of each of the at least m single bacterial cell clone cultures grown in step f2),
h2) selecting at least one single bacterial cell clone culture for each of the m different DNA plasmid species.

Optionally, the method comprises a step of)

i) determining at least one parameter of growth kinetics and/or amount of plasmid DNA of the at least one single bacterial cell clone culture, and
j) selecting one or more bacterial cell clone cultures for each of the m different DNA plasmid species depending on the parameter determined in step i), preferably selecting one bacterial cell clone culture for each of the m different DNA plasmid species.

In another preferred embodiment of the method of the invention, step i) comprises a step of i1) determining a parameter of growth kinetics by measuring the optical density of the bacterial cell clone culture after a time interval, preferably using a microplate reader, or by scattered light online measurement, and/or
i2) determining the amount of plasmid produced per volume and time of bacterial cell culture.

Optionally, the selected one or more bacterial cell clone cultures for each of the m different DNA plasmid species exhibit similar or identical growth kinetics and/or similar or identical DNA production levels, preferably the similar or equal growth kinetics and/or similar identical DNA production levels are as high as possible.

In the method according to the invention, step c1) further comprises a step of k1) inoculating and growing an amount of at least one of the one or more bacterial cell clone cultures selected for each of the m different DNA plasmid species in step j) in a single reaction vessel, or k2) inoculating and growing an amount of at least one of the one or more bacterial cell clone cultures selected for each of the m different DNA plasmid species in step j) in one or more separate reaction vessels for each of the m different DNA plasmid species, optionally wherein one or more bacterial cell clone cultures of the m different DNA plasmid species are grown together in a single reaction vessel. Optionally, wherein equal amounts of each bacterial cell clone culture are inoculated.

Preferably, the amount of each bacterial cell clone culture used for inoculating in step k1 or k2) is selected so that equal or similar amounts of each of the m different DNA plasmid species are obtained.

Preferably, step c1) further comprises a step of l) obtaining the m different DNA plasmid species of the bacterial cell clone cultures grown in step k1) and/or k2), m) optionally linearizing the m different DNA plasmid species obtained in step 1), and n) obtaining the mixture of m different deoxyribonucleic acid (DNA) molecule species.

The method optionally further comprises prior to step a) a step of o) determining a parameter of transcription efficiency for each of the m different deoxyribonucleic acid (DNA) molecule species.

Preferably, in the method of the invention the amount of each of the n different RNA molecule species in the RNA molecule composition is proportional or at least 90% proportional to the amount of the corresponding deoxyribonucleic acid (DNA) molecule species in the mixture of m different deoxyribonucleic acid (DNA) molecule species. "Corresponding DNA molecule species" in the sense of the present invention denotes the DNA molecule which encodes for the respective RNA molecule species. In the same way, the DNA template species corresponds to the respective (linearized) DNA molecule species which is used for RNA in vitro transcription if they encode the same RNA molecule species. Vice versa, the corresponding RNA molecule species to a DNA molecule/template species is a RNA molecule which is encoded by the corresponding DNA molecule/template species.

In another embodiment of the invention, step b) comprises a step of p) purifying the n different RNA molecule species, optionally via HPLC.

In a preferred embodiment, the method further comprises a step of q) qualitatively and/or quantitatively analyzing the RNA molecule composition obtained in step b).

In an optional embodiment, the DNA sequences of the m different deoxyribonucleic acid (DNA) molecule species are at least 80%, more preferably at least 90% and most preferably at least 95%, identical to each other.

Preferably, the DNA plasmid species of the m different deoxyribonucleic acid (DNA) molecule species have the same plasmid backbone and/or the open reading frames of the DNA plasmid species of the m different deoxyribonucleic acid (DNA) molecule species are at least 80%, more preferably at least 90% and most preferably at least 95% identical to each other and/or the open reading frames of the DNA plasmid species of the m different deoxyribonucleic acid (DNA) molecule species vary in their length by a maximum of 100 or 50 nucleotides.

In a preferred embodiment, the RNA sequences of the n different RNA molecule species are at least 80%, more preferably at least 90% and most preferably at least 95% identical to each other.

In a preferred embodiment of the present invention, each of the m different DNA molecule species encodes for one or more of the n different RNA molecule species, wherein each of the n different RNA molecule species encodes for a antigen of different serotypes or strains of a pathogen, for a different allergen, for a different autoimmune antigen, for a different antigen of a pathogen, different adjuvant proteins, for a different isoform or variant of a cancer or tumor antigen, for a different tumor antigen of one patient, for one antibody among a group of antibodies which target different epitopes of a protein or of a group of proteins, for different proteins of a metabolic pathway, for a single protein among a group of proteins which are defect in a subject, or for a different isoform of a protein for molecular therapy.

More preferably, the pathogen is selected from the group consisting of a virus, bacterium, prion, fungus, protozoon, viroid, and parasite.

Even more preferably, pathogen is selected from the group consisting of *Acinetobacter baumannii, Anaplasma genus, Anaplasma phagocytophilum, Ancylostoma braziliense, Ancylostoma duodenale, Arcanobacterium haemolyticum, Ascaris lumbricoides, Aspergillus* genus, Astroviridae, *Babesia* genus, *Bacillus anthracis, Bacillus cereus, Bartonella henselae*, BK virus, *Blastocystis hominis, Blastomyces dermatitidis, Bordetella pertussis, Borrelia burgdorferi, Borrelia* genus, *Borrelia* spp, *Brucella* genus, *Brugia malayi, Bunyaviridae* family, *Burkholderia cepacia* and other *Burkholderia* species, *Burkholderia mallei, Burkholderia pseudomallei*, Caliciviridae family, *Campylobacter* genus, *Candida albicans, Candida* spp, *Chlamydia trachomatis, Chlamydophila pneumoniae, Chlamydophila psittaci*, CJD prion, *Clonorchis sinensis, Clostridium botulinum, Clostridium difficile, Clostridium perfringens, Clostridium perfringens, Clostridium* spp, *Clostridium tetani, Coccidioides* spp, coronaviruses, *Corynebacterium diphtheriae, Coxiella burnetii*, Crimean-Congo hemorrhagic fever virus, *Cryptococcus neoformans, Cryptosporidium* genus, Cytomegalovirus (CMV), Dengue viruses (DEN-1, DEN-2, DEN-3 and DEN-4), *Dientamoeba fragilis*, Ebolavirus (EBOV), *Echinococcus* genus, *Ehrlichia chaffeensis, Ehrlichia ewingii, Ehrlichia genus, Entamoeba histolytica, Enterococcus* genus, Enterovirus genus, Enteroviruses, mainly Coxsackie A virus and Enterovirus 71 (EV71), *Epidermophyton* spp, Epstein-Barr Virus (EBV), *Escherichia coli* O157:H7, O111 and O104:H4, *Fasciola hepatica* and *Fasciola gigantica*, FFI prion, Filarioidea superfamily, Flaviviruses, *Francisella tularensis, Fusobacterium genus, Geotrichum candidum, Giardia intestinalis, Gnathostoma* spp, GSS prion, Guanarito virus, *Haemophilus ducreyi, Haemophilus influenzae, Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Japanese encephalitis virus, JC virus, Junin virus, *Kingella kingae, Klebsiella granulomatis*, Kuru prion, Lassa virus, *Legionella pneumophila, Leishmania* genus,

*Leptospira* genus, *Listeria monocytogenes*, Lymphocytic choriomeningitis virus (LCMV), Machupo virus, *Malassezia* spp, Marburg virus, Measles virus, *Metagonimus yokagawai*, Microsporidia phylum, *Molluscum contagiosum* virus (MCV), Mumps virus, *Mycobacterium leprae* and *Mycobacterium lepromatosis, Mycobacterium tuberculosis, Mycobacterium ulcerans, Mycoplasma pneumoniae, Naegleria fowleri, Necator americanus, Neisseria gonorrhoeae, Neisseria meningitidis, Nocardia asteroides, Nocardia* spp, *Onchocerca volvulus, Orientia tsutsugamushi*, Orthomyxoviridae family (Influenza), *Paracoccidioides brasiliensis, Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari, Rickettsia genus, Rickettsia prowazekii, Rickettsia rickettsii, Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii, Staphylococcus genus, Staphylococcus genus, Streptococcus agalactiae, Streptococcus pneumoniae, Streptococcus pyogenes, Strongyloides stercoralis, Taenia genus, Taenia solium*, Tick-borne encephalitis virus (TBEV), *Toxocara canis* or *Toxocara cati, Toxoplasma gondii, Treponema pallidum, Trichinella spiralis, Trichomonas vaginalis, Trichophyton* spp, *Trichuris trichiura, Trypanosoma brucei, Trypanosoma cruzi, Ureaplasma urealyticum*, Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica, Yersinia pestis*, and *Yersinia pseudotuberculosis*, preferably the pathogen is selected from the group consisting of influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, Rotavirus and Yellow Fever Virus.

In a preferred embodiment, each of the m different DNA molecule species encodes for one or more of the n different RNA molecule species, wherein each of the n different RNA molecule species encodes a different pathogenic antigen or a fragment or variant thereof, selected from the group consisting of influenza haemagglutinin, influenza neuraminidase, influenza nucleoprotein, coronavirus glycoprotein S, prostate specific antigen, outer membrane protein A OmpA, biofilm associated protein Bap, transport protein MucK of *Acinetobacter baumannii* and *Acinetobacter* infections; variable surface glycoprotein (VSG), microtubule-associated protein MAPP15, trans-sialidase (TSA) of *Trypanosoma brucei*; HIV p24 antigen, Human immunodeficiency virus (HIV) envelope proteins Gp120, Gp41, and Gp160, poly-protein GAG, negative factor protein Nef, trans-activator of transcription (Tat) of HIV; galactose-inhibitable adherence protein (GIAP), 29 kDa antigen Eh29, Gal/GalNAc lectin, protein CRT, 125 kDa immunodominant antigen, protein M17, adhesin ADH112 and protein STIRP of *Entamoeba histolytica*; major surface proteins 1 to 5 (MSP1a, MSP1b, MSP2, MSP3, MSP4, MSP5), type IV secreotion system proteins (VirB2, VirB7, VirB11, VirD4) of *Anaplasma* genus; protective Antigen PA, edema factor EF, lethal factor LF, the S-layer homology proteins (SLH) of *Bacillus anthracis*; acranolysin, phospholipase D, collagen-binding protein CbpA of *Arcanobacterium haemolyticum*; nucleocapsid protein (NP), glycoprotein precursor GPC, glycoprotein GP1, glycoprotein GP2 of Junin virus; chitin-protein layer proteins, 14 kDa suarface antigen A14, major sperm protein (MSP), MSP polymerization-organizing protein (MPOP), MSP fiber protein 2 (MFP2), MSP polymerization-activating kinase (MPAK), ABA-1-like protein (ALB), protein ABA-1, cuticulin (CUT-1) of *Ascaris lumbricoides;* 41 kDa allergen Asp v13, allergen Asp f3, major conidial surface protein rodlet A, protease Pep1p, GPI-anchored protein Gel1p, GPI-anchored protein Crf1p of *Aspergillus* genus; family VP26 protein, VP29 protein of Astroviridae; Rhoptry-associated protein 1 (RAP-1), merozoite surface antigens MSA-1, MSA-2 (a1, a2, b, c), 12D3, 11C5, 21B4, P29, variant erythrocyte surface antigen VESA1, Apical Membrane Antigen 1 (AMA-1) of *Babesia* genus; hemolysin, enterotoxin C, PXO1-51, glycolate oxidase, ABC-transporter, penicillin-bingdn protein, zinc transporter family protein, pseudouridine synthase Rsu, plasmid replication protein RepX, oligoendopeptidase F, prophage membrane protein, protein HemK, flagellar antigen H, 28.5-kDa cell surface antigen of *Bacillus cereus*; large T antigen LT, small T antigen, capsid protein VP1, capsid protein VP2 of BK virus; 29 kDa-protein, caspase-3-like antigens, glycoproteins of *Blastocystis hominis*; yeast surface adhesin WI-1 of *Blastomyces dermatitidis*; nucleoprotein N, polymerase L, matrix protein Z, glycoprotein (GP) of Machupo virus; outer surface protein A (OspA), outer surface protein B (OspB), outer surface protein C (OspC), decorin binding protein A (DbpA), decorin binding protein B (DbpB), flagellar filament 41 kDa core protein Fla, basic membrane protein A precursor (BmpA) (Immunodominant antigen P39), outer surface 22 kDa lipoprotein precursor (antigen IPLA7), variable surface lipoprotein vlsE of *Borrelia* genus; Botulinum neurotoxins BoNT/A1, BoNT/A2, BoNT/A3, BoNT/B, BoNT/C, BoNT/D, BoNT/E, BoNT/F, BoNT/G, recombinant botulinum toxin F Hc domain (FHc) of *Clostridium botulinum*; nucleocapsid, glycoprotein precursor of Sabia virus; copper/Zinc superoxide dismutase (SodC), bacterioferritin (Bfr), 50S ribosomal protein Rp1L, OmpA-like transmembrane domain-containing protein Omp31, immunogenic 39-kDa protein M5 P39, zinc ABC transporter periplasmic zinc-bnding protein znuA, periplasmic immunogenic protein Bp26, 30S ribosomal protein S12 RpsL, glyceraldehyde-3-phosphate dehydrogenase Gap, 25 kDa outer-membrane immunogenic protein precursor Omp25, invasion protein B lalB, trigger factor Tig, molecular chaperone DnaK, putative peptidyl-prolyl cis-trans isomerase SurA, lipoprotein Omp19, outer membrane protein MotY Omp16, conserved outer membrane protein D15, malate dehydrogenase (Mdh), component of the Type-IV secretion system (T4SS) VirJ, lipoprotein of unknown function BAB1_0187 of *Brucella* genus; members of the ABC transporter family (LolC, OppA, and PotF), putative lipoprotein releasing system transmembrane protein LolC/E, flagellin FliC, *Burkholderia* intracellular motility A (BimA), bacterial Elongation factor-Tu (EF-Tu), 17 kDa OmpA-like protein, boaA coding protein, boaB coding protein of *Burkholderia cepacia* and other *Burkholderia* species; mycolyl-transferase Ag85A, heat-shock protein 65 (Hsp65), protein TB10.4, 19 kDa antigen, protein PstS3, heat-shock protein 70 (Hsp70) of *Mycobacterium ulcerans*; norovirus major and minor viral capsid proteins VP1 and VP2, genome polyprotein, Sapovirus capsid protein VP1, protein Vp3, geome polyprotein of Caliciviridae family, Norovirus and Sapovirus; major outer membrane protein PorA, flagellin FlaA, surface antigen CjaA, fibronectin binding protein CadF, aspartate/glutamate-binding ABC transporter protein PeblA, protein FspA1, protein FspA2 of *Campylobacter* genus; glycolytic enzyme enolase, secreted aspartyl proteinases SAP1-10, glycophosphatidylinositol (GPI)-linked cell wall protein, protein Hyrl, complement receptor 3-related protein (CR3-RP), adhesin Als3p, heat shock protein 90 kDa (Hsp90), cell surface hydrophobicity protein (CSH) of *Candida albicans* and other *Candida* species; 17-kDa antigen, protein P26, trimeric autotransporter adhesins TAAs, *Bartonella* adhesin A BadA, variably expressed outer-membrane proteins Vomps, protein Pap3, protein HbpA, envelope-associated protease HtrA, protein OMP89, protein GroEL, protein La1B, protein OMP43, dihydrolipoamide succinyltransferase SucB of *Bartonella henselae*; amastigote surface protein-2, amastigote-specific surface protein SSP4, cruzipain, trans-sialidase TS, trypomastigote surface glycol-protein TSA-1, complement regulatory protein CRP-10, protein G4, protein G2, paraxonemal rod protein PAR2, paraflagellar rod component Parl, mucin-associated Surface Proteins MPSP of *Trypanosoma cruzi*; envelope glycoproteins (gB, gC, gE, gH, gI, gK, gL) of Varicella zoster virus (VZV); major outer membrane protein MOMP, probable outer membrane protein PMPC, outer membrane complex protein B OmcB, heat shock proteins Hsp60 and HSP10, protein IncA, proteins from the type III secretion system, ribonucleotide reductase small chain protein NrdB, plasmid protein Pgp3, chlamydial outer protein N (CopN), antigen CT521, antigen CT425, antigen CT043, antigen TC0052, antigen TC0189, antigen TC0582, antigen TC0660, antigen TC0726, antigen TC0816, antigen TC0828 of *Chlamydia trachomatis*; low calcium response protein E (LCrE), serine/threonine-protein kinase PknD, acyl-carrier-protein S-malonyltransferase FabD, single-stranded DNA-binding protein Ssb, major outer membrane protein (MOMP), outer membrane protein 2 (Omp2), polymorphic membrane protein family, such as (Pmp1, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20 and Pmp21 of *Chlamydophila pneumoniae, Chlamydophila pneumoniae* infection; cholera toxin B (CTB), toxin coregulated pilin A (TcpA), toxin coregulated pilin (TcpF), toxin co-regulated pilus biosynthesis ptrotein F (TcpF), cholera enterotoxin subunit A, cholera enterotoxin subunit B, Heat-stable enterotoxin ST, mannose-sensitive hemagglutinin (MSHA), outer membrane protein U Porin (ompU), Poring B protein, polymorphic membrane protein-D of *Vibrio cholerae*; propionyl-CoA carboxylase PCC, 14-3-3 protein, prohibitin, cysteine proteases, glutathione transferases, gelsolin, cathepsin L proteinase CatL, Tegumental Protein 20.8 kDa TP20.8, tegumental protein 31.8 kDa TP31.8, lysophosphatidic acid phosphatase LPAP of *Clonorchis sinensis*; surface layer proteins SLPs, glutamate dehydrogenase antigen GDH, toxin A, toxin B, cysteine protease Cwp84, cysteine protease Cwp13, cysteine protease Cwp19, Cell Wall Protein CwpV, flagellar protein FliC, flagellar protein FliD of *Clostridium difficile; rhinovirus capsid proteins VP*1, VP2, VP3, VP4; coronavirus sprike proteins S, envelope protein E, membrane protein M, nucleocapsid protein N of rhinoviruses and coronaviruses; prion protein Prp (CJD prion); envelope protein Gc, envelope protein Gn, nucleocapsid proteins of Crimean-Congo hemorrhagic fever virus; virulence-associated DEAD-box RNA helicase VAD1, galactoxylomannan-protein GalXM, glucuronoxylomannan GXM, mannoprotein MP of *Cryptococcus neoformans*; acidic ribosomal protein P2 CpP2, mucin antigens Muc1, Muc2, Muc3 Muc4, Muc5, Much, Muc7, surface adherence protein CP20, surface adherence protein CP23, surface protein CP12, surface protein CP21, surface protein CP40, surface protein CP60, surface protein CP15, surface-associated glycopeptides gp40, surface-associated glycopeptides gp15, oocyst wall protein AB, profilin PRF, apyrase of the Crypto-sporidium genus; fatty acid and retinol binding protein-1 (FAR-1), tissue inhibitor of metalloproteinase (TIMP), cysteine proteinase ACEY-1, cysteine proteinase ACCP-1, surface antigen Ac-16, secreted protein 2 ASP-2, metalloprotease 1 MTP-1, aspartyl protease inhibitor API-1, surface-associated antigen SAA-1, adult-specific secreted factor Xa serine protease inhibitor anticoagulant AP, cathepsin D-like aspartic protease ARR-1, for example of *Ancylostoma braziliense* and other pathogens like Cutaneous larva migrans (CLM); cathepsin L-like proteases, 53/25-kDa antigen, 8 kDa family members, cysticercus protein with a marginal trypsin-like activity TsAg5, oncosphere protein TSOL18, oncosphere protein TSOL45-1A, lactate dehydrogenase A LDHA, lactate dehydrogenase B LDHB of *Taenia solium*; pp65 antigen, membrane protein pp15, capsid-proximal tegument protein pp150, protein M45, DNA polymerase UL54, helicase UL105, glycoprotein gM, glycol-protein gN, glycoprotein H, glycoprotein B gB, protein UL83, protein UL94, protein UL99 of Cytomegalovirus (CMV); capsid protein C, premembrane protein prM, membrane protein M, envelope protein E (domain I, domain II, domain II), protein NS1, protein NS2A, protein NS2B, protein NS3, protein NS4A, protein 2K, protein NS4B, protein NS5 of Dengue viruses (DEN-1, DEN-2, DEN-3 and DEN-4)-Flaviviruses; 39 kDa protein of *Dientamoeba fragilis*; diphtheria toxin precursor Tox, diphtheria toxin DT, pilin-specific sortase SrtA, shaft pilin protein SpaA, tip pilin protein SpaC, minor pilin protein SpaB, surface-associated protein DIP1281 of *Corynebacterium diphtheriae*; glycoprotein GP, nucleoprotein NP, minor matrix protein VP24, major matrix protein VP40, transcription activator VP30, polymerase cofactor VP35, RNA polymerase L of Ebolavirus (EBOV); prion protein (vCJD prion, vCJD, nvCJD); UvrABC system protein B, protein Flp1, protein Flp2, protein Flp3, protein TadA, hemoglobin receptor HgbA, outer membrane protein TdhA, protein CpsRA, regulator CpxR, protein SapA, 18 kDa antigen, outer membrane protein NcaA, protein LspA, protein LspA1, protein LspA2, protein LspB, outer membrane component DsrA, lectin DltA, lipoprotein Hlp, major outer membrane protein OMP, outer membrane protein OmpA2 of *Haemophilus ducreyi*; aspartyl protease 1 Pep1, phospholipase B PLB, alpha-mannosidase 1 AMN1, glucanosyl-transferase GEL1, urease URE, peroxisomal matrix protein Pmp1, proline-rich antigen Pra, humal T-cell reative protein TcrP of *Coccidioides immitis* and Cocci-dioides posadasii; allergen Tri r 2, heat shock protein 60 Hsp60, fungal actin Act, antigen Tri r2, antigen Tri r4, antigen Tri t1, protein IV, glycerol-3-phosphate dehydrogenase Gpdl, osmosensor HwSho1A, osmosensor HwSho1B, histidine kinase HwHhk7B, allergen Mala s 1, allergen Mala s 11, thioredoxin Trx Mala s 13, allergen Mala f, allergen Mala s, for examples of *Trichophyton* spp, *Epidermophyton* spp., *Malassezia* spp., *Hortaea werneckii*; protein EG95, protein EG10, protein EG18, protein EgA31, protein EM18, antigen EPC1, antigen B, antigen 5, protein P29, protein 14-3-3, 8-kDa protein, myophilin, heat shock protein 20 (HSP20), glycoprotein GP-89, fatty acid binding protein FAPB of *Echinococcus* genus; major surface protein 2 MSP2, major surface protein 4 MSP4, MSP variant SGV1, MSP variant SGV2, outer membrane protein OMP, outer membrande protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein of the *Ehrlichia* genus; secreted antigen SagA, sagA-like proteins SalA and SalB, collagen adhesin Scm, surface proteins Fms1 EbpA(fm), Fms5 EbpB(fm), Fms9 EpbC(fm) and Fms10, protein EbpC(fm), 96 kDa immunoprotective glycoprotein G1 of the *Enterococcus* genus; genome polyprotein, polymerase 3D, viral capsid protein VP1, viral capsid protein VP2, viral capsid protein VP3, viral capsid protein VP4, protease 2A, protease 3C of the Enterovirus genus; outer membrane proteins OM, 60 kDa outer membrane protein, cell surface antigen OmpA, cell surface antigen OmpB (sca5), 134 kDa outer membrane protein, 31 kDa outer membrane protein, 29.5 kDa outer membrane protein, cell surface protein SCA4, cell surface protein Add (RP827), cell surface protein Adr2 (RP828), cell surface protein SCA1, Invasion protein invA, cell division protein fts, secretion proteins of the sec family, virulence proteins virB, tlyA, tlyC, parvulin-like protein Plp, preprotein translocase SecA, 120-kDa surface protein antigen SPA, 138 kD complex antigen, major 100-kD protein (protein I), intracytoplasmic protein D, protective surface protein antigen SPA (*Rickettsia prowazekii*, Epidemic typhus); Epstein-Barr nuclear antigens (EBNA-1, EBNA-2, EBNA-3A, EBNA-3B, EBNA-3C, EBNA-leader protein (EBNA-LP)), latent membrane proteins (LMP-1, LMP-2A, LMP-2B), early antigen EBV-EA, membrane antigen EBV-MA, viral capsid antigen EBV-VCA, alkaline nuclease EBV-AN, glycoprotein H, glycoprotein gp350, glycoprotein gp110, glycoprotein gp42, glycoprotein gHgL, glycoprotein gB of Epstein-Barr Virus (EBV); cpasid protein VP2, capsid protein VP1, major protein NS1 of Parvovirus B19; pp65 antigen, glycoprotein 105, major capsid protein, envelope glycoprotein H, protein U51 of Human herpesvirus 6 (HHV-6) and Human herpesvirus 7 (HHV-7); thioredoxin-glutathione reductase TGR, cathepsins L1 and L2, Kunitz-type protein KTM, leucine aminopeptidase LAP, cysteine proteinase Fas2, saposin-like protein-2 SAP-2, thioredoxin peroxidases TPx, Prx-1, Prx-2, cathepsin 1 cysteine proteinase CL3, protease cathepsin L CL1, phosphoglycerate kinase PGK, 27-kDa secretory protein, 60 kDa protein HSP35alpha, glutathione transferase GST, 28.5 kDa tegumental antigen 28.5 kDa TA, cathepsin B3 protease CatB3, Type I cystatin stefin-1, cathepsin L5, cathepsin L1g and cathepsin B, fatty acid binding protein FABP, leucine aminopeptidases LAP of *Fasciola hepatica* and *Fasciola gigantica*; prion protein FFI prion; venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, secreted larval acidic proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 of the Filarioidea superfamily; phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, Fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm of *Clostridium perfringens*; leukotoxin lktA, adhesion FadA, outer membrane protein RadD, high-molecular weight arginine-binding protein of *Fusobacterium* genus; phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm, for example of *Clostridium perfringens* and other *Clostridium* species; lipase A, lipase B, peroxidase Dec1 of *Geotrichum candidum*; prion protein GSS prion; cyst wall proteins CWP1, CWP2, CWP3, variant surface protein VSP, VSP1, VSP2, VSP3, VSP4, VSP5, VSP6, 56 kDa antigen, pyruvate ferredoxin oxidoreductase PFOR, alcohol dehydrogenase E ADHE, alpha-giardin, alpha8-giardin, alpha1-guiardin, beta-giardin, cystein proteases, glutathione-S-transferase GST, arginine deiminase ADI, fructose-1,6-bisphosphat aldolase FBA, *Giardia* trophozoite antigens GTA (GTA1, GTA2), ornithine carboxyl transferase OCT, striated fiber-asseblin-like protein SALP, uridine phosphoryl-like protein UPL, alpha-tubulin, beta-tubulin of *Giardia intestinalis*; members of the ABC transporter family (LolC, OppA, and PotF), putative lipoprotein releasing system transmembrane protein LolC/E, flagellin FliC, *Burkholderia* intracellular motility A BimA, bacterial Elongation factor-Tu EF-Tu, 17 kDa OmpA-like protein, boaA coding protein of *Burkholderia mallei*; cyclophilin CyP, 24 kDa third-stage larvae protien GS24, excretion-secretion products ESPs (40, 80, 120 and 208 kDa) of *Gnathostoma spinigerum* and *Gnathostoma hispidum*; pilin proteins, minor pilin-associated subunit pilC, major pilin subunit and variants pilE, pilS, phase variation protein porA, Porin B PorB, protein TraD, Neisserial outer membrane antigen H.8, 70 kDa antigen, major outer membrane protein PI, outer membrane proteins HA and P1B, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR of *Neisseria gonorrhoeae*; outer membrane protein A OmpA, outer membrane protein C OmpC, outer membrane protein K17 OmpK17 of *Klebsiella granulomatis*; fibronectin-binding protein Sfb, fibronectin/fibrinogen-binding protein FBP54, fibronectin-binding protein FbaA, M protein type 1 Emm1, M protein type 6 Emm6, immunoglobulin-binding protein 35 Sib35, Surface protein R28 Spr28, superoxide dismutase SOD, C5a peptidase ScpA, antigen I/II AgI/II, adhesin AspA, G-related alpha2-macroglobulin-binding protein GRAB, surface fibrillar protein M5 of *Streptococcus pyogenes*; C protein β antigen, arginine deiminase proteins, adhesin BibA, 105 kDA protein BPS, surface antigens c, surface antigens R, surface antigens X, trypsin-resistant protein R1, trypsin-resistant protein R3, trypsin-resistant protein R4, surface immunogenic protein Sip, surface protein Rib, Leucine-rich repeats protein LrrG, serine-rich repeat protein Srr-2, C protein alpha-antigen Bca, Beta antigen Bag, surface antigen Epsilon, alpha-like protein ALP1, alpha-like protein ALPS surface antigen delta, alpha-like protein ALP2, alpha-like protein ALPS, alpha-like protein ALP4, Cbeta protein Bac of Streptococcus *agalactiae*; transferrin-binding protein 2 Tbp2, phosphatase P4, outer membrane protein P6, peptidoglycan-associated lipoprotein Pal, protein D, protein E, adherence and penetration protein Hap, outer membrane protein 26 Omp26, outer membrane protein P5 (Fimbrin), outer membrane protein D15, outer membrane protein OmpP2, 5'-nucleotidase NucA, outer membrane protein P1, outer membrane protein P2, outer membrane lipoprotein Pcp, Lipoprotein E, outer membrane protein P4, fuculokinase fucK, [Cu,Zn]-superoxide dismutase SodC, protease HtrA, protein 0145, alpha-galactosylceramide of *Haemophilus influenzae*; polymerase 3D, viral capsid protein VP1, viral capsid protein VP2, viral capsid protein VP3, viral capsid protein VP4, protease 2A, protease 3C (Enteroviruses, mainly Coxsackie A virus and Enterovirus 71 (EV71), Hand, foot and mouth disease (HFMD)); RNA polymerase L, protein L, glycoprotein Gn, glycoprotein Gc, nucleocapsid protein S, envelope glycoprotein G1, nucleoprotein NP, protein N, polyprotein M of Sin Nombre virus, Hantavirus; heat shock protein HspA, heat shock protein HspB, citrate synthase GltA, protein UreB, heat shock protein Hsp60, neutrophil-activating protein NAP, catalase KatA, vacuolating cytotoxin VacA, urease alpha UreA, urease beta Ureb, protein Cpn10, protein groES, heat shock protein Hsp10, protein MopB, cytotoxicity-associated 10 kDa protein CAG, 36 kDa antigen, beta-lactamase HcpA, Beta-lactamase HcpB of *Helicobacter pylori*; integral membrane proteins, aggregation-prone proteins, 0-antigen, toxin-antigens Stx2B, toxin-antigen Stx1B, adhesion-antigen fragment Int28, protein EspA, protein EspB, Intimin, protein Tir, protein IntC300, protein Eae of *Escherichia coli* O157:H7, O111 and O104:H4; RNA polymerase L, protein L, glycoprotein Gn, glycoprotein Gc, nucleocapsid protein S, envelope glycoprotein G1, nucleoprotein NP, protein N, polyprotein M of Bunya-viridae family; glycoprotein G, matrix protein M, nucleoprotein N, fusion protein F, polymerase L, protein W, proteinC, phosphoprotein p, non-structural protein V of Henipavirus, Hendra virus or Nipah virus; polyprotein, glycoproten Gp2, hepatitis A surface antigen HBAg, protein 2A, virus protein VP1, virus protein VP2, virus protein VP3, virus protein VP4, protein P1B, protein P2A, protein P3AB, protein P3D of Hepatitis A Virus; hepatitis B surface antigen HBsAg, Hepatitis B core antigen HbcAg, polymerase, protein Hbx, preS2 middle surface protein, surface protein L, large S protein, virus protein VP1, virus protein VP2, virus protein VP3, virus protein VP4 of Hepatitis B Virus (HBV); envelope glycoprotein E1 gp32 gp35, envelope glycoprotein E2 NS1 gp68 gp70, capsid protein C, core protein Core, polyprotein, virus protein VP1, virus protein VP2, virus protein VP3, virus protein VP4, antigen G, protein NS3, protein NSSA of Hepatitis C Virus; virus protein VP1, virus protein VP2, virus protein VP3, virus protein VP4, large hepaptitis delta antigen, small hepaptitis delta antigen of Hepatitis D Virus; virus protein VP1, virus protein VP2, virus protein VP3, virus protein VP4, capsid protein E2 of Hepatitis E Virus; glycoprotein L UL1, uracil-DNA glycosylase UL2, protein UL3, protein UL4, DNA replication protein UL5, portal protein UL6, virion maturation protein UL7, DNA helicase ULB, replication origin-binding protein UL9, glycoprotein M UL10, protein UL11, alkaline exonuclease UL12, serine-threonine protein kinase UL13, tegument protein UL14, terminase UL15, tegument protein UL16, protein UL17, capsid protein VP23 UL18, major capsid protein VP5 UL19, membrane protein UL20, tegument protein UL21, Glycoprotein H (UL22), Thymidine Kinase UL23, protein UL24, protein UL25, capsid protein P40 (UL26, VP24, VP22A), glycol-protein B (UL27), ICP18.5 protein (UL28), major DNA-binding protein ICP8 (UL29), DNA polymerase UL30, nuclear matrix protein UL31, envelope glycol-protein UL32, protein UL33, inner nuclear membrane protein UL34, capsid protein VP26 (UL35), large tegument protein UL36, capsid assembly protein UL37, VP19C protein (UL38), ribonucleotide reductase (Large subunit) UL39, ribonucleotide reductase (Small subunit) UL40, tegument protein/virion host shutoff VHS protein (UL41), DNA polymerase processivity factor UL42, membrane protein UL43, glycoprotein C (UL44), membrane protein UL45, tegument proteins VP11/12 (UL46), tegument protein VP13/14 (UL47), virion maturation protein VP16 (UL48, Alpha-TIF), envelope protein UL49, dUTP diphosphatase UL50, tegument protein UL51, DNA helicase/primase complex protein UL52, glycoprotein K (UL53), transcriptional regulation protein IE63 (ICP27, UL54), protein UL55, protein UL56, viral replication protein ICP22 (IE68, US1), protein US2, serine/threonine-protein kinase US3, glycoprotein G (US4), glycoprotein J (US5), glycoprotein D (US6), glycoprotein I (US7), glycoprotein E (US8), tegument protein US9, capsid/tegument protein US10, Vmw21 protein (US11), ICP47 protein (IE12, US12), major transcriptional activator ICP4 (IE175, RS1), E3 ubiquitin ligase ICPO (IE110), latency-related protein 1 LRP1, latency-related protein 2 LRP2, neurovirulence factor RL1 (ICP34.5), latency-associated transcript LAT of Herpes simplex virus 1 and 2 (HSV-1 and HSV-2); heat shock protein Hsp60, cell surface protein H1C, dipeptidyl peptidase type IV DppIV, M antigen, 70 kDa protein, 17 kDa histone-like protein of *Histoplasma capsulatum*; fatty acid and retinol binding protein-1 FAR-1, tissue inhibitor of metalloproteinase TIMP (TMP), cysteine proteinase ACEY-1, cysteine proteinase ACCP-1, surface antigen Ac-16, secreted protein 2 ASP-2, metalloprotease 1 MTP-1, aspartyl protease inhibitor API-1, surface-associated antigen SAA-1, surface-associated antigen SAA-2, adult-specific secreted factor Xa, serine protease inhibitor anticoagulant AP, cathepsin D-like aspartic protease ARR-1, glutathione S-transferase GST, aspartic protease APR-1, acetylcholinesterase AChE of *Ancylostoma duodenale* and *Necator americanus*; protein NS1, protein NP1, protein VP1, protein VP2, protein VP3 of Human bocavirus (HBoV); major surface protein 2 MSP2, major surface protein 4 MSP4, MSP variant SGV1, MSP variant SGV2, outer membrane protein OMP, outer membrande protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein of *Ehrlichia ewingii*; major surface proteins 1-5 (MSP1a, MSP1b, MSP2, MSP3, MSP4, MSP5), type IV secreotion system proteins VirB2, VirB7, VirB11, VirD4 of *Anaplasma* phagocytophilum; protein NS1, small hydrophobic protein NS2, SH protein, fusion protein F, glycoprotein G, matrix protein M, matrix protein M2-1, matrix protein M2-2, phosphoprotein P, nucleoprotein N, polymerase L of Human metapneumovirus (hMPV); major surface protein 2 MSP2, major surface protein 4 MSP4, MSP variant SGV1, MSP variant SGV2, outer membrane protein OMP, outer membrande protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein of *Ehrlichia chaffeensis*; replication protein E1, regulatory protein E2, protein E3, protein E4, protein E5, protein E6, protein E7, protein E8, major capsid protein L1, minor capsid protein L2 of Human papillomavirus (HPV); fusion protein F, hemagglutinin-neuramidase HN, glycoprotein G, matrix protein M, phosphoprotein P, nucleoprotein N, polymerase L of Human parainfluenza viruses (HPIV); Hemagglutinin (HA), Neuraminidase (NA), Nucleoprotein (NP), M1 protein, M2 protein, NS1 protein, NS2 protein (NEP protein: nuclear export protein), PA protein, PB1 protein (polymerase basic 1 protein), PB1-F2 protein and PB2 protein of the Orthomyxoviridae family, Influenza virus (flu); genome polyprotein, protein E, protein M, capsid protein C of Japanese encephalitis virus; RTX toxin, type IV pili, major pilus subunit PilA, regulatory transcription factors PilS and PilR, protein sigma54, outer membrane proteins of *Kingella kingae*; prion protein Kuru prion; nucleoprotein N, polymerase L, matrix protein Z, glycoprotein GP of Lassa virus; peptidoglycan-associated lipoprotein PAL, 60 kDa chaperonin Cpn60 (groEL, HspB), type IV pilin PilE, outer membrane protein MIP, major outer membrane protein MompS, zinc metalloproteinase MSP of *Legionella pneumophila*; P4 nuclease, protein WD, ribonucleotide reductase M2, surface membrane glycoprotein Pg46, cysteine proteinase CP, glucose-regulated protein 78 GRP-78, stage-specific S antigen-like protein A2, ATPase F1, beta-tubulin, heat shock protein 70 Hsp70, KMP-11, glycoprotein GP63, protein BT1, nucleoside hydrolase NH, cell surface protein B1, ribosomal protein P1-like protein P1, sterol 24-c-methyltransferase SMT, LACK protein, histone H1, SPB1 protein, thiol specific antioxidant TSA, protein antigen STl1, signal peptidase SP, histone H2B, suface antigen PSA-2, cystein proteinase b Cpb of the *Leishmania* genus; major membrane protein I, serine-rich antigen-45 kDa, 10 kDa caperonin GroES, HSP kDa antigen, amino-oxononanoate synthase AONS, protein recombinase A RecA, Acetyl-/propionyl-coenzyme A carboxylase alpha, alanine racemase, 60 kDa chaperonin 2, ESAT-6-like protein EcxB (L-ESAT-6), protein Lsr2, protein ML0276, Heparin-binding hemagglutinin HBHA, heat-shock protein 65 Hsp65, mycP1 or ML0041 coding protein, htrA2 or ML0176 coding protein, htrA4 or ML2659 coding protein, gcp or ML0379 coding protein, clpC or ML0235 coding protein of *Mycobacterium leprae*; outer membrane protein LipL32, membrane protein LIC10258, membrane protein LP30, membrane protein LIC12238, Ompa-like protein Lsa66, surface protein LigA, surface protein LigB, major outer membrane protein OmpL1, outer membrane protein LipL41, protein LigAni, surface protein LcpA, adhesion protein LipL53, outer membrane protein UpL32, surface protein Lsa63, flagellin FlaB1, membran lipoprotein LipL21, membrane protein pL40, leptospiral surface adhesin Lsa27, outer membrane protein OmpL36, outer membrane protein OmpL37, outer membrane protein OmpL47, outer membrane protein OmpL54, acyltransferase LpxA of the *Leptospira* genus; listeriolysin O precursor Hly (LLO), invasion-associated protein Iap (P60), Listeriolysin regulatory protein PrfA, Zinc metalloproteinase Mpl, Phosphatidylinositol-specific phospholipase C PLC (PlcA, PlcB), 0-acetyltransferase Oat, ABC-transporter permease Im.G_1771, adhesion protein LAP, LAP receptor Hsp60, adhesin LapB, haemolysin listeriolysin O LLO, protein ActA, Internalin A InlA, protein lnlB of *Listeria monocytogenes*; outer surface protein A OspA, outer surface protein OspB, outer surface protein OspC, decorin binding protein A DbpA, decorin binding protein B DbpB, flagellar filament 41 kDa core protein Fla, basic membrane protein A BmpA (Immunodominant antigen P39), outer surface 22 kDa lipoprotein precursor (antigen IPLA7), variable surface lipoprotein vlsE, for example of *Borrelia burgdorferi* and other *Borrelia* species; venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, protein Cox-2 (*Wuchereria bancrofti* and *Brugia malayi*, Lymphatic filariasis (Elephantiasis)); glycoprotein GP, matrix protein Z, polymerase L, nucleoprotein N of Lymphocytic choriomeningitis virus (LCMV); thrombospondin-related anonymous protein TRAP, SSP2 Sporozoite surface protein 2, apical membrane antigen 1 AMA1, rhoptry membrane antigen RMA1, acidic basic repeat antigen ABRA, cell-traversal protein PF, protein Pvs25, merozoite surface protein 1 MSP-1, merozoite surface protein 2 MSP-2, ring-infected erythrocyte surface antigen RESALiver stage antigen 3 LSA-3, protein Eba-175, serine repeat antigen 5 SERA-5, circumsporozoite protein CS, merozoite surface protein 3 MSP3, merozoite surface protein 8 MSP8, enolase PF10, hepatocyte erythrocyte protein 17 kDa HEP17, erythrocyte membrane protein 1 EMP1, protein Kbetamerozoite surface protein 4/5 MSP 4/5, heat shock protein Hsp90, glutamate-rich protein GLURP, merozoite surface protein 4 MSP-4, protein STARP, circumsporozoite protein-related antigen precursor CRA (*Plasmodium* genus, Malaria); nucleoprotein N, membrane-associated protein VP24, minor nucleoprotein VP30, polymerase cofactor VP35, polymerase L, matrix protein VP40, envelope glycoprotein GP of Marburg virus; protein C, matrix protein M, phosphoprotein P, non-structural protein V, hemagglutinin glycoprotein H, polymerase L, nucleoprotein N, fusion protein F of Measles virus; members of the ABC transporter family (LolC, OppA, and PotF), putative lipoprotein releasing system transmembrane protein LolC/E, flagellin FliC, *Burkholderia* intracellular motility A BimA, bacterial Elongation factor-Tu EF-Tu, 17 kDa OmpA-like protein, boaA coding protein, boaB coding protein of *Burkholderia pseudomallei*; pilin proteins, minor pilin-associated subunit pilC, major pilin subunit and variants pilE, pilS, phase variation protein porA, Porin B PorB, protein TraD, Neisserial outer membrane antigen H.8, 70 kDa antigen, major outer membrane protein PI, outer membrane proteins HA and P1B, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR, factor H-binding protein fHbp, adhesin NadA, protein NhbA, repressor FarR of *Neisseria meningitidis;* 66 kDa protein, 22 kDa protein, for example of *Metagonimus* yokagawai; polar tube proteins (34, 75, and 170 kDa in Glugea, 35, 55 and 150 kDa in Encephalitozoon), kinesin-related protein, RNA polymerase II largest subunit, similar of integral membrane protein YIPA, anti-silencing protein 1, heat shock transcription factor HSF, protein kinase, thymidine kinase, NOP-2 like nucleolar protein of Microsporidia phylum; CASP8 and FADD-like apoptosis regulator, Glutathione peroxidase GPX1, RNA helicase NPH-II NPH2, Poly(A) polymerase catalytic subunit PAPL, Major envelope protein P43K, early transcription factor 70 kDa subunit VETFS, early transcription factor 82 kDa subunit VETFL, metalloendopeptidase G1-type, nucleoside triphosphatase I NPH1, replication pro tein A28-like MC134L, RNA polymease 7 kDa subunit RPO7 of *Molluscum contagiosum* virus (MCV); matrix protein M, phosphoprotein P/V, small hydrophobic protein SH, nucleoprotein N, protein V, fusion glycoprotein F, hemagglutinin-neuraminidase HN, RNA polymerase L of Mumps virus; Outer membrane proteins OM, cell surface antigen OmpA, cell surface antigen OmpB (sca5), cell surface protein SCA4, cell surface protein SCA1, intracytoplasmic protein D, crystalline surface layer protein SLP, protective surface protein antigen SPA of *Rickettsia typhi*; adhesin P1, adhesion P30, protein p116, protein P40, cytoskeletal protein HMW1, cytoskeletal protein HMW2, cytoskeletal protein HMW3, MPN152 coding protein, MPN426 coding protein, MPN456 coding protein, MPN-500 coding protein of *Mycoplasma pneumoniae*; NocA, Iron dependent regulatory protein, VapA, VapD, VapF, VapG, caseinolytic protease, filament tip-associated 43-kDa protein, protein P24, protein P61, 15-kDa protein, 56-kDa protein, for example of *Nocardia asteroides* and other *Nocardia* species; venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP, such as peptides N, N1, N2, and N3, activation associated protein-1 ASP-1, Thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 of *Onchocerca volvulus;* 43 kDa secreted glycoprotein, glycoprotein gp0, glycoprotein gp75, antigen Pb27, antigen Pb40, heat shock protein Hsp65, heat shock protein Hsp70, heat shock protein Hsp90, protein P10, triosephosphate isomerase TPI, N-acetyl-glucosamine-binding lectin Paracoccin, 28 kDa protein Pb28 of *Paracoccidioides brasiliensis;* 28-kDa cruzipain-like cystein protease Pw28CCP, for example of *Paragonimus westermani* and other *Paragonimus* species; outer membrane protein OmpH, outer membrane protein Omp28, protein PM1539, protein PM0355, protein PM1417, repair protein MutL, protein BcbC, protein PM0305, formate dehydrogenase-N, protein PM0698, protein PM1422, DNA gyrase, lipoprotein PlpE, adhesive protein Cp39, heme aquisition system receptor HasR, 39 kDa capsular protein, iron-regulated OMP IROMP, outer membrane protein OmpA87, fimbrial protein Ptf, fimbrial subunit protein PtfA, transferrin binding protein Tbpl, esterase enzyme MesA, *Pasteurella multocida* toxin PMT, adhesive protein Cp39 of the *Pasteurella* genus; filamentous hemagglutinin FhaB, adenylate cyclase CyaA, pertussis toxin subunit 4 precursor PtxD, pertactin precursor Prn, toxin subunit 1 PtxA, protein Cpn60, protein brkA, pertussis toxin subunit 2 precursor PtxB, pertussis toxin subunit 3 precursor PtxC, pertussis toxin subunit 5 precursor PtxE, pertactin Prn, protein Fim2, protein Fim3 of *Bordetella pertussis*; F1 capsule antigen, virulence-associated V antigen, secreted effector protein LcrV, V antigen, outer membrane protease Pla, secreted effector protein YopD, putative secreted protein-tyrosine phosphatase YopH, needle complex major subunit YscF, protein kinase YopO, putative autotransporter protein YapF, inner membrane ABC-transporter YbtQ (Irp7), putative sugar binding protein YPO0612, heat shock protein 90 HtpG, putative sulfatase protein YdeN, outer-membrane lipoprotein carrier protein LolA, secretion chaperone YerA, putative lipoprotein YPO0420, hemolysin activator protein HpmB, pesticin/yersiniabactin outer membrane receptor Psn, secreted effector protein YopE, secreted effector protein YopF, secreted effector protein YopK, outer membrane protein YopN, outer membrane protein YopM, Coagulase/fibrinolysin precursor Pla of *Yersinia pestis*; protein PhpA, surface adhesin PsaA, pneumolysin Ply, ATP-dependent protease Clp, lipoate-protein ligase LplA, cell wall surface anchored protein psrP, sortase SrtA, glutamyl-tRNA synthetase GltX, choline binding protein A CbpA, pneumococcal surface protein A PspA, pneumococcal surface protein C PspC, 6-phosphogluconate dehydrogenase Gnd, iron-binding protein PiaA, Murein hydrolase LytB, proteon LytC, protease A1 of *Streptococcus pneumoniae*; major surface protein B, kexin-like protease KEX1, protein A12, 55 kDa antigen P55, major surface glycoprotein Msg of *Pneumocystis jirovecii*; genome polyprotein, polymerase 3D, viral capsid protein VP1, viral capsid protein VP2, viral capsid protein VP3, viral capsid protein VP4, protease 2A, protease 3C of Poliovirus; protein Nfal, exendin-3, secretory lipase, cathepsin B-like protease, cysteine protease, cathepsin, peroxiredoxin, protein CrylAc, for example of *Naegleria fowleri*; agnoprotein, large T antigen, small T antigen, major capsid protein VP1, minor capsid protein Vp2 of JC virus; low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 (Omp2), polymorphic membrane protein family, such as Pmp1, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20, Pmp21 of *Chlamydophila psittaci*; outer membrane protein P1, heat shock protein B HspB, peptide ABC transporter, GTP-binding protein, protein IcmB, ribonuclease R, phosphatas SixA, protein DsbD, outer membrane protein TolC, DNA-binding protein PhoB, ATPase DotB, heat shock protein B (HspB), membrane protein Com1, 28 kDa protein, DNA-3-methyladenine glycosidase I, outer membrane protein OmpH, outer membrane protein AdaA, glycine cleavage system T-protein of *Coxiella burnetii*; nucleoprotein N, large structural protein L, phophoprotein P, matrix protein M, glycoprotein G of Rabies virus; fusionprotein F, nucleoprotein N, matrix protein M, matrix protein M2-1, matrix protein M2-2, phosphoprotein P, small hydrophobic protein SH, major surface glycoprotein G, polymerase L, non-structural protein 1 NS1, non-structural protein 2 NS2 of Respiratory syncytial virus (RSV); genome polyprotein, polymerase 3D, viral capsid protein VP1, viral capsid protein VP2, viral capsid protein VP3, viral capsid protein VP4, protease 2A, protease 3C of Rhinovirus; outer membrane (OM) proteins, cell surface antigen OmpA, cell surface antigen OmpB (sca5), cell surface protein SCA4, cell surface protein SCA1, protein PS120, intracytoplasmic protein D, protective surface protein antigen SPA of the *Rickettsia* genus; outer membrane proteins OM, cell surface antigen OmpA, cell surface antigen OmpB (sca5), cell surface protein SCA4, cell surface protein SCA1, intracytoplasmic protein D of *Rickettsia akari*; envelope glycoprotein GP, polymerase L, nucleoprotein N, non-structural protein NSS of Rift Valley fever virus; outer membrane proteins OM, cell surface antigen OmpA, cell surface antigen OmpB (sca5), cell surface protein SCA4, cell surface protein SCA1, intracytoplasmic protein D of *Rickettsia rickettsii*; non-structural protein 6 NS6, non-structural protein 2 NS2, intermediate capsid protein VP6, inner capsid protein VP2, non-structural protein 3 NS3, RNA-directed RNA polymerase L, protein VP3, non-structural protein 1 NS1, non-structural protein 5 NS5, outer capsid glycoprotein VP7, non-structural glycoprotein 4 NS4, outer capsid protein VP4 of Rotavirus; polyprotein P200, glycoprotein E1, glycoprotein E2, protein NS2, capsid protein C of Rubella virus; chaperonin GroEL (MopA), inositol phosphate phosphatase SopB, heat shock protein HslU, chaperone protein DnaJ, protein TviB, protein IroN, flagellin FliC, invasion protein SipC, glycoprotein gp43, outer membrane protein LamB, outer membrane protein PagC, outer membrane protein TolC, outer membrane protein NmpC, outer membrane protein FadL, transport protein SadA, transferase WgaP, effector proteins SifA, SteC, SseL, SseJ and SseF of the *Salmonella* genus; protein 14, non-structural protein NS7b, non-structural protein NS8a, protein 9b, protein 3a, nucleoprotein N, non-structural protein NS3b, non-structural protein NS6, protein 7a, non-structural protein NS8b, membrane protein M, envelope small membrane protein EsM, replicase polyprotein 1a, spike glycoprotein S, replicase polyprotein lab of SARS coronavirus; serine protease, Atypical *Sarcoptes* Antigen 1 ASA1, glutathione S-transferases (GST), cystein protease, serine protease, apolipoprotein of *Sarcoptes scabiei*; glutathione S-transferases (GST), paramyosin, hemoglbinase SM32, major egg antigen, 14 kDa fatty acid-binding protein Sm14, major larval surface antigen P37, 22.6 kDa tegumental antigen, calpain CANP, triphospate isomerase Tim, surface protein 9B, outer capsid protein VP2, 23 kDa integral membrane protein Sm23, Cu/Zn-superoxide dismutase, glycoprotein Gp, myosin of the *Schistosoma* genus; 60 kDa chaperonin, 56 kDa type-specific antigen, pyruvate phosphate dikinase, 4-hydroxybenzoate octaprenyltransferase of *Orientia tsutsugamushi*; dehydrogenase GuaB, invasion protein Spa32, invasin IpaA, invasin IpaB, invasin IpaC, invasin IpaD, invasin IpaH, invasin IpaJ of the *Shigella* genus; protein P53, virion protein US10 homolog, transcriptional regulator IE63, transcriptional transactivator IE62, protease P33, alpha trans-inducing factor 74 kDa protein, deoxyuridine 5'-triphosphate nucleotidohydrolase, transcriptional transactivator IE4, membrane protein UL43 homolog, nuclear phosphoprotein UL3 homolog, nuclear protein UL4 homolog, replication origin-binding protein, membrane protein 2, phosphoprotein 32, protein 57,DNA polymerase processivity factor, portal protein 54, DNA primase, tegument protein UL14 homolog, tegument protein UL21 homolog, tegument protein UL55 homolog, tripartite terminase subunit UL33 homolog, tripartite terminase subunit UL15 homolog, capsid-binding protein 44, virion-packaging protein 43 of Varicella zoster virus (VZV); truncated 3-beta hydroxy-5-ene steroid dehydrogenase homolog, virion membrane protein A13, protein A19, protein A31, truncated protein A35 homolog, protein A37.5 homolog, protein A47, protein A49, protein A51, semaphorin-like protein A43, serine proteinase inhibitor 1, serine proteinase inhibitor 2, serine proteinase inhibitor 3, protein A6, protein B15, protein C1, protein C5, protein C6, protein F7, protein F8, protein F9, protein F11, protein F14, protein F15, protein F16 of Variola major and Variola minor; adhesin/glycoprotein gp70, proteases of *Sporothrix schenckii*; heme-iron binding protein IsdB, collagen adhesin Cna, clumping factor A (C1fA), protein MecA, fibronectin-binding protein A (FnbA), enterotoxin type A (EntA), enterotoxin type B (EntB), enterotoxin type C EntC1, enterotoxin type C EntC2, enterotoxin type D (EntD), enterotoxin type E (EntE), Toxic shock syndrome toxin-1 (TSST-1), Staphylokinase, Penicillin binding protein 2a (PBP2a, MecA), secretory antigen SssA of the *Staphylococcus* genus, such as *Staphylococcus aureus*; antigen Ss-IR, antigen NIE, strongylastacin, Na+-K+ ATPase Sseat-6, tropomysin SsTmy-1, protein LEC-5, 41 kDa aantigen P5, 41-kDa larval protein, 31-kDa larval protein, 28-kDa larval protein of *Strongyloides stercoralis*; glycerophosphodiester phosphodiesterase GlpQ (Gpd), outer membrane protein TmpB, protein Tp92, antigen TpF1, repeat protein Tpr, repeat protein F TprF, repeat protein G TprG, repeat protein I TprI, repeat protein J TprJ, repeat protein K TprK, treponemal membrane protein A (TmpA), lipoprotein, 15 kDa Tpp15, 47 kDa membrane antigen, miniferritin TpF1, adhesin Tp0751, lipoprotein TP0136, protein TpN17, protein TpN47, outer membrane protein TP0136, outer membrane protein TP0155, outer membrane protein TP0326, outer membrane protein TP0483, outer membrane protein TP0956 of *Treponema pallidum*; Cathepsin L-like proteases, 53/25-kDa antigen, 8 kDa family members, cysticercus protein with a marginal trypsin-like activity TsAg5, oncosphere protein TSOL18, oncosphere protein TSOL45-1A, lactate dehydrogenase A LDHA, lactate dehydrogenase B LDHB of the *Taenia* genus; tetanus toxin TetX, tetanus toxin C TTC, 140 kDa S layer protein, flavoprotein beta-subunit CT3, phospholipase (lecithinase), phosphocarrier protein HPr of *Clostridium tetani*; genome polyprotein, protein E, protein M, capsid protein C of Tick-borne encephalitis virus (TBEV); 58-kDa antigen, 68-kDa antigens, *Toxocara* larvae excretory-secretory antigen TES, 32-kDa glycoprotein, glycoprotein TES-70, glycoprotein GP31, excretory-secretory antigen TcES-57, perienteric fluid antigen Pe, soluble extract antigens Ex, excretory/secretory larval antigens ES, antigen TES-120, polyprotein allergen TBA-1, cathepsin L-like cysteine protease c-cp1-1, 26-kDa protein of *Toxocara canis* or *Toxocara cati*; microneme proteins, such as MIC1, MIC2, MICS, MIC4, MICS, MICE, MIC7, or MIC8, rhoptry protein Rop2, rhoptry proteins, such as Rop1, Rop2, Rop3, Rop4, Rop5, Rop6, Rop7, Rop16, or Rjop17, protein SR1, surface antigen P22, major antigen p24, major surface antigen p30, dense granule proteins, such as GRA1, GRA2, GRAS, GRA4, GRAS, GRA6, GRA7, GRAB, GRA9, or GRA10, 28 kDa antigen, surface antigen SAG1, SAG2 related antigen, nucleoside-triphosphatase 1, nucleoside-triphosphatase 2, protein Stt3, HesB-like domain-containing protein, rhomboid-like protease 5, toxomepsin 1 of *Toxoplasma gondii;* 43 kDa secreted glycoprotein, 53 kDa secreted glycoprotein, paramyosin, antigen Ts21, antigen Ts87, antigen p46000, TSL-1 antigens, caveolin-1 CAV-1, 49 kDa newborn larva antigen, prosaposin homologue, serine protease, serine proteinase inhibitor, 45-kDa glycoprotein Gp45 of *Trichinella spiralis*; Myb-like transcriptional factors (Myb1, Myb2, Myb3), adhesion protein AP23, adhesion protein AP33, adhesin protein AP33-3, adhesins AP51, adhesin AP65, adhesion protein AP65-1, alpha-actinin, kinesin-associated protein, teneurin, 62 kDa proteinase, subtilisin-like serine protease SUB1, cysteine proteinase gene 3 CP3, alpha-enolase Enol, cysteine proteinase CP30, heat shock proteins Hsp70 and Hsp60, immunogenic protein P270 of *Trichomonas vaginalis*; beta-tubulin, 47-kDa protein, secretory leucocyte-like proteinase-1 SLP-1, 50-kDa protein TT50, 17 kDa antigen, 43/47 kDa protein of *Trichuris trichiura*; protein ESAT-6 (EsxA), 10 kDa filtrate antigen EsxB, secreted antigen 85-B FBPB, fibronectin-binding protein A FbpA (Ag85A), serine protease PepA, PPE family protein PPE18, fibronectin-binding protein D FbpD, immunogenic protein MPT64, secreted protein MPT51, catalase-peroxidase-peroxynitritase T KATG, periplasmic phosphate-binding lipoprotein PSTS3 (PBP-3, Phos-1), iron-regulated heparin binding hemagglutinin Hbha, PPE family protein PPE14, PPE family protein PPE68, protein Mtb72F, protein Apa, immunogenic protein MPT63, periplasmic phosphate-binding lipoprotein PSTS1 (PBP-1), molecular chaperone DnaK, cell surface lipoprotein Mpt83, lipoprotein P23, phosphate transport system permease protein pstA, 14 kDa antigen, fibronectin-binding protein C FbpC1, Alanine dehydrogenase TB43, Glutamine synthetase 1, ESX-1 protein, protein CFP10, TB10.4 protein, protein MPT83, protein MTB12, protein MTBE, Rpf-like proteins, protein MTB32, protein MTB39, crystallin, heat-shock protein HSP65, protein PST-S, for example of *Mycobacterium tuberculosis*; outer membrane protein FobA, outer membrane protein FobB, intracellular growth locus lglC1, intracellular growth locus IglC2, aminotransferase Wbtl, chaperonin GroEL, 17 kDa major membrane protein TUL4, lipoprotein LpnA, chitinase family 18 protein, isocitrate dehydrogenase, Nif3 family protein, type IV pili glycosylation protein, outer membrane protein to1C, FAD binding family protein, type IV pilin multimeric outer membrane protein, two component sensor protein KdpD, chaperone protein DnaK, protein TolQ of *Francisella tularensis*; MB antigen, urease, protein GyrA, protein GyrB, protein ParC, protein ParE, lipid associated membrane proteins LAMP, thymidine kinase TK, phospholipase PL-A1, phospholipase PL-A2, phospholipase PL-C, surface-expressed 96-kDa antigen of *Ureaplasma urealyticum*; non-structural polyprotein, structural polyprotein, capsid protein CP, protein E1, protein E2, protein E3, protease P1, protease P2, protease P3 of Venezuelan equine encephalitis virus; glycoprotein GP, matrix protein Z, polymerase L, nucleoprotein N of Guanarito virus; polyprotein, protein E, protein M, capsid protein C, protease NS3, protein NS1, protein NS2A, protein AS2B, brotein NS4A, protein NS4B, protein NS5 of West Nile virus; capsid protein CP, protein E1, protein E2, protein E3, protease P2 of Western equine encephalitis virus; genome polyprotein, protein E, protein M, capsid protein C, protease NS3, protein NS1, protein NS2A, protein AS2B, protein NS4A, protein NS4B, protein NS5 of Yellow fever virus; putative Yop targeting protein YobB, effector protein YopD, effector protein YopE, protein YopH, effector protein YopJ, protein translocation protein YopK, effector protein YopT, protein YpkA, flagellar biosyntheses protein FlhA, peptidase M48, potassium efflux system KefA, transcrip-tional regulator RovA, adhesin Ifp, translocator portein LcrV, protein PcrV, invasin Inv, outer membrane protein OmpF-like porin, adhesin YadA, protein kinase C, phospholipase C1, protein PsaA, mannosyltransferase-like protein WbyK, protein YscU, antigen YPMa of *Yersinia pseudotuberculosis*; effector protein YopB, 60 kDa chaperonin, protein WbcP, tyrosin-protein phosphatase YopH, protein YopQ, entero-toxin, Galactoside permease, reductaase NrdE, protein YasN, Invasin Inv, adhesin YadA, outer membrane porin F OmpF, protein UspA1, protein EibA, protein Hia, cell surface protein Ail, chaperone SycD, protein LcrD, protein LcrG, protein LcrV, protein SycE, protein YopE, regulator protein TyeA, protein YopM, protein YopN, protein YopO, protein YopT, protein YopD, protease ClpP, protein MyfA, protein FilA, and protein PsaA of *Yersinia enterocolitica.*

Preferably, the cancer or tumor is selected from the group consisting of Acute lymphoblastic leukemia, Acute myeloid leukemia, Adrenocortical carcinoma, AIDS-related cancers, AIDS-related lymphoma, Anal cancer, Appendix cancer, Astro-cytoma, Basal cell carcinoma, Bile duct cancer, Bladder cancer, Bone cancer, Osteo-sarcoma/Malignant fibrous histiocytoma, Brainstem glioma, Brain tumor, cerebellar astrocytoma, cerebral astrocytoma/malignant glioma, ependymoma, medullo-blastoma, supratentorial primitive neuroectodermal tumors, visual pathway and hypothalamic glioma, Breast cancer, Bronchial adenomas/carcinoids, Burkitt lymphoma, childhood Carcinoid tumor, gastrointestinal Carcinoid tumor, Carcinoma of unknown primary, primary Central nervous system lymphoma, childhood Cerebellar astrocytoma, childhood Cerebral astrocytoma/Malignant glioma, Cervical cancer, Childhood cancers, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Ewing's sarcoma in the Ewing family of tumors, Childhood Extracranial germ cell tumor, Extragonadal Germ cell tumor, Extrahepatic bile duct cancer, Intraocular melanoma, Retinoblastoma, Gallbladder cancer, Gastric (Stomach) cancer, Gastrointestinal Carcinoid Tumor, Gastrointestinal stromal tumor (GIST), extracranial, extragonadal, or ovarian Germ cell tumor, Gestational trophoblastic tumor, Glioma of the brain stem, Childhood Cerebral Astrocytoma, Childhood Visual Pathway and Hypothalamic Glioma, Gastric carcinoid, Hairy cell leukemia, Head and neck cancer, Heart cancer, Hepatocellular (liver) cancer, Hodgkin lymphoma, Hypopharyngeal cancer, childhood Hypothalamic and visual pathway glioma, Intraocular Melanoma, Islet Cell Carcinoma (Endocrine Pancreas), Kaposi sarcoma, Kidney cancer (renal cell cancer), Laryngeal Cancer, Leukemias, acute lymphoblastic Leukemia, acute myeloid Leukemia, chronic lymphocytic Leukemia, chronic myelogenous Leukemia, hairy cell Leukemia, Lip and Oral Cavity Cancer, Liposarcoma, Liver Cancer, Non-Small Cell Lung Cancer, Small Cell Lung Cancer, Lymphomas, AIDS-related Lymphoma, Burkitt Lymphoma, cutaneous T-Cell Lymphoma, Hodgkin Lymphoma, Non-Hodgkin Lymphomas, Primary Central Nervous System Lymphoma, Waldenström Macroglobulinemia, Malignant Fibrous Histiocytoma of Bone/Osteosarcoma, Childhood Medulloblastoma, Melanoma, Intraocular (Eye) Melanoma, Merkel Cell Carcinoma, Adult Malignant Mesothelioma, Childhood Mesothelioma, Metastatic Squamous Neck Cancer with Occult Primary, Mouth Cancer, Childhood Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Chronic Myelogenous Leukemia, Adult Acute Myeloid Leukemia, Childhood Acute Myeloid Leukemia, Multiple Myeloma (Cancer of the Bone-Marrow), Chronic Myeloproliferative Disorders, Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, islet cell Pancreatic cancer, Paranasal sinus and nasal cavity cancer, Parathyroid cancer, Penile cancer, Pharyngeal cancer, Pheochromo-cytoma, Pineal astrocytoma, Pineal germinoma, childhood Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Cancer of the Renal pelvis and ureter, Retinoblastoma, childhood Rhabdomyosarcoma, Salivary gland cancer, Sarcoma of the Ewing family of tumors, Kaposi Sarcoma, soft tissue Sarcoma, uterine Sarcoma, Sézary syndrome, Skin cancer (nonmelanoma), Skin cancer (melanoma), Merkel cell Skin carcinoma, Small intestine cancer, Squamous cell carcinoma, metastatic Squamous neck cancer with occult primary, childhood Supratentorial primitive neuroectodermal tumor, Testicular cancer, Throat cancer, childhood Thymoma, Thymoma and Thymic carcinoma, Thyroid cancer, childhood Thyroid cancer, Transitional cell cancer of the renal pelvis and ureter, gestational Trophoblastic tumor, Urethral cancer, endometrial Uterine cancer, Uterine sarcoma, Vaginal cancer, childhood Visual pathway and hypothalamic glioma, Vulvar cancer, Waldenström macroglobulinemia, and childhood Wilms tumor (kidney cancer).

Preferably, each of the m different DNA molecule species encodes for one or more of the n different RNA molecule species, wherein each of the n different RNA molecule species encodes a different cancer or tumor antigen, or a fragment or variant thereof, selected from the group consisting of 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMM-PRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R17I, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylgluco-saminyltransferase-V, Neo-PAP, Neo-PAP/m, NFYC/m, NGEP, NMP22, NPM/ALK, N-Ras/m, NSE, NY-ESO-B, NY-ESO-1, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PAP, PART-1, PATE, PDEF, Pim-1-Kinase, Pin-1, Pml/PARalpha, POTE, PRAME, PRDXS/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP-1, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGFR1, VEGFR-2/FLK-1, and WT1. Such tumour antigens preferably may be selected from the group consisting of p53, CA125, EGFR, Her2/neu, hTERT, PAP, MAGE-A1, MAGE-A3, Mesothelin, MUC-1, GP100, MART-1, Tyrosinase, PSA, PSCA, PSMA, STEAP-1, VEGF, VEGFR1, VEGFR2, Ras, CEA or WT1, and more preferably from PAP, MAGE-A3, WT1, and MUC-1, preferably selected from the group consisting of MAGE-A1, e.g. MAGE-A1 according to accession number M77481, MAGE-A2, MAGE-A3, MAGE-A6, e.g. MAGE-A6 according to accession number NM_005363, MAGE-C1, MAGE-C2, melan-A, e.g. melan-A according to accession number NM_005511, GP100, e.g. GP100 according to accession number M77348, tyrosinase, e.g. tyrosinase according to accession number NM_000372, surviving, e.g. survivin according to accession number AF077350, CEA, e.g. CEA according to accession number NM_004363, Her-2/neu, e.g. Her-2/neu according to accession number M11730, WT1, e.g. WT1 according to accession number NM_000378, PRAME, e.g. PRAME according to accession number NM_006115, EGFRI (epidermal growth factor receptor 1), e.g. EGFRI (epidermal growth factor receptor 1) according to accession number AF288738, MUC1, mucin-1, e.g. mucin-1 according to accession number NM_002456, SEC61G, e.g. SEC61G according to accession number NM_014302, hTERT, e.g. hTERT accession number NM_198253, 5 T4, e.g. 5T4 according to accession number NM_006670, TRP-2, e.g. TRP-2 according to accession number NM_001922, STEAP1, PCA, PSA, and PSMA.

In a preferred embodiment of the present invention, the method further comprises a step of complexing the RNA molecules (all or only a part of the molecules) according to the invention with one or more cationic or polycationic compounds, preferably with cationic or polycationic polymers, cationic or polycationic peptides or proteins, e.g. protamine, cationic or polycationic polysaccharides and/or cationic or polycationic lipids.

Also provided is a RNA molecule composition produced by the method according to the invention and a pharmaceutical composition comprising the RNA molecule composition according to the invention and a pharmaceutically acceptable excipient. In a preferred embodiment, the RNA molecules produced according to the method of the invention are mRNA molecules.

In a preferred embodiment of the present invention, the RNA molecule composition according to the invention comprises at least one RNA molecule being complexed with one or more member selected from the group consisting of cationic and polycationic compounds, preferably selected from the group consisting of cationic and polycationic polymers, cationic and polycationic peptides and proteins, preferably protamine, cationic and polycationic polysaccharides, and cationic and polycationic lipids.

Optionally, the N/P ratio (the ratio of moles of the amine groups of cationic polymers to those of the phosphate ones of RNA) of the at least one RNA molecule to the one or more cationic or polycationic compounds is in the range of 0.1 to 20, preferably in the range of 0.3 to 4, of 0.5 to 2, of 0.7 to 2 and more preferably of 0.7 to 1.5.

In another preferred embodiment, the at least one RNA molecule is complexed with one or more cationic or polycationic compounds in a weight ratio in the range from 6:1 (w/w) to 0.25:1 (w/w), more preferably from 5:1 (w/w) to 0.5:1 (w/w), even more preferably from 4:1 (w/w) to 1:1 (w:w) or from 3:1 (w/w) to 1:1 (w/w), and most preferably in a weight ratio in the range from 3:1 (w/w) to 2:1 (w/w) of RNA to cationic or polycationic compound and/or with a polymeric carrier; or optionally in a nitrogen/phosphate ratio (N/P ratio) of RNA to cationic or polycationic compound and/or polymeric carrier in the range of about 0.1-10, preferably in a range of 0.3-4 or 0.3-1, and most preferably in a range of 0.5-1 or 0.7-1, and even most preferably in a range of 0.3-0.9 or 0.5-0.9.

In another embodiment, the RNA molecule composition may comprise at least one RNA molecule complexed with one or more cationic or polycationic compounds (also denoted as complexed RNA molecule), and at least one free RNA molecule. Optionally, the nucleic acid sequence of the at least one complexed RNA molecule is identical to the at least one free RNA molecule.

The molar ratio of complexed RNA molecules to the free RNA molecules is selected from a molar ratio of 0.001:1 to 1:0.001, preferably a ratio of about 1:1.

In a preferred embodiment, the ratio of the complexed RNA molecules to the (free) RNA molecules is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of the complexed RNA molecules to the free RNA molecules is in a ratio of 1:1 (w/w).

In another preferred embodiment, the at least one complexed RNA molecule may be complexed with one or more lipids, thereby forming liposomes, lipid nanoparticles and/or lipoplexes.

Further provided is a pharmaceutical container comprising the RNA composition according to to the invention or the pharmaceutical composition according to to the invention. Optionally, the pharmaceutical container is a syringe, vial, infusion bottle, ampoule or carpoule.

Also provided is the RNA molecule (composition) of the invention or the pharmaceutical composition according to of the invention for use as a medicament.

In a preferred embodiment, the RNA molecule composition or the pharmaceutical composition is for use in the treatment or prophylaxis of a disease selected from the group consisting of genetic diseases, allergies, autoimmune diseases, infectious diseases, neoplasms, cancer and tumor-related diseases, inflammatory diseases, diseases of the blood and blood-forming organs, endocrine, nutritional and metabolic diseases, diseases of the nervous system, inherited diseases, diseases of the circulatory system, diseases of the respiratory system, diseases of the digestive system, diseases of the skin and subcutaneous tissue, diseases of the musculoskeletal system and connective tissue, and diseases of the genitourinary system, independently if they are inherited or acquired and combinations thereof.

Moreover provided is the use of the RNA molecule composition or of the pharmaceutical composition as immunotherapeutic agent, gene-therapeutic agent or as vaccine.

Definitions

For the sake of clarity and readability, the following definitions are provided. Any technical feature mentioned for these definitions may be read on each and every embodiment of the invention. Additional definitions and explanations may be specifically provided in the context of these embodiments. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art. Standard techniques are used for nucleic acid and peptide synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, N.Y.), which are provided throughout this document.

Enzyme: Enzymes are catalytically active biomolecules that perform biochemical reactions such as DNA dependent RNA transcription (e.g., RNA polymerases), or double stranded DNA digestion (e.g., restriction endonucleases). Enzymes are typically composed of amino acids and/or RNA (ribozymes, snRNA).

Protein: A protein typically comprises one or more peptides or polypeptides. A protein is typically folded into a 3-dimensional form, which may be required for the protein to exert its biological function. The sequence of a protein or peptide is typically understood to be the order, i.e. the succession of its amino acids.

Nucleic acid: The term nucleic acid means any DNA- or RNA-molecule and is used synonymous with polynucleotide. Furthermore, modifications or derivatives of the nucleic acid as defined herein are explicitly included in the general term “nucleic acid”. For example, peptide nucleic acid (PNA) is also included in the term “nucleic acid”.

RNA, mRNA: RNA is the usual abbreviation for ribonucleic acid. It is a nucleic acid molecule, i.e. a polymer consisting of nucleotide monomers. These nucleotides are usually adenosine-monophosphate, uridine-monophosphate, guanosine-monophosphate and cytidine-monophosphate monomers, which are connected to each other along a so-called backbone. The backbone is formed by phosphodiester bonds between the sugar, i.e. ribose, of a first and a phosphate moiety of a second, adjacent monomer. The specific order of the monomers, i.e. the order of the bases linked to the sugar/phosphate-backbone, is called the RNA-sequence. Usually RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA, which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, optionally a 5'UTR, an open reading frame, optionally a 3'UTR and a poly(A) sequence. Aside from messenger RNA, several non-coding types of RNA exist which may be involved in regulation of transcription and/or translation, and immunostimulation. In the context of the invention the term “RNA” or “RNA molecule (species)” further encompass other coding RNA molecules, such as viral RNA, retroviral RNA and replicon RNA, small interfering RNA (siRNA), antisense RNA, CRISPR RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

According to a preferred embodiment, step a) of the inventive method comprises the selection of an RNA sequence. The selected RNA sequence typically comprises an RNA sequence, which corresponds to an RNA molecule, which is produced by the inventive method. The selected RNA sequence may be a coding RNA, which encodes a protein sequence or a fragment or variant thereof, preferably selected from therapeutically active proteins or peptides, including adjuvant proteins, tumor antigens, pathogenic antigens (e.g. selected, from animal antigens, from viral antigens, from protozoal antigens, from bacterial antigens), allergenic antigens, autoimmune antigens, or further antigens, from allergens, from antibodies, from immunostimulatory proteins or peptides, from antigen-specific T-cell receptors, biologies, cell penetrating peptides, secreted proteins, plasma membrane proteins, cytoplasmic or cytoskeletal proteins, intracellular membrane bound proteins, nuclear proteins, proteins associated with human disease, targeting moieties or those proteins encoded by the human genome, for which no therapeutic indication has been identified but which nonetheless have utility in areas of research and discovery. The coding RNAs may be e.g. mRNAs, viral RNAs, or replicon RNAs.

Alternatively, the selected RNA sequence may be any further RNA as defined herein, particularly a small interfering RNA (siRNA), an antisense RNA, a CRISPR RNA, a ribozyme, an aptamer, a riboswitch, an immunostimulating RNA, a transfer RNA (tRNA), a ribosomal RNA (rRNA), a small nuclear RNA (snRNA), a small nucleolar RNA (snoRNA), a microRNA (miRNA), or a Piwi-interacting RNA (piRNA).

If the target RNA sequence that is selected encodes a peptide or a protein, the coding sequence may be readily identified by one of skill in the art by using public and private databases, e.g. GenBank.

In preferred embodiments, the RNA molecules produced by the inventive method comprises naturally occuring and/or modified nucleotides. Several modifications are known in the art, which can be applied to a nucleotide comprised in the RNA obtained by using the inventive method. In a preferred embodiment, the invention thus provides a method for providing modified RNA molecules, preferably as defined herein, more preferably RNA molecules comprising at least one modification as described herein.

Chemical modifications: The term "RNA modification" as used herein may refer to chemical modifications comprising backbone modifications as well as sugar modifications or base modifications.

In this context, a modified RNA molecule as defined herein may contain nucleotide analogues/modifications, e.g. backbone modifications, sugar modifications or base modifications. A backbone modification in connection with the present invention is a modification, in which phosphates of the backbone of the nucleotides contained in an RNA molecule as defined herein are chemically modified. A sugar modification in connection with the present invention is a chemical modification of the sugar of the nucleotides of the RNA molecule as defined herein. Furthermore, a base modification in connection with the present invention is a chemical modification of the base moiety of the nucleotides of the RNA molecule. In this context, nucleotide analogues or modifications are preferably selected from nucleotide analogues, which are applicable for transcription and/or translation.

Sugar Modifications: The modified nucleosides and nucleotides, which may be incorporated into a modified RNA molecule as described herein, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R═H, alkyl, cycloalkyl, aryl, aralkyl, heteroaryl or sugar); polyethyleneglycols (PEG), —$O(CH_2CH_2O)nCH_2CH_2OR$; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. $NH_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified RNA molecule can include nucleotides containing, for instance, arabinose as the sugar.

Backbone Modifications: The phosphate backbone may further be modified in the modified nucleosides and nucleotides, which may be incorporated into a modified RNA molecule as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications: The modified nucleosides and nucleotides, which may be incorporated into a modified RNA molecule as described herein can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-aminopurine-riboside-5'-triphosphate; 2-aminoadenosine-5'-triphosphate, 2'-amino-2'-deoxy-cytidine-triphosphate, 2-thiocytidine-5'-triphosphate, 2-thiouridine-5'-triphosphate, 2'-fluorothymidine-5'-triphosphate, 2'-O-methyl inosine-5'-triphosphate 4-thio-uridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-bromo-2'-deoxycytidine-5'-triphosphate, 5-bromo-2'-deoxyuridine-5'-triphosphate, 5-iodocytidine-5'-triphosphate, 5-iodo-2'-deoxycytidine-5'-triphosphate, 5-iodouridine-5'-triphosphate, 5-iodo-2'-deoxyuridine-5'-triphosphate, 5-methylcytidine-5'-triphosphate, 5-methyluridine-5'-triphosphate, 5-propynyl-2'-deoxycytidine-5'-tri-phosphate, 5-propynyl-2'-deoxyuridine-5'-triphosphate, 6-azacytidine-5'-triphosphate, 6-azauridine-5'-triphosphate, 6-chloropurineriboside-5'-triphosphate, 7-deaza-adenosine-5'-triphosphate, 7-deazaguanosine-5'-triphosphate, 8-azaadenosine- 5'-tri-phosphate, 8-azidoadenosine-5'-triphosphate, benzimidazole-riboside-5'-triphos-phate, N1-methyladenosine-5'-triphosphate, N1-methylguanosine-5'-triphosphate, N6-methyladenosine-5'-triphosphate, O6-methylguanosine-5'-triphosphate, pseudo-uridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudo-uridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydro-pseudouridine, 2-thio-dihydrouridine, 2-thio-dihydropseudouridine, 2-methoxy-uridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diamino-purine, 1-methyladenosine, N6-methyladenosine, N6-isopentenyladenosine, N6-(cis-hydroxyisopentenyl)adenosine, 2-methylthio-N6-(cis-hydroxyisopentenyl) adeno-sine, N6-glycinylcarbamoyladenosine, N6-threonylcarbamoyladenosine, 2-methyl-thio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group. In specific embodiments, a modified nucleoside is 5'-O-(1-thiophosphate)-adenosine, 5'-O-(1-thiophosphate)-cytidine, 5'-O-(1-thiophosphate)-guanosine, 5'-O-(1-thiophosphate)-uridine or 5'-O-(1-thiophosphate)-pseudouridine.

In further specific embodiments, a modified RNA may comprise nucleoside modifications selected from 6-aza-cytidine, 2-thio-cytidine, α-thio-cytidine, pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, pyrrolo-cytidine, inosine, α-thio-guanosine, 6-methyl-guanosine, 5-methyl-cytdine, 8-oxo-guanosine, 7-deaza-guanosine, N1-methyl-adenosine, 2-amino-6-chloro-purine, N6-methyl-2-amino-purine, pseudo-iso-cytidine, 6-chloro-purine, N6-methyl-adenosine, α-thio-adenosine, 8-azido-adenosine, 7-deaza-adenosine.

DNA: DNA is the usual abbreviation for deoxyribonucleic acid. It is a nucleic acid molecule, i.e. a polymer consisting of nucleotide monomers. These nucleotides are usually deoxy-adenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerized by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single-stranded or double-stranded. In the double stranded form, the nucleotides of the first strand typically hybridize with the nucleotides of the second strand, e.g. by A/T-base-pairing and G/C-base-pairing.

Identity of the RNA/DNA molecule species or DNA plasmid species: The identity of the DNA plasmid species describes the aspect that the practitioner may need to know which of the m different DNA molecule species or DNA plasmid species is present in the mixture, transformed in a particular bacterial cell clone or present in a particular bacterial cell (clone) culture. This is in some embodiments required to make sure that a member of all species is present in the culture, clone or mixture. The identity of the RNA or DNA species can be determined by sequencing, digest with specific restriction endonucleases showing a characteristic pattern on an agarose gel, PCR or else. The skilled person is well familiar with further methods for determining the identity of a RNA or DNA molecule/plasmid species.

Template DNA: As used herein, the term “template DNA” (or “DNA template”) typically relates to a DNA molecule comprising a nucleic acid sequence encoding the RNA sequence to be in vitro transcribed. The template DNA is used as template for RNA in vitro transcription in order to produce the RNA encoded by the template DNA. Therefore, the template DNA comprises all elements necessary for RNA in vitro transcription, particularly a promoter element for binding of a DNA dependent RNA polymerase as e.g. T3, T7 and SP6 RNA polymerases 5' of the DNA sequence encoding the target RNA sequence. Furthermore the template DNA may comprise primer binding sites 5' and/or 3' of the DNA sequence encoding the target RNA sequence to determine the identity of the DNA sequence encoding the target RNA sequence e.g. by PCR or DNA sequencing. As used herein, the term ‘template DNA’ may also refer to a DNA vector, such as a plasmid DNA, which comprises a nucleic acid sequence encoding the RNA sequence. Further, the “template DNA” in the context of the present invention may be a linear or a circular DNA molecule.

Target (RNA) Sequence: A “target sequence” as used herein is typically understood as the sequence of the RNA, which is encoded by the nucleic acid sequence comprised in the template DNA. The target sequence is thus the sequence to be synthesized by RNA in vitro transcription, e.g. a protein-coding sequence or another RNA as defined herein like isRNA, antisense RNA etc.

Linear (template) DNA plasmid: The linear (template) DNA plasmid is obtained by contacting the plasmid DNA with a restriction enzyme under suitable conditions so that the restriction enzyme cuts the plasmid DNA at its recognition site(s) and disrupts the plasmid structure. Hence, the linear template DNA comprises a free 5' end and a free 3' end, which are not linked to each other. If the plasmid DNA contains only one recognition site for the restriction enzyme, the linear template DNA has the same number of nucleotides as the plasmid DNA. If the plasmid DNA contains more than one recognition site for the restriction enzyme, the linear template DNA has a smaller number of nucleotides than the plasmid DNA. The linear template DNA is then the fragment of the plasmid DNA, which contains the elements necessary for RNA in vitro transcription that is a promoter element for RNA transcription and the template DNA element. The DNA sequence encoding the target RNA sequence of the linear template DNA determines the sequence of the transcribed RNA by the rules of base-pairing.

Sequence of a nucleic acid molecule/nucleic acid sequence: The sequence of a nucleic acid molecule is typically understood to be the particular and individual order, i.e. the succession of its nucleotides.

Sequence of amino acid molecules/amino acid sequence: The sequence of a protein or peptide is typically understood to be the order, i.e. the succession of its amino acids.

Sequence identity: Two or more sequences are identical if they exhibit the same length and order of nucleotides or amino acids. The percentage of identity typically describes the extent, to which two sequences are identical, i.e. it typically describes the percentage of nucleotides that correspond in their sequence position to identical nucleotides of a reference sequence. For the determination of the degree of identity, the sequences to be compared are considered to exhibit the same length, i.e. the length of the longest sequence of the sequences to be compared. This means that a first sequence consisting of 8 nucleotides/amino acids is 80% identical to a second sequence consisting of 10 nucleotides/amino acids comprising the first sequence. In other words, in the context of the present invention, identity of sequences preferably relates to the percentage of nucleotides/amino acids of a sequence, which have the same position in two or more sequences having the same length. Gaps are usually regarded as non-identical positions, irrespective of their actual position in an alignment.

Open reading frame: An open reading frame (ORF) in the context of the invention may typically be a sequence of several nucleotide triplets which may be translated into a peptide or protein. An open reading frame preferably contains a start codon, i.e. a combination of three subsequent nucleotides coding usually for the amino acid methionine (ATG or AUG), at its 5'-end and a subsequent region which usually exhibits a length which is a multiple of 3 nucleotides. An ORF is preferably terminated by a stop codon (e.g., TAA, TAG, TGA). Typically, this is the only stop codon of the open reading frame. Thus, an open reading frame in the context of the present invention is preferably a nucleotide sequence, consisting of a number of nucleotides that may be divided by three, which starts with a start codon (e.g. ATG or AUG) and which preferably terminates with a stop codon (e.g., TAA, TGA, or TAG or UAA, UAG, UGA, respectively). The open reading frame may be isolated or it may be incorporated in a longer nucleic acid sequence, for example in a vector or an mRNA. An open reading frame may also be termed “protein coding region” or “coding region”.

Epitope: (also called “antigen determinant”) can be distinguished in T cell epitopes and B cell epitopes. T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form. B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Fragment of a sequence: A fragment of a sequence may typically be a shorter portion of a full-length sequence of e.g. a nucleic acid molecule or an amino acid sequence. Accordingly, a fragment, typically, consists of a sequence that is identical to the corresponding stretch within the full-length sequence. A preferred fragment of a sequence in the context of the present invention, consists of a continuous stretch of entities, such as nucleotides or amino acids corresponding to a continuous stretch of entities in the molecule the fragment is derived from, which represents at least 5%, 10%, 20%, preferably at least 30%, more preferably at least 40%, more preferably at least 50%, even more preferably at least 60%, even more preferably at least 70%, and most preferably at least 80% of the total (i.e. full-length) molecule from which the fragment is derived. Preferably, a fragment of a protein comprises at least one epitope of the protein. Furthermore a fragment of a nucleic acid sequence encodes preferably at least one epitope of a protein.

Sequence-optimized reaction mix: A reaction mix for use in an in vitro transcription reaction of an RNA molecule of a given sequence comprising the four nucleoside triphosphates (NTPs) GTP, ATP, CTP and UTP, wherein the fraction (2) of each of the four nucleoside triphosphates (NTPs) in the sequence-optimized reaction mix corresponds to the fraction (1) of the respective nucleotide in said RNA molecule, a buffer, a DNA template, and an RNA polymerase. If a ribonucleotide is not present in said RNA molecule, the corresponding nucleoside triphosphate is also not present in the sequence-optimized reaction mix.

Sequence-optimized nucleoside triphosphate (NTP) mix: A mixture of nucleoside triphosphates (NTPs) for use in an in vitro transcription reaction of an RNA molecule of a given sequence comprising the four nucleoside triphosphates (NTPs) GTP, ATP, CTP and UTP, wherein the fraction (2) of each of the four nucleoside triphosphates (NTPs) in the sequence-optimized nucleoside triphosphate (NTP) mix corresponds to the fraction (1) of the respective nucleotide in said RNA molecule. If a ribonucleotide is not present in the RNA molecule, the corresponding nucleoside triphosphate is also not present in the sequence-optimized nucleoside triphosphate (NTP) mix.

RNA yield: The "RNA yield" is the amount of RNA product obtained in an RNA in vitro transcription reaction. The RNA yield can be expressed as the RNA concentration (g/ml or mol/l). Multiplication of the RNA concentration with the reaction volume gives the absolute amount of RNA (in grams or moles).

Plasmid: The term "plasmid" or "vector" refers to a nucleic acid molecule, preferably to an artificial nucleic acid molecule. A plasmid in the context of the present invention is suitable for incorporating or harboring a desired nucleic acid sequence, such as a nucleic acid sequence comprising an open reading frame. Thus, the plasmid may comprise a sequence corresponding, e.g., to a desired mRNA sequence or a part thereof, such as a sequence corresponding to the open reading frame and the 3'-UTR of an mRNA. A transcription plasmid may be used for production of expression products such as RNA, e.g. mRNA, or peptides, polypeptides or proteins. For example, a transcription plasmid may comprise sequences needed for transcription of a sequence stretch of the vector, such as a promoter sequence, e.g. an RNA polymerase promoter sequence. A plasmid in the context of the present invention is typically a DNA plasmid which serves as template in the in vitro transcription step of the method of the invention. Preferably, a plasmid in the sense of the present application comprises a cloning site, a selection marker, such as an antibiotic resistance factor, and a sequence suitable for multiplication of the plasmid, such as an origin of replication.

In vitro transcribed RNA: An "in vitro transcribed RNA" is an RNA molecule that has been synthesized from a template DNA, commonly a linearized and purified plasmid (template) DNA, a PCR product, or an oligonucleotide. RNA synthesis occurs in a cell free ("in vitro") assay catalyzed by DNA dependent RNA polymerases. In a process called RNA in vitro transcription, virtually all nucleotides analogues into RNA. Particular examples of DNA dependent RNA polymerases are the T7, T3, and SP6 RNA polymerases. An in vitro transcribed RNA may comprise elements such as 5'-cap, optionally a 5'UTR, an open reading frame, optionally a 3'UTR and a poly(A) sequence. Aside from proteinogenic messenger RNA, several non-coding types of RNA exist which may be involved in regulation of transcription and/or translation. Such All RNA molecules as defined herein may also be synthesized by RNA in vitro transcription.

RNA in vitro transcription: The term "RNA in vitro transcription" (or 'in vitro transcription') relates to a process wherein RNA, in particular mRNA, is synthesized in a cell-free system (in vitro). Preferably, cloning vectorsDNA, particularly plasmid DNA vectors are applied as template for the generation of RNA transcripts. These cloning vectors are generally designated as transcription vector. RNA may be obtained by DNA dependent in vitro transcription of an appropriate DNA template, which according to the present invention is preferably a linearized plasmid DNA template. The promoter for controlling RNA in vitro transcription can be any promoter for any DNA dependent RNA polymerase. Particular examples of DNA dependent RNA polymerases are the T7, T3, and SP6 RNA polymerases. A DNA template for RNA in vitro RNA transcription may be obtained by cloning of a nucleic acid, in particular cDNA corresponding to the respective RNA to be in vitro transcribed, and introducing it into an appropriate vector for RNA in vitro transcription, for example in plasmid circular plasmid DNA. The cDNA may be obtained by reverse transcription of mRNA or chemical synthesis. Moreover, the DNA template for in vitro RNA synthesis may also be obtained by gene synthesis. Preferably cloning vectors are used for RNA in vitro RNA transcription, which are generally designated transcription vectors.

Transformation: In the context of the present invention, transformation comprises the (non-viral) transfer of DNA, most commonly plasmid DNA into competent bacteria. Common transformation techniques comprise heat-shock transformation of chemically competent bacteria (most commonly *Escherichia coli*) and electro-shock transformation of electro competent bacteria, commonly referred to as electroporation. Following that, transformed bacteria are selectively cultured in a suitable medium (e.g., LB-medium) containing antibiotics. The resistance against the antibiotics is transferred by the resistance gene, encoded by the plasmid. After transformation, usually single bacterial cell clones are isolated before growing the bacteria in large-scale by applying the transformed cells on agar plates comprising the respective antibiotic. After growing the cells, usually overnight, single colonies of bacteria may be used for inoculating larger amounts of a suitable medium with the respective antibiotics for further testing.

Polymerase chain reaction (PCR): The polymerase chain reaction (PCR) is a technology in molecular biology used to amplify a a piece of DNA across several orders of magnitude, generating thousands to millions of copies of a particular DNA sequence. Developed in 1983 by Kary Mullis (Bartlett, J. M. S.; Stirling, D. (2003). "A Short History of the Polymerase Chain Reaction". PCR Protocols. Methods in Molecular Biology 226 (2nd ed.). pp. 3-6) PCR is now a common and often indispensable technique used in medical and biological research labs for a variety of applications. The method relies on thermal cycling, consisting of cycles of repeated heating and cooling of the reaction for DNA melting and enzymatic replication of the DNA. Primers (short DNA fragments) containing sequences complementary to the target sequence along with a heat-stable DNA polymerase, such as Taq polymerase, enable selective and repeated amplification. As PCR progresses, the DNA generated is itself used as a template for replication, setting in motion a chain reaction in which the DNA template is exponentially amplified. The DNA polymerase enzymatically assembles a new DNA strand from DNA building-blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample through a defined series of temperature steps. In the first step, the two strands of the DNA double helix are physically separated at a high temperature in a process called DNA melting. In the second step, the temperature is lowered and the two DNA strands become templates for DNA polymerase to selectively amplify the target DNA. The selectivity of PCR results from the use of primers that are complementary to the DNA region targeted for amplification under specific thermal cycling conditions.

Quantitative Polymerase chain reaction (qPCR) or real-time polymerase chain reaction: A real-time polymerase chain reaction is a laboratory technique of molecular biology based on the polymerase chain reaction (PCR), which is used to amplify and simultaneously detect or quantify a targeted DNA molecule. The procedure follows the general principle of polymerase chain reaction (PCR); its key feature is that the amplified DNA is detected as the reaction progresses in "real time". Two common methods for the detection of products in quantitative PCR are: (1) non-specific fluorescent dyes that intercalate with any double-stranded DNA, and (2) sequence-specific DNA probes consisting of oligonucleotides that are labelled with a fluorescent reporter, which permits detection only after hybridization of the probe with its complementary sequence to quantify nucleic acids. Quantitative PCR is carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and DNA polymerase. The PCR process generally consists of a series of temperature changes that are repeated 25-40 times. These cycles normally consist of three stages: the first, at around 95° C., allows the separation of the nucleic acid's double chain; the second, at a temperature of around 50-60° C., allows the binding of the primers with the DNA template; the third, at between 68-72° C., facilitates the polymerization carried out by the DNA polymerase. Due to the small size of the fragments the last step is usually omitted in this type of PCR as the enzyme is able to increase their number during the change between the alignment stage and the denaturing stage. In addition, some thermal cyclers add another short temperature phase lasting only a few seconds to each cycle, with a temperature of, for example, 80° C., in order to reduce the noise caused by the presence of primer dimers when a non-specific dye is used. The temperatures and the timings used for each cycle depend on a wide variety of parameters, such as: the enzyme used to synthesize the DNA, the concentration of divalent ions and deoxyribonucleotides (dNTPs) in the reaction and the bonding temperature of the primers. The type of quantitative PCR technique used depends on the DNA sequence in the samples, the technique can either use non-specific fluorochromes or hybridization probes.

HPLC: High-performance liquid chromatography (HPLC; formerly referred to as high-pressure liquid chromatography), is a technique in analytic chemistry used to separate the components in a mixture, to identify each component, and to quantify each component. It relies on pumps to pass a pressurized liquid solvent containing the sample mixture through a column filled with a solid adsorbent material. Each component in the sample interacts slightly differently with the adsorbent material, causing different flow rates for the different components and leading to the separation of the components as they flow out the column. HPLC is distinguished from traditional ("low pressure") liquid chromatography because operational pressures are significantly higher (50-350 bar), while ordinary liquid chromatography typically relies on the force of gravity to pass the mobile phase through the column. Due to the small sample amount separated in analytical HPLC, typical column dimensions are 2.1-4.6 mm diameter, and 30-250 mm length. Also HPLC columns are made with smaller sorbent particles (2-50 micrometer in average particle size). This gives HPLC superior resolving power when separating mixtures, which is why it is a popular chromatographic technique. The schematic of an HPLC instrument typically includes a sampler, pumps, and a detector. The sampler brings the sample mixture into the mobile phase stream which carries it into the column. The pumps deliver the desired flow and composition of the mobile phase through the column. The detector generates a signal proportional to the amount of sample component emerging from the column, hence allowing for quantitative analysis of the sample components. A digital microprocessor and user software control the HPLC instrument and provide data analysis. Some models of mechanical pumps in a HPLC instrument can mix multiple solvents together in ratios changing in time, generating a composition gradient in the mobile phase. Various detectors are in common use, such as UV/Vis, photodiode array (PDA) or based on mass spectrometry. Most HPLC instruments also have a column oven that allows for adjusting the temperature the separation is performed at.

DNA Sequencing: DNA sequencing is the process of determining the precise order of nucleotides within a DNA molecule. It includes any method or technology that is used to determine the order of the four bases—adenine, guanine, cytosine, and thymine—in a strand of DNA. It includes Maxam-Gilbert sequencing, Sanger sequencing (chain-termination sequencing), next generation sequencing, cycle sequencing, capillary electrophoresis DNA sequencing, single-molecule real-time sequencing, Ion Torrent sequencing, pyrosequencing, sequencing by synthesis, sequencing by ligation.

RNA Sequencing: In order to sequence RNA, the usual method is first to reverse transcribe the sample to generate cDNA fragments. This can then be sequenced as described above for DNA Sequencing.

RNA polymerase/DNA-dependent RNA polymerase: RNA polymerase (RNAP or RNApol), also known as DNA-dependent RNA polymerase, is an enzyme that produces primary transcript RNA. In cells, RNAP is necessary for constructing RNA chains using DNA genes as templates, a process called transcription. RNA polymerase enzymes are essential to life and are found in all organisms and many viruses. In chemical terms, RNAP is a nucleotidyl transferase that polymerizes ribonucleotides at the 3' end of an RNA transcript. Particularly preferred in the context of the present invention are T3, T7 and Sp6 RNA polymerases.

Purification: as used herein, the term "purification" or "purifying" is understood to mean that the desired RNA or DNA in a sample is separated and/or isolated from impurities, intermediates, byproducts and/or reaction components present therein or that the impurities, intermediates, byproducts and/or reaction components are at least depleted from the sample comprising the RNA or DNA. Non-limiting examples of undesired constituents of RNA- or DNA-containing samples which therefore need to be depleted may comprise degraded fragments or fragments which have arisen as a result of premature termination of transcription, or also excessively long transcripts if plasmids are not completely linearized. Furthermore, intermediates may be depleted from the sample such as e.g. template DNA. Additionally, reaction components such as enzymes, proteins, bacterial DNA and RNA, small molecules such as spermidine, buffer components etc. may have to be depleted from the RNA/DNA sample. In addition, impurities such as, organic solvents, and nucleotides or other small molecules may be separated. Ideally, the RNA has a higher purity and/or integrity after purification than the starting material. The purity may be determined by methods commonly known to the skilled person, e.g. by gas chromatography, quantitative PCR, analytical HPLC or gel electrophoresis.

Tangential Flow Filtration (TFF) or Crossflow Filtration: Crossflow filtration (also known as tangential flow filtration)

is a type of filtration. Crossflow filtration is different from dead-end filtration in which the feed is passed through a membrane or bed, the solids being trapped in the filter and the filtrate being released at the other end. Cross-flow filtration gets its name because the majority of the feed flow travels tangentially across the surface of the filter, rather than into the filter. The principal advantage of this is that the filter cake (which can blind the filter) is substantially washed away during the filtration process, increasing the length of time that a filter unit can be operational. It can be a continuous process, unlike batch-wise dead-end filtration. This type of filtration is typically selected for feeds containing a high proportion of small particle size solids (where the permeate is of most value) because solid material can quickly block (blind) the filter surface with dead-end filtration. Applied pressure causes one portion of the flow stream to pass through the membrane (filtrate/permeate) while the remainder (retentate) is recirculated back to the feed reservoir. The general working principle of TFF can be found in literature, see e.g. Fernandez et al. (A BIOTECHNOLOGICA, Bd. 12, 1992, Berlin, Pages 49-56) or Rathore, A S et al (Prep Biochem Biotechnol. 2011; 41(4):398-421). The primary applications for TFF are concentration, diafiltration (desalting and buffer/solvent exchange), and fractionation of large from small biomolecules. Membranes with different molecular weight cutoffs (MWCO) may be used for TFF. In the context of the present invention ultrafiltration membranes are preferably used for TFF. Two basic filter configurations are generally used for TFF. In cartridge filters (often called hollow fiber filters), the membrane forms a set of parallel hollow fibers. The feed stream passes through the lumen of the fibers and the permeate is collected from outside the fibers. Cartridges are characterized in terms of fiber length, lumen diameter and number of fibers, as well as filter pore size. In cassette filters, several flat sheets of membrane are held apart from each other and from the cassette housing by support screens. The feed stream passes into the space between two sheets and permeate is collected from the opposite side of the sheets. Cassettes are characterized in terms of flow path length and channel height, as well as membrane pore size. The channel height is determined by the thickness of the support screen. Both cartridges and cassettes are constructed from materials chosen for mechanical strength, chemical and physical compatibility, and low levels of extractable and/or toxic compounds.

Ultrafiltration: Ultrafiltration is a filtration method using a membrane in which forces like pressure or concentration gradients lead to a separation through a semipermeable membrane. Suspended solids and solutes of high molecular weight are retained in the so-called retentate, while water and low molecular weight solutes pass through the membrane in the permeate. This separation process is used in industry and research for purifying and concentrating macromolecular ($10^3$-$10^6$ Da) solutions. Ultra-filtration is not fundamentally different from microfiltration. Both of these separate based on size exclusion or particle capture. Ultrafiltration membranes are defined by the molecular weight cut-off (MWCO) of the membrane of between 2 and 100 nm (which corresponds to a MWCO between 1 and 1000 kDa). Ultrafiltration is applied in cross-flow or dead-end mode.

Concentration: Concentration is a simple process that involves removing fluid from a solution while retaining the solute molecules. The concentration of the solute increases in direct proportion to the decrease in solution volume, i.e. halving the volume effectively doubles the concentration.

Mixture of m different DNA molecule species: The term "mixture of m different DNA molecule species" denotes a composition comprising m DNA molecules which may differ with respect to their DNA sequence and/or their sequence length. Identical DNA molecules in the mixture belong to the same DNA molecule species. The DNA molecules of different species differ with respect to their DNA sequence and/or their sequence length. Hence, a "species" denotes a group of the same DNA molecules which do not differ in their DNA sequence and/or their sequence length. Each of the m different DNA molecule species encodes one or more of the n different RNA. In the mixture, identical, similar or different amounts of each species may be present, preferably the amounts are identical or similar. The integer m denotes the number of different DNA molecule species which are present in the mixture and can be 1, 2, 3, 4, 5, 6, 7, 8, 9, 10, 11, 12, 13, 14, 15, 16, 17, 18, 19, 20, 21 and so forth. Theoretically, there is no upper limit for m. However, usually m is in the range of 1 to 100, preferably in the range 3 to 50, more preferably 5 to 25. Most preferably, m is at least 2, 3, 4, 5, 6, 7, 8, 9, 10 and so forth. In general, m is identical, similar or lower than n. In a preferred embodiment m is identical to n.

n different RNA molecule species: The term "n different RNA molecule species" denotes a number of n RNA molecules which may differ with respect to their RNA sequence and/or their sequence length. Hence, a "species" denotes a group of the same RNA molecules which do not differ in their RNA sequence and/or their sequence length. Preferably, each of the n different RNA molecule species encodes one target peptide/protein. In the RNA molecule composition of the invention, identical, similar or different amounts of each species may be present, preferably the amounts are identical or similar. The integer n denotes the number of different RNA molecule species which are present in the composition and can be 2, 3, 4, 5, 6, 7, 8, 9, 10, 11, 12, 13, 14, 15, 16, 17, 18, 19, 20, 21 and so forth. Theoretically, there is no upper limit for n. However, usually n is in the range of 2 to 100, preferably in the range 3 to 50, more preferably 5 to 25. Preferably, n is identical to m.

Similar: The term "similar" is used when determinants do not need to be identical, i.e. 100% the same. To be still similar, a parameter should not differ more than 20%, preferably not more that 15%, more preferably not more than 10%, not more than 5%, even more preferably not more than 2% and most preferably not more than 1% from a second determined parameter. "Similar" with respect to the at least one parameter of growth kinetics, such as the optical density ($OD_{600}$) of the cell culture denotes that the parameters of the two or more compared bacterial cell clone cultures do not differ more than 20%, preferably not more that 15%, more preferably not more than 10%, not more than 5%, even more preferably not more than 2% and most preferably not more than 1% from each other. "Similar" with respect to the at least one parameter of amount of plasmid DNA, such as in μg DNA/ml cell culture, denotes that the compared amounts should not differ more than 20%, preferably not more that 15%, more preferably not more than 10%, not more than 5%, even more preferably not more than 2% and most preferably not more than 1% from each other. The method of production according to the invention may typically yield 100-600 μg DNA/mL bacterial cell culture medium. "Similar" with respect to the amounts of each of the m different DNA plasmid species denotes that the amounts should not differ more than 20%, preferably not more that 15%, more preferably not more than 10%, not more than 5%, even more preferably not more than 2% and most preferably not more than 1% from a second determined parameter from the highest amount determined for one species of the mixture of m different DNA plasmid species.

Bacterial amplification: "Bacterial amplification" denotes a process which is also described in the method of the invention, wherein the DNA as plasmid DNA is transformed into bacterial cells and grown until the stationary phase is reached. The bacterial cells are harvested, subsequently, and the plasmid DNA purified from the harvest using standard purifications kits which are commercially available.

Enzymatic amplification: Enzymatic amplification of the DNA molecule species to be used as template in the RNA in vitro transcription method can be done e.g. by rolling circle amplification as described by Gusev et al. (Am J Pathol. 2001; 159(1):63-9) and Monsur Ali et al. (Chem. Soc. Rev., 2014, 43, 3324).

Pharmaceutically acceptable excipient: The term "pharmaceutically acceptable excipient" includes any material, which when combined with the RNA molecule species retains the activity of the RNA molecules and is non-reactive with a subject's immune system. Examples include, but are not limited to, any of the standard pharmaceutical excipients such as a buffer system, like phosphate buffered saline solution, surfactants, water, emulsions such as oil/water emulsion, and various types of wetting agents, starch, milk, sugar, certain types of clay, gelatin, stearic acid or salts thereof, magnesium or calcium stearate, talc, vegetable fats or oils, gums, glycols, or other known excipients.

Gene therapy: Gene therapy may typically be understood to mean a treatment of a patient's body or isolated elements of a patient's body, for example isolated tissues/cells, by nucleic acids encoding a peptide or protein. It may typically comprise at least one of the steps of a) administration of a nucleic acid, preferably an artificial nucleic acid molecule as defined herein, directly to the patient—by whatever administration route—or in vitro to isolated cells/tissues of the patient, which results in transfection of the patient's cells either in vivo/ex vivo or in vitro; b) transcription and/or translation of the introduced nucleic acid molecule; and optionally c) re-administration of isolated, transfected cells to the patient, if the nucleic acid has not been administered directly to the patient.

(Genetic) vaccination: "Genetic vaccination" or "vaccination" may typically be understood to be vaccination by administration of a nucleic acid molecule encoding an antigen or an immunogen or fragments thereof. The nucleic acid molecule may be administered to a subject's body or to isolated cells of a subject. Upon transfection of certain cells of the body or upon transfection of the isolated cells, the antigen or immunogen may be expressed by those cells and subsequently presented to the immune system, eliciting an adaptive, i.e. antigen-specific immune response. Accordingly, genetic vaccination typically comprises at least one of the steps of a) administration of a nucleic acid, preferably an artificial nucleic acid molecule as defined herein, to a subject, preferably a patient, or to isolated cells of a subject, preferably a patient, which usually results in transfection of the subject's cells, either in vivo or in vitro; b) transcription and/or translation of the introduced nucleic acid molecule; and optionally c) re-administration of isolated, transfected cells to the subject, preferably the patient, if the nucleic acid has not been administered directly to the patient.

Immunotherapy: The term "immunotherapy" is to be understood according to the general understanding of the skilled person in the fields of medicine and therapy. Also used in this context are the terms "biologic therapy" or "biotherapy". It is the treatment of a disease by inducing, enhancing, or suppressing an immune response in a patient's body and comprises in particular cancer immunotherapy. Immunotherapy is also being applied in many other disease areas, including allergy, rheumatoid disease, autoimmunity and transplantation, as well as in many infections, such as HIV/AIDS and hepatitis.

Protein replacement therapy: The term "protein replacement therapy" is to be understood according to the general understanding of the skilled person in the fields of medicine and therapy and denotes, in its broadest sense, that a protein which is absent in a patient or not available in the necessary amount is provided to the patient or "replaced". In general, this is done by administering to the patient an intravenous infusion containing the enzyme. Enzyme replacement therapy is e.g. available for lysosomal diseases, such as Gaucher disease, Fabry disease, MPS I, MPS II (Hunter syndrome), MPS VI and Glycogen storage disease type II. Enzyme replacement therapy does not affect the underlying genetic defect, but increases the concentration of the deficient enzyme.

Pharmaceutically effective amount: A pharmaceutically effective amount in the context of the invention is typically understood to be an amount that is sufficient to induce a pharmaceutical effect, such as an immune response, altering a pathological level of an expressed peptide or protein, or substituting a lacking gene product, e.g., in case of a pathological situation.

DETAILED DESCRIPTION OF THE INVENTION

To solve the above mentioned problems in the art the present invention provides a method for producing a ribonucleic acid (RNA) molecule composition comprising n different RNA molecule species, the method comprising the following steps:

a) RNA in vitro transcription of a mixture of m different deoxyribonucleic acid (DNA) molecule species in a single reaction vessel in parallel, i.e. simultaneously, wherein each of the m different DNA molecule species encodes one or more of the n different RNA molecule species thereby generating the n different RNA molecule species, and b) obtaining the RNA molecule composition comprising n different RNA molecule species generated in step a), wherein n is an integer of at least 2, and wherein m is an integer of at least 1. In a particularly preferred embodiment, each of the n different RNA molecule species encodes for a different peptide or protein, preferably an antigen as mentioned herein below. In a very preferred embodiment, the RNA molecule species are mRNA molecule species.

Step a) is performed in the same reaction vessel in parallel, i.e. simultaneously. A reaction vessel can be any suitable reaction vessel for in vitro transcription known to the skilled person. In parallel means that all m different DNA molecule species are present together in the reaction vessel and are transcribed in parallel, i.e. simultaneously. Thereby the n different RNA molecule species are produced in parallel, i.e. simultaneously, and depending on the amount of the corresponding m different DNA molecule species. Preferably, the ratio of the n different RNA molecule species to each other after finishing the RNA in vitro transcription reaction is the same as between the m different DNA molecule species.

In a preferred embodiment, prior to the RNA in vitro transcription step a) a step of generating the mixture of m different DNA molecule species by bacterial amplification (step c1), and/or polymerase chain reaction (PCR) (step c2), and/or chemical DNA synthesis (step c3) and/or using enzymatic amplification, for example by rolling circle amplification (step c4) is performed.

If the mixture of m different DNA molecule species is generated by PCR (step c2), cDNA (complementary to the target RNA molecule species sequence) or any DNA comprising the cDNA (e.g. a plasmid vector comprising the cDNA) may be used as template. In this case, the 5'-primer used for PCR preferably comprises the sequence of a promoter of DNA-dependent RNA polymerase to generate a PCR product comprising at least a promoter for a DNA-dependent RNA polymerase and the DNA sequence encoding the target RNA sequence. This synthesized or amplified PCR product may then be used as mixture of m different DNA molecule species as template for RNA in vitro transcription. As a quality measure, the transcription efficiencies of the individual PCR amplified templates may be determined. The respective ratio may be 1:1 for all different DNA molecule species, however, the ratio may also differ between the different DNA molecule species, depending on the desired amount for each target peptide/protein which is encoded by the respective RNA molecule species.

In particular, the mixture of m different DNA molecule species (also denoted as "template cocktails") may be generated by on-chip PCR or using dbDNA templates with subsequent RNA in vitro transcription.

For on-chip PCR, the m different DNA molecule species which encode one or more of the n different RNA molecule species are immobilized on a DNA chip (e.g. abtainable from TWIST bioscience, San Francisco, Calif., USA). The m different DNA molecule species may be immobilized by physical adsorption, covalent bonding and treptavidin-Biotin interactions. Preparative PCR is e.g. described in Example 10. The obtained PCR product is optionally purified (e.g. PureMessenger®; WO2008077592) and used for RNA in vitro transcription to generate the n different RNA molecule species.

Alternatively, the mixture of m different DNA molecule species for subsequent RNA in vitro transcription may be generated by an in vitro cell free process for amplifying DNA templates and converting the amplified DNA molecules into closed linear "doggybone" DNAs (dbDNA) (Touchlight Genetics, London, UK). Rolling circle DNA template amplification and generation of dbDNA are performed as described in WO 2010/086626. The obtained dbDNA templates are then typically individually linearized using an appropriate restriction enzyme (e.g., EcoRI), purified, and mixed to generate linearized m different DNA molecule species as template mixture (e.g., mix-4, mix-5; e.g. see Table 2). The linearized template mixture is used for RNA in vitro transcription (essentially performed according to Example 9).

Subsequently, the RNA molecules may be subjected to quantitative and qualitative measurements (e.g., RNA AGE, RT-qPCR, NGS, and spectrometry). A purification step may follow and, optionally, a formulation step is performed (e.g., protamine complexation, LNP encapsulation).

Alternatively, the mixture of m different DNA molecule species may be synthesized chemically (that is, without enzymatic amplification, step c3). In such an embodiment, the different synthetized DNA templates would be mixed together in respective ratios before starting the RNA in vitro transcription. As a quality measure, the transcription efficiencies of the individual templates may be determined. This embodiment is particularly preferred for small-scale RNA production e.g., in the context of personalized RNA cocktails. The respective ratio may be 1:1 for all different DNA molecule species, however, the ratio may also differ between the different DNA molecule species, depending on the desired amount for each target peptide/protein which is encoded by the respective RNA molecule species.

Alternatively, the mixture of m different DNA molecule species may be generated by rolling circle amplification (step c4). A suitable plasmid DNA comprising the cDNA (e.g. a plasmid vector comprising the cDNA) may be used for by rolling circle amplification as described by Gusev et al. (Am J Pathol. 2001; 159(1):63-9) and Monsur Ali et al. (Chem. Soc. Rev., 2014, 43, 3324). As a quality measure, the transcription efficiencies of the individual templates may be determined. The respective ratio may be 1:1 for all different DNA molecule species, however, the ratio may also differ between the different DNA molecule species, depending on the desired amount for each target peptide/protein which is encoded by the respective RNA molecule species.

Preferably, the mixture of m different DNA molecule species is generated by bacterial amplification as in step c1). For this purpose, a bacterial cell culture is transformed with at least one single DNA plasmid species of the mixture of m different DNA plasmid species, wherein each DNA plasmid species encodes one or more of the n different RNA molecule species (step d). In this case, the DNA molecule species in step a) are DNA plasmid species. The DNA molecule species as well as the DNA plasmid species both encode for the respective RNA molecule species. However in contrast to the DNA molecule species, the DNA plasmid species are further characterized by the typical features of plasmid DNA as known to the skilled person and as defined above. Preferably, all of the m different DNA plasmid species are transformed in separate transformation steps, i.e. step c1) of the method of the invention further a step d1) of transforming m single bacterial cell cultures each with a single DNA plasmid species of the m different DNA plasmid species, wherein the single DNA plasmid species encodes one or more of the n different RNA molecule species.

In one embodiment, all of the m different DNA plasmid species are transformed together in a single transformation step i.e. step c1) of the method of the invention further a step d2) of transforming a single bacterial cell culture with a mixture of m different DNA plasmid species, wherein each DNA plasmid species encodes one or more of the n different RNA molecule species.

The method further optionally comprises a step of e) isolating at least one single bacterial cell clone for each DNA plasmid species of the mixture of m different DNA plasmid species and growing each of the at least one single bacterial cell clone isolated in step e) in a separate bacterial cell clone culture. Thereby, bacterial cell clones are separated which may or may not contain different DNA plasmid(s).

Plasmid DNA vectors for synthesis of the template DNA plasmid species are preferably selected depending on the host organism. For production/replication/amplifcation of plasmid DNA, bacteria, particularly *Escherichia coli* (*E. coli*) are used. Many plasmids are commercially available for such uses, including pDP (Ambion), pGEM (Promega), pBluescript (Stratagene), pCRII (Invitrogen), pUC57, pJ204 (from DNA 2.0) and pJ344 (from DNA 2.0), pUC18, pBR322 and pUC19.

Commonly, cDNA encoding or corresponding to the RNA sequence of interest (target RNA sequence) is inserted into a plasmid that typically contains a number of features (possible features listed below). These include a gene that makes the bacterial cells resistant to particular antibiotics (normally kanamycin or ampicillin), an origin of replication to allow bacterial cells to replicate the plasmid DNA, and a multiple cloning site (MCS, or polylinker). A multiple cloning site is a short region containing several commonly used restriction sites allowing the easy insertion of DNA fragments at this location, such as a DNA sequence encoding at least one of the n different RNA molecule species.

Although a very large number of host organisms and molecular cloning vectors are in use, the great majority of molecular cloning experiments begin with a laboratory strain of the bacterium *E. coli* and a plasmid cloning vector. *E. coli* and plasmid vectors are in common use because they are technically sophisticated, versatile, widely available, and offer rapid growth of recombinant organisms with minimal equipment.

Particularly useful cloning vectors for *E. coli* are vectors based on pUC19 or pBR322 (J. Vieira. Gene. Vol. 19, No. 3, October 1982, p. 259-268, ISSN 0378-1119. PMID 6295879; Sue Lin-Chao et al., *Molecular Microbiology.* 6, Nr. 22, November 1992, ISSN 0950-382X, S. 3385-3393, doi:10.1111/j.1365-2958.1992.tb02206.x, PMID 1283002, C.Helmer-Citterich et al. (1988). *The EMBO journal* 7(2), 557-66; C. Yanisch-Perron et al. (1985), *Gene.* Vol. 33, p. 103-119. PMID 2985470; F. Bolivar et al., Gene. 2, 95-113 (1977); L. Covarrubias et al., *Gene.* 13, 25-35 (1981)).

For the use as template in RNA in vitro transcription reactions, the DNA plasmid typically carries a binding site for a DNA-dependent RNA polymerase, preferably for T3, T7 or SP6 polymerase (T3-, T7-, or SP6 promoter).

To increase the transcription, translation and/or stability further elements can optionally be included in the plasmid:
a 5'-UTR (particularly preferred are TOP-UTRs according to WO 2013/143700 and WO 2013/143699);
a Kozak sequence, or another translation initiation element (CCR(A/G)CCAUGG, where R is a purine (adenine or guanine) three bases upstream of the start codon (AUG), which is followed by another 'G'. 5'UTR also have been known to form secondary structures, which are involved in elongation factor binding);
a 3'-UTR (particularly preferred are UTRs from stable RNAs particularly from albumin gene, an α-globin gene, a β-globin gene, a tyrosine hydroxylase gene, a lipoxygenase gene, and a collagen alpha gene according to WO 2013/143700; a poly(A) sequence; a poly(C) sequence; and/or a stem-loop sequences, e.g. histone stem-loop sequences according to WO 2012/019780.

Particularly preferred are plasmids based on the DNA plasmid pUC19. The different variants (pCV19, pCV26, pCV32, and pCV22 min) differ in restriction sites and 5'- and/or 3'-UTRs. Vectors are preferably based on pCV26 as shown in FIG. 3 in PCT/EP2015/000959.

The desired DNA sequence encoding at least one of the n different RNA molecule species is introduced into the plasmid backbone using standard methods from the field of molecular technology which are well known to the skilled person and e.g. described in PCT/EP2015/000959.

Different methods for transformation of DNA plasmid molecules are well known to a person skilled in the art, comprising electroporation of electro-competent cells or heat shock transformation of chemically competent cells. Preferred herein is the transformation of chemical competent cells by heat shock, using strains comprising e.g. DH5alpha, DH10B, Machl, OmniMax 2, Stb12, Top 10, or Top 10F.

For example, 1-10 ng, preferably (4-5 ng) purified plasmid are mixed with 50 μl chemical competent cells, e.g. $CaCl_2$-competent cells, preferably DH5 alpha. The mixture is incubated for at least 30 minutes at 0-5° C. Subsequently, the mixture is incubated for 20 s at 42° C. After the heat shock the mixture is incubated at 0-5° C. for several minutes.

For plating the cells, 900 μL LB-medium is added; incubated for 1-3 h at 37° C. and plated on LB agar plates containing antibiotics e.g. ampicillin or kanamycin, dependent on the antibiotic resistance gene encoded on the plasmid, and incubated 12-24 h at 37° C.

The transformation efficacy is evaluated based on the number of colonies formed. *E. coli* cells are transformed for each of the m different DNA plasmid molecules. Only bacteria that take up copies of the plasmid survive, since the plasmid makes them resistant (ampicillin resistance). In particular, the resistance genes are expressed (used to make a protein) and the expressed protein either breaks down the antibiotics or prevents it from inhibiting certain bacterial pathways. In this way, the antibiotics act as a filter to select only the bacteria containing the plasmid DNA. Now these bacteria can be grown in large amounts, harvested, and lysed to isolate the plasmid of interest.

Preferably the bacterial cells are *Escherichia coli* (*E. coli*).

After step d1), the following method steps:
e1) isolating at least one single bacterial cell clone of each of the m single bacterial cell cultures transformed in step d1),
f1) growing each of the single bacterial cell clones isolated in step e1) in a separate bacterial cell culture,
g1) optionally determining the DNA sequence of the DNA plasmid species of each of the bacterial cell clone cultures grown in step f1),
h1) selecting at least one bacterial cell clone culture for each of the m different DNA plasmid species.

After step d2), the method may further comprise the following steps:
e2) isolating at least m single bacterial cell clones, and
f2) growing each of the at least m single bacterial cell clones isolated in step e2) in a separate bacterial cell clone culture,
g2) determining the DNA sequence of the DNA plasmid species of each of the at least m single bacterial cell clone cultures grown in step f2),
h2) selecting at least one single bacterial cell clone culture for each of the m different DNA plasmid species.

In a preferred embodiment, the mixture of plasmid DNA is homogeneous, that is, all DNA plasmid species are present in identical or similar amounts, potentially generating a homogeneous mixture of RNA molecule species. In other words, the amount of each of the m different DNA molecules species employed in step a) is identical or at least similar. Thereby, in theory, identical or at least similar amounts of each of the n different RNA molecules in the RNA composition should be achieved. Similar amounts mean that the amounts of the single DNA or RNA species do not vary for more than 20%, preferably for more than 15%, more preferably for more than 10% or 5% or even more preferably do not differ for more than 2% based on the total amount of the DNA or RNA molecules in the mixture or composition.

This embodiment is particularly preferred if an RNA molecule composition comprising n RNA molecules species encoding different variants of the same target peptide/protein, e.g., an antigen shall be provided e.g., the same antigen of different serotypes of a pathogen.

In another preferred embodiment, the RNA molecule species differ in their amount in the RNA molecule composition. This embodiment may be preferred if a first target peptide/protein is e.g. an antigen which is encoded by a first RNA molecule species that is much more potent than a second antigen which is encoded by a second RNA molecule species. If, for example, the first antigen is as double as potent as the second antigen, the amount of the RNA encoding the first antigen could be half of the amount of the RNA encoding the second antigen. Also in the context of molecular therapy or protein replacement therapy, it may be preferred to generate RNA compositions wherein respective RNA species in said composition differ in their amount.

It should be noted that in a preferred embodiment, the number of molecules of each RNA molecule species is proportional to the number of molecules of the respective DNA molecule species in the mixture of m different DNA molecule species for RNA in vitro transcription. In case of the bacterial generation of the mixture of m different DNA molecule species, the number of molecules of each DNA plasmid species is proportional to the number of molecules of the respective DNA molecule species in the mixture of m different DNA molecule species. Hence, if different amounts of the n different RNA molecule species are desired, there are different points in the method where the practitioner can influence the final amount of each RNA molecule species in the RNA molecule composition. These points will be described below.

In one preferred embodiment bacterial amplification is particularly preferred for which transformation of the particular template plasmid DNAs in a microbial host, i.e. a bacterial cell, preferably an *E. coli* cell, has to be performed. To produce sufficient amounts of each plasmid DNA as template for RNA in vitro transcription, it is particularly preferred that the bacterial clones bearing different plasmids are cultivated together in one fermentation vessel as a co-culture.

One important point for the co-culture of several clones comprising different plasmid DNA is the inoculation step. Depending on parameters such as the number of transferred cells or the vital status of the microbes (early/mid/late exponential, stationary phase), cultivation results may vary (Huber et al. Microbial Cell Factories, 2009, 8:42). In a co-culture this differences in the inoculation step may influence the population ratio during the fermentation in an undesired way. A suitable inoculation method is e.g. described in Huber et al. BMC Biotechnology, 2010, 10:22.

In a particularly preferred embodiment homogeneous growth and productivity of all cultivated clones is required for best possible homogeneity among all plasmid DNA species (that is: bacteria clones bearing respective plasmids should grow equally in the co-culture to achieve similar amounts of DNA plasmid).

The following measures may be taken if homogeneous DNA plasmid species production is desired:

(I) Even though, each plasmid species encodes a different target RNA species, it is preferred that there are only minimal differences in the plasmid sequences. This means that the sequences of the m different DNA plasmid and molecules species are homogeneous, i.e. are at least 80%, at least 85%, at least 90%, at least 95%, at least 97% or preferably at least 99% identical to each other. The plasmid backbones are at least 80%, at least 85%, at least 90%, at least 95%, at least 97%, preferably at least 99% and most preferably 100% identical and the open reading frames (ORF) of the m different deoxyribonucleic acid (DNA) plasmid or molecule species are should be of similar length, i.e. should vary in their length by a maximum of 100 nucleotides, 50 nucleotides, 40 nucleotides, 30 nucleotides, preferably a maximum of 20 nucleotides, more preferably a maximum of 10 nucleotides, 7 nucleotides or even more preferably a maximum of 5 nucleotides, with only minimal changes of the nucleotide sequence, i.e. at least 80%, to each other. In another preferred embodiment, the RNA sequences of the n different RNA molecule species are at least 80% identical, at least 85%, at least 90%, at least 95%, at least 97% or preferably at least 99% identical to each other.

Hence, the metabolic burden due to plasmid replication is preferably the same for all bacterial cell clones and major differences in microbial growth and plasmid DNA replication can be avoided by the above measures. Moreover, the similar length of the open reading frames allows the use of HPLC as a purification method for the resulting RNA mixture (e.g. as disclosed in WO 2008/077592 A1, the HPCL purification methods described therein are incorporated herein by reference). The above described measures are in particular applicable to the embodiments where RNA molecules species encode different variants of the same antigen, e.g., the same antigen of different serotypes or strains of a pathogen.

If the RNA composition for example is provided as individual gene therapy for a patient e.g. lacking different enzymes of a metabolic pathway, the RNA molecule sequences and therefore necessarily the DNA molecule and plasmid species sequences may vary in length for more than 50 nucleotides or have a sequence identity below 80%. In such cases, measures as will be described below can be taken to achieve the desired amount of each RNA molecule species in the RNA molecule composition. Also for RNA molecule compositions comprising highly varying different RNA molecule species, the method of the invention is applicable. Also in this embodiment, growth and production behavior of the transformed cells are tested. If no cultures having an identical or similar growth behavior and/or being producing an identical or similar amount of plasmid DNA per time interval and volume of cell culture, respective amounts of bacterial cell culture are used for inoculating the bacterial cell culture for production in larger scale for RNA in vitro transcription.

For such products, alternative purification procedures have to be adapted (e.g., oligo d(T) capture).

Clearly the m different DNA molecule species in the mixture may be generated via different methods, i.e. by PCR, bacterial amplification of plasmid DNA and chemical synthesis (as disclosed above).

(II) Before plasmid DNA production in a co-culture to produce enough of each DNA molecule species for the RNA in vitro transcription, all clones are analyzed for their individual growth and production behavior in an independent screening, i.e. at least one parameter of growth kinetics and/or amount of plasmid DNA of the at least one single bacterial cell clone culture is determined. Hence, the method of the invention further comprises a step of i) determining at least one parameter of growth kinetics and/or amount of plasmid DNA of the at least one single bacterial cell clone culture, and j) selecting one or more bacterial cell clone cultures for each of the m different DNA plasmid species depending on the parameter determined in step i), preferably selecting one bacterial cell clone culture for each of the m different DNA plasmid species. Optionally, step i) comprises a step of i1) determining a parameter of growth kinetics by measuring the optical density of the bacterial cell clone culture after a time interval, preferably using a microplate reader, or by scattered light online measurement, and/or i2) determining the amount of plasmid produced per volume and time of bacterial cell culture.

Preferably, this is done in a high-throughput manner in multi-well plate format (e.g., 24 well plate, 48 well plate, 96 well plate). Each clone is pre-cultivated separately in one culture well of a microtiter plate inoculated from a glycerol stock. Afterwards, a second set of cultivations is inoculated from this pre-culture plate for the individual clone characterization. The growing of bacterial cell cultures, culturing conditions, like temperature (e.g. 30° C. or 37° C.), stiffing speed, and time, suitable growth, media and selection markers are well known to the skilled person.

Growth kinetics can be recorded photometrically, e.g. by measurement of the optical density at different time points using a microplate reader, e.g. after 2 h, after 4 h, after 6 h, after 8 h, after 10 h, after 12, h after 18 h, after 24 h and so forth. Microbial growth can also be followed by optical signals, i.e. by scattered light online measurement in special devices (microplate reader). Additionally, plasmid DNA titer quantification is done at the end of cultivation. Glycerol stocks are optionally generated from clones that show uniform growth and production characteristics.

Based on the results of the above mentioned analysis of the growth characteristics of bacterial clones, desired clones, preferably clones that show similar growth characteristics, are selected and used for a co-culture (that is, a fermentation procedure comprising bacteria bearing pDNA (=plasmid DNA species) clones encoding different RNA molecule species).

Hence, in a preferred embodiment of the method of the invention the selected one or more bacterial cell clone cultures for each of the m different DNA plasmid species exhibit similar or identical growth kinetics and/or similar or identical DNA production levels, preferably the similar or equal growth kinetics and/or similar identical DNA production levels are as high as possible.

Optionally, step c1) of the method of the invention further comprises a step of k1) inoculating and growing an amount of at least one of the one or more bacterial cell clone cultures selected for each of the m different DNA plasmid species in step j) in a single reaction vessel, or k2) inoculating and growing an amount of at least one of the one or more bacterial cell clone cultures selected for each of the m different DNA plasmid species in step j) in one or more separate reaction vessels for each of the m different DNA plasmid species, optionally wherein one or more bacterial cell clone cultures of the m different DNA plasmid species are grown together in a single reaction vessel.

For this purpose of DNA plasmid species production, the selected, preferably uniformly growing and producing bacterial cell clones may optionally be applied to a multi-step fermentation step consisting of:

(I) Pre-cultivation in shake flasks (e.g. having a culture volume of 100, 250 or 500 mL) or a small bioreactor applying a mineral or complex medium (such as LB, TB, or M9 medium) inoculated from glycerol stocks (glycerol stocks of uniformly growing clones; one clone per DNA plasmid species)

(II) Main cultivation in a production-scale bioreactor applying a mineral or complex medium, e.g. LB, TB, or M9, inoculated from the pre-culture. The main cultivation may starts with an initial phase for biomass generation followed by a growth limited plasmid production phase triggered by a temperature shift. Alternatively, all other high-yield fermentation procedures commonly known in the art may be applied. Since all clones show the same growth and production behavior, all plasmid DNA variants are potentially produced in similar amounts. The culture volume of the production-scale bioreactor is principally not limited, typical volumes range between 1 L to 1000 L.

In one preferred embodiment of the present invention, identical amounts of each bacterial cell clone culture are inoculated. Alternatively, the amount of each bacterial cell clone culture used for inoculating in step k1 or k2) is selected so that identical or similar amounts of each of the m different DNA plasmid species are obtained. The latter alternative is applicable in cases where the single bacterial cell clones exhibit different growth kinetics (i.e. vary more than 20% from each other) and/or differ in the produced amount of plasmid DNA (i.e. amounts differ more than 20% in yield). In such cases, the amount of pre-culture which is used for inoculating the production scale culture volume in step k1) or k2) can be varied to harmonize the produced amount of all DNA plasmid species.

In another embodiment of the present invention, different amounts of each bacterial cell clone culture are inoculated. The amount of each bacterial cell clone culture used for inoculating in step k1) or k2) is selected so that the desired amounts of each of the m different DNA plasmid species are obtained.

For each bacterial clone, a test RNA in vitro transcription may be performed to characterize the transcription efficiency (This is particularly useful for divergent DNA molecule/plasmid species that are not similar in length and sequence). Based on the transcription efficiency, the respective template mixture can be generated. This embodiment is also suitable for PCR-based templates after purification.

In a preferred embodiment, the DNA plasmid/molecule mixture is analyzed regarding its identity and its composition e.g. via sequencing, e.g. Next Generation Sequencing (NGS; e.g., Illumina), PCR, qPCR or restriction mapping in order to confirm the identity and quantity of each individual DNA molecule species.

In another preferred embodiment, step c1) of the method of the invention further comprises a step of 1) obtaining the m different DNA plasmid species of the bacterial cell clone cultures grown in step k1) and/or k2). This step is done using standard method known in the art for purifying and isolating plasmid DNA from bacterial cells. The method may optionally comprise a step m) of linearizing the m different DNA plasmid species obtained in step 1), Preferably after step 1) and the optional step m), a step of n) obtaining the mixture of m different deoxyribonucleic acid (DNA) molecule species is performed. In an alternative embodiment, the m different DNA plasmid species are generated in separate fermentations and mixed together after plasmid DNA extraction before starting the RNA in vitro transcription.

Linearization is performed using commercially available restriction endonucleases, such as EcoRI if the used plasmid bears one EcoRI restriction site for plasmid DNA linearization. If the respective restriction site, such as an EcoRI restriction site, is present in the target sequence, this site is eliminated, previously. Appropriate reaction conditions can be found in the manufacturer's manual. Successful linearization may be controlled e.g. by agarose gel electrophoresis.

The isolated plasmid DNA is typically linearized by a specific, preferably singular, enzymatic restriction to provide a defined linear template for the following RNA in vitro transcription step a). This ensures a defined termination of the in vitro RNA transcription procedure by avoiding transcriptional read-through. The linearized DNA plasmid species are also denoted DNA molecule species and are preferably purified and the content and yield of the linear DNA is determined.

Preferred endonucleases for linearizing the pDNA template include BciVI, Xbal, Spel, HindIII, Notl, EcoRI, Ndel, AfIII, Hindlll, and Sapl. The most preferred restriction enzyme is EcoRI.

Particularly preferred are the following conditions:

Composition of One Reaction:

1 μg plasmid DNA 0.5 μl reaction buffer 3 units restriction enzyme

Add. 5 μl with WFI (water for injection)

The composition is calculated according to the amount of plasmid DNA used for linearization (at least 1000 reactions, preferably 10000 reactions). The reaction is incubated for 4 to 5 hours at 37° C.

The linearized template DNA is preferably purified. Different methods can be used, e.g. phenol/chloroform extraction with subsequent alcohol precipitation, chromatographic methods, filtration methods, or silica-based DNA capture methods. This purification step also ensures the reduction of impurities (e.g. proteins) from the previous manufacturing steps, including *E. coli* proteins, restriction enzymes and BSA (contained in reaction buffers).

In this context, phenol/chloroform/isoamylalcohol precipitation with subsequent isopropanol precipitation is preferred. These methods are described in Sambrook et al., Molecular Cloning, Second Edition, 1989, Cold Spring Harbor Laboratory Press). After precipitation, the plasmid DNA is resuspended in a suitable buffer, preferably water for injection.

Linear template plasmid DNA is preferably analyzed for successful/complete linearization. The band uniqueness and band size of the linear plasmid DNA are preferably analyzed via agarose gel electrophoresis. Alternatively, any other method known in the art for determining DNA fragments may be used, in particular the methods as described in PCT/EP2015/000959, incorporated herein by reference.

Therefore, in a preferred embodiment the method of the invention also includes analyzing for successful linearization of DNA plasmid species.

Exemplary methods for analyzing DNA fragments after step n) of the invention, for instance, agarose gel electrophoresis, polyacrylamide gel electrophoresis, chip gel electrophoresis, capillary electrophoresis, fluorescence-based automatic DNA-fragment analysis and HPLC (e.g. WAVE™ DNA Fragment Analysis System). Particularly preferred is agarose gel electrophoresis as described in Sambrook et al., Molecular Cloning, a laboratory manual, 2nd edition, Cold Spring Harbor Laboratory Press 1989. 6.

Prior to step a), the method of the invention may further comprise a step of a test transcription in small scale. A small scale transcription test with linear DNA molecule species into RNA via a polymerization reaction by RNA polymerase is preferably performed. This small scale test RNA in vitro transcription is performed to estimate the expected yield of in vitro transcribed RNA and to analyze the identity of the in vitro transcribed RNA.

A RNA in vitro transcription reaction commonly contains, but is not limited to, DNA molecule species as template, a suitable buffer (HEPES, Tris-HCl pH 7.5), DNA dependent RNA polymerase (e.g. T7, T3, SP6), a suitable nucleotide mixture (natural and/or modified nucleotides), DTT, spermidine, NaCl, $MgCl_2$, RNAse inhibitor and pyrophosphatase.

Subsequently, the in vitro transcribed RNA is preferably purified. Different methods for RNA purification are known in the art including phenol/chloroform/isoamylalcohol extraction with subsequent ethanol or isopropanol precipitation, precipitation with alcohol and a monovalent cation such as sodium or ammonium ion, LiCl precipitation, chromatographic methods or filtration methods.

In this context, LiCl precipitation is particularly preferred. LiCl precipitation is preferably performed by adding 50% of the volume 8 M LiCl. The reaction is mixed and incubated at room temperature. Subsequently the reaction is centrifuged, the supernatant discarded and the RNA pellet washed with 75% ethanol. After drying the RNA is preferably resuspended in water.

The concentration of the test RNA in vitro transcription is preferably determined by photometry as described in PCT/EP2015/000959. Therefore, the yield of in vitro transcribed RNA can be estimated.

The RNA identity in the (test) in vitro transcription is preferably determined by any method known in the art, particularly by any method described in PCT/EP2015/000959. Particularly preferred is agarose gel electrophoresis as described in PCT/EP2015/000959, incorporated herein by reference.

Below, preferred steps are described for controlling the quality of the template DNA molecule/plasmid species comprising a nucleic acid sequence encoding the RNA molecule species. In particular, this section relates to preferred steps for determination of the DNA molecule content, determination of the identity of the DNA molecule sequence encoding the target RNA molecule sequences and/or determination of the purity of the DNA molecule/plasmid species.

The concentration of the isolated template plasmid DNA molecules (dsDNA) is preferably determined by a standard photometric method for nucleic acids via measurement of the absorption. Moreover, the OD 260/280 value is preferably determined which measures the purity of a nucleic acid sample. For pure DNA, A260/280 is approximately 1.8.

To confirm that the obtained DNA plasmid/molecule species comprise the nucleic acid sequences encoding the RNA molecule species sequences, PCR with appropriate primers may be performed. Primers located in the nucleic acid sequence encoding the target RNA sequence or primers located outside of the nucleic acid sequence encoding the target RNA sequence may be used for PCR.

If a plasmid DNA plasmid species is used as template for the RNA in vitro transcription in step a), also primers located on the backbone of the plasmid DNA vector may be used, e.g. standard primers such as M13, Sp6, or T7 primers flanking the insert DNA sequence encoding the target RNA molecule species sequences.

The resulting PCR-amplified products may be analyzed by any method known in the art such as by gel electrophoresis e.g. agarose gel electrophoresis, DNA sequencing or chromatography e.g. HPLC). Particularly preferred is the analysis by agarose gel electrophoresis or HPLC.

In one aspect, the present invention provides PCR used as a method for analysis of template DNA molecule/plasmid species, for controlling the identity of the DNA sequence encoding the target RNA molecule species sequences. Particularly, this method is used as a quality control for the production of template DNA in the method for producing the RNA molecule composition according to the invention, preferably in the production process of in vitro transcribed RNA.

Alternatively or additionally to other methods, such as PCR, restriction analysis of the template plasmid DNA vector comprising the insert DNA sequence encoding the target RNA sequence is preferably conducted and the resulting fragments of the plasmid DNA vector are analyzed to confirm that the template plasmid DNA vector contains the insert DNA sequence encoding the target RNA molecule species sequence.

Restriction enzymes specifically bind to and cleave double-stranded DNA at specific sites within or adjacent to a particular sequence known as the recognition site. Most of the restriction enzymes recognize a specific sequence of nucleotides that are four, five or six nucleotides in length and display twofold symmetry. Some cleave both strands exactly at the axis of symmetry, generating fragments of DNA that carry blunt ends; others cleave each strand at similar locations on opposite sides of the axis of symmetry, creating fragments of DNA that carry single-stranded termini (See Definitions).

The reaction conditions used for the restriction digestion are dependent on the used restriction enzymes. Particularly, the salt concentration differs depending on the used restriction enzyme. Therefore, the manufacturer of restriction enzymes optimized buffers for their restriction enzymes.

Preferred conditions for a restriction reaction with one restriction enzyme are:

0.5 μg plasmid DNA (0.2-2 μg plasmid DNA)
1.5 μl 10× reaction buffer
1 μl restriction enzyme (1 μl normally comprises 1 u)
Add. 15 μl WFI (water for injection)

Preferred conditions for a restriction reaction with two restriction enzymes are:

0.5 μg plasmid DNA (0.2-2 μg plasmid DNA)
1.5 μl 10× reaction buffer
1 μl restriction enzyme 1 (1 μl normally comprises 1 u)
1 μl restriction enzyme 2 (1 μl normally comprises 1 u)
Add. 15 μl WFI (water for injection)

The restriction reaction is typically mixed as shown above and incubated preferably for 1-4 hours at 37° C.

In this context, it is particularly preferred that restriction enzymes are combined, which cut 5'- and 3' of the insert DNA sequence. Alternatively, a specific combination of restriction enzymes is chosen dependent on the insert DNA sequence. In this case, it is particularly preferred to choose a restriction enzyme, which cuts only once in the DNA plasmid backbone and a restriction enzyme, which cuts once in the insert DNA sequence.

It is particularly preferred to perform at least one, 2, 3, 4 or 5 different restriction reactions using different restriction enzyme(s) (combinations) in order to control the identity of the insert DNA sequence comprising the nucleic acid sequence encoding the target RNA sequence.

After step n), the m different DNA plasmid species are extracted from the bacterial host cells via conventional, commercially available plasmid preparation kits or customized purification processes applying different filtration and chromatography steps. After purification, the plasmid DNA mixture is analyzed regarding its identity and its composition via sequencing, Next Generation Sequencing (NGS; e.g., Illumina), PCR, qPCR or restriction mapping in order to confirm the identity and quantity of each individual plasmid.

The identity of the insert DNA sequence contained in the template plasmid DNA vector is e.g. controlled by enzymatic restriction and subsequent analyzed preferably via agarose gel electrophoresis. For this purpose, template plasmid DNA is incubated with a certain number of specific restriction enzymes (preferably in at least five independent reactions) leading to a specific fragmentation of the template plasmid DNA vector. Subsequently, the restricted DNA samples are analyzed by separation of the obtained fragments of different sizes e.g. on an agarose gel or by e.g. by HPLC. The received fragmentation pattern of the DNA is compared to the theoretically expected restriction pattern.

Automated DNA sequencing of the insert DNA molecule species sequence of the plasmid DNA or of the PCR product encoding the target RNA molecule species sequence may be performed to confirm the identity of the DNA sequence encoding the target RNA molecule species sequence. The DNA sequencing may be performed by any method known in the art, particularly by any method defined herein or in PCT/EP2015/000959. Selection of appropriate primers for DNA sequencing ensures that the complete length of the DNA sequence encoding the target RNA sequence is completely covered for both complementary strands of the DNA primers (primers flanking the DNA sequence encoding the target RNA sequence e.g. the insert DNA sequence, located on the backbone of the plasmid, e.g., M13 forward, and M13 reverse). The received sequence information is compared to the expected sequence of the DNA sequence encoding the target RNA sequence.

Therefore, it is particularly preferred in the context of the present invention to confirm or to control the identity of the DNA molecule/plasmid species sequence encoding one or more of the RNA molecule species.

After the fermentation, plasmid DNA is extracted from the host cells via conventional, commercially available plasmid preparation kits or customized purification processes applying different filtration and chromatography steps. After purification, the plasmid DNA mixture is analyzed regarding its identity and its composition via sequencing, Next Generation Sequencing (NGS; e.g., Illumina), PCR, qPCR or restriction mapping in order to confirm the identity and quantity of each individual plasmid.

DNA molecule/plasmid species (also referred herein as "template DNA" or "DNA template") may further be controlled with respect to RNA-contamination. Preferably, the template DNA e.g. plasmid DNA species is incubated with RNase A. Afterwards the concentration of the purified template DNA is determined again and the difference before and after RNase treatment is calculated.

The following reaction is particularly preferred:

1-20 μg template DNA, preferably 10-15 μg template DNA are incubated with 1 μl RNAse A (1 g/l) for 1 h at 37° C.

Nucleotides are separated e.g. by alcohol precipitation, chromatography, preferably on Sephadex columns.

Preferably, the concentration of the isolated template DNA, preferably after RNase A digestion, is determined by a standard photometric method for nucleic acids via measurement of the absorption at 260 nm (OD260) (see above).

Calculation of the percentage of template DNA contained in the template DNA preparation:

$$\%\ \text{template}\ DNA = \frac{\text{concentration of nucleic acids after}\ RNase\ A\ \text{digestion}}{\text{concentration of nucleic acids before}\ RNase\ A\ \text{digestion}} \times 100\%$$

A test for bacterial endotoxins is preferably carried out in order to determine the presence and/or the amount of endotoxins in the template DNA preparation. Preferably, endotoxins of gram-negative bacterial origin are detected and/or quantified by using amoebocyte lysate from horseshoe crab (Limulus *polyphemus* or *Tachypleus tridentatus*). The principle has been discovered by Levin (Levin, J. 1979. The reaction between bacterial endotoxin and amebocyte lysate, p. 131-146. In E. Cohen (ed.), Biomedical Applications of the Horseshoe Crab (Limulidae), Progress in Clinical and Biological Research, Vol. 29. Alan R. Liss, Inc., NewYork).

In general, there are at least three techniques for performing this test: the gel-clot technique, which is based on gel formation; the turbidimetric technique, based on the development of turbidity after cleavage of an endogenous substrate; and the chromo-genic technique, based on the development of colour after cleavage of a synthetic peptide-chromogen complex.

Preferred is the LAL-test. The amount of endotoxins per volume of plasmid DNA is determined and evaluated via kinetic-turbidometric LAL (Limulus-Amoebocyte-Lysate) test according to Ph. Eur. 2.6.14 (Pharmacopoeia *Europaea*).

The total protein content per volume of template plasmid DNA is preferably calculated. Several different methods are known in the art for detection of protein, including UV absorbance measurements at 280 nm (due to the presence of aromatic amino acids), the Lowry assay, the Biuret assay, the Bradford assay, and the BCA (Bichinonic Acid) assay.

The BCA (Bichinonic Acid) assay, a colorimetric method of detection is based on complexation of proteins with copper and BCA. The total protein concentration contained in the RNA is measured via absorption at 562 nm compared to a protein standard (BSA). The principle of the bicinchoninic acid (BCA) assay is similar to the Lowry procedure (Lowry, O. H. et al, J. Biol. Chem., 193, 265-275 (1951)). Both rely on the formation of a $Cu^{2+}$-protein complex under alkaline conditions, followed by reduction of the $Cu^{2+}$ to $Cu^{+}$. The amount of reduction is proportional to the protein present. It has been shown that cysteine, cystine, tryptophan, tyrosine, and the peptide bond are able to reduce $Cu^{2+}$ to $Cu^{+}$. BCA forms a purple-blue complex with $Cu^{+}$ in alkaline environments, thus providing a basis to monitor the reduction of alkaline $Cu^{2+}$ by proteins at absorbance maximum 562 nm.

Another method, which can be used for the determination of protein is the Bradford method. The Bradford assay, a colorimetric protein assay, is based on an absorbance shift of the dye Coomassie Brilliant Blue G-250 in which under acidic conditions the red form of the dye is converted into its bluer form to bind to the protein being assayed. The (bound) form of the dye has an absorption spectrum maximum historically held to be at 595 nm. The cationic (unbound) forms are green or red. The binding of the dye to the protein stabilizes the blue anionic form. The increase of absorbance at 595 nm is proportional to the amount of bound dye, and thus to the amount (concentration) of protein present in the sample.

Particularly preferred is the BCA assay. For performing a BCA assay, several commercially available kits may be used.

To determine sterility of the template DNA preparation, a PCR using universal bacterial primers (detecting universal occurring genes in bacteria) may be performed. Moreover, a plating assay may be conducted.

Particularly preferred is a plating assay according to PhEur 2.6.12.: For determina-tion of the bioburden the presence/absence of bacteria is tested under aerobe and anaerobe conditions after plating the plasmid DNA on agar- and/or glucose plates and incubation for several days (e.g. 5 and 7 days, respectively). The bioburden is assessed by counting the bacteria clones grown on bacteria plates.

For this purpose, different media for plating can be used. Tryptic Soy Agar (TSA) (Soybean Casein Digest Agar (CSA)) and Sabouraud Glucose (2%) Agar plates are particularly preferred.

In case *E. coli* is used for amplification of the template plasmid DNA, the residual *E. coli* DNA is preferably determined.

Residual *E coli* DNA may be detected via PCR, preferably via quantitative PCR (qPCR) using primers and probes specific for *E. coli* genes. In this context primers and probes specific for any genomic sequence or gene comprised in the respective bacterial strain (e.g. *E. coli* strain) is particularly useful to perform a PCR or qPCR to determine residual bacterial DNA.

Plasmid DNA is checked for residual *E. coli* DNA. For this purpose quantitative PCR (qPCR) is performed with the plasmid DNA sample together with a positive and a negative control and the calculated number of copies of genomic *E. coli* DNA is assessed. For this purpose an *E. coli* specific gene is amplified and quantified. Preferably the Light Cycler from Roche is used in combination with FastStart DNA MasterPlus Hybridization Probes.

The template DNA (e.g. the linear template plasmid DNA species) is preferably analyzed for RNase contamination using commercially available RNase detection kits, including RNaseAlert® (Applied Biosystems), RNase contamination assay (New England Biolabs) or an assay where the incubation of the template DNA with a reference RNA serves as a readout for RNase contamination.

The template DNA may be analyzed for RNase contamination by using the RNaseAlert® kit, which utilizes an RNA substrate tagged with a fluorescent reporter molecule (fluor) on one end and a quencher of that reporter on the other. In the absence of RNases, the physical proximity of the quencher dampens fluorescence from the fluor. In the presence of RNases, the RNA substrate is cleaved, and the fluor and quencher are spatially separated in solution. This causes the fluor to emit a bright green signal when excited by light of the appropriate wavelength. Fluorescence can be readily detected with a filter-based or monochromator-based fluorometer.

The template DNA may be alternatively analyzed for RNAse contamination by using an RNase Contamination Assay Kit (New England Biolabs) which detects general RNase activities including non-enzyme based RNA degradation due to heavy metal contamination in samples and high pH. The assay probe is a fluorescein labeled RNA transcript (300-mer). After incubation with a pDNA sample the integrity of the RNA probe is analyzed on denaturing PAGE followed by SYBR Gold staining or preferably by scanning with a FAM/Fluorescein capable imaging system.

In a preferred embodiment, the template DNA is analyzed for RNase contamination by incubation of the template DNA (preferably the linear template plasmid DNA) with a reference RNA and subsequent analysis via RNA agarose gel electrophoresis. In case of absence of RNase both the linear DNA and the reference RNA can be detected on the agarose gel, in case of RNase contamination, only the DNA band can be detected.

The linearized DNA molecule species mixture is then used as a template in step a) of RNA in vitro transcription using e.g. a DNA dependent T7 RNA polymerase in the presence of a nucleotide mixture.

The obtained mixture of m different deoxyribonucleic acid (DNA) molecule species may then be used in step a) of RNA in vitro transcription.

As a quality control for the obtained mixture of m different DNA plasmid/molecule species, DNA plasmid/molecules are extracted from the bacterial cells via conventional, commercially available plasmid preparation kits or customized purification processes applying different filtration and chromatography steps known to the skilled person.

Preferably, the method further comprises prior to step a) a step of o) determining a parameter of transcription efficiency for each of the m different deoxyribonucleic acid (DNA) molecule species.

The RNA in vitro transcription is preferably performed using a DNA dependent T7 RNA polymerase in the presence of a nucleotide mixture. For preferred embodiments, where the n different RNA molecules species have highly similar sequences (similar G:C:U:A ratio), a sequence optimized NTP mix can be applied in order to optimize the RNA/NTP yield, as disclosed.

The RNA in vitro transcription reaction typically comprises a transcription buffer, nucleotide triphosphates (NTPs), an RNase inhibitor and a DNA-dependent RNA polymerase. The NTPs can be selected from, but are not limited to those described herein including naturally occurring and modified NTPs. The DNA-dependent RNA polymerase can be selected from, but is not limited to, T7 RNA polymerase, T3 RNA polymerase, SP6 RNA polymerase and mutant polymerases such as, but not limited to, polymerases able to incorporate modified nucleic acids. Particularly preferred is T7 RNA polymerase as an enzyme for RNA in vitro transcription.

During polymerization, the mRNA may be co-transcriptionally capped at the 5' end with a cap analogue as defined herein (e.g. N7-MeGpppG).

As transcription buffer, following buffers are preferred: 40 mM Tris pH 7.5 or 80 mM HEPES.

Template DNA: 10-500 μg/ml, particularly preferred are 50 μg/ml

Nucleotide triphosphates of the desired chemistry are used, including naturally occuring nucleotides (e.g. at least one of the nucleotides ATP, CTP, UTP and GTP) and/or modified nucleotides, preferably modified nucleotides as described herein, or any combination thereof. ATP, CTP, UTP and GTP are preferably used in a concentration of 0.5-10 mM, preferably in a concentration of 3-5 mM and most preferably in a concentration of 4 mM.

Useful cap analogs include, but are not limited to, N7-MeGpppG (=m7G(5')ppp(5')G), m7G(5')ppp(5')A, ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine. If 5'-CAP (cap analog) is used, the concentration of GTP is preferably decreased compared to the other used nucleotides. Furthermore the cap analog is used in a concentration which is at least the same as the concentration of ATP, CTP and UTP.

The ratio of cap analog:GTP can be varied from 10:1 to 1:1 to balance the percentage of capped products with the efficiency of the transcription reaction, preferably a ratio of cap analog:GTP of 4:1-5:1 is used. In this context it is particularly preferred to use 5.8 mM Cap analog and 1.45 mM GTP if ATP, UTP and CTP are used in a concentration of 4 mM.

$MgCl_2$ can optionally be added to transcription reaction. Preferred is a concentration of 1-100 mM. Particularly preferred is a concentration of 5-30 mM and most preferably 12-24 mM $MgCl_2$ is used.

Spermidine can optionally be added to the transcription reaction, preferably 1-10 mM, most preferably 2 mM spermidine.

Dithiothreitol (DTT) can optionally be added to the transcription reaction, preferably at a concentration of 1-100 mM, more preferably 10-100 mM, most preferably 40 mM.

An RNase inhibitor can optionally be added to the transcription reaction, preferably 0.1-1 U/μl, most preferably 0.2 U/μl.

*E. coli* pyrophosphatase can optionally be added to the transcription reaction, preferably in a concentration of 1-10 U/μg template DNA, and most preferably in a concentration of 5 U/μg template DNA. This ensures that magnesium, which is essential for transcription, remains in solution and does not precipitate as magnesium pyrophosphate.

The following viral DNA-dependent RNA polymerases can be used: T3, T7 and Sp6 polymerases. 1-1000 Units/μg DNA can be used. Preferably in a concentration of 100 U/μg DNA.

BSA can optionally be used, preferably in a concentration of 1-1000 μg/ml, most preferably in a concentration of 100 μg/ml. Most preferably, BSA is not present in the transcription reaction.

Most preferably, the RNA in vitro transcription reaction comprises the following components:

template DNA mixture
4 mM ATP, CTP and UTP
1.45 mM GTP,
5.8 mM CAP analogue
80 mM HEPES or Tris HCl
24 mM $MgCl_2$
2 mM Spermidine
40 mM DTT
5 u pyrophosphatase
4 u RNase inhibitor
100 u T7 RNA polymerase The RNA in vitro transcription reaction is preferably incubated at 37° C., more preferably for at least 4 hours.

Further, preferably the amount of each of the n different RNA molecule species in the RNA molecule composition is proportional or at least 90% proportional to the amount of the corresponding DNA molecule species in the mixture of m different DNA molecule species.

In another preferred embodiment, step b) of the method of the invention further comprises a step of p) purifying the n different RNA molecule species, optionally via HPLC and optionally, a step of q) qualitatively and quantitatively analyzing the RNA molecule composition obtained in step b). For purification of the mixture of n different RNA molecule species, LiCl precipitation, and/or TFF (PCT/EP2015/062002, incorporated herein by reference) and/or HPLC methods (PureMessenger®; WO 2008/077592 A1, incorporated herein by reference) may be applied. Alternatively, affinity chromatography applying a Poly(T) resin can be used. The purified RNA is optionally qualitatively and/or quantitatively analyzed.

Step p) of purifying the n different RNA molecule species may comprise the removal of template DNA, i.e. the DNA molecule species are separated from the RNA molecule species. In one embodiment, the RNA molecules are removed chromatographically using a polyA capture, e.g., oligo dT, based affinity purification step. The RNA molecules bind to the affinity substrate, while the DNA molecules flow through and are removed. However, particularly preferred is the enzymatic removal of DNA molecules using DNAse I.

In a preferred embodiment, the RNA molecules obtained by the inventive method may further be capped. As an alternative to co-transcriptional capping using CAP analogs, the RNA may be capped enzymatically. In particular embodiments, the RNA obtained by the inventive method may further be polyadenylated via incubation with a bacterial poly (A) polymerase (polynucleotide adenylyltransferase) e.g., from *E. coli* together with ATP in the respective buffer The step p) of RNA purification may include any purification method known in the art such as alcohol precipitation, chromatography, such as HPLC, or LiCl precipitation, wherein LiCl precipitation is preferred. Further details on purification methods of RNA can be taken from PCT/EP2015/000959, PCT/EP2015/062002, WO 2008/077592 A1, incorporated herein by reference.

In a preferred embodiment, the RNA molecule concentration/RNA content/RNA amount is determined as described below and in PCT/EP2015/000959, which is incorporated herein by reference.

The RNA content is preferably determined by spectrometric analysis. Spectrophoto-metric analysis is based on the principles that nucleic acids absorb ultraviolet light in a specific pattern. In the case of DNA and RNA, a sample that is exposed to ultraviolet light at a wavelength of 260 nanometers (nm) will absorb that ultraviolet light. The resulting effect is that less light will strike the photodetector and this will produce a higher optical density (OD).

An optical density of 1 measured at 260 nm corresponds to a concentration of 40 μg/ml single stranded RNA.

The yield of the test transcription is evaluated measurement of the absorption at 260 nm (OD260).

The RNA molecule species indentity can be determined by various methods as will be explained in detail below:

i) Determination of Transcript Length and Transcript Uniqueness

The correct transcript length and transcript uniqueness is preferably confirmed in order to verify identity and purity of the RNA obtained in step b) of the inventive method.

The band uniqueness and band size of mRNA is preferably analyzed by agarose gel electrophoresis, capillary gel electrophoresis, polyacrylamide gel electrophoresis or HPLC. Particularly preferred is agarose gel electrophoresis.

Electrophoresis through agarose gels is a method to separate RNA. The RNA can be determined in the agarose gel by addition of the fluorescent intercalating dye ethidium bromide or other commercially available dyes (SybrSafe DNA stain, Cybr Green, Orange DNA loading dye)

As running usually 1×MOPS buffer is used (MOPS, 0.74% Formaldehyde, in ultra-pure water)

For the preparation of the agarose gel, 0.5-3% (w/v) agarose or more preferably 1.2% (w/v) agarose is melted in 1× running buffer.

The solution is poured into a mold and allowed to harden. When an electric field is applied across the gel, RNA, which is negatively charged, migrates to the anode. As running buffer the same buffer as used for preparation of the agarose gel is used.

Loading buffer (e.g. Gel loading buffer with ethidium bromide (10 mg/1)) is added to the sample and loaded on the agarose gel. After gel running the RNA can be determined, for example, by ultraviolet light. The RNA length can be compared to the predicted length and therefore allows the determination if the correct DNA sequence encoding the target RNA sequence is integrated into the plasmid.

Alternatively, polyacrylamide gel electrophoresis, capillary gel electrophoresis, or HPLC may be used.

ii) Determination of RNA Identity by RNAse Treatment with Subsequent Analysis of the Degraded Product In a preferred embodiment, RNA identity is confirmed by a test, which uses RNAse A digestion of a sample of the RNA obtained in step b) of the inventive method. The digested RNA is preferably compared with an untreated sample on an RNA gel electrophoresis.

In this context, it is particularly preferred to digest 1 μg RNA transcript with 10 μg RNAse A.

iii) Determination of RNA Identity by RT-PCR with Subsequent Analysis of the Product Via-Agarose Gelelectrophoresis In a first step, the RNA is preferably converted into complementary DNA (cDNA) using the enzyme reverse transcriptase. In a second step, the resulting cDNA is amplified via PCR (polymerase chain reaction) using appropriate primers to provide a PCR product of a certain size. The PCR product is analyzed via agarose gel electrophoresis for correct band size.

RT-PCR using the RNA as a template is preferably used to determine the size of the RNA product. For reverse transcription, kits are commercially available.

Afterwards, produced cDNA is amplified with target-specific primers and product band sizes are analysed in a conventional DNA agarose gel electrophoresis.

iv) Determination of RNA Identity by Reverse Transcription Sequencing:

The RNA transcript can be characterized by reverse transcription sequencing. The RNA product is incubated with a common reverse transcriptase, a set of primers, and dNTPs to obtain cDNA samples. The cDNA serve as a template for PCR to amplify the cDNA. The PCR product is then characterized by analysis using a sequencing procedure as defined herein such as Sanger sequencing or bidirectional sequencing.

v) Determination of RNA Identity by Oligonucleotide Mapping:

The RNA obtained in step b) of the inventive method is preferably incubated with various nucleotide probes under conditions sufficient to allow hybridization of the probes to the RNA to form duplexes, where each of the nucleotide probes includes a sequence complementary to a different region of the RNA transcript.

The formed duplexes are then contacted with an RNase (such as RNase H or RNase Tl) under conditions sufficient to allow RNase digestion of the duplexes to form reaction products.

Next, the reaction products are analyzed, for example by using a procedure such as reverse phase high performance liquid chromatography (RP-HPLC), anion exchange HPLC (AEX), or RP-HPLC coupled to mass spectrometry (MS). Finally, the RNA is characterized by using the analysis of the reaction products to determine the sequence of the RNA.

vi) Determination of RNA Identity by RNA Sequencing.

In a preferred embodiment, the identity of the RNA may be determined by RNA sequencing. Methods for RNA sequence analysis are known in the art and may be used herein.

vii) Determination of RNA Integrity

The relative integrity of the RNA obtained in step b) of the invention is preferably determined as the percentage of full-length RNA (i.e. non-degraded RNA) with respect to the total amount of RNA (i.e. full-length RNA and degraded RNA fragments (which appear as smears in gel electrophoresis)).

viii) Determination of pH

Potentiometric determination of the pH content using a conventional volt-meter, according to the european pharmacopedia (PhEur) 2.2.3 is preferably used to determine the pH value in the RNA preparation.

ix) Determination of Osmolality

In a preferred embodiment, the osmolality of the RNA obtained in step b) of the inventive method is determined. The measurement of the osmolality is performed using a conventional osmometry device according to PhEur 2.2.35.

x) Determination of Bioburden/Microbial Content

To determine sterility of the RNA preparation, an RT-PCR using universal bacterial primers (detecting universal occurring genes in bacteria) may be performed. Moreover, a plating assay may be conducted.

Particularly preferred is a plating assay according to PhEur 2.6.12.: For determination of the bioburden the presence/absence of bacteria is tested under aerobe and anaerobe conditions after plating the RNA on agar- and/or glucose plates and incubation for several days (e.g. 5 and 7 days, respectively). The bioburden is assessed by counting the bacteria clones grown on bacteria plates.

For this purpose, different media for plating can be used. Tryptic Soy Agar (TSA) (Soybean Casein Digest Agar (CSA)) and Sabouraud Glucose (2%) Agar plates are particularly preferred.

xi) Determination of Endotoxin Contamination:

A test for bacterial endotoxins is preferably used to detect or quantify endotoxins of gram-negative bacterial origin by using amoebocyte lysate from horseshoe crab (*Limulus polyphemus* or *Tachypleus tridentatus*). The principle has been discovered by Levin (Levin, J. 1979. The reaction between bacterial endotoxin and amebocyte lysate, p. 131-146. In E. Cohen (ed.), Biomedical Applications of the Horseshoe Crab (Limulidae), Progress in Clinical and Biological Research, Vol. 29. Alan R. Liss, Inc., NewYork).

In general, there are 3 techniques for performing this test: the gel-clot technique, which is based on gel formation; the turbidimetric technique, based on the development of turbidity after cleavage of an endogenous substrate; and the chromogenic technique, based on the development of colour after cleavage of a synthetic peptide-chromogen complex Preferred is the LAL-test. The amount of endotoxins per volume of RNA is determined and evaluated via kinetic-turbidometric LAL (Limulus-Amoebocyte-Lysate) test according to Ph. Eur. 2.6.14 (Pharmacopoea *Europaea*).

xii) Determination of Protein Contamination:

The total protein content per volume of RNA obtained in step b) of the inventive method is calculated.

Several different methods in the art are known for detection of protein, including UV absorbance measurements at 280 nm (due to the presence of aromatic amino acids), the Lowry assay, the Biuret assay, the Bradford assay, and the BCA (Bichinonic Acid) assay.

The BCA (Bichinonic Acid) assay, a colorimetric method of detection based on complexation of proteins with copper and BCA. The total protein concentration contained in the RNA is measured via absorption at 562 nm compared to a protein standard (BSA). The principle of the bicinchoninic acid (BCA) assay is similar to the Lowry procedure (Lowry, O. H. et al, J. Biol. Chem., 193, 265-275 (1951)). Both rely on the formation of a $Cu^{2+}$-protein complex under alkaline conditions, followed by reduction of the $Cu^{2+}$ to $Cu^{+}$. The amount of reduction is proportional to the protein present. It has been shown that cysteine, cystine, tryptophan, tyrosine, and the peptide bond are able to reduce $Cu^{2+}$ to $Cu^{+}$. BCA forms a purple-blue complex with $Cu^{+}$ in alkaline environments, thus providing a basis to monitor the reduction of alkaline $Cu^{2+}$ by proteins at absorbance maximum 562 nm.

Another method which could be used for the determination of protein is the Bradford method. The Bradford assay, a colorimetric protein assay, is based on an absorbance shift of the dye Coomassie Brilliant Blue G-250 in which under acidic conditions the red form of the dye is converted into its bluer form to bind to the protein being assayed. The (bound) form of the dye has an absorption spectrum maximum historically held to be at 595 nm. The cationic (unbound) forms are green or red. The binding of the dye to the protein stabilizes the blue anionic form. The increase of absorbance at 595 nm is proportional to the amount of bound dye, and thus to the amount (concentration) of protein present in the sample.

Particularly preferred is the BCA assay. For performing a BCA assay, several commercially available kits may be used.

xiii) Determination of Plasmid DNA Contamination:

Residual plasmid DNA may optionally be detected by PCR or quantitative PCR as described herein using specific primers and probes for DNA plasmid used for RNA in vitro transcription. Particularly preferred is the detection of residual plasmid DNA via quantitative PCR as described herein using specific primers and probes for the ampicillin gene hosted in the production vector. The probes are used as positive control and thus for calculation of the plasmid DNA concentration.

xiv) Determination of Bacterial DNA Contamination:

Residual bacterial DNA may optionally be detected e.g. by PCR or quantitative PCR using specific primers and probes for bacterial genomic sequences. Particularly preferred is the detection of residual bacterial DNA is detected via quantitative PCR using specific primers and probes for an *E. coli* gene. The probes are preferably used as positive control and thus for calculation of the bacterial DNA concentration.

xv) Determination of Residual Solvent Contamination

Residual solvents are preferably analyzed based on the PhEur 2.2.28 method via headspace gas chromatography using the standard addition method. Samples are heated to 80° C., equilibrated, and the gas phase is injected and analyzed using FID (flame ionization detection).

The analysis preferably includes acetonitrile, chlorophorm, triethylammonium acetate (TEAA), isopropanol, and phenol.

As outlined above, certain quality controls can optionally be implemented to e.g. analyze the growth characteristics of bacterial clones or to characterize the performance of plasmid DNAs, or other DNA templates (e.g., generated using PCR) in RNA in vitro transcription. Moreover, quality controls can optionally be implemented to analyze the composition of the DNA template mixture and/or the in vitro transcribed RNA molecule composition, both quantitatively and qualitatively. Additionally, suitable quality controls during the process of template production and RNA production can be used in the context of the present invention, as disclosed in PCT/EP2015/000959 and WO 2014/144039, both are incorporated herein by reference. A method for purifying RNA molecule mixtures can e.g. be taken from PCT/EP2015/000959, PCT/EP2015/062002, WO 2008/077592, the content of which is incorporated herein by reference.

Preferably, each of the m different DNA molecule species encodes for one or more of the n different RNA molecule species, wherein each of the n different RNA molecule species encodes for a antigen of different serotypes or strains of a pathogen, for a different allergen, for a different autoimmune antigen, for a different antigen of a pathogen, for a different isoform or variant of a cancer or tumor antigen, for a different tumor antigen of one patient, for one antibody among a group of antibodies which target different epitopes of a protein or of a group of proteins, for different proteins of a metabolic pathway, for a single protein among a group of proteins which are defect in a subject, or for a different isoform of a protein for molecular therapy.

More preferably, the pathogen is selected from the group consisting of a virus, bacterium, protozoon, prion, fungus, viroid, and parasite.

Preferably, the pathogen is selected from the group consisting of *Acinetobacter baumannii, Anaplasma genus, Anaplasma phagocytophilum, Ancylostoma braziliense, Ancylostoma duodenale, Arcanobacterium haemolyticum, Ascaris lumbricoides, Aspergillus* genus, Astroviridae, *Babesia* genus, *Bacillus anthracis, Bacillus cereus, Bartonella henselae*, BK virus, *Blastocystis hominis, Blastomyces dermatitidis, Bordetella pertussis, Borrelia burgdorferi, Borrelia genus, Borrelia* spp, *Brucella* genus, *Brugia malayi, Bunyaviridae family, Burkholderia cepacia* and other *Burkholderia* species, *Burkholderia mallei, Burkholderia pseudomallei*, Caliciviridae family, *Campylobacter* genus, *Candida albicans, Candida* spp, *Chlamydia trachomatis, Chlamydophila pneumoniae, Chlamydophila psittaci*, CJD prion, *Clonorchis sinensis, Clostridium botulinum, Clostridium difficile, Clostridium perfringens, Clostridium perfringens, Clostridium* spp, *Clostridium tetani, Coccidioides* spp, coronaviruses, *Corynebacterium diphtheriae, Coxiella burnetii*, Crimean-Congo hemorrhagic fever virus, *Cryptococcus neoformans*, Crypto-sporidium genus, Cytomegalovirus (CMV), Dengue viruses (DEN-1, DEN-2, DEN-3 and DEN-4), *Dientamoeba fragilis*, Ebolavirus (EBOV), *Echinococcus* genus, *Ehrlichia chaffeensis, Ehrlichia ewingii, Ehrlichia genus, Entamoeba histolytica, Enterococcus* genus, Enterovirus genus, Enteroviruses, mainly Coxsackie A virus and Enterovirus 71 (EV71), *Epidermophyton* spp, Epstein-Ban Virus (EBV), *Escherichia coli* O157:H7, O111 and O104:H4, *Fasciola hepatica* and *Fasciola gigantica*, FFI prion, Filarioidea superfamily, Flaviviruses, *Francisella tularensis, Fusobacterium genus, Geotrichum candidum, Giardia intestinalis, Gnathostoma* spp, GSS prion, Guanarito virus, *Haemophilus ducreyi, Haemophilus influenzae, Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Japanese encephalitis virus, JC virus, Junin virus, *Kingella kingae, Klebsiella granulomatis*, Kuru prion, Lassa virus, *Legionella pneumophila, Leishmania* genus, *Leptospira* genus, *Listeria monocytogenes*, Lymphocytic choriomeningitis virus (LCMV), Machupo virus, *Malassezia* spp, Marburg virus, Measles virus, *Metagonimus yokagawai*, Microsporidia phylum, *Molluscum contagiosum* virus (MCV), Mumps virus, *Mycobacterium leprae* and *Mycobacterium* lepromatosis, *Mycobacterium tuberculosis, Mycobacterium ulcerans, Mycoplasma pneumoniae, Naegleria fowleri, Necator americanus, Neisseria gonorrhoeae, Neisseria meningitidis, Nocardia asteroides, Nocardia* spp, *Onchocerca volvulus, Orientia tsutsugamushi*, Orthomyxoviridae family (Influenza), *Paracoccidioides brasiliensis, Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari, Rickettsia genus, Rickettsia prowazekii, Rickettsia rickettsii, Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii, Staphylococcus* genus, *Staphylococcus* genus, *Streptococcus agalactiae, Streptococcus pneumoniae, Streptococcus pyogenes, Strongyloides stercoralis, Taenia genus, Taenia solium*, Tick-borne encephalitis virus (TBEV), *Toxocara canis* or *Toxocara cati, Toxoplasma gondii, Treponema pallidum, Trichinella spiralis, Trichomonas vaginalis, Trichophyton* spp, *Trichuris trichiura, Trypanosoma brucei, Trypanosoma cruzi, Ureaplasma urealyticum*, Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica, Yersinia pestis*, and *Yersinia pseudotuberculosis*, preferably the pathogen is selected from the group consisting of influenza virus, respiratory syncytial virus (RSV), Herpes simplex virus (HSV), human Papilloma virus (HPV), Human immunodeficiency virus (HIV), *Plasmodium, Staphylococcus aureus, Dengue virus, Chlamydia trachomatis*, Cytomegalovirus (CMV), Hepatitis B virus (HBV), *Mycobacterium tuberculosis*, Rabies virus, Rotavirus and Yellow Fever Virus.

In another preferred embodiment of the method of the invention, each of the m different DNA molecule species encodes for one or more of the n different RNA molecule species, wherein each of the n different RNA molecule species encodes a different pathogenic antigen selected from the group consisting of (organism of origin and corresponding disease given in brackets) influenza haemagglutinin, influenza neuraminidase, influenza nucleoprotein, coronavirus glycoprotein S, prostate specific antigen, outer membrane protein A OmpA, biofilm associated protein Bap, transport protein MucK (*Acinetobacter baumannii, Acinetobacter* infections)); variable surface glycoprotein VSG, microtubule-associated protein MAPP15, trans-sialidase TSA (*Trypanosoma brucei*, African sleeping sickness (African trypanosomiasis)); HIV p24 antigen, HIV envelope proteins (Gp120, Gp41, Gp160), polyprotein GAG, negative factor protein Nef, trans-activator of transcription Tat (HIV (Human immunodeficiency virus), AIDS (Acquired immunodeficiency syndrome)); galactose-inhibitable adherence protein GIAP, 29 kDa antigen Eh29, Gal/GalNAc lectin, protein CRT, 125 kDa immunodominant antigen, protein M17, adhesin ADH112, protein STIRP (*Entamoeba histolytica*, Amoebiasis); Major surface proteins 1-5 (MSP1a, MSP1b, MSP2, MSP3, MSP4, MSP5), type IV secreotion system proteins (VirB2, VirB7, VirB11, VirD4) (*Anaplasma* genus, Anaplasmosis); protective Antigen PA, edema factor EF, lethal facotor LF, the S-layer homology proteins SLH (*Bacillus anthracis*, Anthrax); acranolysin, phospholipase D, collagen-binding protein CbpA (*Arcanobacterium haemolyticum, Arcanobacterium haemolyticum* infection); nucleocapsid protein NP, glycoprotein precursor GPC, glycoprotein GP1, glycoprotein GP2 (Junin virus, Argentine hemorrhagic fever); chitin-protein layer proteins, 14 kDa suarface antigen A14, major sperm protein MSP, MSP polymerization-organizing protein MPOP, MSP fiber protein 2 MFP2, MSP polymerization-activating kinase MPAK, ABA-1-like protein ALB, protein ABA-1, cuticulin CUT-1 (*Ascaris lumbricoides*, Ascariasis); 41 kDa allergen Asp v13, allergen Asp f3, major conidial surface protein rodlet A, protease Pep1p, GPI-anchored protein Gellp, GPI-anchored protein Crf1p (*Aspergillus* genus, Aspergillosis); family VP26 protein, VP29 protein (Astroviridae, Astrovirus infection); Rhoptry-associated protein 1 RAP-1, merozoite surface antigens MSA-1, MSA-2 (a1, a2, b, c), 12D3, 1105, 21B4, P29, variant erythrocyte surface antigen VESA1, Apical Membrane Antigen 1 AMA-1 (*Babesia* genus, Babesiosis); hemolysin, enterotoxin C, PXO1-51, glycolate oxidase, ABC-transporter, penicillin-bingdn protein, zinc transporter family protein, pseudouridine synthase Rsu, plasmid replication protein RepX, oligoendopeptidase F, prophage membrane protein, protein HemK, flagellar antigen H, 28.5-kDa cell surface antigen (*Bacillus cereus, Bacillus cereus* infection); large T antigen LT, small T antigen, capsid protein VP1, capsid protein VP2 (BK virus, BK virus infection); 29 kDa-protein, caspase-3-like antigens, glycoproteins (*Blastocystis hominis, Blastocystis hominis* infection); yeast surface adhesin WI-1 (*Blastomyces dermatitidis*, Blastomycosis); nucleoprotein N, polymerase L, matrix protein Z, glycoprotein GP (Machupo virus, Bolivian hemorrhagic fever); outer surface protein A OspA, outer surface protein OspB, outer surface protein OspC, decorin binding protein A DbpA, decorin binding protein B DbpB, flagellar filament 41 kDa core protein Fla, basic membrane protein A precursor BmpA (Immunodominant antigen P39), outer surface 22 kDa lipoprotein precursor (antigen IPLA7), variable surface lipoprotein vlsE (*Borrelia* genus, *Borrelia* infection); Botulinum neurotoxins BoNT/A1, BoNT/A2, BoNT/A3, BoNT/B, BoNT/C, BoNT/D, BoNT/E, BoNT/F, BoNT/G, recombinant botulinum toxin F Hc domain FHc (*Clostridium botulinum*, Botulism (and Infant botulism)); nucleocapsid, glycoprotein precursor (Sabia virus, Brazilian hemorrhagic fever); copper/Zinc superoxide dismutase SodC, bacterioferritin Bfr, 50S ribosomal protein RplL, OmpA-like transmembrane domain-containing protein Omp31, immunogenic 39-kDa protein M5 P39, zinc ABC transporter periplasmic zinc-bnding protein znuA, periplasmic immunogenic protein Bp26, 30S ribosomal protein S12 RpsL, glyceraldehyde-3-phosphate dehydrogenase Gap, 25 kDa outer-membrane immunogenic protein precursor Omp25, invasion protein B lalB, trigger factor Tig, molecular chaperone DnaK, putative peptidyl-prolyl cis-trans isomerase SurA, lipoprotein Omp19, outer membrane protein MotY Omp16, conserved outer membrane protein D15, malate dehydrogenase Mdh, component of the Type-IV secretion system (T4SS) VirJ, lipoprotein of unknown function BAB1_0187 (*Brucella* genus, Brucellosis); members of the ABC transporter family (Lo1C, OppA, and PotF), putative lipoprotein releasing system transmembrane protein Lo1C/E, flagellin FliC, *Burkholderia* intracellular motility A BimA, bacterial Elongation factor-Tu EF-Tu, 17 kDa OmpA-like protein, boaA coding protein, boaB coding protein (*Burkholderia cepacia* and other *Burkholderia* species, *Burkholderia* infection); mycolyl-transferase Ag85A, heat-shock protein Hsp65, protein TB10.4, 19 kDa antigen, protein PstS3, heat-shock protein Hsp70 (*Mycobacterium ulcerans*, Buruli ulcer); norovirus major and minor viral capsid proteins VP1 and VP2, genome polyprotein, Sapoviurus capsid protein VP1, protein Vp3, geome polyprotein (Caliciviridae family, Calicivirus infection (Norovirus and Sapovirus)); major outer membrane protein PorA, flagellin FlaA, surface antigen CjaA, fibronectin binding protein CadF, aspartate/glutamate-binding ABC transporter protein PeblA, protein FspA 1, protein FspA2 (*Campylobacter* genus, Campylobacteriosis); glycolytic enzyme enolase, secreted aspartyl proteinases SAP1-10, glycophosphatidylinositol (GPI)-linked cell wall protein, protein Hyr 1, complement receptor 3-related protein CR3-RP, adhesin Als3p, heat shock protein 90 kDa hsp90, cell surface hydrophobicity protein CSH (usually *Candida albicans* and other *Candida* species, Candidiasis); 17-kDa antigen, protein P26, trimeric autotransporter adhesins TAAs, *Bartonella* adhesin A BadA, variably expressed outer-membrane proteins Vomps, protein Pap3, protein HbpA, envelope-associated protease HtrA, protein OMP89, protein GroEL, protein La1B, protein OMP43, dihydrolipoamide succinyltransferase SucB (*Bartonella henselae*, Cat-scratch disease); amastigote surface protein-2, amastigote-specific surface protein SSP4, cruzipain, trans-sialidase TS, trypomastigote surface glycoprotein TSA-1, complement regulatory protein CRP-10, protein G4, protein G2, paraxonemal rod protein PAR2, paraflagellar rod component Parl, mucin-Associated Surface Proteins MPSP (*Trypanosoma cruzi*, Chagas Disease (American trypanosomiasis)); envelope glycoproteins (gB, gC, gE, gH, gI, gK, gL) (Varicella zoster virus (VZV), Chickenpox); major outer membrane protein MOMP, probable outer membrane protein PMPC, outer membrane complex protein B OmcB, heat shock proteins Hsp60 HSP10, protein *IncA*, proteins from the type III secretion system, ribonucleotide reductase small chain protein NrdB, plasmid protein Pgp3, chlamydial outer protein N CopN, antigen CT521, antigen CT425, antigen CT043, antigen TC0052, antigen TC0189, antigen TC0582, antigen TC0660, antigen TC0726, antigen TC0816, antigen TC0828 (*Chlamydia trachomatis, Chlamydia*); low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 Omp2, polymorphic membrane protein family (Pmp1, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20, Pmp21) (*Chlamydophila pneumoniae, Chlamydophila pneumoniae* infection); cholera toxin B CTB, toxin coregulated pilin A TcpA, toxin coregulated pilin TcpF, toxin co-regulated pilus biosynthesis ptrotein F TcpF, cholera enterotoxin subunit A, cholera enterotoxin subunit B, Heat-stable enterotoxin ST, mannose-sensitive hemagglutinin MSHA, outer membrane protein U Porin ompU, Poring B protein, polymorphic membrane protein-D (*Vibrio cholerae*, Cholera); propionyl-CoA carboxylase PCC, 14-3-3 protein, prohibitin, cysteine proteases, glutathione transferases, gelsolin, cathepsin L proteinase CatL, Tegumental Protein 20.8 kDa TP20.8, tegumental protein 31.8 kDa TP31.8, lysophosphatidic acid phosphatase LPAP, (*Clonorchis sinensis*, Clonorchiasis); surface layer proteins SLPs, glutamate dehydrogenase antigen GDH, toxin A, toxin B, cysteine protease Cwp84, cysteine protease Cwp13, cysteine protease Cwp19, Cell Wall Protein CwpV, flagellar protein FliC, flagellar protein FliD (*Clostridium difficile, Clostridium difficile* infection); rhinoviruses: capsid proteins VP1, VP2, VP3, VP4; coronaviruses: sprike proteins S, envelope proteins E, membrane proteins M, nucleocapsid proteins N (usually rhinoviruses and coronaviruses, Common cold (Acute viral rhinopharyngitis; Acute coryza)); prion protein Prp (CJD prion, Creutzfeldt-Jakob disease (CJD)); envelope protein Gc, envelope protein Gn, nucleocapsid proteins (Crimean-Congo hemorrhagic fever virus, Crimean-Congo hemorrhagic fever (CCHF)); virulence-associated DEAD-box RNA helicase VAD1, galactoxylomannan-protein GalXM, glucuronoxylomannan GXM, mannoprotein MP (*Cryptococcus neoformans*, Cryptococcosis); acidic ribosomal protein P2 CpP2, mucin antigens Muc1, Muc2, Muc3 Muc4, Muc5, Muc6, Muc7, surface adherence protein CP20, surface adherence protein CP23, surface protein CP12, surface protein CP21, surface protein CP40, surface protein CP60, surface protein CP15, surface-associated glycopeptides gp40, surface-associated glycopeptides gp15, oocyst wall protein AB, profilin PRF, apyrase (*Cryptosporidium* genus, Cryptosporidiosis); fatty acid and retinol binding protein-1 FAR-1, tissue inhibitor of metalloproteinase TIMP (TMP), cysteine proteinase ACEY-1, cysteine proteinase ACCP-1, surface antigen Ac-16, secreted protein 2 ASP-2, metalloprotease 1 MTP-1, aspartyl protease inhibitor API-1, surface-associated antigen SAA-1, adult-specific secreted factor Xa serine protease inhibitor anticoagulant AP, cathepsin D-like aspartic protease ARR-1 (usually *Ancylostoma braziliense*; multiple other parasites, Cutaneous larva migrans (CLM)); cathepsin L-like proteases, 53/25-kDa antigen, 8 kDa family members, cysticercus protein with a marginal trypsin-like activity TsAg5, oncosphere protein TSOL18, oncosphere protein TSOL45-1A, lactate dehydrogenase A LDHA, lactate dehydrogenase B LDHB (*Taenia solium*, Cysticercosis); pp65 antigen, membrane protein pp15, capsid-proximal tegument protein pp150, protein M45, DNA polymerase UL54, helicase UL105, glycoprotein gM, glycoprotein gN, glcoprotein H, glycoprotein B gB, protein UL83, protein UL94, protein UL99 (Cytomegalovirus (CMV), Cytomegalovirus infection); capsid protein C, premembrane protein prM, membrane protein M, envelope protein E (domain I, domain II, domain II), protein NS1, protein NS2A, protein NS2B, protein NS3, protein NS4A, protein 2K, protein NS4B, protein NS5 (Dengue viruses (DEN-1, DEN-2, DEN-3 and DEN-4)-Flaviviruses, Dengue fever); 39 kDa protein (*Dientamoeba fragilis*, Dientamoebiasis); diphtheria toxin precursor Tox, diphteria toxin DT, pilin-specific sortase SrtA, shaft pilin protein SpaA, tip pilin protein SpaC, minor pilin protein SpaB, surface-associated protein DIP1281 (*Corynebacterium diphtheriae*, Diphtheria); glycoprotein GP, nucleoprotein NP, minor matrix protein VP24, major matrix protein VP40, transcription activator VP30, polymerase cofactor VP35, RNA polymerase L (Ebolavirus (EBOV), Ebola hemorrhagic fever); prion protein (vCJD prion, Variant Creutzfeldt-Jakob disease (vCJD, nvCJD)); UvrABC system protein B, protein Flp1, protein Flp2, protein Flp3, protein TadA, hemoglobin receptor HgbA, outer membrane protein TdhA, protein CpsRA, regulator CpxR, protein SapA, 18 kDa antigen, outer membrane protein NcaA, protein LspA, protein LspA1, protein LspA2, protein LspB, outer membrane component DsrA, lectin DltA, lipoprotein Hlp, major outer membrane protein OMP, outer membrane protein OmpA2 (*Haemophilus ducreyi*, Chancroid); aspartyl protease 1 Pep1, phospholipase B PLB, alpha-mannosidase 1 AMN1, glucanosyltransferase GEL1, urease URE, peroxisomal matrix protein Pmp1, proline-rich antigen Pra, human T-cell reactive protein TcrP (*Coccidioides immitis* and *Coccidioides* posadasii, Coccidioidomycosis); allergen Tri r 2, heat shock protein 60 Hsp60, fungal actin Act, antigen Tri r2, antigen Tri r4, antigen Tri t1, protein IV, glycerol-3-phosphate dehydrogenase Gpdl, osmosensor HwSho1A, osmosensor HwSho1B, histidine kinase HwHhk7B, allergen Mala s 1, allergen Mala s 11, thioredoxin Trx Mala s 13, allergen Mala f, allergen Mala s (usually *Trichophyton* spp, *Epidermophyton* spp., *Malassezia* spp., *Hortaea werneckii*, Dermatophytosis); protein EG95, protein EG10, protein EG18, protein EgA31, protein EM18, antigen EPC1, antigen B, antigen 5, protein P29, protein 14-3-3, 8-kDa protein, myophilin, heat shock protein 20 HSP20, glycoprotein GP-89, fatty acid binding protein FAPB (*Echinococcus* genus, Echinococcosis); major surface protein 2 MSP2, major surface protein 4 MSP4, MSP variant SGV1, MSP variant SGV2, outer membrane protein OMP, outer membrane protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia* genus, Ehrlichiosis); secreted antigen SagA, sagA-like proteins SalA and SalB, collagen adhesin Scm, surface proteins Fms1 (EbpA(fm), Fms5 (EbpB(fm), Fms9 (EpbC(fm) and Fms10, protein EbpC(fm), 96 kDa immunoprotective glycoprotein G1 (*Enterococcus* genus, *Enterococcus* infection); genome polyprotein, polymerase 3D, viral capsid protein VP1, viral capsid protein VP2, viral capsid protein VP3, viral capsid protein VP4, protease 2A, protease 3C (Enterovirus genus, Enterovirus infection); outer membrane proteins OM, 60 kDa outer membrane protein, cell surface antigen OmpA, cell surface antigen OmpB (sca5), 134 kDa outer membrane protein, 31 kDa outer membrane protein, 29.5 kDa outer membrane protein, cell surface protein SCA4, cell surface protein Add (RP827), cell surface protein Adr2 (RP828), cell surface protein SCA1, Invasion protein invA, cell division protein fts, secretion proteins sec 0family, virulence proteins virB, tlyA, tlyC, parvulin-like protein Plp, preprotein translocase SecA, 120-kDa surface protein antigen SPA, 138 kD complex antigen, major 100-kD protein (protein I), intracytoplasmic protein D, protective surface protein antigen SPA (*Rickettsia prowazekii*, Epidemic typhus); Epstein-Barr nuclear antigens (EBNA-1, EBNA-2, EBNA-3A, EBNA-3B, EBNA-3C, EBNA-leader protein (EBNA-LP)), latent membrane proteins (LMP-1, LMP-2A, LMP-2B), early antigen EBV-EA, membrane antigen EBV-MA, viral capsid antigen EBV-VCA, alkaline nuclease EBV-AN, glycoprotein H, glycoprotein gp350, glycoprotein gp110, glycoprotein gp42, glycoprotein gHgL, glycoprotein gB (Epstein-Ban Virus (EBV), Epstein-Ban Virus Infectious Mononucleosis); cpasid protein VP2, capsid protein VP1, major protein NS1 (Parvovirus B19, Erythema infectiosum (Fifth disease)); pp65 antigen, glycoprotein 105, major capsid protein, envelope glycoprotein H, protein U51 (Human herpesvirus 6 (HHV-6) and Human herpesvirus 7 (HHV-7), Exanthem subitum); thioredoxin-glutathione reductase TGR, cathepsins L1 and L2, Kunitz-type protein KTM, leucine aminopeptidase LAP, cysteine proteinase Fas2, saposin-like protein-2 SAP-2, thioredoxin peroxidases TPx, Prx-1, Prx-2, cathepsin 1 cysteine proteinase CL3, protease cathepsin L CL1, phosphoglycerate kinase PGK, 27-kDa secretory protein, 60 kDa protein HSP35alpha, glutathione transferase GST, 28.5 kDa tegumental antigen 28.5 kDa TA, cathepsin B3 protease CatB3, Type I cystatin stefin-1, cathep sin L5, cathepsin Llg and cathepsin B, fatty acid binding protein FABP, leucine aminopeptidases LAP (*Fasciola hepatica* and *Fasciola gigantica*, Fasciolosis); prion protein (FFI prion, Fatal familial insomnia (FFI)); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, secreted larval acidic proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 (Filarioidea superfamily, Filariasis); phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, Fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm (*Clostridium perfringens*, Food poisoning by *Clostridium perfringens*); leukotoxin lktA, adhesion FadA, outer membrane protein RadD, high-molecular weight arginine-binding protein (*Fusobacterium* genus, *Fusobacterium* infection); phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm (usually *Clostridium perfringens*; other *Clostridium* species, Gas gangrene (Clostridial myonecrosis)); lipase A, lipase B, peroxidase Dec1 (*Geotrichum candidum*, Geotrichosis); prion protein (GSS prion, Gerstmann-Sträussler-Scheinker syndrome (GSS)); cyst wall proteins CWP1, CWP2, CWP3, variant surface protein VSP, VSP1, VSP2, VSP3, VSP4, VSPS, VSP6, 56 kDa antigen, pyruvate ferredoxin oxidoreductase PFOR, alcohol dehydrogenase E ADHE, alpha-giardin, alpha8-giardin, alpha1-guiardin, beta-giardin, cystein proteases, glutathione-S-transferase GST, arginine deiminase ADI, fructose-1,6-bisphosphat aldolase FBA, *Giardia* trophozoite antigens GTA (GTA1, GTA2), ornithine carboxyl transferase OCT, striated fiber-asseblin-like protein SALP, uridine phosphoryl-like protein UPL, alpha-tubulin, beta-tubulin (*Giardia intestinalis*, Giardiasis); members of the ABC transporter family (Lo1C, OppA, and PotF), putative lipoprotein releasing system transmembrane protein Lo1C/E, flagellin FliC, *Burkholderia* intracellular motility A BimA, bacterial Elongation factor-Tu EF-Tu, 17 kDa OmpA-like protein, boaA coding protein (*Burkholderia mallei*, Glanders); cyclophilin CyP, 24 kDa third-stage larvae protien GS24, excretion-secretion products ESPs (40, 80, 120 and 208 kDa) (*Gnathostoma spinigerum* and *Gnathostoma hispidum*, Gnathostomiasis); pilin proteins, minor pilin-associated subunit pi1C, major pilin subunit and variants pilE, pilS, phase variation protein porA, Porin B PorB, protein TraD, Neisserial outer membrane antigen H.8, 70 kDa antigen, major outer membrane protein PI, outer membrane proteins HA and P1B, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR (*Neisseria gonorrhoeae*, Gonorrhea); outer membrane protein A OmpA, outer membrane protein C OmpC, outer membrane protein K17 OmpK17 (*Klebsiella granulomatis*, Granuloma inguinale (Donovanosis)); fibronectin-binding protein Sfb, fibronectin/fibrinogen-binding protein FBP54, fibronectin-binding protein FbaA, M protein type 1 Emm1, M protein type 6 Emm6, immunoglobulin-binding protein 35 Sib35, Surface protein R28 Spr28, superoxide dismutase SOD, C5a peptidase ScpA, antigen I/II AgI/II, adhesin AspA, G-related alpha2-macroglobulin-binding protein GRAB, surface fibrillar protein M5 (*Streptococcus pyogenes*, Group A streptococcal infection); C protein β antigen, arginine deiminase proteins, adhesin BibA, 105 kDA protein BPS, surface antigens c, surface antigens R, surface antigens X, trypsin-resistant protein R1, trypsin-resistant protein R3, trypsin-resistant protein R4, surface immunogenic protein Sip, surface protein Rib, Leucine-rich repeats protein LrrG, serine-rich repeat protein Srr-2, C protein alpha-antigen Bca, Beta antigen Bag, surface antigen Epsilon, alpha-like protein ALP1, alpha-like protein ALPS surface antigen delta, alpha-like protein ALP2, alpha-like protein ALPS, alpha-like protein ALP4, Cbeta protein Bac (*Streptococcus agalactiae*, Group B streptococcal infection); transferrin-binding protein 2 Tbp2, phosphatase P4, outer membrane protein P6, peptidoglycan-associated lipoprotein Pal, protein D, protein E, adherence and penetration protein Hap, outer membrane protein 26 Omp26, outer membrane protein P5 (Fimbrin), outer membrane protein D15, outer membrane protein OmpP2, 5'-nucleotidase NucA, outer membrane protein P1, outer membrane protein P2, outer membrane lipoprotein Pcp, Lipoprotein E, outer membrane protein P4, fuculokinase fucK, [Cu,Zn]-superoxide dismutase SodC, protease HtrA, protein 0145, alpha-galactosylceramide (*Haemophilus influenzae, Haemophilus influenzae* infection); polymerase 3D, viral capsid protein VP1, viral capsid protein VP2, viral capsid protein VP3, viral capsid protein VP4, protease 2A, protease 3C (Enteroviruses, mainly Coxsackie A virus and Enterovirus 71 (EV71), Hand, foot and mouth disease (HFMD)); RNA polymerase L, protein L, glycoprotein Gn, glycoprotein Gc, nucleocapsid protein S, envelope glycoprotein G1, nucleoprotein NP, protein N, polyprotein M (Sin Nombre virus, Hantavirus, Hantavirus Pulmonary Syndrome (HPS)); heat shock protein HspA, heat shock protein HspB, citrate synthase GltA, protein UreB, heat shock protein Hsp60, neutrophil-activating protein NAP, catalase KatA, vacuolating cytotoxin VacA, urease alpha UreA, urease beta Ureb, protein Cpn10, protein groES, heat shock protein Hsp10, protein MopB, cytotoxicity-associated 10 kDa protein CAG, 36 kDa antigen, beta-lactamase HcpA, Beta-lactamase HcpB (*Helicobacter pylori, Helicobacter pylori* infection); integral membrane proteins, aggregation-prone proteins, 0-antigen, toxin-antigens Stx2B, toxin-antigen Stx1B, adhesion-antigen fragment Int28, protein EspA, protein EspB, Intimin, protein Tir, protein IntC300, protein Eae (*Escherichia coli* O157:H7, O111 and O104:H4, Hemolytic-uremic syndrome (HUS)); RNA polymerase L, protein L, glycoprotein Gn, glycoprotein Gc, nucleocapsid protein S, envelope glycoprotein G1, nucleoprotein NP, protein N, polyprotein M (*Bunyaviridae* family, Hemorrhagic fever with renal syndrome (HFRS)); glycoprotein G, matrix protein M, nucleoprotein N, fusion protein F, polymerase L, protein W, proteinC, phosphoprotein p, non-structural protein V (Henipavirus (Hendra virus Nipah virus), Henipavirus infections); polyprotein, glycoproten Gp2, hepatitis A surface antigen HBAg, protein 2A, virus protein VP1, virus protein VP2, virus protein VP3, virus protein VP4, protein P1B, protein P2A, protein P3AB, protein P3D (Hepatitis A Virus, Hepatitis A); hepatitis B surface antigen HBsAg, Hepatitis B core antigen HbcAg, polymerase, protein Hbx, preS2 middle surface protein, surface protein L, large S protein, virus protein VP1, virus protein VP2, virus protein VP3, virus protein VP4 (Hepatitis B Virus (HBV), Hepatitis B); envelope glycoprotein E1 gp32 gp35, envelope glycoprotein E2 NS1 gp68 gp70, capsid protein C, core protein Core, polyprotein, virus protein VP1, virus protein VP2, virus protein VP3, virus protein VP4, antigen G, protein NS3, protein NS5A, (Hepatitis C Virus, Hepatitis C); virus protein VP1, virus protein VP2, virus protein VP3, virus protein VP4, large hepaptitis delta antigen, small hepaptitis delta antigen (Hepatitis D Virus, Hepatitis D); virus protein VP1, virus protein VP2, virus protein VP3, virus protein VP4, capsid protein E2 (Hepatitis E Virus, Hepatitis E); glycoprotein L UL1, uracil-DNA glycosylase UL2, protein UL3, protein UL4, DNA replication protein UL5, portal protein UL6, virion maturation protein UL7, DNA helicase ULB, replication origin-binding protein UL9, glycoprotein M UL10, protein UL11, alkaline exonuclease UL12, serine-threonine protein kinase UL13, tegument protein UL14, terminase UL15, tegument protein UL16, protein UL17, capsid protein VP23 UL18, major capsid protein VP5 UL19, membrane protein UL20, tegument protein UL21, Glycoprotein H (UL22), Thymidine Kinase UL23, protein UL24, protein UL25, capsid protein P40 (UL26, VP24, VP22A), glycoprotein B (UL27), ICP18.5 protein (UL28), major DNA-binding protein ICP8 (UL29), DNA polymerase UL30, nuclear matrix protein UL31, envelope glycoprotein UL32, protein UL33, inner nuclear membrane protein UL34, capsid protein VP26 (UL35), large tegument protein UL36, capsid assembly protein UL37, VP19C protein (UL38), ribonucleotide reductase (Large subunit) UL39, ribonucleotide reductase (Small subunit) UL40, tegument protein/virion host shutoff VHS protein (UL41), DNA polymerase processivity factor UL42, membrane protein UL43, glycoprotein C (UL44), membrane protein UL45, tegument proteins VP11/12 (UL46), tegument protein VP13/14 (UL47), virion maturation protein VP16 (UL48, Alpha-TIF), envelope protein UL49, dUTP diphosphatase UL50, tegument protein UL51, DNA helicase/primase complex protein UL52, glycoprotein K (UL53), transcriptional regulation protein IE63 (ICP27, UL54), protein UL55, protein UL56, viral replication protein ICP22 (1E68, US1), protein US2, serine/threonine-protein kinase US3, glycoprotein G (US4), glycoprotein J (US5), glycoprotein D (US6), glycoprotein I (US7), glycoprotein E (US8), tegument protein US9, capsid/tegument protein US10, Vmw21 protein (US11), ICP47 protein (IE12, US12), major transcriptional activator ICP4 (IE175, RS1), E3 ubiquitin ligase ICP0 (IE110), latency-related protein 1 LRP1, latency-related protein 2 LRP2, neurovirulence factor RL1 (ICP34.5), latency-associated transcript LAT (Herpes simplex virus 1 and 2 (HSV-1 and HSV-2), Herpes simplex); heat shock protein Hsp60, cell surface protein H1C, dipeptidyl peptidase type IV DppIV, M antigen, 70 kDa protein, 17 kDa histone-like protein (*Histoplasma capsulatum*, Histoplasmosis); fatty acid and retinol binding protein-1 FAR-1, tissue inhibitor of metalloproteinase TIMP (TMP), cysteine proteinase ACEY-1, cysteine proteinase ACCP-1, surface antigen Ac-16, secreted protein 2 ASP-2, metalloprotease 1 MTP-1, aspartyl protease inhibitor API-1, surface-associated antigen SAA-1, surface-associated antigen SAA-2, adult-specific secreted factor Xa, serine protease inhibitor anticoagulant AP, cathepsin D-like aspartic protease ARR-1, glutathione S-transferase GST, aspartic protease APR-1, acetylcholinesterase AChE (*Ancylostoma duodenale* and *Necator americanus*, Hookworm infection); protein NS1, protein NP1, protein VP1, protein VP2, protein VP3 (Human bocavirus (HBoV), Human bocavirus infection); major surface protein 2 MSP2, major surface protein 4 MSP4, MSP variant SGV1, MSP variant SGV2, outer membrane protein OMP, outer membrane protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia ewingii, Human ewingii* ehrlichiosis); major surface proteins 1-5 (MSP1a, MSP1b, MSP2, MSP3, MSP4, MSP5), type IV secreotion system proteins VirB2, VirB7, VirB11, VirD4 (*Anaplasma phagocytophilum*, Human granulocytic anaplasmosis (HGA)); protein NS1, small hydrophobic protein NS2, SH protein, fusion protein F, glycoprotein G, matrix protein M, matrix protein M2-1, matrix protein M2-2, phosphoprotein P, nucleoprotein N, polymerase L (Human metapneumovirus (hMPV), Human metapneumovirus infection); major surface protein 2 MSP2, major surface protein 4 MSP4, MSP variant SGV1, MSP variant SGV2, outer membrane protein OMP, outer membrande protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia chaffeensis*, Human monocytic ehrlichiosis); replication protein E1, regulatory protein E2, protein E3, protein E4, protein E5, protein E6, protein E7, protein E8, major capsid protein L1, minor capsid protein L2 (Human papillomavirus (HPV), Human papillomavirus (HPV) infection); fusion protein F, hemagglutinin-neuramidase HN, glycoprotein G, matrix protein M, phosphoprotein P, nucleoprotein N, polymerase L (Human parainfluenza viruses (HPIV), Human parainfluenza virus infection); Hemagglutinin (HA), Neuraminidase (NA), Nucleoprotein (NP), M1 protein, M2 protein, NS1 protein, NS2 protein (NEP protein: nuclear export protein), PA protein, PB1 protein (polymerase basic 1 protein), PB1-F2 protein and PB2 protein (Orthomyxoviridae family, Influenza virus (flu)); genome polyprotein, protein E, protein M, capsid protein C (Japanese encephalitis virus, Japanese encephalitis); RTX toxin, type IV pili, major pilus subunit PilA, regulatory transcription factors PilS and PilR, protein sigma54, outer membrane proteins (*Kingella kingae, Kingella kingae* infection); prion protein (Kuru prion, Kuru); nucleoprotein N, polymerase L, matrix protein Z, glycoprotein GP (Lassa virus, Lassa fever); peptidoglycan-associated lipoprotein PAL, 60 kDa chaperonin Cpn60 (groEL, HspB), type IV pilin PilE, outer membrane protein MIP, major outer membrane protein MompS, zinc metalloproteinase MSP (*Legionella pneumophila*, Legionellosis (Legionnaires' disease, Pontiac fever)); P4 nuclease, protein WD, ribonucleotide reductase M2, surface membrane glycoprotein Pg46, cysteine proteinase CP, glucose-regulated protein 78 GRP-78, stage-specific S antigen-like protein A2, ATPase F1, beta-tubulin, heat shock protein 70 Hsp70, KMP-11, glycoprotein GP63, protein BT1, nucleoside hydrolase NH, cell surface protein B1, ribosomal protein P1-like protein P1, sterol 24-c-methyltransferase SMT, LACK protein, histone H1, SPB1 protein, thiol specific antioxidant TSA, protein antigen STl1, signal peptidase SP, histone H2B, suface antigen PSA-2, cystein proteinase b Cpb (*Leishmania* genus, Leishmaniasis); major membrane protein I, serine-rich antigen-45 kDa, 10 kDa caperonin GroES, HSP kDa antigen, amino-oxononanoate synthase AONS, protein recombinase A RecA, Acetyl-/propionyl-coenzyme A carboxylase alpha, alanine racemase, 60 kDa chaperonin 2, ESAT-6-like protein EcxB (L-ESAT-6), protein Lsr2, protein ML0276, Heparin-binding hemagglutinin HBHA, heat-shock protein 65 Hsp65, mycP1 or ML0041 coding protein, htrA2 or ML0176 coding protein, htrA4 or ML2659 coding protein, gcp or ML0379 coding protein, clpC or ML0235 coding protein (*Mycobacterium leprae* and *Mycobacterium* lepromatosis, Leprosy); outer membrane protein LipL32, membrane protein LIC10258, membrane protein LP30, membrane protein LIC12238, Ompa-like protein Lsa66, surface protein LigA, surface protein LigB, major outer membrane protein OmpL1, outer membrane protein LipL41, protein LigAni, surface protein LcpA, adhesion protein LipL53, outer membrane protein UpL32, surface protein Lsa63, flagellin FlaB1, membran lipoprotein LipL21, membrane protein pL40, leptospiral surface adhesin Lsa27, outer membrane protein OmpL36, outer membrane protein OmpL37, outer membrane protein OmpL47, outer membrane protein OmpL54, acyltransferase LpxA (*Leptospira* genus, Leptospirosis); listeriolysin O precursor Hly (LLO), invasion-associated protein Iap (P60), Listeriolysin regulatory protein PrfA, Zinc metalloproteinase Mpl, Phosphatidylinositol-specific phospholipase C PLC (PlcA, PlcB), 0-acetyltransferase Oat, ABC-transporter permease Im.G_1771, adhesion protein LAP, LAP receptor Hsp60, adhesin LapB, haemolysin listeriolysin O LLO, protein ActA, Internalin A In1A, protein 1n1B (*Listeria monocytogenes*, Listeriosis); outer surface protein A OspA, outer surface protein OspB, outer surface protein OspC, decorin binding protein A DbpA, decorin binding protein B DbpB, flagellar filament 41 kDa core protein Fla, basic membrane protein A BmpA (Immunodominant antigen P39), outer surface 22 kDa lipoprotein precursor (antigen IPLA7), variable surface lipoprotein vlsE (usually *Borrelia burgdorferi* and other *Borrelia* species, Lyme disease (Lyme borreliosis)); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, protein Cox-2 (*Wuchereria bancrofti* and *Brugia malayi*, Lymphatic filariasis (Elephantiasis)); glycoprotein GP, matrix protein Z, polymerase L, nucleoprotein N (Lymphocytic choriomeningitis virus (LCMV), Lymphocytic choriomeningitis); thrombospondin-related anonymous protein TRAP, SSP2 Sporozoite surface protein 2, apical membrane antigen 1 AMA1, rhoptry membrane antigen RMA1, acidic basic repeat antigen ABRA, cell-traversal protein PF, protein Pvs25, merozoite surface protein 1 MSP-1, merozoite surface protein 2 MSP-2, ring-infected erythrocyte surface antigen RESALiver stage antigen 3 LSA-3, protein Eba-175, serine repeat antigen 5 SERA-5, circumsporozoite protein CS, merozoite surface protein 3 MSP3, merozoite surface protein 8 MSP8, enolase PF10, hepatocyte erythrocyte protein 17 kDa HEP17, erythrocyte membrane protein 1 EMP1, protein Kbetamerozoite surface protein 4/5 MSP 4/5, heat shock protein Hsp90, glutamate-rich protein GLURP, merozoite surface protein 4 MSP-4, protein STARP, circumsporozoite protein-related antigen precursor CRA (*Plasmodium* genus, Malaria); nucleoprotein N, membrane-associated protein VP24, minor nucleoprotein VP30, polymerase cofactor VP35, polymerase L, matrix protein VP40, envelope glycoprotein GP (Marburg virus, Marburg hemorrhagic fever (MHF)); protein C, matrix protein M, phosphoprotein P, non-structural protein V, hemagglutinin glycoprotein H, polymerase L, nucleoprotein N, fusion protein F (Measles virus, Measles); members of the ABC transporter family (Lo1C, OppA, and PotF), putative lipoprotein releasing system transmembrane protein Lo1C/E, flagellin FliC, *Burkholderia* intracellular motility A BimA, bacterial Elongation factor-Tu EF-Tu, 17 kDa OmpA-like protein, boaA coding protein, boaB coding protein (*Burkholderia pseudomallei*, Melioidosis (Whitmore's disease)); pilin proteins, minor pilin-associated subunit pi1C, major pilin subunit and variants pilE, pilS, phase variation protein porA, Porin B PorB, protein TraD, Neisserial outer membrane antigen H.8, 70 kDa antigen, major outer membrane protein PI, outer membrane proteins HA and P1B, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR, factor H-binding protein fHbp, adhesin NadA, protein NhbA, repressor FarR (*Neisseria meningitidis*, Meningococcal disease); 66 kDa protein, 22 kDa protein (usually *Metagonimus* yokagawai, Metagonimiasis); polar tube proteins (34, 75, and 170 kDa in Glugea, 35, 55 and 150 kDa in Encephalitozoon), kinesin-related protein, RNA polymerase II largest subunit, similar of integral membrane protein YIPA, anti-silencing protein 1, heat shock transcription factor HSF, protein kinase, thymidine kinase, NOP-2 like nucleolar protein (Microsporidia phylum, Microsporidiosis); CASP8 and FADD-like apoptosis regulator, Glutathione peroxidase GPX1, RNA helicase NPH-II NPH2, Poly(A) polymerase catalytic subunit PAPL, Major envelope protein P43K, early transcription factor 70 kDa subunit VETFS, early transcription factor 82 kDa subunit VETFL, metalloendopeptidase G1-type, nucleoside triphosphatase I NPH1, replication protein A28-like MC134L, RNA polymease 7 kDa subunit RPO7 (*Molluscum contagiosum* virus (MCV), *Molluscum contagiosum* (MC)); matrix protein M, phosphoprotein P/V, small hydrophobic protein SH, nucleoprotein N, protein V, fusion glycoprotein F, hemagglutinin-neuraminidase HN, RNA polymerase L (Mumps virus, Mumps); Outer membrane proteins OM, cell surface antigen OmpA, cell surface antigen OmpB (sca5), cell surface protein SCA4, cell surface protein SCA1, intracytoplasmic protein D, crystalline surface layer protein SLP, protective surface protein antigen SPA (*Rickettsia typhi*, Murine typhus (Endemic typhus)); adhesin P1, adhesion P30, protein p116, protein P40, cytoskeletal protein HMW1, cytoskeletal protein HMW2, cytoskeletal protein HMW3, MPN152 coding protein, MPN426 coding protein, MPN456 coding protein, MPN-500coding protein (*Mycoplasma pneumoniae, Mycoplasma* pneumonia); NocA, Iron dependent regulatory protein, VapA, VapD, VapF, VapG, caseinolytic protease, filament tip-associated 43-kDa protein, protein P24, protein P61, 15-kDa protein, 56-kDa protein (usually *Nocardia asteroides* and other *Nocardia* species, Nocardiosis); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 (*Onchocerca volvulus*, Onchocerciasis (River blindness)); 43 kDa secreted glycoprotein, glycoprotein gp0, glycoprotein gp75, antigen Pb27, antigen Pb40, heat shock protein Hsp65, heat shock protein Hsp70, heat shock protein Hsp90, protein P10, triosephosphate isomerase TPI, N-acetyl-glucosamine-binding lectin Paracoccin, 28 kDa protein Pb28 (*Paracoccidioides brasiliensis*, Paracoccidioidomycosis (South American blastomycosis)); 28-kDa cruzipain-like cystein protease Pw28CCP (usually *Paragonimus westermani* and other *Paragonimus* species, Paragonimiasis); outer membrane protein OmpH, outer membrane protein Omp28, protein PM1539, protein PM0355, protein PM1417, repair protein MutL, protein BcbC, prtein PM0305, formate dehydrogenase-N, protein PM0698, protein PM1422, DNA gyrase, lipoprotein PlpE, adhesive protein Cp39, heme aquisition system receptor HasR, 39 kDa capsular protein, iron-regulated OMP TROMP, outer membrane protein OmpA87, fimbrial protein Ptf, fimbrial subunit protein PtfA, transferrin binding protein Tbp1, esterase enzyme MesA, *Pasteurella multocida* toxin PMT, adhesive protein Cp39 (*Pasteurella* genus, Pasteurellosis); "filamentous hemagglutinin FhaB, adenylate cyclase CyaA, pertussis toxin subunit 4 precursor PtxD, pertactin precursor Prn, toxin subunit 1 PtxA, protein Cpn60, protein brkA, pertussis toxin subunit 2 precursor PtxB, pertussis toxin subunit 3 precursor PtxC, pertussis toxin subunit 5 precursor PtxE, pertactin Prn, protein Fim2, protein Fim3;" (*Bordetella pertussis*, Pertussis (Whooping cough)); "F1 capsule antigen, virulence-associated V antigen, secreted effector protein LcrV, V antigen, outer membrane protease Pla, secreted effector protein YopD, putative secreted protein-tyrosine phosphatase YopH, needle complex major subunit YscF, protein kinase YopO, putative autotransporter protein YapF, inner membrane ABC-transporter YbtQ (Irp7), putative sugar binding protein YPO0612, heat shock protein 90 HtpG, putative sulfatase protein YdeN, outer-membrane lipoprotein carrier protein Lo1A, secretion chaperone YerA, putative lipoprotein YP00420, hemolysin activator protein HpmB, pesticin/yersiniabactin outer membrane receptor Psn, secreted effector protein YopE, secreted effector protein YopF, secreted effector protein YopK, outer membrane protein YopN, outer membrane protein YopM, Coagulase/fibrinolysin precursor Pla;" (*Yersinia pestis*, Plague); protein PhpA, surface adhesin PsaA, pneumolysin Ply, ATP-dependent protease Clp, lipoate-protein ligase Lp1A, cell wall surface anchored protein psrP, sortase SrtA, glutamyl-tRNA synthetase GltX, choline binding protein A CbpA, pneumococcal surface protein A PspA, pneumococcal surface protein C PspC, 6-phosphogluconate dehydrogenase Gnd, iron-binding protein PiaA, Murein hydrolase LytB, proteon LytC, protease A1 (*Streptococcus pneumoniae*, Pneumococcal infection); major surface protein B, kexin-like protease KEX1, protein A12, 55 kDa antigen P55, major surface glycoprotein Msg (*Pneumocystis jirovecii, Pneumocystis* pneumonia (PCP)); genome polyprotein, polymerase 3D, viral capsid protein VP1, viral capsid protein VP2, viral capsid protein VP3, viral capsid protein VP4, protease 2A, protease 3C (Poliovirus, Poliomyelitis); protein Nfal, exendin-3, secretory lipase, cathepsin B-like protease, cysteine protease, cathepsin, peroxiredoxin, protein CrylAc (usually *Naegleria fowleri*, Primary amoebic meningoencephalitis (PAM)); agnoprotein, large T antigen, small T antigen, major capsid protein VP1, minor capsid protein Vp2 (JC virus, Progressive multifocal leukoencephalopathy); low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 Omp2, polymorphic membrane protein family (Pmp1, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20, Pmp21) (*Chlamydophila psittaci*, Psittacosis); outer membrane protein P1, heat shock protein B HspB, peptide ABC transporter, GTP-binding protein, protein IcmB, ribonuclease R, phosphatas SixA, protein DsbD, outer membrane protein TolC, DNA-binding protein PhoB, ATPase DotB, heat shock protein B HspB, membrane protein Com1, 28 kDa protein, DNA-3-methyladenine glycosidase I, pouter membrane protein OmpH, outer membrane protein AdaA, glycine cleavage system T-protein (*Coxiella burnetii*, Q fever); nucleoprotein N, large structural protein L, phophoprotein P, matrix protein M, glycoprotein G (Rabies virus, Rabies); fusionprotein F, nucleoprotein N, matrix protein M, matrix protein M2-1, matrix protein M2-2, phophoprotein P, small hydrophobic protein SH, major surface glycoprotein G, polymerase L, non-structural protein 1 NS1, non-structural protein 2 NS2 (Respiratory syncytial virus (RSV), Respiratory syncytial virus infection); genome polyprotein, polymerase 3D, viral capsid protein VP1, viral capsid protein VP2, viral capsid protein VP3, viral capsid protein VP4, protease 2A, protease 3C (Rhinovirus, Rhinovirus infection); outer membrane proteins OM, cell surface antigen OmpA, cell surface antigen OmpB (sca5), cell surface protein SCA4, cell surface protein SCA1, protein PS120, intracytoplasmic protein D, protective surface protein antigen SPA (*Rickettsia* genus, Rickettsial infection); outer membrane proteins OM, cell surface antigen OmpA, cell surface antigen OmpB (sca5), cell surface protein SCA4, cell surface protein SCA1, intracytoplasmic protein D (*Rickettsia akari*, Rickettsialpox); envelope glycoprotein GP, polymerase L, nucleoprotein N, non-structural protein NSS (Rift Valley fever virus, Rift Valley fever (RVF)); outer membrane proteins OM, cell surface antigen OmpA, cell surface antigen OmpB (sca5), cell surface protein SCA4, cell surface protein SCA1, intracytoplasmic protein D (*Rickettsia rickettsii*, Rocky mountain spotted fever (RMSF)); "non-structural protein 6 NS6, non-structural protein 2 NS2, intermediate capsid protein VP6, inner capsid protein VP2, non-structural protein 3 NS3, RNA-directed RNA polymerase L, protein VP3, non-structural protein 1 NS1, non-structural protein 5 NS5, outer capsid glycoprotein VP7, non-structural glycoprotein 4 NS4, outer capsid protein VP4;" (Rotavirus, Rotavirus infection); polyprotein P200, glycoprotein E1, glycoprotein E2, protein NS2, capsid protein C (Rubella virus, Rubella); chaperonin GroEL (MopA), inositol phosphate phosphatase SopB, heat shock protein HslU, chaperone protein DnaJ, protein TviB, protein IroN, flagellin FliC, invasion protein SipC, glycoprotein gp43, outer membrane protein LamB, outer membrane protein PagC, outer membrane protein TolC, outer membrane protein NmpC, outer membrane protein FadL, transport protein SadA, transferase WgaP, effector proteins SifA, SteC, SseL, SseJ and SseF (*Salmonella* genus, *Salmonellosis*); "protein 14, non-structural protein NS7b, non-structural protein NS8a, protein 9b, protein 3a, nucleoprotein N, non-structural protein NS3b, non-structural protein NS6, protein 7a, non-structural protein NS8b, membrane protein M, envelope small membrane protein EsM, replicase polyprotein 1a, spike glycoprotein S, replicase polyprotein lab;" (SARS coronavirus, SARS (Severe Acute Respiratory Syndrome)); serin protease, Atypical *Sarcoptes* Antigen 1 ASA1, glutathione S-transferases GST, cystein protease, serine protease, apolipoprotein (*Sarcoptes scabiei*, Scabies); glutathione S-transferases GST, paramyosin, hemoglbinase SM32, major egg antigen, 14 kDa fatty acid-binding protein Sm14, major larval surface antigen P37, 22.6 kDa tegumental antigen, calpain CANP, triphospate isomerase Tim, surface protein 9B, outer capsid protein VP2, 23 kDa integral membrane protein Sm23, Cu/Zn-superoxide dismutase, glycoprotein Gp, myosin (*Schistosoma* genus, Schistosomiasis (Bilharziosis)); 60 kDa chaperonin, 56 kDa type-specific antigen, pyruvate phosphate dikinase, 4-hydroxybenzoate octaprenyltransferase (*Orientia tsutsugamushi*, Scrub typhus); dehydrogenase GuaB, invasion protein Spa32, invasin IpaA, invasin IpaB, invasin IpaC, invasin IpaD, invasin IpaH, invasin IpaJ (*Shigella* genus, Shigellosis (Bacillary dysentery)); protein P53, virion protein US10 homolog, transcriptional regulator IE63, transcriptional transactivator IE62, protease P33, alpha trans-inducing factor 74 kDa protein, deoxyuridine 5'-triphosphate nucleotidohydrolase, transcriptional transactivator IE4, membrane protein UL43 homolog, nuclear phosphoprotein UL3 homolog, nuclear protein UL4 homolog, replication origin-binding protein, membrane protein 2, phosphoprotein 32, protein 57,DNA polymerase processivity factor, portal protein 54, DNA primase, tegument protein UL14 homolog, tegument protein UL21 homolog, tegument protein UL55 homolog, tripartite terminase subunit UL33 homolog, tripartite terminase subunit UL15 homolog, capsid-binding protein 44, virion-packaging protein 43 (Varicella zoster virus (VZV), Shingles (Herpes zoster)); truncated 3-beta hydroxy-5-ene steroid dehydrogenase homolog, virion membrane protein A13, protein A19, protein A31, truncated protein A35 homolog, protein A37.5 homolog, protein A47, protein A49, protein A51, semaphorin-like protein A43, serine proteinase inhibitor 1, serine proteinase inhibitor 2, serine proteinase inhibitor 3, protein A6, protein B15, protein C1, protein C5, protein C6, protein F7, protein F8, protein F9, protein F11, protein F14, protein F15, protein F16 (Variola major or Variola minor, Smallpox (Variola)); adhesin/glycoprotein gp70, proteases (*Sporothrix schenckii*, Sporotrichosis); heme-iron binding protein IsdB, collagen adhesin Cna, clumping factor A ClfA, protein MecA, fibronectin-binding protein A FnbA, enterotoxin type A EntA, enterotoxin type B EntB, enterotoxin type C EntC1, enterotoxin type C EntC2, enterotoxin type D EntD, enterotoxin type E EntE, Toxic shock syndrome toxin-1 TSST-1, Staphylokinase, Penicillin binding protein 2a PBP2a (MecA), secretory antigen SssA (*Staphylococcus* genus, Staphylococcal food poisoning); heme-iron binding protein IsdB, collagen adhesin Cna, clumping factor A ClfA, protein MecA, fibronectin-binding protein A FnbA, enterotoxin type A EntA, enterotoxin type B EntB, enterotoxin type C EntC1, enterotoxin type C EntC2, enterotoxin type D EntD, enterotoxin type E EntE, Toxic shock syndrome toxin-1 TSST-1, Staphylokinase, Penicillin binding protein 2a PBP2a (MecA), secretory antigen SssA (*Staphylococcus* genus e.g. *aureus*, Staphylococcal infection); antigen Ss-IR, antigen NIE, strongylastacin, Na+-K+ ATPase Sseat-6, tropomysin SsTmy-1, protein LEC-5, 41 kDa aantigen P5, 41-kDa larval protein, 31-kDa larval protein, 28-kDa larval protein (*Strongyloides stercoralis*, Strongyloidiasis); glycerophosphodiester phosphodiesterase GlpQ (Gpd), outer membrane protein TmpB, protein Tp92, antigen TpF1, repeat protein Tpr, repeat protein F TprF, repeat protein G TprG, repeat protein I TprI, repeat protein J TprJ, repeat protein K TprK, treponemal membrane protein A TmpA, lipoprotein, 15 kDa Tpp15, 47 kDa membrane antigen, miniferritin TpF1, adhesin Tp0751, lipoprotein TP0136, protein TpN17, protein TpN47, outer membrane protein TP0136, outer membrane protein TP0155, outer membrane protein TP0326, outer membrane protein TP0483, outer membrane protein TP0956 (*Treponema pallidum*, Syphilis); Cathepsin L-like proteases, 53/25-kDa antigen, 8 kDa family members, cysticercus protein with a marginal trypsin-like activity TsAg5, oncosphere protein TSOL18, oncosphere protein TSOL45-1A, lactate dehydrogenase A LDHA, lactate dehydrogenase B LDHB (*Taenia* genus, Taeniasis); tetanus toxin TetX, tetanus toxin C TTC, 140 kDa S layer protein, flavoprotein beta-subunit CT3, phospholipase (lecithinase), phosphocarrier protein HPr (*Clostridium tetani*, Tetanus (Lockjaw)); genome polyprotein, protein E, protein M, capsid protein C (Tick-borne encephalitis virus (TBEV), Tick-borne encephalitis); 58-kDa antigen, 68-kDa antigens, *Toxocara* larvae excretory-secretory antigen TES, 32-kDa glycoprotein, glycoprotein TES-70, glycoprotein GP31, excretory-secretory antigen TcES-57, perienteric fluid antigen Pe, soluble extract antigens Ex, excretory/secretory larval antigens ES, antigen TES-120, polyprotein allergen TBA-1, cathepsin L-like cysteine protease c-cp1-1, 26-kDa protein (*Toxocara canis* or *Toxocara cati*, Toxocariasis (Ocular Larva Migrans (OLM) and Visceral Larva Migrans (VLM))); microneme proteins (MIC1, MIC2, MICS, MIC4, MICS, MICE, MIC7, MIC8), rhoptry protein Rop2, rhoptry proteins (Rop1, Rop2, Rop3, Rop4, Rop5, Rop6, Rop7, Rop16, Rjop17), protein SR1, surface antigen P22, major antigen p24, major surface antigen p30, dense granule proteins (GRA1, GRA2, GRAS, GRA4, GRAS, GRA6, GRA7, GRAB, GRA9, GRA10), 28 kDa antigen, surface antigen SAG1, SAG2 related antigen, nucleoside-triphosphatase 1, nucleoside-triphosphatase 2, protein Stt3, HesB-like domain-containing protein, rhomboid-like protease 5, toxomepsin 1 (*Toxoplasma gondii*, Toxoplasmosis); 43 kDa secreted glycoprotein, 53 kDa secreted glycoprotein, paramyosin, antigen Ts21, antigen Ts87, antigen p46000, TSL-1 antigens, caveolin-1 CAV-1, 49 kDa newborn larva antigen, prosaposin homologue, serine protease, serine proteinase inhibitor, 45 kDa glycoprotein Gp45 (*Trichinella spiralis*, Trichinellosis); Myb-like transcriptional factors (Myb1, Myb2, Myb3), adhesion protein AP23, adhesion protein AP33, adhesin protein AP33-3, adhesins AP51, adhesin AP65, adhesion protein AP65-1, alpha-actinin, kinesin-associated protein, teneurin, 62 kDa proteinase, subtilisin-like serine protease SUB1, cysteine proteinase gene 3 CP3, alpha-enolase Enol, cysteine proteinase CP30, heat shock proteins (Hsp70, Hsp60), immunogenic protein P270, (*Trichomonas vaginalis*, Trichomoniasis); beta-tubulin, 47-kDa protein, secretory leucocyte-like proteinase-1 SLP-1, 50-kDa protein TT50, 17 kDa antigen, 43/47 kDa protein (*Trichuris trichiura*, Trichuriasis (Whipworm infection)); protein ESAT-6 (EsxA), 10 kDa filtrate antigen EsxB, secreted antigen 85-B FBPB, fibronectin-binding protein A FbpA (Ag85A), serine protease PepA, PPE family protein PPE18, fibronectin-binding protein D FbpD, immunogenic protein MPT64, secreted protein MPT51, catalase-peroxidase-peroxynitritase T KATG, periplasmic phosphate-binding lipoprotein PSTS3 (PBP-3, Phos-1), iron-regulated heparin binding hemagglutinin Hbha, PPE family protein PPE14, PPE family protein PPE68, protein Mtb72F, protein Apa, immunogenic protein MPT63, periplasmic phosphate-binding lipoprotein PSTS1 (PBP-1), molecular chaperone DnaK, cell surface lipoprotein Mpt83, lipoprotein P23, phosphate transport system permease protein pstA, 14 kDa antigen, fibronectin-binding protein C FbpC1, Alanine dehydrogenase TB43, Glutamine synthetase 1, ESX-1 protein, protein CFP10, TB10.4 protein, protein MPT83, protein MTB12, protein MTBE, Rpf-like proteins, protein MTB32, protein MTB39, crystallin, heat-shock protein HSP65, protein PST-S (usually *Mycobacterium tuberculosis*, Tuberculosis); outer membrane protein FobA, outer membrane protein FobB, intracellular growth locus 1glC1, intracellular growth locus IglC2, aminotransferase Wbtl, chaperonin GroEL, 17 kDa major membrane protein TUL4, lipoprotein LpnA, chitinase family 18 protein, isocitrate dehydrogenase, Nif3 family protein, type IV pili glycosylation protein, outer membrane protein tolC, FAD binding family protein, type IV pilin multimeric outer membrane protein, two component sensor protein KdpD, chaperone protein DnaK, protein TolQ (*Francisella tularensis*, Tularemia); "MB antigen, urease, protein GyrA, protein GyrB, protein ParC, protein ParE, lipid associated membrane proteins LAMP, thymidine kinase TK, phospholipase PL-A1, phospholipase PL-A2, phospholipase PL-C, surface-expressed 96-kDa antigen;" (*Ureaplasma urealyticum, Ureaplasma urealyticum* infection); non-structural polyprotein, structural polyprotein, capsid protein CP, protein E1, protein E2, protein E3, protease P1, protease P2, protease P3 (Venezuelan equine encephalitis virus, Venezuelan equine encephalitis); glycoprotein GP, matrix protein Z, polymerase L, nucleoprotein N (Guanarito virus, Venezuelan hemorrhagic fever); polyprotein, protein E, protein M, capsid protein C, protease NS3, protein NS1, protein NS2A, protein AS2B, protein NS4A, protein NS4B, protein NS5 (West Nile virus, West Nile Fever); cpasid protein CP, protein E1, protein E2, protein E3, protease P2 (Western equine encephalitis virus, Western equine encephalitis); genome polyprotein, protein E, protein M, capsid protein C, protease NS3, protein NS1, protein NS2A, protein AS2B, protein NS4A, protein NS4B, protein NS5 (Yellow fever virus, Yellow fever); putative Yop targeting protein YobB, effector protein YopD, effector protein YopE, protein YopH, effector protein YopJ, protein translocation protein YopK, effector protein YopT, protein YpkA, flagellar biosyntheses protein FlhA, peptidase M48, potassium efflux system KefA, transcriptional regulator RovA, adhesin Ifp, translocator portein LcrV, protein PcrV, invasin Inv, outer membrane protein OmpF-like porin, adhesin YadA, protein kinase C, phospholipase C1, protein PsaA, mannosyltransferase-like protein WbyK, protein YscU, antigen YPMa (*Yersinia pseudotuberculosis, Yersinia pseudotuberculosis* infection); effector protein YopB, 60 kDa chaperonin, protein WbcP, tyrosin-protein phosphatase YopH, protein YopQ, enterotoxin, Galactoside permease, reductase NrdE, protein YasN, Invasin Inv, adhesin YadA, outer membrane porin F OmpF, protein UspA1, protein EibA, protein Hia, cell surface protein Ail, chaperone SycD, protein LcrD, protein LcrG, protein LcrV, protein SycE, protein YopE, regulator protein TyeA, protein YopM, protein YopN, protein YopO, protein YopT, protein YopD, protease ClpP, protein MyfA, protein FilA, and protein PsaA (*Yersinia enterocolitica*, Yersiniosis) (given in brackets is the particular pathogen or the family of pathogens of which the antigen(s) is/are derived and the infectious disease with which the pathogen is associated).

In particularly preferred embodiments the pathogenic antigen is selected from

- HIV p24 antigen, HIV envelope proteins (Gp120, Gp41, Gp160), polyprotein GAG, negative factor protein Nef, trans-activator of transcription Tat if the infectious disease is HIV, preferably an infection with Human immunodeficiency virus,
- major outer membrane protein MOMP, probable outer membrane protein PMPC, outer membrane complex protein B OmcB, heat shock proteins Hsp60 HSP10, protein IncA, proteins from the type III secretion system, ribonucleotide reductase small chain protein NrdB, plasmid protein Pgp3, chlamydial outer protein N CopN, antigen CT521, antigen CT425, antigen CT043, antigen TC0052, antigen TC0189, antigen TC0582, antigen TC0660, antigen TC0726, antigen TC0816, antigen TC0828 if the infectious disease is an infection with *Chlamydia trachomatis,*
- pp65 antigen, membrane protein pp15, capsid-proximal tegument protein pp150, protein M45, DNA polymerase UL54, helicase UL105, glycoprotein gM, glycoprotein gN, glycoprotein H, glycoprotein B gB, protein UL83, protein UL94, protein UL99 if the infectious disease is Cytomegalovirus infection, preferably an infection with Cytomegalovirus (CMV);
- capsid protein C, premembrane protein prM, membrane protein M, envelope protein E (domain I, domain II, domain II), protein NS1, protein NS2A, protein NS2B, protein NS3, protein NS4A, protein 2K, protein NS4B, protein NS5 if the infectious disease is Dengue fever, preferably an infection with Dengue viruses (DEN-1, DEN-2, DEN-3 and DEN-4)-Flaviviruses;
- hepatitis B surface antigen HBsAg, Hepatitis B core antigen HbcAg, polymerase, protein Hbx, preS2 middle surface protein, surface protein L, large S protein, virus protein VP1, virus protein VP2, virus protein VP3, virus protein VP4 if the infectious disease is Hepatits B, preferably an infection with Hepatitis B Virus (HBV);
- replication protein E1, regulatory protein E2, protein E3, protein E4, protein E5, protein E6, protein E7, protein E8, major capsid protein L1, minor capsid protein L2 if the infectious disease is Human papillomavirus (HPV) infection, preferably an infection with Human papillomavirus (HPV);
- fusion protein F, hemagglutinin-neuramidase HN, glycoprotein G, matrix protein M, phosphoprotein P, nucleoprotein N, polymerase L if the infectious disease is Human parainfluenza virus infection, preferably an infection with Human parainfluenza viruses (HPIV);
- Hemagglutinin (HA), Neuraminidase (NA), Nucleoprotein (NP), M1 protein, M2 protein, NS1 protein, NS2 protein (NEP protein: nuclear export protein), PA protein, PB1 protein (polymerase basic 1 protein), PB1-F2 protein and PB2 protein (Orthomyxoviridae family, Influenza virus (flu));
- nucleoprotein N, large structural protein L, phosphoprotein P, matrix protein M, glycoprotein G if the infectious disease is Rabies, preferably an infection with Rabies virus;
- fusionprotein F, nucleoprotein N, matrix protein M, matrix protein M2-1, matrix protein M2-2, phosphoprotein P, small hydrophobic protein SH, major surface glycoprotein G, polymerase L, non-structural protein 1 NS1, non-structural protein 2 NS2 if the infectious disease is Respiratory syncytial virus infection, preferably an infection with Respiratory syncytial virus (RSV);
- secretory antigen SssA (*Staphylococcus* genus, Staphylococcal food poisoning); secretory antigen SssA (*Staphylococcus* genus e.g. *aureus*, Staphylococcal infection); molecular chaperone DnaK, cell surface lipoprotein Mpt83, lipoprotein P23, phosphate transport system permease protein pstA, 14 kDa antigen, fibronectin-binding protein C FbpC1, Alanine dehydrogenase TB43, Glutamine synthetase 1, ESX-1 protein, protein CFP10, TB10.4 protein, protein MPT83, protein MTB12, protein MTB8, Rpf-like proteins, protein MTB32, protein MTB39, crystallin, heat-shock protein HSP65, protein PST-S if the infectious disease is Tuberculosis, preferably an infection with *Mycobacterium tuberculosis;* genome polyprotein, protein E, protein M, capsid protein C, protease NS3, protein NS1, protein NS2A, protein AS2B, protein NS4A, protein NS4B, protein NS5 if the infectious disease is Yellow fever, preferably an infection with Yellow fever virus.

The n different RNA molecule species may also each encode for a different isoform or variant of a cancer or tumor antigen selected from the group consisting of 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD1, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gpl 00, GPC3, GPNMB/m, HAGE, HAST-2, hepsin, Her2/neu, HERV-K-MEL, HLA-A*0201-R1 71, HLA-A1 1/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, MEI/m, mesothelin, MG50/PXDN, MMP1 1, MN/CA IX-antigen, MRP-3, MUC-1, MUC-2, MUM-1/m, MUM-2/m, MUM-3/m, myosin class 1/m, NA88-A, N-acetylglucosaminyltransferase-V, Neo-PAP, Neo-PAP/m, NFYC/m, NGEP, NMP22, NPM/ALK, N-Ras/m, NSE, NY-ESO-B, NY-ESO-1, OA1, OFA-iLRP, OGT, OGT/m, OS-9, OS-9/m, osteocalcin, osteopontin, pi 5, p190 minor bcr-abl, p53, p53/m, PAGE-4, PAI-1, PAI-2, PAP, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK m, RAGE-1, RBAF600/m, RHAMM/CD1 68, RU1, RU2, S-100, SAGE, SART-1, SART-2, SART-3, SCC, SIRT2/m, Sp17, SSX-1, SSX-2/HOM-MEL-40, SSX-4, STAMP-1, STEAP-1, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGFR1, VEGFR-2/FLK-1, and WT1.

The n different RNA molecule species may also each encode a different allergen associated with allergy or an allergic disease (allergens or allergenic antigens).

The n different RNA molecule species may also each encode for a different autoimmune self-antigens (autoantigens).

The n different RNA molecule species may also each encode a different therapeutic antibody selected from the group consisting of antibodies which are used inter alia for the treatment of cancer or tumour diseases, immune disorders, infectious diseases, Alzheimer's disease, asthma, and antibodies which are used for the treatment of diverse disorders, e.g. osteoporosis, tooth decay, idiopathic pulmonary fibrosis, focal segmental glomerulosclerosis, pain, muscular dystrophy, and Neovascular age-related macular degeneration.

The n different RNA molecule species may also each encode a different isoform or variant of a therapeutic protein selected from the goup consisting of a therapeutic protein which can be used inter alia in the treatment of metabolic or endocrine disorders.

These and other proteins are understood to be therapeutic, as they are meant to treat the subject by replacing its defective endogenous production of a functional protein in sufficient amounts. Accordingly, such therapeutic proteins are typically mammalian, in particular human proteins.

For the treatment of blood disorders, diseases of the circulatory system, diseases of the respiratory system, cancer or tumour diseases, infectious diseases or immunedeficiencies therapeutic proteins may be encoded by the n different RNA molecule species.

The n different RNA molecule species may also each encode a different isoform or variant of adjuvant proteins.

Furthermore, the RNA composition may be used for reprogramming of somatic cells into pluri- or omnipotent stem cells. For this purpose several factors are described, particularly Oct-3/4, Sox gene family (Sox1, Sox2, Sox3, and Sox15), Klf family (Klf1, Klf2, Klf4, and Klf5), Myc family (c-myc, L-myc, and N-myc), Nanog, and LIN28.

Preferably, infectious diseases in the sense of the invention are preferably selected from the group consisting of viral, bacterial, protozoological and prion infectious diseases. Such infectious diseases are typically selected from the list consisting of *Acinetobacter* infections, African sleeping sickness (African trypanosomiasis), AIDS (Acquired immunodeficiency syndrome), Amoebiasis, Anaplasmosis, Anthrax, Appendicitis, *Arcanobacterium haemolyticum* infections, Argentine hemorrhagic fever, Ascariasis, Aspergillosis, Astrovirus infections, Athlete's foot, Babesiosis, *Bacillus cereus* infections, Bacterial meningitis, Bacterial pneumonia, Bacterial vaginosis (BV), *Bacteroides* infections, Balantidiasis, *Baylisascaris* infections, Bilharziosis, BK virus infections, Black *piedra, Blastocystis hominis* infections, Blastomycosis, Bolivian hemorrhagic fever, *Borrelia* infectionss (Borreliosis), Botulism (and Infant botulism), Bovine tapeworm, Brazilian hemorrhagic fever, Brucellosis, *Burkholderia* infections, Buruli ulcer, Calicivirus infections (Norovirus and Sapovirus), Campylobacteriosis, Candidiasis (Candidosis), Canine tapeworm infections, Cat-scratch disease, Chagas Disease (American trypanosomiasis), Chancroid, Chickenpox, *Chlamydia* infections, *Chlamydia trachomatis* infections, *Chlamydophila pneumoniae* infections, Cholera, Chromoblastomycosis, Climatic bubo, Clonorchiasis, *Clostridium difficile* infections, Coccidioidomycosis, Cold, Colorado tick fever (CTF), Common cold (Acute viral rhinopharyngitis; Acute coryza), Condyloma *acuminata*, Conjunctivitis, Creutzfeldt-Jakob disease (CJD), Crimean-Congo hemorrhagic fever (CCHF), Cryptococcosis, Cryptosporidiosis, Cutaneous larva migrans (CLM), Cutaneous Leishmaniosis, Cyclosporiasis, Cysticercosis, Cytomegalovirus infections, Dengue fever, Dermatophytosis, Dienta-moebiasis, Diphtheria, Diphyllobothriasis, Donavanosis, Dracunculiasis, Early summer meningoencephalitis (FSME), Ebola hemorrhagic fever, Echinococcosis, Ehrlichiosis, Enterobiasis (Pinworm infections), *Enterococcus* infections, Enterovirus infections, Epidemic typhus, Epiglottitis, Epstein-Barr Virus Infectious Mono-nucleosis, Erythema infectiosum (Fifth disease), Exanthem subitum, Fasciolopsiasis, Fasciolosis, Fatal familial insomnia (FFI), Fifth disease, Filariasis, Fish poisoning (Ciguatera), Fish tapeworm, Flu, Food poisoning by *Clostridium perfringens*, Fox tapeworm, Free-living amebic infections, *Fusobacterium* infections, Gas gangrene, Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infections, Group B streptococcal infections, *Haemophilus influenzae* infections, Hand foot and mouth disease (HFMD), Hantavirus Pulmonary Syndrome (HPS), *Helicobacter pylori* infections, Hemolytic-uremic syndrome (HUS), Hemorrhagic fever with renal syndrome (HFRS), Henipavirus infections, Hepatitis A, Hepatitis B, Hepatitis C, Hepatitis D, Hepatitis E, Herpes simplex, Herpes simplex type I, Herpes simplex type II, Herpes zoster, Histoplasmosis, Hollow warts, Hookworm infections, Human bocavirus infections, Human *ewingii* ehrlichiosis, Human granulocytic anaplasmosis (HGA), Human metapneumovirus infections, Human monocytic ehrlichiosis, Human papillomavirus (HPV) infections, Human parainfluenza virus infections, Hymenolepiasis, Influenza, Isosporiasis, Japanese encephalitis, Kawasaki disease, Keratitis, *Kingella kingae* infections, Kuru, Lambliasis (Giardiasis), Lassa fever, Legionellosis (Legionnaires' disease, Pontiac fever), Leishmaniasis, Leprosy, Leptospirosis, Lice, Listeriosis, Lyme borreliosis, Lyme disease, Lymphatic filariasis (Elephantiasis), Lymphocytic choriomeningitis, Malaria, Marburg hemorrhagic fever (MHF), Marburg virus, Measles, Melioidosis (Whitmore's disease), Meningitis, Meningococcal disease, Metagonimiasis, Microsporidiosis, Miniature tapeworm, Miscarriage (prostate inflammation), *Molluscum contagiosum* (MC), Mononucleosis, Mumps, Murine typhus (Endemic typhus), Mycetoma, *Mycoplasma hominis, Mycoplasma* pneumonia, Myiasis, Nappy/diaper dermatitis, Neonatal conjunctivitis (*Ophthalmia neonatorum*), Neonatal sepsis (Chorioamnionitis), Nocardiosis, Noma, Norwalk virus infections, Onchocerciasis (River blindness), Osteomyelitis, Otitis media, Paracoccidio-idomycosis (South American blastomycosis), *Paragonimiasis, Paratyphus, Pasteurellosis, Pediculosis capitis* (Head lice), *Pediculosis corporis* (Body lice), *Pediculosis pubis* (Pubic lice, Crab lice), Pelvic inflammatory disease (PID), Pertussis (Whooping cough), Pfeiffer's glandular fever, Plague, Pneumococcal infections, Pneumocystis pneumonia (PCP), Pneumonia, Polio (childhood lameness), Poliomyelitis, Porcine tapeworm, *Prevotella* infections, Primary amoebic meningoencephalitis (PAM), Progressive multifocal leukoencephalopathy, Pseudo-croup, Psittacosis, Q fever, Rabbit fever, Rabies, Rat-bite fever, Reiter's syndrome, Respiratory syncytial virus infections (RSV), Rhinosporidiosis, Rhinovirus infections, Rickettsial infections, Rickettsialpox, Rift Valley fever (RVF), Rocky mountain spotted fever (RMSF), Rotavirus infections, Rubella, *Salmonella* paratyphus, *Salmonella* typhus, *Salmonellosis*, SARS (Severe Acute Respiratory Syndrome), Scabies, Scarlet fever, Schistosomiasis (Bilharziosis), Scrub typhus, Sepsis, Shigellosis (Bacillary dysentery), Shingles, Smallpox (Variola), Soft chancre, Sporotrichosis, Staphylococcal food poisoning, Staphylococcal infections, Strongyloidiasis, Syphilis, Taeniasis, Tetanus, Three-day fever, Tick-borne encephalitis, Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea *versicolor* (*Pityriasis versicolor*), Toxocariasis (Ocular Larva Migrans (OLM) and Visceral Larva Migrans (VLM)), Toxoplasmosis, Trichinellosis, Trichomoniasis, Trichuriasis (Whipworm infections), Tripper, Trypanosomiasis (sleeping sickness), Tsutsugamushi disease, Tuberculosis, Tularemia, Typhus, Typhus fever, *Ureaplasma urealyticum* infections, Vaginitis (Colpitis), Variant Creutzfeldt-Jakob disease (vCJD, nvCJD), Venezuelan equine encephalitis, Venezuelan hemorrhagic fever, Viral pneumonia, Visceral Leishmaniosis, Warts, West Nile Fever, Western equine encephalitis, White piedra (Tinea blanca), Whooping cough, Yeast fungus spots, Yellow fever, *Yersinia pseudotuberculosis* infections, Yersiniosis, and Zygomycosis.

Cancer and tumor-related diseases are selected from the group consisting of Acute lymphoblastic leukemia, Acute myeloid leukemia, Adrenocortical carcinoma, AIDS-related cancers, AIDS-related lymphoma, Anal cancer, Appendix cancer, Astro-cytoma, Basal cell carcinoma, Bile duct cancer, Bladder cancer, Bone cancer, Osteo-sarcoma/Malignant fibrous histiocytoma, Brainstem glioma, Brain tumor, cerebellar astrocytoma, cerebral astrocytoma/malignant glioma, ependymoma, medullo-blastoma, supratentorial primitive neuroectodermal tumors, visual pathway and hypothalamic glioma, Breast cancer, Bronchial adenomas/carcinoids, Burkitt lymphoma, childhood Carcinoid tumor, gastrointestinal Carcinoid tumor, Carcinoma of unknown primary, primary Central nervous system lymphoma, childhood Cerebellar astrocytoma, childhood Cerebral astrocytoma/Malignant glioma, Cervical cancer, Childhood cancers, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Ewing's sarcoma in the Ewing family of tumors, Childhood Extracranial germ cell tumor, Extragonadal Germ cell tumor, Extrahepatic bile duct cancer, Intraocular melanoma, Retinoblastoma, Gallbladder cancer, Gastric (Stomach) cancer, Gastrointestinal Carcinoid Tumor, Gastrointestinal stromal tumor (GIST), extracranial, extragonadal, or ovarian Germ cell tumor, Gestational trophoblastic tumor, Glioma of the brain stem, Childhood Cerebral Astrocytoma, Childhood Visual Pathway and Hypothalamic Glioma, Gastric carcinoid, Hairy cell leukemia, Head and neck cancer, Heart cancer, Hepatocellular (liver) cancer, Hodgkin lymphoma, Hypopharyngeal cancer, childhood Hypothalamic and visual pathway glioma, Intraocular Melanoma, Islet Cell Carcinoma (Endocrine Pancreas), Kaposi sarcoma, Kidney cancer (renal cell cancer), Laryngeal Cancer, Leukemias, acute lymphoblastic Leukemia, acute myeloid Leukemia, chronic lymphocytic Leukemia, chronic myelogenous Leukemia, hairy cell Leukemia, Lip and Oral Cavity Cancer, Liposarcoma, Liver Cancer, Non-Small Cell Lung Cancer, Small Cell Lung Cancer, Lymphomas, AIDS-related Lymphoma, Burkitt Lymphoma, cutaneous T-Cell Lymphoma, Hodgkin Lymphoma, Non-Hodgkin Lymphomas, Primary Central Nervous System Lymphoma, Waldenström Macroglobulinemia, Malignant Fibrous Histiocytoma of Bone/Osteosarcoma, Childhood Medulloblastoma, Melanoma, Intraocular (Eye) Melanoma, Merkel Cell Carcinoma, Adult Malignant Mesothelioma, Childhood Mesothelioma, Metastatic Squamous Neck Cancer with Occult Primary, Mouth Cancer, Childhood Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Chronic Myelogenous Leukemia, Adult Acute Myeloid Leukemia, Childhood Acute Myeloid Leukemia, Multiple Myeloma (Cancer of the Bone-Marrow), Chronic Myeloproliferative Disorders, Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, islet cell Pancreatic cancer, Paranasal sinus and nasal cavity cancer, Parathyroid cancer, Penile cancer, Pharyngeal cancer, Pheochromo-cytoma, Pineal astrocytoma, Pineal germinoma, childhood Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Cancer of the Renal pelvis and ureter, Retinoblastoma, childhood Rhabdo-myosarcoma, Salivary gland cancer, Sarcoma of the Ewing family of tumors, Kaposi Sarcoma, soft tissue Sarcoma, uterine Sarcoma, Sézary syndrome, Skin cancer (nonmelanoma), Skin cancer (melanoma), Merkel cell Skin carcinoma, Small intestine cancer, Squamous cell carcinoma, metastatic Squamous neck cancer with occult primary, childhood Supratentorial primitive neuroectodermal tumor, Testi-cular cancer, Throat cancer, childhood Thymoma, Thymoma and Thymic carcinoma, Thyroid cancer, childhood Thyroid cancer, Transitional cell cancer of the renal pelvis and ureter, gestational Trophoblastic tumor, Urethral cancer, endometrial Uterine cancer, Uterine sarcoma, Vaginal cancer, childhood Visual pathway and hypothalamic glioma, Vulvar cancer, Waldenström macroglobulinemia, and childhood Wilms tumor (kidney cancer).

Autoimmune disease selected from Addison disease (autoimmune adrenalitis, Morbus Addison), alopecia areata, Addison's anemia (Morbus Biermer), autoimmune hemolytic anemia (AIHA), autoimmune hemolytic anemia (AIHA) of the cold type (cold hemagglutinine disease, cold autoimmune hemolytic anemia (AIHA) (cold agglutinin disease), (CHAD)), autoimmune hemolytic anemia (AIHA) of the warm type (warm AIHA, warm autoimmune haemolytic anemia (AIHA)), autoimmune hemolytic Donath-Landsteiner anemia (paroxysmal cold hemo-globinuria), antiphospholipid syndrome (APS), atherosclerosis, autoimmune arthritis, arteriitis temporalis, Takayasu arteriitis (Takayasu's disease, aortic arch disease), temporal arteriitis/giant cell arteriitis, autoimmune chronic gastritis, autoimmune infertility, autoimmune inner ear disease (AIED), Basedow's disease (Morbus Basedow), Bechterew's disease (Morbus Bechterew, ankylosing spondylitis, spondylitis ankylosans), Behcet's syndrome (Morbus Behcet), bowel disease including autoimmune inflammatory bowel disease (including colitis ulcerosa (Morbus Crohn, Crohn's disease), cardiomyopathy, particularly autoimmune cardiomyopathy, idiopathic dilated cardiomyopathy (DCM), celiac sprue dermatitis (gluten mediated enteropathia), chronic fatigue immune dysfunction syndrome (CFIDS), chronic inflammatory demyelinating polyneuropathy (CIDP), chronic polyarthritis, Churg-Strauss syndrome, cicatricial pemphigoid, Cogan syndrome, CREST syndrome (syndrom with Calcinosis cutis, Raynaud phenomenon, motility disorders of the esophagus, sklerodaktylia and teleangiectasia), Crohn's disease (Morbus Crohn, colitis ulcerosa), dermatitis herpetiformis during, dermatologic autoimmune diseases, dermatomyositis, Diabetes, Diabetes mellitus Type 1 (type I diabetes, insuline dependent Diabetes mellitus), Diabetes mellitus Type 2 (type II diabetes), essential mixed cryoglobulinemia, essential mixed cryoglobulinemia, fibromyalgia, fibromyositis, Goodpasture syndrome (anti-GBM mediated glomerulonephritis), graft versus host disease, Guillain-Barré syndrome (GBM, Polyradikuloneuritis), haematologic autoimmune diseases, Hashimoto thyroiditis, hemophilia, acquired hemophilia, hepatitis, autoimmune hepatitis, particularly autoimmune forms of chronic hepatitis, idiopathic pulmonary fibrosis (IPF), idiopathic thrombocytopenic purpura, Immuno-thrombocytopenic purpura (Morbus Werlhof; ITP), IgA nephropathy, infertility, autoimmune infertility, juvenile rheumatoid arthritis (Morbus Still, Still syndrome), Lambert-Eaton syndrome, lichen planus, lichen sclerosus, lupus erythematosus, systemic lupus erythematosus (SLE), lupus erythematosus (discoid form), Lyme arthritis (Lyme disease, *borrelia* arthritis), Ménierè's disease (Morbus Ménierè); mixed connective tissue disease (MCTD), multiple sclerosis (MS, encephalomyelitis disseminate, Charcot's disease), Myasthenia gravis (myasthenia, MG), myosits, polymyositis, neural autoimmune diseases, neurodermitis, pemphigus vulgaris, bullous pemphigoid, scar forming pemphigoid; polyarteriitis *nodosa* (periarteiitis *nodosa*), polychondritis (panchon-dritis), polyglandular (autoimmune) syndrome (PGA syndrome, Schmidt's syn-drome), Polymyalgia rheumatica, primary agammaglobulinemia, primary biliary cirrhosis PBC, primary autoimmune cholangitis), progressive systemic sclerosis (PSS), Psoriasis, Psoriasis vulgaris, Raynaud's phenomena, Reiter's syndrome (Morbus Reiter, urethral conjunctive synovial syndrome)), rheumatoid arthritis (RA, chronic polyarthritis, rheumatic disease of the joints, rheumatic fever), sarcoidosis (Morbus Boeck, Besnier-Boeck-Schaumann disease), stiff-man syndrome, Sclero-dermia, Scleroderma, Sjögren's syndrome, sympathetic ophtalmia; Transient gluten intolerance, transplanted organ rejection, uveitis, autoimmune uveiitis, Vasculitis, Vitiligo, (leucoderma, piebold skin), and Wegner's disease (Morbus Wegner, Wegner's granulomatosis), or a fragment, variant or derivative of said autoimmune self-antigen.

Preferably, diseases as mentioned herein are preferably selected from infectious diseases, neoplasms (e.g. cancer or tumour diseases), diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system.

In this context particularly preferred are inherited diseases selected from 1p36 deletion syndrome; 18p deletion syndrome; 21-hydroxylase deficiency; 45, X (Turner syndrome); 47, XX,+21 (Down syndrome); 47, XXX (triple X syndrome); 47, XXY (Klinefelter syndrome); 47, XY,+21 (Down syndrome); 47, XYY syndrome; 5-ALA dehydratase-deficient *porphyria* (ALA dehydratase deficiency); 5-aminolaevulinic dehydratase deficiency *porphyria* (ALA dehydratase deficiency); 5p deletion syndrome (Cri du chat) 5p-syndrome (Cri du chat); A-T (ataxia-telangiectasia); AAT (alpha-1 antitrypsin deficiency); Absence of vas deferens (congenital bilateral absence of vas deferens); Absent vasa (congenital bilateral absence of vas deferens); aceruloplasminemia; ACG2 (achondrogenesis type II); ACH (achondroplasia); Achondrogenesis type II; achondroplasia; Acid beta-glucosidase deficiency (Gaucher disease type 1); Acrocephalosyndactyly (Apert) (Apert syndrome); acrocephalosyndactyly, type V (Pfeiffer syndrome); Acrocephaly (Apert syndrome); Acute cerebral Gaucher's disease (Gaucher disease type 2); acute intermittent *porphyria*; ACY2 deficiency (Canavan disease); AD (Alzheimer's disease); Adelaide-type craniosynostosis (Muenke syndrome); Adenomatous Polyposis *Coli* (familial adenomatous polyposis); Adenomatous Polyposis of the Colon (familial adeno-matous polyposis); ADP (ALA dehydratase deficiency); adenylosuccinate lyase deficiency; Adrenal gland disorders (21-hydroxylase deficiency); Adrenogenital syndrome (21-hydroxylase deficiency); Adrenoleukodystrophy; AIP (acute inter-mittent *porphyria*); AIS (androgen insensitivity syndrome); AKU (alkaptonuria); ALA dehydratase *porphyria* (ALA dehydratase deficiency); ALA-D *porphyria* (ALA dehydratase deficiency); ALA dehydratase deficiency; Alcaptonuria (alkaptonuria); Alexander disease; alkaptonuria; Alkaptonuric ochronosis (alkaptonuria); alpha-1 antitrypsin deficiency; alpha-1 proteinase inhibitor (alpha-1 antitrypsin deficiency); alpha-1 related emphysema (alpha-1 antitrypsin deficiency); Alpha-galactosidase A deficiency (Fabry disease); ALS (amyotrophic lateral sclerosis); Alstrom syndrome; ALX (Alexander disease); Alzheimer disease; Amelogenesis Imperfecta; Amino levulinic acid dehydratase deficiency (ALA dehydratase deficiency); Aminoacylase 2 deficiency (Canavan disease); amyotrophic lateral sclerosis; Anderson-Fabry disease (Fabry disease); androgen insensitivity syndrome; Anemia; Anemia, hereditary sideroblastic (X-linked sideroblastic anemia); Anemia, sex-linked hypo-chromic sideroblastic (X-linked sideroblastic anemia); Anemia, splenic, familial (Gaucher disease); Angelman syndrome; Angiokeratoma Corporis Diffusum (Fabry's disease); Angiokeratoma diffuse (Fabry's disease); Angiomatosis retinae (von Hippel-Lindau disease); ANH1 (X-linked sideroblastic anemia); APC resistance, Leiden type (factor V Leiden thrombophilia); Apert syndrome; AR deficiency (androgen insensitivity syndrome); AR-CMT2 ee (Charcot-Mare-Tooth disease, type 2); Arachnodactyly (Marfan syndrome); ARNSHL (Nonsyndromic deafness autosomal recessive); Arthro-ophthalmopathy, hereditary progressive (Stickler syndrome COL2A1); Arthrochalasis multiplex congenita (Ehlers-Danlos syndrome arthrochalasia type); AS (Angelman syndrome); Asp deficiency (Canavan disease); Aspa deficiency (Canavan disease); Aspartoacylase deficiency (Canavan disease); ataxia-telangiectasia; Autism-Dementia-Ataxia-Loss of Purposeful Hand Use syndrome (Rett syndrome); autosomal dominant juvenile ALS (amyotrophic lateral sclerosis, type 4); Autosomal dominant opitz G/BBB syndrome (22q11.2 deletion syndrome); autosomal recessive form of juvenile ALS type 3 (Amyotrophic lateral sclerosis type 2); Autosomal recessive nonsyndromic hearing loss (Nonsyndromic deafness autosomal recessive); Autosomal Recessive Sensorineural Hearing Impairment and Goiter (Pendred syndrome); AxD (Alexander disease); Ayerza syndrome (primary pulmonary hypertension); B variant of the Hexosaminidase GM2 gangliosidosis (Sandhoff disease); BANF (neurofibromatosis 2); Beare-Stevenson cutis gyrata syndrome; Benign paroxysmal peritonitis (Mediterranean fever, familial); Benjamin syndrome; beta thalassemia; BH4 Deficiency (tetrahydrobiopterin deficiency); Bilateral Acoustic Neurofibromatosis (neurofibromatosis 2); biotinidase deficiency; bladder cancer; Bleeding disorders (factor V Leiden thrombophilia); Bloch-Sulzberger syndrome (incontinentia pigmenti); Bloom syndrome; Bone diseases; Bone marrow diseases (X-linked sideroblastic anemia); Bonnevie-Ullrich syndrome (Turner syndrome); Bourneville disease (tuberous sclerosis); Bourneville phakomatosis (tuberous sclerosis); Brain diseases (prion disease); breast cancer; Birt-Hogg-Dube syndrome; Brittle bone disease (osteo-genesis imperfecta); Broad Thumb-Hallux syndrome (Rubinstein-Taybi syndrome); Bronze Diabetes (hemochromatosis); Bronzed cirrhosis (hemochromatosis); Bulbospinal muscular atrophy, X-linked (Kennedy disease); Burger-Grutz syndrome (lipoprotein lipase deficiency, familial); CADASIL; CGD Chronic Granulomatous Disorder; Camptomelic dysplasia; Canavan disease; Cancer; Cancer Family syndrome (hereditary nonpolyposis colorectal cancer); Cancer of breast (breast cancer); Cancer of the bladder (bladder cancer); Carboxylase Deficiency, Multiple, Late-Onset (biotinidase deficiency); Cardiomyopathy (Noonan syndrome); Cat cry syndrome (Cri du chat); CAVD (congenital bilateral absence of vas deferens); Caylor cardiofacial syndrome (22q11.2 deletion syndrome); CBAVD (congenital bilateral absence of vas deferens); Celiac Disease; CEP (congenital erythropoietic *porphyria*); Ceramide trihexosidase deficiency (Fabry disease); Cerebelloretinal Angiomatosis, familial (von Hippel-Lindau disease); Cerebral arteriopathy with subcortical infarcts and leukoencephalopathy (CADASIL); Cerebral autosomal dominant ateriopathy with subcortical infarcts and leukoencephalopathy (CADASIL); Cerebral sclerosis (tuberous sclerosis); Cerebroatrophic Hyperammonemia (Rett syndrome); Cerebroside Lipidosis syndrome (Gaucher disease); CF (cystic fibrosis); CH (congenital hypothyroidism); Charcot disease (amyotrophic lateral sclerosis); Charcot-Marie-Tooth disease; Chondrodystrophia (achondroplasia); Chondrodys-trophy syndrome (achondroplasia); Chondrodystrophy with sensorineural deafness (otospondylomegaepiphyseal dysplasia); Chondrogenesis imperfecta (achondro-genesis, type II); Choreoathetosis self-mutilation hyperuricemia syndrome (Lesch-Nyhan syndrome); Classic Galactosemia (galactosemia); Classical Ehlers-Danlos syndrome (Ehlers-Danlos syndrome #classical type); Classical Phenylketonuria (phenylketonuria); Cleft lip and palate (Stickler syndrome); Cloverleaf skull with thanatophoric dwarfism (Thanatophoric dysplasia #type 2); CLS (Coffin-Lowry syndrome); CMT (Charcot-Marie-Tooth disease); Cockayne syndrome; Coffin-Lowry syndrome; collagenopathy, types II and XI; Colon Cancer, familial Nonpolyposis (hereditary nonpolyposis colorectal cancer); Colon cancer, familial (familial adenomatous polyposis); Colorectal Cancer; Complete HPRT deficiency (Lesch-Nyhan syndrome); Complete hypoxanthine-guanine phosphoribosy transferase deficiency (Lesch-Nyhan syndrome); Compression neuropathy (hereditary neuropathy with liability to pressure palsies); Congenital adrenal hyperplasia (21-hydroxylase deficiency); congenital bilateral absence of vas deferens (Congenital absence of the vas deferens); Congenital erythropoietic *porphyria*; Congenital heart disease; Congenital hypomyelination (Charcot-Marie-Tooth disease Type 1/Charcot-Marie-Tooth disease Type 4); Congenital hypothyroidism; Congenital methemoglobinemia (Methemoglobinemia Congenital methaemoglobi-naemia); Congenital osteosclerosis (achondroplasia); Congenital sideroblastic anaemia (X-linked sideroblastic anemia); Connective tissue disease; Conotruncal anomaly face syndrome (22q11.2 deletion syndrome); Cooley's Anemia (beta thalassemia); Copper storage disease (Wilson disease); Copper transport disease (Menkes disease); Coproporphyria, hereditary (hereditary coproporphyria); Coproporphyrinogen oxidase deficiency (hereditary coproporphyria); Cowden syndrome; CPO deficiency (hereditary coproporphyria); CPRO deficiency (hereditary coproporphyria); CPX deficiency (hereditary coproporphyria); Craniofacial dysarthrosis (Crouzon syndrome); Craniofacial Dysostosis (Crouzon syndrome); Cretinism (congenital hypothyroidism); Creutzfeldt-Jakob disease (prion disease); Cri du chat (Crohn's disease, fibrostenosing); Crouzon syndrome; Crouzon syndrome with acanthosis *nigricans* (Crouzonodermoskeletal syndrome); Crouzono-dermoskeletal syndrome; CS (Cockayne syndrome)(Cowden syndrome); Curschmann-Batten-Steinert syndrome (myotonic dystrophy); cutis gyrata syndrome of Beare-Stevenson (Beare-Stevenson cutis gyrata syndrome); Disorder Mutation Chromosome; D-glycerate dehydrogenase deficiency (hyperoxaluria, primary); Dappled metaphysis syndrome (spondyloepimetaphyseal dysplasia, Strudwick type); DAT—Dementia Alzheimer's type (Alzheimer disease); Genetic hypercalciuria (Dent's disease); DBMD (muscular dystrophy, Duchenne and Becker types); Deafness with goiter (Pendred syndrome); Deafness-retinitis pigmentosa syndrome (Usher syndrome); Deficiency disease, Phenylalanine Hydroxylase (phenyl-ketonuria); Degenerative nerve diseases; de Grouchy syndrome 1 (De Grouchy Syndrome); Dejerine-Sottas syndrome (Charcot-Marie-Tooth disease); Delta-aminolevulinate dehydratase deficiency *porphyria* (ALA dehydratase deficiency); Dementia (CADASIL); demyelinogenic leukodystrophy (Alexander disease); Dermatosparactic type of Ehlers-Danlos syndrome (Ehlers-Danlos syndrome dermatosparaxis type); Dermatosparaxis (Ehlers-Danlos syndrome dermatosparaxis type); developmental disabilities; dHMN (Amyotrophic lateral sclerosis type 4); DHMN-V (distal spinal muscular atrophy, type V); DHTR deficiency (androgen insensitivity syndrome); Diffuse Globoid Body Sclerosis (Krabbe disease); DiGeorge syndrome; Dihydrotestosterone receptor deficiency (androgen insensitivity syn-drome); distal spinal muscular atrophy, type V; DM1 (Myotonic dystrophy type1); DM2 (Myotonic dystrophy type2); Down syndrome; DSMAV (distal spinal muscular atrophy, type V); DSN (Charcot-Marie-Tooth disease type 4); DSS (Charcot-Marie-Tooth disease, type 4); Duchenne/Becker muscular dystrophy (muscular dystrophy, Duchenne and Becker types); Dwarf, achondroplastic (achondroplasia); Dwarf, thanatophoric (thanatophoric dysplasia); Dwarfism; Dwarfism-retinal atrophy-deafness syndrome (Cockayne syndrome); dysmyelinogenic leukodystrophy (Alexander disease); Dystrophia myotonica (myotonic dystrophy); dystrophia retinae pigmentosa-dysostosis syndrome (Usher syndrome); Early-Onset familial alzheimer disease (EOFAD) (Alzheimer disease); EDS (Ehlers-Danlos syndrome); Ehlers-Danlos syndrome; Ekman-Lobstein disease (osteogenesis imperfecta); Entrapment neuropathy (hereditary neuropathy with liability to pressure palsies); Epiloia (tuberous sclerosis); EPP (erythropoietic protoporphyria); Erythroblastic anemia (beta thalassemia); Erythrohepatic protoporphyria (erythropoietic protoporphyria); Erythroid 5-aminolevulinate synthetase deficiency (X-linked sideroblastic anemia); Erythropoietic *porphyria* (congenital erythropoietic *porphyria*); Erythropoietic protoporphyria; Erythropoietic uroporphyria (congenital erythropoietic *porphyria*); Eye cancer (retinoblastoma FA—Friedreich ataxia); Fabry disease; Facial injuries and disorders; Factor V Leiden thrombophilia; FALS (amyotrophic lateral sclerosis); familial acoustic neuroma (neurofibromatosis type II); familial adenomatous polyposis; familial Alzheimer disease (FAD) (Alzheimer disease); familial amyotrophic lateral sclerosis (amyotrophic lateral sclerosis); familial dysautonomia; familial fat-induced hypertriglyceridemia (lipoprotein lipase deficiency, familial); familial hemochromatosis (hemochromatosis); familial LPL deficiency (lipoprotein lipase deficiency, familial); familial nonpolyposis colon cancer (hereditary nonpoly-posis colorectal cancer); familial paroxysmal polyserositis (Mediterranean fever, familial); familial PCT (*porphyria* cutanea *tarda*); familial pressure sensitive neuro-pathy (hereditary neuropathy with liability to pressure palsies); familial primary pulmonary hypertension (FPPH) (primary pulmonary hypertension); Familial Turner syndrome (Noonan syndrome); familial vascular leukoencephalopathy (CADASIL); FAP (familial adenomatous polyposis); FD (familial dysautonomia); Female pseudo-Turner syndrome (Noonan syndrome); Ferrochelatase deficiency (erythropoietic protoporphyria); ferroportin disease (Haemochromatosis type 4); Fever (Mediterranean fever, familial); FG syndrome; FGFR3-associated coronal synostosis (Muenke syndrome); Fibrinoid degeneration of astrocytes (Alexander disease); Fibrocystic disease of the pancreas (cystic fibrosis); FMF (Mediterranean fever, familial); Folling disease (phenylketonuria); fra(X) syndrome (fragile X syndrome); fragile X syndrome; Fragilitas ossium (osteogenesis imperfecta); FRAXA syndrome (fragile X syndrome); FRDA (Friedreich's ataxia); Friedreich ataxia (Friedreich's ataxia); Friedreich's ataxia; FXS (fragile X syndrome); G6PD deficiency; Galactokinase deficiency disease (galactosemia); Galactose-1-phosphate uridyl-transferase deficiency disease (galactosemia); galactosemia; Galactosylceramidase deficiency disease (Krabbe disease); Galactosylceramide lipidosis (Krabbe disease); galactosylcerebrosidase deficiency (Krabbe disease); galactosylsphingosine lipidosis (Krabbe disease); GALC deficiency (Krabbe disease); GALT deficiency (galactosemia); Gaucher disease; Gaucher-like disease (pseudo-Gaucher disease); GBA deficiency (Gaucher disease type 1); GD (Gaucher's disease); Genetic brain disorders; genetic emphysema (alpha-1 antitrypsin deficiency); genetic hemochromatosis (hemochromatosis); Giant cell hepatitis, neonatal (Neonatal hemochromatosis); GLA deficiency (Fabry disease); Glioblastoma, retinal (retinoblastoma); Glioma, retinal (retinoblastoma); globoid cell leukodystrophy (GCL, GLD) (Krabbe disease); globoid cell leukoencephalopathy (Krabbe disease); Glucocerebrosidase deficiency (Gaucher disease); Glucocerebrosidosis (Gaucher disease); Glucosyl cerebroside lipidosis (Gaucher disease); Glucosylceramidase deficiency (Gaucher disease); Glucosylceramide beta-glucosidase deficiency (Gaucher disease); Glucosylceramide lipidosis (Gaucher disease); Glyceric aciduria (hyperoxaluria, primary); Glycine encephalopathy (Nonketotic hyperglycinemia); Glycolic aciduria (hyperoxaluria, primary); GM2 gangliosidosis, type 1 (Tay-Sachs disease); Goiter-deafness syndrome (Pendred syndrome); Graefe-Usher syndrome (Usher syndrome); Gronblad-Strandberg syndrome (pseudoxanthoma elasticum); Guenther *porphyria* (congenital erythropoietic *porphyria*); Gunther disease (congenital erythropoietic *porphyria*); Haemochromatosis (hemochromatosis); Hallgren syndrome (Usher syndrome); Harlequin Ichthyosis; Hb S disease (sickle cell anemia); HCH (hypochondroplasia); HCP (hereditary coproporphyria); Head and brain malformations; Hearing disorders and deafness; Hearing problems in children; HEF2A (hemochromatosis type 2); HEF2B (hemochromatosis type 2); Hematoporphyria (*porphyria*); Heme synthetase deficiency (erythropoietic protoporphyria); Hemochromatoses (hemochromatosis); hemochromatosis; hemoglobin M disease (methemoglobinemia beta-globin type); Hemoglobin S disease (sickle cell anemia); hemophilia; HEP (hepatoerythropoietic *porphyria*); hepatic AGT deficiency (hyperoxaluria, primary); hepatoerythropoietic *porphyria*; Hepatolenticular degeneration syndrome (Wilson disease); Hereditary arthro-ophthalmopathy (Stickler syndrome); Hereditary coproporphyria; Hereditary dystopic lipidosis (Fabry disease); Hereditary hemochromatosis (HHC) (hemo-chromatosis); Hereditary Inclusion Body Myopathy (skeletal muscle regeneration); Hereditary iron-loading anemia (X-linked sideroblastic anemia); Hereditary motor and sensory neuropathy (Charcot-Marie-Tooth disease); Hereditary motor neuro-nopathy (spinal muscular atrophy); Hereditary motor neuronopathy, type V (distal spinal muscular atrophy, type V); Hereditary Multiple Exostoses; Hereditary non-polyposis colorectal cancer; Hereditary periodic fever syndrome (Mediterranean fever, familial); Hereditary Polyposis *Coli* (familial adenomatous polyposis); Hereditary pulmonary emphysema (alpha-1 antitrypsin deficiency); Hereditary resistance to activated protein C (factor V Leiden thrombophilia); Hereditary sensory and autonomic neuropathy type III (familial dysautonomia); Hereditary spastic paraplegia (infantile-onset ascending hereditary spastic paralysis); Hereditary spinal ataxia (Friedreich ataxia); Hereditary spinal sclerosis (Friedreich ataxia); Herrick's anemia (sickle cell anemia); Heterozygous OSMED (Weissenbacher-Zweymüller syndrome); Heterozygous otospondylomegaepiphyseal dysplasia (Weissenbacher-Zweymüller syndrome); HexA deficiency (Tay-Sachs disease); Hexosaminidase A deficiency (Tay-Sachs disease); Hexosaminidase alpha-subunit deficiency (variant B) (Tay-Sachs disease); HFE-associated hemochromatosis (hemochromatosis); HGPS (Progeria); Hippel-Lindau disease (von Hippel-Lindau disease); HLAH (hemochromatosis); HMN V (distal spinal muscular atrophy, type V); HMSN (Charcot-Marie-Tooth disease); HNPCC (hereditary nonpolyposis colorectal cancer); HNPP (hereditary neuropathy with liability to pressure palsies); homocystinuria; Homogentisic acid oxidase deficiency (alkaptonuria); Homogentisic acidura (alkaptonuria); Homozygous *porphyria* cutanea *tarda* (hepatoerythropoietic *porphyria*); HP1 (hyperoxaluria, primary); HP2 (hyperoxaluria, primary); HPA (hyperphenylalaninemia); HPRT—Hypoxanthine-guanine phosphoribosyltransferase deficiency (Lesch-Nyhan syndrome); HSAN type III (familial dysautonomia); HSAN3 (familial dysautonomia); HSN-III (familial dysautonomia); Human dermatosparaxis (Ehlers-Danlos syndrome #dermatosparaxis type); Huntington's disease; Hutchinson-Gilford progeria syndrome (progeria); Hyperandrogenism, nonclassic type, due to 21-hydroxylase deficiency (21-hydroxylase deficiency); Hyperchylomicronemia, familial (lipoprotein lipase deficiency, familial); hyper-glycinemia with ketoacidosis and leukopenia (propionic acidemia); Hyperlipo-proteinemia type I (lipoprotein lipase deficiency, familial); hyperoxaluria, primary; hyperphenylalaninaemia (hyperphenylalaninemia); hyperphenylalaninemia; Hypo-chondrodysplasia (hypochondroplasia); hypochondrogenesis; hypochondroplasia; Hypochromic anemia (X-linked sideroblastic anemia); Hypocupremia, congenital; Menkes syndrome); hypoxanthine phosphoribosyltransferse (HPRT) deficiency (Lesch-Nyhan syndrome); IAHSP (infantile-onset ascending hereditary spastic paralysis); idiopathic hemochromatosis (hemochromatosis, type 3); Idiopathic neonatal hemochromatosis (hemochromatosis, neonatal); Idiopathic pulmonary hypertension (primary pulmonary hypertension); Immune system disorders (X-linked severe combined immunodeficiency); Incontinentia Pigmenti; Infantile cerebral Gaucher's disease (Gaucher disease type 2); Infantile Gaucher disease (Gaucher disease type 2); infantile-onset ascending hereditary spastic paralysis; Infertility; inherited emphysema (alpha-1 antitrypsin deficiency); Inherited human transmissible spongiform encephalopathies (prion disease); inherited tendency to pressure palsies (hereditary neuropathy with liability to pressure palsies); Insley-Astley syndrome (otospondylomegaepiphyseal dysplasia); Intermittent acute *porphyria* syndrome (acute intermittent *porphyria*); Intestinal polyposis-cutaneous pigmentation syndrome (Peutz-Jeghers syndrome); IP (incontinentia pigmenti); Iron storage disorder (hemochromatosis); Isodicentric 15 (idic15); Isolated deafness (nonsyndromic deafness); Jackson-Weiss syndrome; JH (Haemochromatosis type 2); Joubert syndrome; JPLS (Juvenile Primary Lateral Sclerosis); juvenile amyotrophic lateral sclerosis (Amyotrophic lateral sclerosis type 2); Juvenile gout, choreoathetosis, mental retardation syndrome (Lesch-Nyhan syndrome); juvenile hyperuricemia syndrome (Lesch-Nyhan syndrome); JWS (Jackson-Weiss syndrome); KD (X-linked spinal-bulbar muscle atrophy); Kennedy disease (X-linked spinal-bulbar muscle atrophy); Kennedy spinal and bulbar muscular atrophy (X-linked spinal-bulbar muscle atrophy); Kerasin histiocytosis (Gaucher disease); Kerasin lipoidosis (Gaucher disease); Kerasin thesaurismosis (Gaucher disease); ketotic glycinemia (propionic acidemia); ketotic hyperglycinemia (propionic acidemia); Kidney diseases (hyperoxaluria, primary); Klinefelter syndrome; Klinefelter's syndrome; Kniest dysplasia; Krabbe disease; Lacunar dementia (CADASIL); Langer-Saldino achondrogenesis (achondrogenesis, type II); Langer-Saldino dysplasia (achondrogenesis, type II); Late-onset Alzheimer disease (Alzheimer disease type 2); Late-onset familial Alzheimer disease (AD2) (Alzheimer disease type 2); late-onset Krabbe disease (LOKD) (Krabbe disease); Learning Disorders (Learning disability); Lentiginosis, perioral (Peutz-Jeghers syndrome); Lesch-Nyhan syndrome; Leukodystrophies; leukodystrophy with Rosenthal fibers (Alexander disease); Leukodystrophy, spongiform (Canavan disease); LFS (Li-Fraumeni syndrome); Li-Fraumeni syndrome; Lipase D deficiency (lipoprotein lipase deficiency, familial); LIPD deficiency (lipoprotein lipase deficiency, familial); Lipidosis, cerebroside (Gaucher disease); Lipidosis, ganglioside, infantile (Tay-Sachs disease); Lipoid histiocytosis (kerasin type) (Gaucher disease); lipoprotein lipase deficiency, familial; Liver diseases (galactosemia); Lou Gehrig disease (amyotrophic lateral sclerosis); Louis-Bar syndrome (ataxia-telangiectasia); Lynch syndrome (hereditary nonpolyposis colorectal cancer); Lysyl-hydroxylase deficiency (Ehlers-Danlos syndrome kyphoscoliosis type); Machado-Joseph disease (Spinocerebellar ataxia type 3); Male breast cancer (breast cancer); Male genital disorders; Male Turner syndrome (Noonan syndrome); Malignant neoplasm of breast (breast cancer); malignant tumor of breast (breast cancer); Malignant tumor of urinary bladder (bladder cancer); Mammary cancer (breast cancer); Marfan syndrome 15; Marker X syndrome (fragile X syndrome); Martin-Bell syndrome (fragile X syndrome); McCune-Albright syndrome; McLeod syndrome; MEDNIK; Mediterranean Anemia (beta thalassemia); Mediterranean fever, familial; Mega-epiphyseal dwarfism (otospondylomegaepiphyseal dysplasia); Menkea syndrome (Menkes syndrome); Menkes syndrome; Mental retardation with osteocartilaginous abnormalities (Coffin-Lowry syndrome); Metabolic disorders; Metatropic dwarfism, type II (Kniest dysplasia); Metatropic dysplasia type II (Kniest dysplasia); Methemoglobinemia beta-globin type; methylmalonic acidemia; MFS (Marfan syndrome); MHAM (Cowden syndrome); MK (Menkes syndrome); Micro syndrome; Microcephaly; MMA (methylmalonic acidemia); MNK (Menkes syndrome); Monosomy 1p36 syndrome (1p36 deletion syndrome); monosomy X (Turner syndrome); Motor neuron disease, amyotrophic lateral sclerosis (amyotrophic lateral sclerosis); Movement disorders; Mowat-Wilson syndrome; Mucopolysaccharidosis (MPS I); Mucoviscidosis (cystic fibrosis); Muenke syndrome; Multi-Infarct dementia (CADASIL); Multiple carboxylase deficiency, late-onset (biotinidase deficiency); Multiple hamartoma syndrome (Cowden syndrome); Multiple neurofibromatosis (neurofibromatosis); Muscular dystrophy; Muscular dystrophy, Duchenne and Becker type; Myotonia atrophica (myotonic dystrophy); Myotonia dystrophica (myotonic dystrophy); myotonic dystrophy; Myxedema, congenital (congenital hypothyroidism); Nance-Insley syndrome (otospondylomegaepiphyseal dysplasia); Nance-Sweeney chondrodysplasia (otospondylomegaepiphyseal dysplasia); NBIA1 (pantothenate kinase-associated neurodegeneration); Neill-Dingwall syndrome (Cockayne syndrome); Neuroblastoma, retinal (retinoblastoma); Neurodegeneration with brain iron accumulation type 1 (pantothenate kinase-associated neuro-degeneration); Neurofibromatosis type I; Neurofibromatosis type II; Neurologic diseases; Neuromuscular disorders; neuronopathy, distal hereditary motor, type V (Distal spinal muscular atrophy type V); neuronopathy, distal hereditary motor, with pyramidal features (Amyotrophic lateral sclerosis type 4); NF (neurofibromatosis); Niemann-Pick (Niemann-Pick disease); Noack syndrome (Pfeiffer syndrome); Nonketotic hyperglycinemia (Glycine encephalopathy); Non-neuronopathic Gaucher disease (Gaucher disease type 1); Non-phenylketonuric hyperphenylalaninemia (tetrahydrobiopterin deficiency); nonsyndromic deafness; Noonan syndrome; Norrbottnian Gaucher disease (Gaucher disease type 3); Ochronosis (alkaptonuria); Ochronotic arthritis (alkaptonuria); OI (osteogenesis imperfecta); OSMED (otospondylomegaepiphyseal dysplasia); osteogenesis imperfecta; Osteopsathyrosis (osteogenesis imperfecta); Osteosclerosis congenita (achondroplasia); Oto-spondylomegaepiphyseal dysplasia (otospondylomegaepiphyseal dysplasia); otospondylo-megaepiphyseal dysplasia; Oxalosis (hyperoxaluria, primary); Oxaluria, primary (hyperoxaluria, primary); pantothenate kinase-associated neurodegeneration; Patau Syndrome (Trisomy 13); PBGD deficiency (acute intermittent *porphyria*); PCC deficiency (propionic acidemia); PCT (*porphyria* cutanea *tarda*); PDM (Myotonic dystrophy #type 2); Pendred syndrome; Periodic disease (Mediterranean fever, familial); Periodic peritonitis (Mediterranean fever, familial); Periorificial lentiginosis syndrome (Peutz-Jeghers syndrome); Peripheral nerve disorders (familial dysautonomia); Peripheral neurofibromatosis (neurofibromatosis 1); Peroneal muscular atrophy (Charcot-Marie-Tooth disease); peroxisomal alanine:glyoxylate aminotransferase deficiency (hyperoxaluria, primary); Peutz-Jeghers syndrome; Pfeiffer syndrome; Phenylalanine hydroxylase deficiency disease (phenylketonuria); phenylketonuria; Pheochromocytoma (von Hippel-Lindau disease); Pierre Robin syndrome with fetal chondrodysplasia (Weissenbacher-Zweymüller syndrome); Pigmentary cirrhosis (hemochromatosis); PJS (Peutz-Jeghers syndrome); PKAN (pantothenate kinase-associated neurodegeneration); PKU (phenylketonuria); Plumboporphyria (ALA deficiency *porphyria*); PMA (Charcot-Marie-tooth disease); polyostotic fibrous dysplasia (McCune-Albright syndrome); polyposis *coli* (familial adenomatous polyposis); polyposis, hamartomatous intestinal (Peutz-Jeghers syndrome); polyposis, intestinal, II (Peutz-Jeghers syndrome); polyps-and-spots syndrome (Peutz-Jeghers syndrome); Porphobilinogen synthase deficiency (ALA deficiency *porphyria*); *porphyria*; porphyrin disorder (*porphyria*); PPH (primary pulmonary hypertension); PPDX deficiency (variegate *porphyria*); Prader-Labhart-Willi syndrome (Prader-Willi syndrome); Prader-Willi syndrome; presenile and senile dementia (Alzheimer disease); primary hemochromatosis (hemochromatosis); primary hyperuricemia syndrome (Lesch-Nyhan syndrome); primary pulmonary hypertension; primary senile degenerative dementia (Alzheimer disease); prion disease; procollagen type EDS VII, mutant (Ehlers-Danlos syndromearthrochalasia type); progeria (Hutchinson Gilford Progeria Syndrome); Progeria-like syndrome (Cockayne syndrome); progeroid nanism (Cockayne syndrome); progressive chorea, chronic hereditary (Huntington) (Huntington's disease); progressive muscular atrophy (spinal muscular atrophy); progressively deforming osteogenesis imperfecta with normal sclerae (Osteogenesis imperfect type III); PROMM (Myotonic dystrophy type 2); propionic academia; propionyl-CoA carboxylase deficiency (propionic acidemia); protein C deficiency; protein S deficiency; protoporphyria (erythropoietic protoporphyria); protoporphyrinogen oxidase deficiency (variegate *porphyria*); proximal myotonic dystrophy (Myotonic dystrophytype 2); proximal myotonic myopathy (Myotonic dystrophy type 2); pseudo-Gaucher disease; pseudo-Ullrich-Turner syndrome (Noonan syndrome); pseudoxanthoma elasticum; psychosine lipidosis (Krabbe disease); pulmonary arterial hypertension (primary pulmonary hypertension); pulmonary hypertension (primary pulmonary hypertension); PWS (Prader-Willi syndrome); PXE—pseudoxanthoma elasticum (pseudoxanthoma elasticum); Rb (retinoblastoma); Recklinghausen disease, nerve (neurofibromatosis 1); Recurrent polyserositis (Mediterranean fever, familial); Retinal disorders; Retinitis pigmentosa-deafness syndrome (Usher syndrome); Retinoblastoma; Rett syndrome; RFALS type 3 (Amyotrophic lateral sclerosis type 2); Ricker syndrome (Myotonic dystrophy type 2); Riley-Day syndrome (familial dysautonomia); Roussy-Levy syndrome (Charcot-Marie-Tooth disease); RSTS (Rubinstein-Taybi syndrome); RTS (Rett syndrome) (Rubinstein-Taybi syndrome); RTT (Rett syndrome); Rubinstein-Taybi syndrome; Sack-Barabas syndrome (Ehlers-Danlos syndrome, vascular type); SADDAN; sarcoma family syndrome of Li and Fraumeni (Li-Fraumeni syndrome); sarcoma, breast, leukemia, and adrenal gland (SBLA) syndrome (Li-Fraumeni syndrome); SBLA syndrome (Li-Fraumeni syndrome); SBMA (X-linked spinal-bulbar muscle atrophy); SCD (sickle cell anemia); Schwannoma, acoustic, bilateral (neurofibromatosis 2); SCIDX1 (X-linked severe combined immunodeficiency); sclerosis *tuberosa* (tuberous sclerosis); SDAT (Alzheimer disease); SED congenita (spondyloepiphyseal dysplasia congenita); SED Strudwick (spondyloepimetaphyseal dysplasia, Strudwick type); SEDc (spondylo-epiphyseal dysplasia congenita); SEMD, Strudwick type (spondyloepimetaphyseal dysplasia, Strudwick type); senile dementia (Alzheimer disease type 2); severe achondroplasia with developmental delay and acanthosis *nigricans* (SADDAN); Shprintzen syndrome (22q11.2 deletion syndrome); sickle cell anemia; skeleton-skin-brain syndrome (SADDAN); Skin pigmentation disorders; SMA (spinal muscular atrophy); SMED, Strudwick type (spondyloepimetaphyseal dysplasia, Strudwick type); SMED, type I (spondyloepimetaphyseal dysplasia, Strudwick type); Smith Lemli Opitz Syndrome; South-African genetic *porphyria* (variegate *porphyria*); spastic paralysis, infantile onset ascending (infantile-onset ascending hereditary spastic paralysis); Speech and communication disorders; sphingolipidosis, Tay-Sachs (Tay-Sachs disease); spinal-bulbar muscular atrophy; spinal muscular atrophy; spinal muscular atrophy, distal type V (Distal spinal muscular atrophy type V); spinal muscular atrophy, distal, with upper limb predominance (Distal spinal muscular atrophy type V); spinocerebellar ataxia; spondyloepimetaphyseal dysplasia, Strudwick type; spondyloepiphyseal dysplasia congenital; spondyloepiphyseal dysplasia (collagenopathy, types II and XI); spondylometaepiphyseal dysplasia congenita, Strudwick type (spondyloepimetaphyseal dysplasia, Strudwick type); spondylometaphyseal dysplasia (SMD)

(spondyloepimetaphyseal dysplasia, Strudwick type); spondylometaphyseal dysplasia, Strudwick type (spondyloepimeta-physeal dysplasia, Strudwick type); spongy degeneration of central nervous system (Canavan disease); spongy degeneration of the brain (Canavan disease); spongy degeneration of white matter in infancy (Canavan disease); sporadic primary pulmonary hypertension (primary pulmonary hypertension); SSB syndrome (SADDAN); steely hair syndrome (Menkes syndrome); Steinert disease (myotonic dystrophy); Steinert myotonic dystrophy syndrome (myotonic dystrophy); Stickler syndrome; stroke (CADASIL); Strudwick syndrome (spondyloepimetaphyseal dysplasia, Strudwick type); subacute neuronopathic Gaucher disease (Gaucher disease type 3); Swedish genetic *porphyria* (acute intermittent *porphyria*); Swedish *porphyria* (acute intermittent *porphyria*); Swiss cheese cartilage dysplasia (Kniest dysplasia); Tay-Sachs disease; TD—thanatophoric dwarfism (thanatophoric dysplasia); TD with straight femurs and cloverleaf skull (thanatophoric dysplasia Type 2); Telangiectasia, cerebello-oculocutaneous (ataxia-telangiectasia); Testicular feminization syndrome (androgen insensitivity syndrome); tetrahydrobiopterin deficiency; TFM—testicular feminization syndrome (androgen insensitivity syndrome); thalassemia *intermedia* (beta thalassemia); Thalassemia Major (beta thalassemia); thanatophoric dysplasia; thiamine-responsive megaloblastic anemia with diabetes mellitus and sensorineural deafness; Thrombophilia due to deficiency of cofactor for activated protein C, Leiden type (factor V Leiden thrombophilia); Thyroid disease; Tomaculous neuropathy (hereditary neuropathy with liability to pressure palsies); Total HPRT deficiency (Lesch-Nyhan syndrome); Total hypo-xanthine-guanine phosphoribosyl transferase deficiency (Lesch-Nyhan syndrome); Tourette's Syndrome; Transmissible dementias (prion disease); Transmissible spongiform encephalopathies (prion disease); Treacher Collins syndrome; Trias fragilitis ossium (osteogenesis imperfect Type I); triple X syndrome; Triplo X syndrome (triple X syndrome); Trisomy 21 (Down syndrome); Trisomy X (triple X syndrome); Troisier-Hanot-Chauffard syndrome (hemochromatosis); TS (Turner syndrome); TSD (Tay-Sachs disease); TSEs (prion disease); tuberose sclerosis (tuberous sclerosis); tuberous sclerosis; Turner syndrome; Turner syndrome in female with X chromosome (Noonan syndrome); Turner's phenotype, karyotype normal (Noonan syndrome); Turner's syndrome (Turner syndrome); Turner-like syndrome (Noonan syndrome); Type 2 Gaucher disease (Gaucher disease type 2); Type 3 Gaucher disease (Gaucher disease type 3); UDP-galactose-4-epimerase deficiency disease (galactosemia); UDP glucose 4-epimerase deficiency disease (galactosemia); UDP glucose hexose-1-phosphate uridylyltransferase deficiency (galactosemia); Ullrich-Noonan syndrome (Noonan syndrome); Ullrich-Turner syndrome (Turner syndrome); Undifferentiated deafness (nonsyndromic deafness); UPS deficiency (acute intermittent *porphyria*); Urinary bladder cancer (bladder cancer); UROD deficiency (*porphyria* cutanea *tarda*); Uroporphyrinogen decarboxylase deficiency (*porphyria* cutanea *tarda*); Uroporphyrinogen synthase deficiency (acute intermittent *porphyria*); UROS deficiency (congenital erythropoietic *porphyria*); Usher syndrome; UTP hexose-1-phosphate uridylyl-transferase deficiency (galactosemia); Van Bogaert-Bertrand syndrome (Canavan disease); Van der Hoeve syndrome (osteogenesis imperfect Type I); variegate *porphyria*; Velocardiofacial syndrome (22q11.2 deletion syndrome); VHL syndrome (von Hippel-Lindau disease); Vision impairment and blindness (Alstrom syndrome); Von Bogaert-Bertrand disease (Canavan disease); von Hippel-Lindau disease; Von Recklenhausen-Applebaum disease (hemochromatosis); von Recklinghausen disease (neurofibromatosis 1); VP (variegate *porphyria*); Vrolik disease (osteogenesis imperfecta); Waardenburg syndrome; Warburg Sjo Fledelius Syndrome (Micro syndrome); WD (Wilson disease); Weissenbacher-Zweymüller syndrome; Wilson disease; Wilson's disease (Wilson disease); Wolf-Hirschhorn syndrome; Wolff Periodic disease (Mediterranean fever, familial); WZS (Weissenbacher-Zweymüller syndrome); Xeroderma Pigmentosum; X-linked mental retardation and macroorchidism (fragile X syndrome); X-linked primary hyperuricemia (Lesch-Nyhan syndrome); X-linked severe combined immunodeficiency; X-linked sideroblastic anemia; X-linked spinal-bulbar muscle atrophy (Kennedy disease); X-linked uric aciduria enzyme defect (Lesch-Nyhan syndrome); X-SCID (X-linked severe combined immunodeficiency); XLSA (X-linked sideroblastic anemia); XSCID (X-linked severe combined immunodeficiency); XXX syndrome (triple X syndrome); XXXX syndrome (48, XXXX); XXXXX syndrome (49, XXXXX); XXY syndrome (Klinefelter syndrome); XXY trisomy (Klinefelter syndrome); XYY karyotype (47,XYY syndrome); XYY syndrome (47,XYY syndrome); and YY syndrome (47,XYY syndrome).

In a preferred embodiment of the present invention, the method further comprises a step of complexing the RNA molecules (all or only a part of the molecules) according to the invention with one or more cationic or polycationic compounds, preferably with cationic or polycationic polymers, cationic or polycationic peptides or proteins, e.g. protamine, cationic or polycationic polysaccharides and/or cationic or polycationic lipids.

Also provided is an RNA molecule composition produced by the method according to the invention and a pharmaceutical composition comprising the RNA molecule composition according to the invention and a pharmaceutically acceptable excipient. Pharmaceutically acceptable excipient comprise all substances which are usually used in a pharmaceutical composition. Examples are physiologically acceptable buffering agents, like phosphate buffers (preferably sodium monohydrogen phosphate-sodium dihydrogen phosphate system), citrate buffers, lactate buffers, acetate buffers, carbonate buffers, BisTris, MES, and Glycine-HCl; surfactants like polyoxy ethylene sorbitan alkyl esters; polyols, e.g. a sugar alcohol, like mannitol or sorbitol. The pH of the RNA molecule composition is preferably in the range of 6 to 8, more preferably in the range of 6.5 to 7.5.

In a preferred embodiment, the RNA molecules in the RNA molecule composition according to the invention are all or partially complexed with one or more cationic or polycationic compounds, preferably with cationic or polycationic polymers, cationic or polycationic peptides or proteins, e.g. protamine, cationic or polycationic polysaccharides and/or cationic or polycationic lipids.

According to a preferred embodiment, the RNA molecules of the composition according to the present invention may be all or partially complexed with lipids to form one or more liposomes, lipoplexes, or lipid nanoparticles. Therefore, in one embodiment, the RNA molecule composition comprises liposomes, lipoplexes, and/or lipid nanoparticles.

Lipid-based formulations have been increasingly recognized as one of the most promising delivery systems for RNA due to their biocompatibility and their ease of large-scale production. Cationic lipids have been widely studied as synthetic materials for delivery of RNA. After mixing together, nucleic acids are condensed by cationic lipids to form lipid/nucleic acid complexes known as lipoplexes. These lipid complexes are able to protect genetic material from the action of nucleases and deliver it into cells by interacting with the negatively charged cell membrane.

Lipoplexes can be prepared by directly mixing positively charged lipids at physiological pH with negatively charged nucleic acids.

Conventional liposomes consist of a lipid bilayer that can be composed of cationic, anionic, or neutral (phospho)lipids and cholesterol, which encloses an aqueous core. Both the lipid bilayer and the aqueous space can incorporate hydrophobic or hydrophilic compounds, respectively. Liposome characteristics and behaviour in vivo can be modified by addition of a hydrophilic polymer coating, e.g. polyethylene glycol (PEG), to the liposome surface to confer steric stabilization. Furthermore, liposomes can be used for specific targeting by attaching ligands (e.g., antibodies, peptides, and carbohydrates) to its surface or to the terminal end of the attached PEG chains.

Liposomes are colloidal lipid-based and surfactant-based delivery systems composed of a phospholipid bilayer surrounding an aqueous compartment. They may be present as spherical vesicles and can range in size from 20 nm to a few microns. Cationic lipid-based liposomes are able to complex with negatively charged nucleic acids via electrostatic interactions, resulting in complexes that offer biocompatibility, low toxicity, and the possibility of the large-scale production required for in vivo clinical applications. Liposomes can fuse with the plasma membrane for uptake; once inside the cell, the liposomes are processed via the endocytic pathway and the genetic material is then released from the endosome/carrier into the cytoplasm. Liposomes have long been perceived as drug delivery vehicles because of their superior biocompatibility, given that liposomes are basically analogs of biological membranes, and can be prepared from both natural and synthetic phospholipids.

Cationic liposomes have been traditionally the most commonly used non-viral delivery systems for oligonucleotides, including plasmid DNA, antisense oligos, and siRNA/small hairpin RNA-shRNA). Cationic lipids, such as DOTAP, (1,2-dioleoyl-3-trimethylammonium-propane) and DOTMA (N-E1-(2,3-dioleoyloxy)propyll-N,N,N-trimethyl-ammonium methyl sulfate) can form complexes or lipoplexes with negatively charged nucleic acids to form nanoparticles by electrostatic interaction, providing high in vitro transfection efficiency. Furthermore, neutral lipid-based nanoliposomes for RNA delivery as e.g. neutral 1,2-dioleoyl-sn-glycero-3-phosphatidylcholine (DOPC)-based nanoliposomes were developed.

Therefore, in one embodiment the RNA molecules are complexed with cationic lipids and/or neutral lipids and thereby form liposomes, lipid nanoparticles, lipoplexes or neutral lipid-based nanoliposomes.

In a preferred embodiment, the RNA molecules in the RNA molecule composition according to the invention are formulated together with a cationic or polycationic compound and/or with a polymeric carrier. Accordingly, in a further embodiment of the invention, it is preferred that the RNA molecules as defined herein or any other nucleic acid comprised in the inventive (pharmaceutical) composition or vaccine is associated with or complexed with a cationic or polycationic compound or a polymeric carrier, optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w) of RNA or nucleic acid to cationic or polycationic compound and/or with a polymeric carrier; or optionally in a nitrogen/phosphate (N/P) ratio of RNA molecule or nucleic acid to cationic or polycationic compound and/or polymeric carrier in the range of about 0.1-10, preferably in a range of about 0.3-4 or 0.3-1, and most preferably in a range of about 0.5-1 or 0.7-1, and even most preferably in a range of about 0.3-0.9 or 0.5-0.9. More preferably, the N/P ratio of RNA to the one or more polycations is in the range of about 0.1 to 10, including a range of about 0.3 to 4, of about 0.5 to 2, of about 0.7 to 2 and of about 0.7 to 1.5.

Therein, the RNA and RNA molecules as defined herein or any other nucleic acid comprised in the (pharmaceutical) composition or vaccine according to the invention can also be associated with a vehicle, transfection or complexation agent for increasing the transfection efficiency and/or the immunostimulatory properties of the RNA/mRNA according to the invention or of optionally comprised further included nucleic acids.

Cationic or polycationic compounds, being particularly preferred agents in this context include protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, pIsl, FGF, Lactoferrin, Transportan, Buforin-2, Bac715-24, SynB, SynB(1), pVEC, hCT-derived peptides, SAP, or histones. More preferably, the mRNA/RNA according to the invention is complexed with one or more polycations, preferably with protamine or oligofectamine, most preferably with protamine. In this context, protamine is particularly preferred.

Additionally, preferred cationic or polycationic proteins or peptides may be selected from the following proteins or peptides having the following total formula (I):

$$(Arg)_l;(Lys)_j;(His)_h;(Orn)_o;(Xaa)_x, \quad \text{(formula (I))}$$

wherein l+j+h+o+x=8-15, and l, j, h or o independently from each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. In this context, the disclosure of WO 2009/030481 is incorporated herewith by reference.

Further preferred cationic or polycationic compounds, which can be used as transfection or complexation agents may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethyl-ammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(-trimethylammonioacetyl)diethanolamine chloride, CLIP1: rac-[(2,3-dioctadecyloxy-propyl)(2-hydroxyethyl)]-dimethylammonium chloride, CLIP6: rac-[2(2,3-dihexa-decyloxypropyl-oxymethyloxy)ethyl]trimethylammonium, CLIP9: rac-2(2,3-dihexa-decyloxypropyl-oxysuccinyloxy)ethyl-trimethylammonium, oligofectamine, or cationic or polycationic polymers, e.g. modified polyaminoacids, such as alpha-aminoacid-polymers or reversed polyamides, etc., modified polyethylenes, such as PVP (poly (N-ethyl-4-vinylpyridinium bromide)), etc., modified acrylates, such as pDMAEMA (poly(dimethylaminoethyl methylacrylate)), etc., modified amido-amines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly (ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

According to a preferred embodiment, the RNA molecule composition of the present invention comprises the RNA molecules as defined herein and a polymeric carrier. A polymeric carrier used according to the invention might be a polymeric carrier formed by disulfide-crosslinked cationic components. The disulfide-crosslinked cationic components may be the same or different from each other. The polymeric carrier can also contain further components. It is also particularly preferred that the polymeric carrier used according to the present invention comprises mixtures of cationic peptides, proteins or polymers and optionally further components as defined herein, which are crosslinked by disulfide bonds as described herein. In this context, the disclosure of WO 2012/013326 is incorporated herewith by reference.

In this context, the cationic components, which form basis for the polymeric carrier by disulfide-crosslinkage, are typically selected from any suitable cationic or polycationic peptide, protein or polymer suitable for this purpose, particular any cationic or polycationic peptide, protein or polymer capable of complexing the mRNA as defined herein or a further nucleic acid comprised in the composition, and thereby preferably condensing the (m)RNA or the nucleic acid. The cationic or polycationic peptide, protein or polymer, is preferably a linear molecule, however, branched cationic or polycationic peptides, proteins or polymers may also be used.

Every disulfide-crosslinking cationic or polycationic protein, peptide or polymer of the polymeric carrier, which may be used to complex the RNA molecules according to the invention or any further nucleic acid comprised in the (pharmaceutical) composition or vaccine of the present invention, contains at least one —SH moiety, most preferably at least one cysteine residue or any further chemical group exhibiting an —SH moiety, capable of forming a disulfide linkage upon condensation with at least one further cationic or polycationic protein, peptide or polymer as cationic component of the polymeric carrier as mentioned herein.

As defined above, the polymeric carrier, which may be used to complex the RNA molecules of the present invention or any further nucleic acid comprised in the (pharmaceutical) composition or vaccine according to the invention may be formed by disulfide-crosslinked cationic (or polycationic) components. Preferably, such cationic or polycationic peptides or proteins or polymers of the polymeric carrier, which comprise or are additionally modified to comprise at least one —SH moiety, are selected from, proteins, peptides and polymers as defined herein for complexation agent.

In a further particular embodiment, the polymeric carrier which may be used to complex the RNA molecules as defined herein or any further nucleic acid comprised in the (pharmaceutical) composition or vaccine according to the invention may be selected from a polymeric carrier molecule according to generic formula (II):

$$L\text{-}P1\text{-}S\text{—}[S\text{-}P2\text{-}S]_k\text{—}S\text{-}P3\text{-}L \qquad \text{formula (II)}$$

wherein,

P1 and P3 are different or identical to each other and represent a linear or branched hydrophilic polymer chain, each P1 and P3 exhibiting at least one —SH— moiety, capable to form a disulfide linkage upon condensation with component P2, or alternatively with (AA), $(AA)_x$, or $[(AA)_x]_z$ if such components are used as a linker between P1 and P2 or P3 and P2) and/or with further components (e.g. (AA), $(AA)_x$, $[(AA)_x]_z$ or L), the linear or branched hydrophilic polymer chain selected independent from each other from polyethylene glycol (PEG), poly-N-(2-hydroxypropyl) methacrylamide, poly-2-(methacryloyloxy)ethyl phosphorylcholines, poly(hydroxyalkyl L-asparagine), poly(2-(methacryloyloxy)ethyl phosphoryl-choline), hydroxyethylstarch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

P2 is a cationic or polycationic peptide or protein, e.g. as defined above for the polymeric carrier formed by disulfide-crosslinked cationic components, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20; or is a cationic or polycationic polymer, e.g. as defined above for the polymeric carrier formed by disulfide-crosslinked cationic components, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each P2 exhibiting at least two —SH-moieties, capable to form a disulfide linkage upon condensation with further components P2 or component(s) P1 and/or P3 or alternatively with further components (e.g. (AA), (AA)x, or [(AA) x]z);

—S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components P1 and P2, P2 and P2, or P2 and P3, or optionally of further components as defined herein (e.g. L, (AA), (AA)x, [(AA)x]z, etc); The —SH-moiety may be part of the structure of these components or added by a modification as defined below;

L is an optional ligand, which may be present or not, and may be selected independent from the other from RGD, transferrin, folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues), or any further protein as defined herein, etc.;

k is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, ora range of about 3 to 15, 4 to 15, 5 to 15, or 10 to 15, or a range of about 6 to 11 or 7 to 10. Most preferably, k is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

In this context, the disclosure of WO 2011/026641 is incorporated herewith by reference. Each of hydrophilic polymers P1 and P3 typically exhibits at least one —SH-moiety, wherein the at least one —SH-moiety is capable to form a disulfide linkage upon reaction with component P2 or with component (AA) or (AA)x, if used as linker between P1 and P2 or P3 and P2 as defined below and optionally with a further component, e.g. L and/or (AA) or (AA)x, e.g. if two or more —SH-moieties are contained. The following subformulae "P1-S—S-P2" and "P2-S—S-P3" within generic formula (II) above (the brackets are omitted for better readability), wherein any of S, P1 and P3 are as defined herein, typically represent a situation, wherein one-SH-moiety of hydrophilic polymers P1 and P3 was condensed with one —SH-moiety of component P2 of generic formula (II) above, wherein both sulphurs of these —SH-moieties form a disulfide bond —S—S— as defined herein in formula (II). These —SH-moieties are typically provided by each of the hydrophilic polymers P1 and P3, e.g. via an internal cysteine or any further (modified) amino acid or compound which carries a —SH moiety. Accordingly, the subformulae "P1-S—S-P2" and "P2-S—S-P3" may also be written as "P1-Cys-Cys-P2" and "P2-Cys-Cys-P3", if the —SH-moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine. Likewise, the terms "—S-Cys" and "—Cys-S" indicate a disulfide bond between a —SH containing moiety and a cysteine, which may also be written as "—S—(S-Cys)" and "-(Cys-S)—S". Alternatively, the hydrophilic polymers P1 and P3 may be modified with a —SH moiety, preferably via a chemical reaction with a compound carrying a —SH moiety, such that each of the hydrophilic polymers P1 and P3 carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers P1 and P3 as defined herein. Such non-amino compounds may be attached to the hydrophilic polymers P1 and P3 of formula (II) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g maleinimide moieties, α,β-unsatured carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow Sn-type substitution reactions (e.g halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers P1 and P3. As defined herein, each of hydrophilic polymers P1 and P3 typically exhibits at least one —SH-moiety preferably at one terminal end, but may also contain two or even more —SH-moieties, which may be used to additionally attach further components as defined herein, preferably further functional peptides or proteins e.g. a ligand, an amino acid component (AA) or (AA)x, antibodies, cell penetrating peptides or enhancer peptides (e.g. TAT, KALA), etc.

Preferably, the inventive composition comprises at least one RNA molecule as defined herein, which is complexed with one or more polycations, and at least one free RNA, wherein the at least one complexed RNA is preferably identical to the at least one free RNA. In this context, it is particularly preferred that the composition of the present invention comprises the RNA molecule according to the invention that is complexed at least partially with a cationic or polycationic compound and/or a polymeric carrier, preferably cationic proteins or peptides. In this context, the disclosure of WO 2010/037539 and WO 2012/113513 is incorporated herein by reference. "Partially" means that only a part of the RNA molecules as defined herein is complexed in the composition according to the invention with a cationic compound and that the rest of the RNA molecules as defined herein is (comprised in the inventive (pharmaceutical) composition or vaccine) in uncomplexed form ("free"). Preferably, the molar ratio of the complexed RNA molecules to the free RNA molecules is selected from a molar ratio of about 0.001:1 to about 1:0.001, including a ratio of about 1:1. More preferably the ratio of complexed RNA molecules to free RNA molecules (in the (pharmaceutical) composition or vaccine of the present invention) is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed RNA molecules to free RNA molecules in the inventive pharmaceutical composition or vaccine is selected from a ratio of about 1:1 (w/w).

The complexed RNA molecules in the (pharmaceutical) composition or vaccine according to the present invention, are preferably prepared according to a first step by complexing the RNA molecules according to the invention with a cationic or polycationic compound and/or with a polymeric carrier, preferably as defined herein, in a specific ratio to form a stable complex. In this context, it is highly preferable, that no free cationic or polycationic compound or polymeric carrier or only a negligibly small amount thereof remains in the component of the complexed RNA molecules after complexing the RNA molecules. Accordingly, the ratio of the RNA molecules and the cationic or polycationic compound and/or the polymeric carrier in the component of the complexed RNA molecules is typically selected in a range so that the RNA molecules are entirely complexed and no free cationic or polycationic compound or polymeric carrier or only a negligibly small amount thereof remains in the composition.

Preferably the ratio of the RNA molecules as defined herein to the cationic or polycationic compound and/or the polymeric carrier, preferably as defined herein, is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the RNA molecules as defined herein to the cationic or polycationic compound and/or the polymeric carrier, preferably as defined herein, in the component of the complexed RNA molecules, may also be calculated on the basis of the nitrogen/phosphate ratio (N/P-ratio) of the entire complex. In the context of the present invention, an N/P-ratio is preferably in the range of about 0.1-10, preferably in a range of about 0.3-4 and most preferably in a range of about 0.5-2 or 0.7-2 regarding the ratio of RNA molecules: cationic or polycationic compound and/or polymeric carrier, preferably as defined herein, in the complex, and most preferably in a range of about 0.7-1.5, 0.5-1 or 0.7-1, and even most preferably in a range of about 0.3-0.9 or 0.5-0.9, preferably provided that the cationic or polycationic compound in the complex is a cationic or polycationic cationic or polycationic protein or peptide and/or the polymeric carrier as defined above. In this specific embodiment the complexed RNA molecules as defined herein are also encompassed in the term “adjuvant component”.

In other embodiments, the composition according to the invention comprising the RNA molecules as defined herein may be administered naked without being associated with any further vehicle, transfection or complexation agent.

It has to be understood and recognized, that according to the present invention, the inventive composition may comprise at least one naked RNA molecule as defined herein and/or at least one formulated/complexed RNA molecule as defined herein, wherein every formulation and/or complexation as disclosed above may be used.

The invention also provides a pharmaceutical container comprising the RNA molecule composition or the pharmaceutical composition according to the invention. The pharmaceutical container is preferably a syringe, vial, infusion bottle, ampoule or carpoule.

Also provided is the RNA molecule composition or the pharmaceutical composition according to the invention for use as a medicament, preferably for use in the treatment or prophylaxis of a disease selected from the group consisting of genetic diseases, allergies, autoimmune diseases, infectious diseases, neoplasms, cancer and tumor-related diseases, inflammatory diseases, diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system, independently if they are inherited or acquired, and combinations thereof.

Also provided is the use of the RNA molecule composition as immunotherapeutic agent, gene-therapeutic agent or as vaccine.

DESCRIPTION OF THE FIGURES

FIG. 1: Percent identity matrix of the pDNA sequences (FIG. 1A) and the RNA sequences (FIG. 1B). The matrix is based on sequence identity values using multiple sequence alignments (Clustal 12.1). SEQ ID NOs are indicated.

In FIG. 2A, DH5alpha was used as a host. Three groups that show similar growth characteristics were identified (g1, g2, g3). In FIG. 2B, a CopyCutter™ strain was used as a host. All pDNA cultures exhibited similar growth characteristics. A detailed description of the experiment is provided in Example 7.

FIG. 4A shows a scheme of the CoStock and CoInoc co-cultivation strategies. FIG. 4B shows an overlay of the growth characteristics for different replicates (co-cultivations of 4 and 5 different clones). A detailed description of the experiment is provided in Example 8.

FIG. 5 shows RNA agarose gel electrophoresis of the obtained RNA molecule compositions using a pDNA mixture as template. A detailed description of the experiment is provided in Example 9.

FIG. 8 shows RNA agarose gel electrophoresis of the obtained RNA molecule compositions using a PCR amplified DNA mixture as a template. A detailed description of the experiment is provided in Example 10.

EXAMPLES

Figure 2:
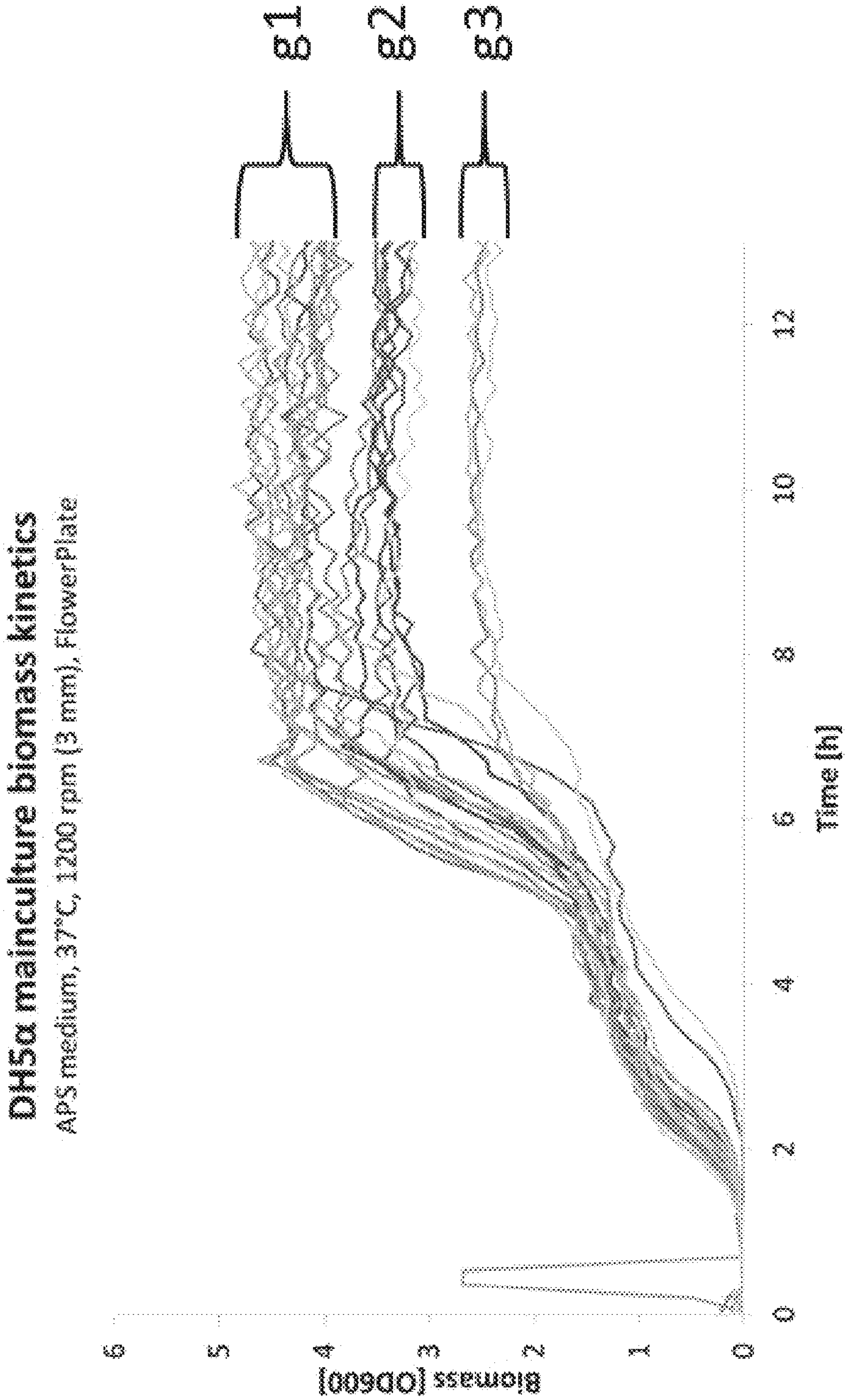
FIG. 2: Overlay of growth curves ($OD_{600}$) of different pDNA clones.
Figure 2:
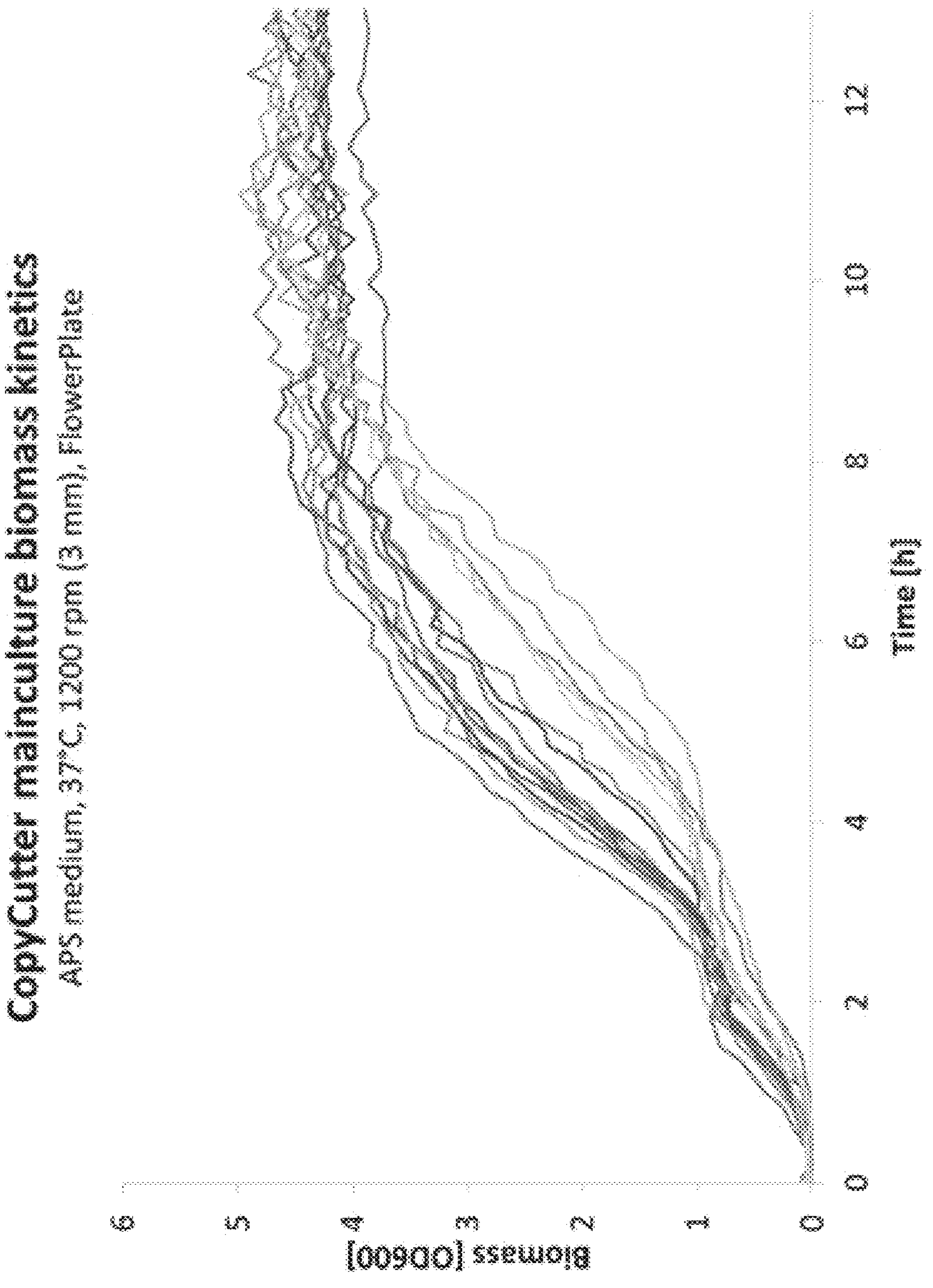
Figure 3A:
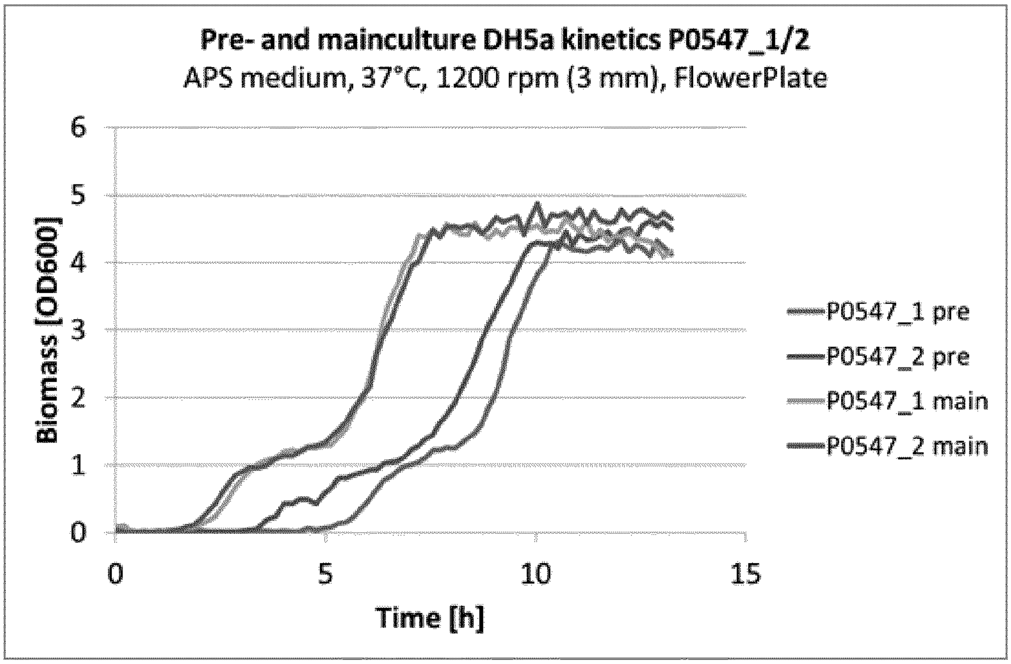
FIG. 3: Pre- and main culture growth kinetics for DH5alpha (A) and CopyCutter™ (B) clones show that growth characteristics of clones are robust. A detailed description of the experiment is provided in Example 7. A: DH5alpha and B: CopyCutter™ clones
Figure 3A:
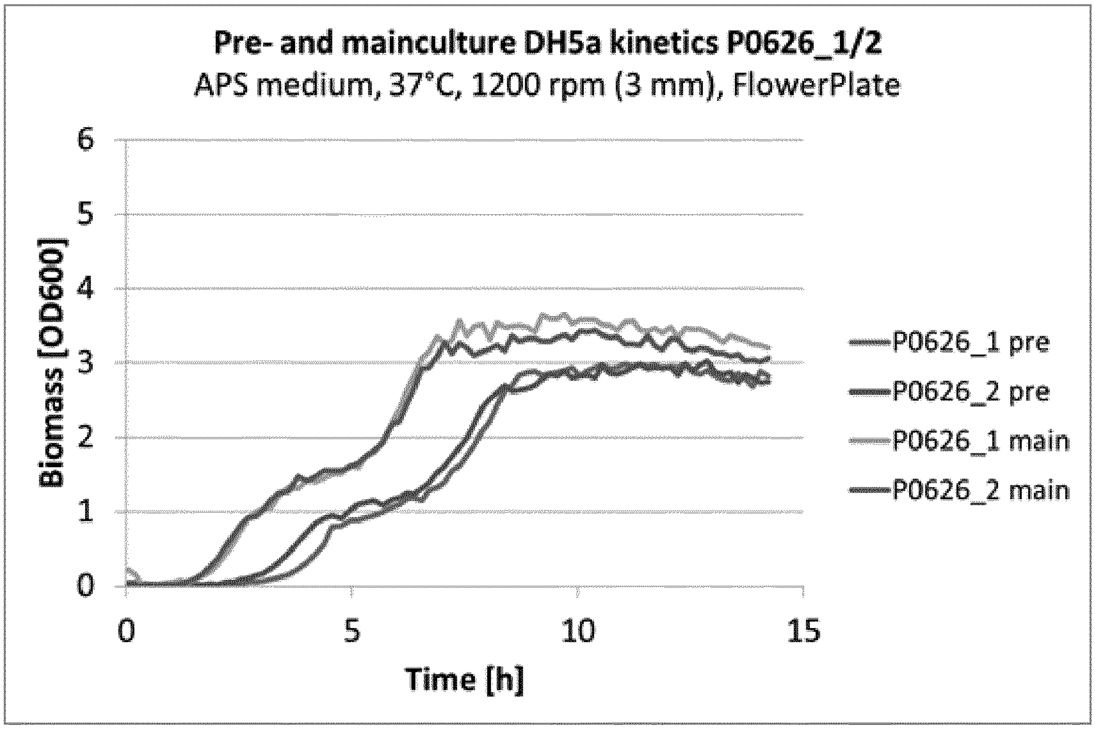
Figure 3B:
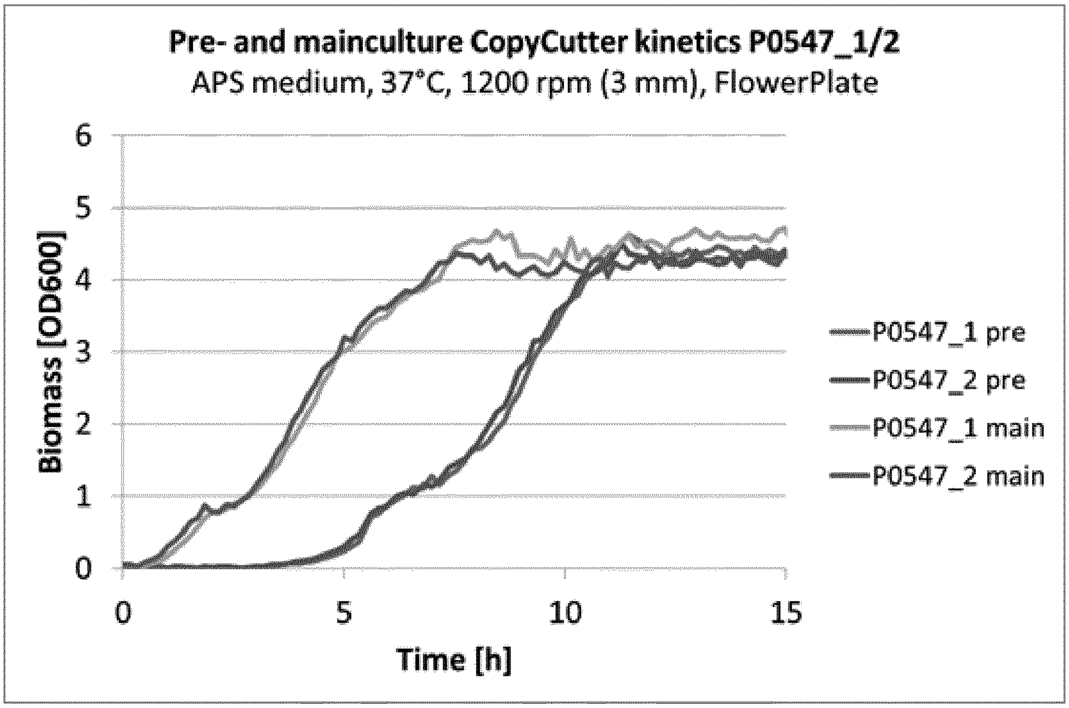
Figure 3B:
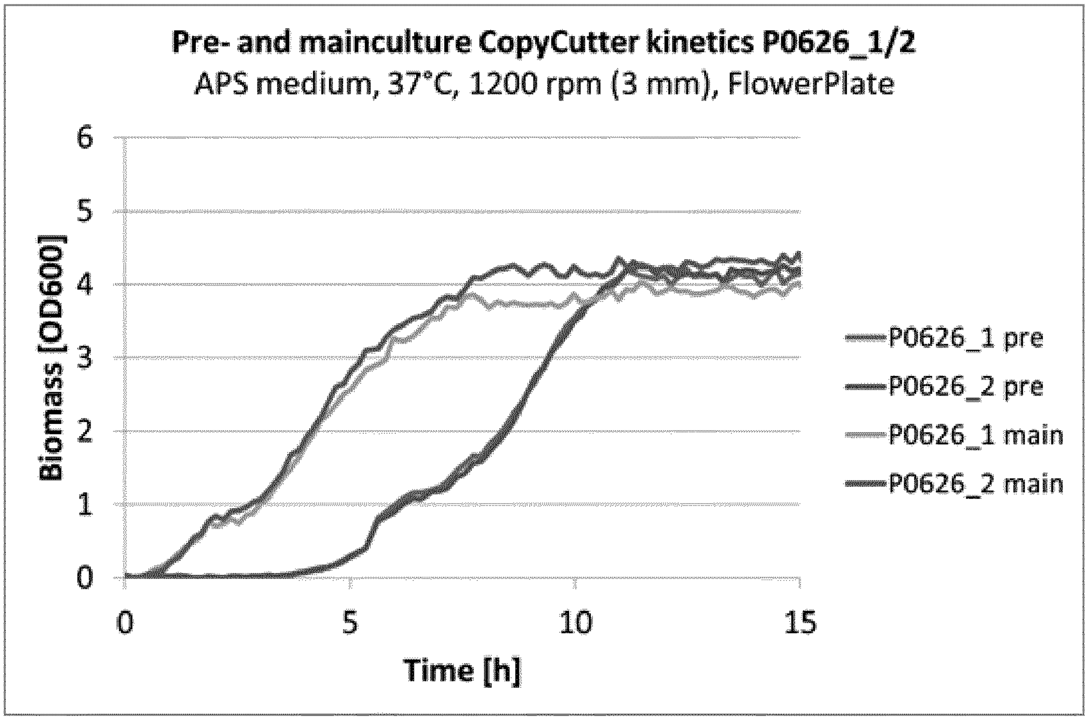

The following examples are intended to illustrate the invention in a further way. They are merely illustrative and not intended to limit the subject matter of the invention.

Example 1: Preparation of DNA Encoding HA Proteins of Several Serotypes

For the present examples, DNA sequences encoding different heamagglutinin proteins, a glycoprotein found on the surface of influenza viruses (Influenza A and Influenza B), were generated. For the present examples, several HA proteins of various serotypes were used (see Table 1 below). The DNA sequences were prepared by modifying the wild type encoding DNA sequence by introducing a GC-optimized sequence for stabilization. Sequences were introduced into the same vector backbone, a pUC19 derived vector and modified to comprise a 5'-UTR derived from the 32L4 ribosomal protein (32L4 TOP 5'-UTR) and a 3'-UTR derived from albumin, a histone-stem-loop structure, and a stretch of 64 adenosines at the 3'-terminal end. The respective plasmid DNA sequences as well as the corresponding RNA sequences are provided in the sequence protocol (SEQ ID NOs: 1-14 (RNA sequences) and SEQ ID NOs: 15-28 (plasmid DNA sequences). The generated sequences show high sequence similarity (Sequence identity matrix of plasmid DNA sequences and expected RNA sequences provided in FIG. 1). The obtained plasmid DNA constructs were transformed and propagated in bacteria (*Escherichia coli*) and glycerol stocks were prepared using common protocols known in the art.

TABLE 1

HA-constructs used in the experiment

| SEQ ID NO of RNA | SEQ ID NO of pDNA | HA protein description | Length of pDNA | Length of RNA | GC content of the RNA |
|---|---|---|---|---|---|
| 1 | 15 | H1N1 Influenza A virus (Puerto Rico/1934) | 3952 | 1915 | 60.78 |
| 2 | 16 | H1N1 Influenza A virus (Netherlands/2009) | 3955 | 1918 | 60.84 |
| 3 | 17 | H1N1 Influenza A virus (California/2009) | 3955 | 1918 | 61.00 |
| 4 | 18 | H5N1 Influenza A virus (NIBRG-14) | 3949 | 1912 | 60.25 |
| 5 | 19 | H5N1 Influenza A virus (Vietnam 2004) | 3961 | 1924 | 60.34 |
| 6 | 20 | H5N1 Influenza A virus (Bavaria/2006) | 3961 | 1924 | 60.60 |
| 7 | 21 | H1N1 Influenza A virus (Brisbane/2007) | 3952 | 1915 | 60.78 |
| 8 | 22 | H3N2 Influenza A virus (Uruguay/2007) | 3955 | 1918 | 60.74 |
| 9 | 23 | H3N2 Influenza A virus (Hongkong/1968) | 3955 | 1918 | 61.52 |
| 10 | 24 | H2N2 Influenza A virus (Japan/1957) | 3943 | 1906 | 61.12 |
| 11 | 25 | H7N7 Influenza A virus (Bratislava/1979) | 3946 | 1909 | 62.28 |
| 12 | 26 | H1N1 Influenza A virus (Netherlands2009)-wBB (California2009) | 3955 | 1918 | 60.85 |
| 13 | 27 | HA Influenza B virus (Brisbane 2008) | 4012 | 1975 | 63.39 |
| 14 | 28 | H1N1 Influenza A virus (California2009)-wBB (Netherlands2009) | 3955 | 1918 | 61.00 |

Example 2: Screening of the Growth Behavior of Individual Clones

The goal of this experiment is to evaluate the individual growth and production behavior of bacteria cultures bearing plasmids obtained in Example 1. This analysis is necessary to identify uniformly growing clones from HA plasmid DNAs (see Table 1) which guarantees that all plasmid DNA variants are produced in similar amounts (see Example 3).

2.1. Pre-Cultivation from Glycerol Stocks

For each bacterial clone, 1 ml LB medium (containing 100 μg/ml ampicillin) is inoculated with the respective glycerol stock and incubated for 16 h at 37° C. in a shaking incubator. Following that, 10 μl of the individual bacterial culture is transferred to solid LB medium (supplemented with 100 μg/ml ampicillin) and incubated for 16 h at 37° C. to obtain single discrete colonies. Single discrete colonies from each plate are taken to inoculate 1 ml of liquid LB medium (containing 100 μg/ml ampicillin) for pre-cultivation prior to the screening main culture. In this way, first growth synchronization is achieved.

2.2. Screening of Growth Performance in Microtiter Plate

After determination of pre-cultures' biomass concentrations by optical density measurement in a plate reader, the respective volume of each clone is transferred to inoculate 1 mL of liquid TB medium (containing 100 μg/ml ampicillin) to a uniform initial cell density of 0.1. The growth of the individual clones is monitored in a special microtiter plate with a transparent bottom using online measurements (scattered light and dissolved oxygen tension (DOT) measurement). The recorded online signals allow for a detailed determination of growth kinetics such as lag phase duration, growth rate, and final biomass formation. After cultivation, plasmid titer quantification and next generation sequencing is performed. Uniformly growing clones are identified and used to generate glycerol stocks. Subsequently, those clones are used for large-scale plasmid DNA production.

2.3. Screening of RNA In Vitro Transcription Performance of Individual Clones

The DNA plasmids are enzymatically linearized using EcoRI and transcribed in vitro using DNA dependent T7 RNA polymerase in the presence of a nucleotide mixture under respective buffer conditions. To assess the transcription efficiency of individual clones over time, samples taken at different time points are analyzed quantitatively.

2.4. In Vitro and In Vivo Characterization of Individual mRNA Constructs

Expression analysis of individual mRNAs (in vitro translation, in-vitro expression and analysis by western blot, FACS, and ELISA.

Individual analysis of antigenicity of antigens

Example 3: Large-Scale Plasmid DNA Production

From each HA antigen (see Table 1), one uniformly growing pre-selected clone is taken (glycerol stocks) to inoculate a heterologous pre-culture (containing clones from each antigen) in shake flasks (200 ml LB medium containing 100 μg/ml ampicillin) for 16 h at 37° C. 100 ml of that pre-culture is taken to inoculate a production-scale fermenter (Eppendorf BioFlo415, volume 15 liter).

To obtain optimal bacteria growth, feeding solution (LB medium comprising ampicillin (100 μg/ml) with 2% glucose) is constantly fed into the fermenter tank. During fermentation, standard parameters are precisely regulated and continuously monitored (e.g., pH: 7.0, temperature: 37° C.). The cell density is controlled by photometric determination at 600 nm. The fermentation procedure is stopped after 20 hours of incubation time. The bacterial culture is centrifuged down at 6000 g for 15 minutes at room temperature, the supernatant is discarded and the cell pellet used for plasmid DNA isolation.

Since all clones show the same growth and production behavior, all plasmid DNA species are potentially produced in similar amounts.

Example 4: Plasmid DNA Preparation and Quality Controls

The obtained bacterial cell pellet (see example 3) is used for plasmid preparation, using a commercially available endotoxin free plasmid DNA giga-preparation kit (Macherey Nagel). After purification, the plasmid DNA mixture is analyzed regarding its identity and quantity via next generation sequencing (NGS), qPCR or restriction mapping in order to confirm the presence of each individual antigen encoding plasmid in the respective amounts.

Additionally, plasmid DNA content and purity are determined via UV absorption and anion exchange chromatography.

Example 5: RNA In Vitro Transcription

The DNA plasmid mixture is enzymatically linearized using EcoRI and transcribed in vitro using DNA dependent T7 RNA polymerase in the presence of a nucleotide mixture under respective buffer conditions. The obtained mRNA mixture is purified using PureMessenger® (CureVac, Tübingen, Germany; WO 2008/077592 A1) and used for in vitro and in vivo experiments.

Example 6: Formulation of a Polyvalent HA Vaccine 6.1. Formulation with Protamine The mRNA mixture is furthermore complexed with protamine prior to use in in vivo vaccination. The mRNA formulation consists of a mixture of 50% free mRNA and 50% mRNA complexed with protamine at a weight ratio of 2:1 (according to WO/2010/037539). First, mRNA is complexed with protamine by addition of protamine-Ringer's lactate solution to mRNA. After incubation for 10 minutes, when the complexes were stably generated, free mRNA is added, and the final concentration of the vaccine is adjusted with Ringer's lactate solution.

6.2. LNP Encapsulation

A lipid nanoparticle (LNP)-encapsulated mRNA mixture is prepared using an ionizable amino lipid (cationic lipid), phospholipid, cholesterol and a PEGylated lipid. LNPs are prepared as follows. Cationic lipid, DSPC, cholesterol and PEG-lipid are solubilized in ethanol. Briefly, the mRNA mixture is diluted to a total concentration of 0.05 mg/mL in 50 mM citrate buffer, pH 4. Syringe pumps are used to mix the ethanolic lipid solution with the mRNA mixture at a ratio of about 1:6 to 1:2 (vol/vol). The ethanol is then removed and the external buffer replaced with PBS by dialysis. Finally, the lipid nanoparticles are filtered through a 0.2 μm pore sterile filter. Lipid nanoparticle particle diameter size is determined by quasi-elastic light scattering using a Malvern Zetasizer Nano (Malvern, UK).

Example 7: Cultivation and Characterization of Growth Behaviour of Different pDNA Strains 12 different HA pDNA constructs (obtained according to Example 1) were propagated in DH5alpha and CopyCutter™ *E. coli* strains and characterized for their growth behavior.

7.1 Re-Transformation of pDNA in *Escherichia coli:*

For the re-transformation of pDNA (obtained according to Example 1) harboring influenza antigen coding sequences (SEQ ID NOs: 1-11, 13), 123 μl SOC medium was prepared and maintained at 37° C. 25 μl competent cells (DH5alpha and CopyCutter™) were thawed on ice, mixed, and 2 μL of the respective pDNA were added. After incubation on ice for 30 min, cells were heat shocked for 30 s at 42° C. Then, cells were cooled on ice for 2 min. After adding 123 μL SOC medium, cells were incubated for 37° C. for 60 min and 500 rpm. Afterwards, cells were plated on 1.5% agarose LB APS ampicillin [100 mg/L] and incubated over night at 37° C. to allow growth of discrete colonies.

7.2 Characterization of Growth Behavior of Obtained Clones:

For screening of growth characteristics of clones, 48 multi-well BOH flower plates with optodes for pH and DO were used. The cultivation and characterization of growth was performed with main cultures on DH5alpha and CopyCutter™ hosts. For inoculation of the pre-culture, two discrete colonies per transformation were picked and transferred into separate wells in 1.2 mL LB APS ampicillin [100 mg/L]. The 48 well flower plate was sealed with a gas permeable sealing foil with evaporation reduction and cultivated in a Biolector® (m2p-labs) microbioreactor (Conditions: 37° C.; 1200 rpm shaking frequency; 20.95% 02; humidity of 85%; Well readout: cycle time 10 min; biomass gain of 25; $pO_2$ gain of 38; pH gain of 22). The plate was incubated until an $OD_{600}$ between 0.4 and 0.7 was reached. Main-cultures were inoculated with pre-cultures to a final $OD_{600}$ of 0.05-0.1 in 1.1 ml LB APS ampicillin [100 mg/L], CopyCutter™ clones were additionally treated with induction solution. The cultivation was continued with the same cultivation settings, until all clones reached the stationary phase. Cells were harvested for pDNA preparation. After characterization of DH5α and CopyCutter™ clones, glycerol stocks of all clones with a final OD600 of 1.0 were prepared for further experiments. FIG. 2 shows the growth characteristics of each individual main culture for DH5alpha and CopyCutter™ strains. FIG. 2 shows a comparison of the growth kinetics of pre- and main-culture for two different clones per pDNA construct for DH5alpha and CopyCutter™ strains.

7.3 Results:

The results of FIG. 2 show that several analyzed clones show similar growth characteristics, both for DH5alpha strain and CopyCutter™ strain. For example, DH5alpha clones can be grouped in three characteristic groups that may potentially be cultured together (g1, g2, g3). CopyCutter™ clones show a more balanced and homogeneous growth characteristics. These clones may potentially be grouped and cultured together. The data suggests that it is feasible to generate a co-culture of clones for producing a pDNA template mixture for RNA in vitro transcription which would dramatically economize and streamline the RNA production process.

The results in FIG. 3 show that the growth characteristics of different clones that carry the same pDNA constructs are comparable to each other, suggesting that the characterization of the growth behavior is robust and therefore suitable to assess and predict the growth behavior also for a setting of a co-cultivation.

Summarizing the above, the data shows that co-culturing of groups of clones is applicable in (industrial) production of RNA mixtures.

Example 8: Co-Cultivation and Characterization of Different Clone Mixes

Based on the results of Example 7, CopyCutter™ clones with similar growth characteristics were selected and used to co-cultivate different influenza antigen clones and to produce a pDNA template mixture. In one setup, four different pDNAs ("4-mix") were selected for co-culturing (A; B; C; D), in another setup, five different pDNAs ("5-mix") were selected for co-culturing (A; B; C; D; E); the selected constructs show high similarity in sequence length, GC content and sequence similarity on the RNA level (see Table 2 and Table 3).

TABLE 2

Overview of the 4-mix and 5-mix selected for co-culturing

| Antigen | pDNA length | GC content RNA in % | SEQ ID NO RNA | SEQ ID NO pDNA |
|---|---|---|---|---|
| | | 4-mix | | |
| A | 3955 | 60.84 | 2 | 16 |
| B | 3961 | 60.34 | 5 | 19 |
| C | 3955 | 60.74 | 8 | 22 |
| D | 3943 | 61.12 | 10 | 24 |
| | | 5-mix | | |
| A | 3955 | 60.84 | 2 | 16 |
| B | 3961 | 60.34 | 5 | 19 |
| C | 3955 | 60.74 | 8 | 22 |
| D | 3943 | 61.12 | 10 | 24 |
| E | 4012 | 63.39 | 13 | 27 |

TABLE 3

Sequence identity matrix (in %) of 4-mix and 5-mix sequences on the pDNA level

| | E | C | A | B | D |
|---|---|---|---|---|---|
| E | 100 | 82.27 | 81.90 | 82.11 | 82.33 |
| C | 82.27 | 100 | 84.38 | 84.37 | 84.29 |
| A | 81.90 | 84.38 | 100 | 88.76 | 89.03 |
| B | 82.11 | 84.37 | 88.76 | 100 | 90.91 |
| D | 82.33 | 84.29 | 89.03 | 90.91 | 100 |

Two concepts of co-cultivation were tested: the co-stock ("CoStock") and the co-inocula ("Colnoc") strategies (see FIG. 4A). In the CoStock strategy, the glycerol stocks of the respective clones were mixed in equimolar ratios and used as inoculum for a pre-culture (1.2 mL LB APS ampicillin [100 mg/L]). For a mixture of 4 clones, 15 μL from each glycerol stock ($OD_{600}$=1) was used (60 μL in total). For a mixture of 5 clones, 12.5 μL from each glycerol stock ($OD_{600}$=1) was used (60 μL in total). After the pre-cultures reached an $OD_{600}$ of 10, the pre-cultures were used as inocula for a main-culture. In the Colnoc strategy, 60 μL of each individual glycerol stock ($OD_{600}$=1) was used as inoculum for individual pre-cultures (1.2 mL LB APS ampicillin [100 mg/L]). Cultivation of each clone was performed separately in a pre-culture until the individual cultures reached an $OD_{600}$ of 10. A mixture of said pre-cultures was used for the inoculation of a main-culture.

The main cultures in both strategies were grown to a concentration of $OD_{600}$ 0.2. To each main-culture, the CopyCutter™ induction solution was added. When the respective cultures reached the late log-phase after approximately 7 h, cells were harvested. Afterwards, the pDNA was extracted, measured with spectrophotometry, and quantitatively analyzed (restriction analysis, sequencing, quantitative PCR). Growth characteristics of the respective co-culture replicates (CoStock strategy and Colnoc strategy with several replicates) were monitored as outlined in Example 7. The results are shown in FIG. 4B.

Figure 4:
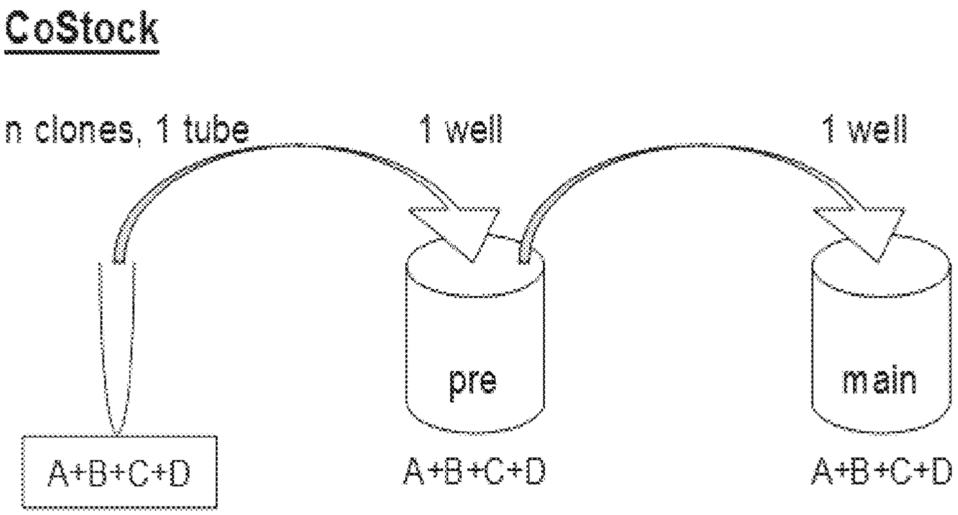
FIG. 4.
Figure 4:
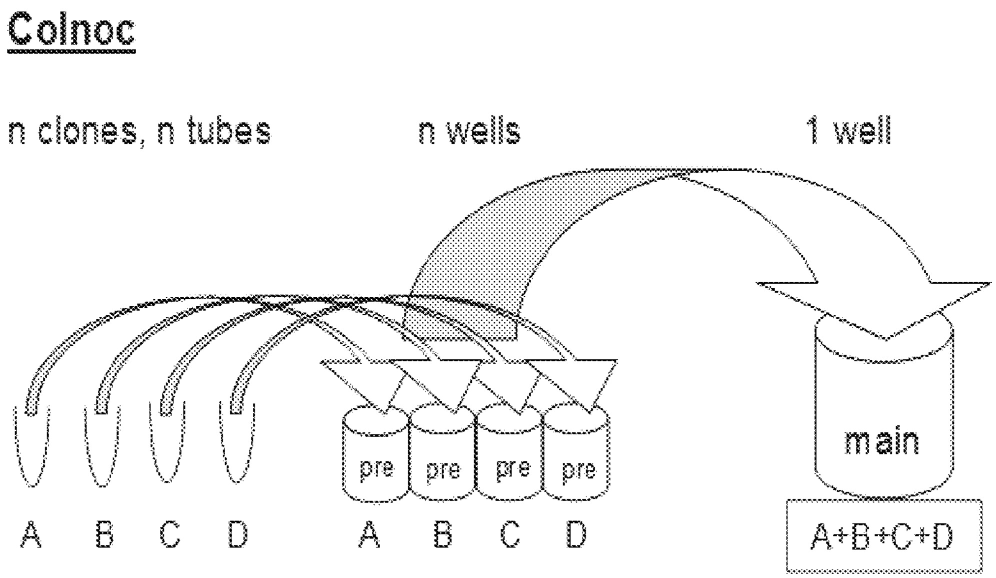
Figure 4:
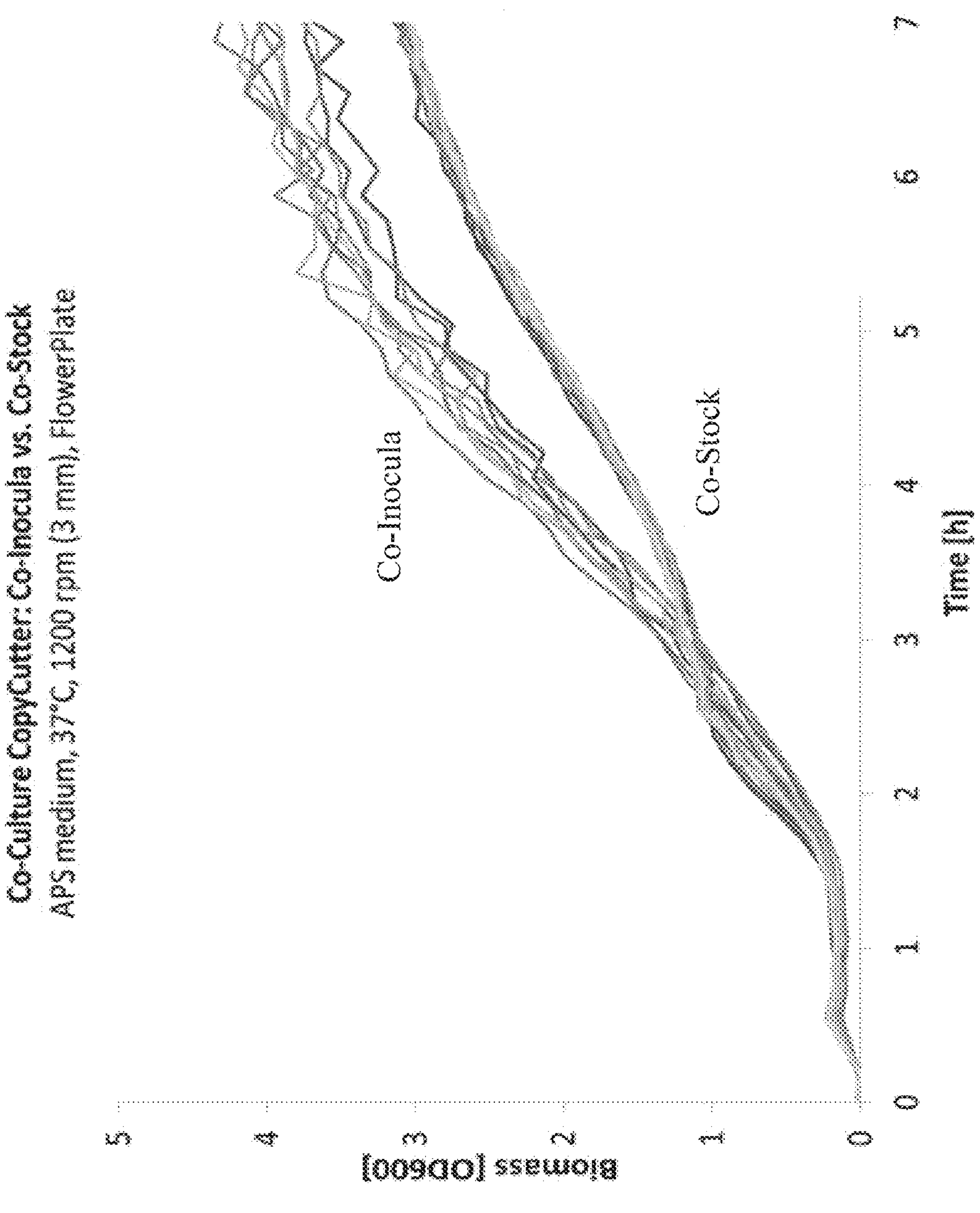

Results:

FIG. 4 shows that major differences for the respective tested setups (Colnoc strategy, CoStock strategy, 4-mix, and 5-mix) could not be observed, suggesting that the overall growth characteristics of the respective co-cultures were comparable to each other. In that experiment, the CoStock culture replicates showed a very homogeneous growth behavior with very small inter-sample variation.

Summarizing the above, the data shows that co-culturing of several different clones works in a robust and reproducible way. Therefore, the generation of a pDNA mixture for RNA in vitro transcription can be obtained by bacterial amplification in a co-culture which streamlines and improves the production process of RNA mixture based therapeutics.

Example 9: RNA In Vitro Transcription Using pDNA Template Mixtures

The aim of the experiment was to show that an mRNA mixture can be generated in one reaction by RNA in vitro transcription using a pDNA cocktail as a template. In the present example, a 4-mix and 5-mix RNA mixture was produced (see Table 2 and 3).

9.1 Generation of pDNA Template Mixtures:

First, the pDNAs of mix-4 and mix-5 (see Table 2) were separately linearized (200 μg pDNA each) using 60 μL EcoRI (10 U/μL) enzyme in the respective digestion buffer. The reactions were incubated for 4-5 h at 37° C. Linearized pDNAs were recovered using isopropanol precipitation. The obtained linearized pDNA samples were re-dissolved in WFI and analyzed for completeness of linearization using agarose gel electrophoresis. The linearized pDNA templates were used to generate pDNA mix-4 and mix-5 mixtures (0.09 μg/μL linearized pDNA each).

Figure 5:
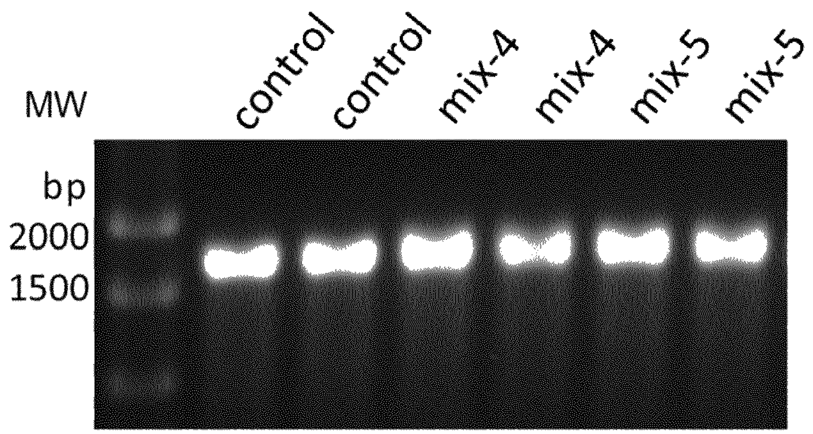
FIG. 5.

9.2 RNA In Vitro Transcription Using pDNA Template Mixtures:

RNA in vitro transcription was performed with the respective mix-4 and mix-5 pDNA mixtures (25 μg/mL DNA in total) in the presence of a sequence-optimized NTP-mix (13.45 mM) comprising cap analog (4×GTP), 2500 U/mL T7 Polymerase, 24 mM $MgCl_2$, 5 U/mL Pyrophosphatase (PPase), and 0.2 U/μL Ribolock in Tris-HCl transcription buffer. The reactions were incubated at 37° C. After 90 minutes incubation time, Tris-HCl transcription buffer and NTPs were added (26.9 mM final NTP concentration) and incubated at 37° C. for additional 5 h. Afterwards, DNA template was removed using a DNaseI digest. The digestion reaction was stopped with 25 mM EDTA and samples were subjected to LiCl precipitation. Precipitated RNA was re-dissolved in WFI. Following that the RNA was analyzed using RNA agarose gel electrophoresis (see FIG. 5). The composition of the RNA mixture was quantitatively and qualitatively analyzed (see FIG. 6). Moreover the obtained RNA composition is chracterized using NGS and qPCR. The obtained mRNA mixture may further be formulated according to Example 6.

9.3 Results:

RNA agarose gel electrophoresis (see FIG. 5A) showed that RNA was produced in comparable amounts for the control reaction (single RNA preparation), the mix-4 and mix-5 reactions. Defined bands were visible for the standard, mix-4 and mix-5 between in the expected size. Moreover, side-products could not be determined and no variation in band intensity in the respective duplicates could be observed. The data demonstrates that it is feasible to generate a RNA mixture in one RNA in vitro transcription reaction using a pDNA mixture as template. In addition the data demonstrates that the RNA in vitro reaction yields the expected product in a robust, clean and reproducible manner.

Figure 6:
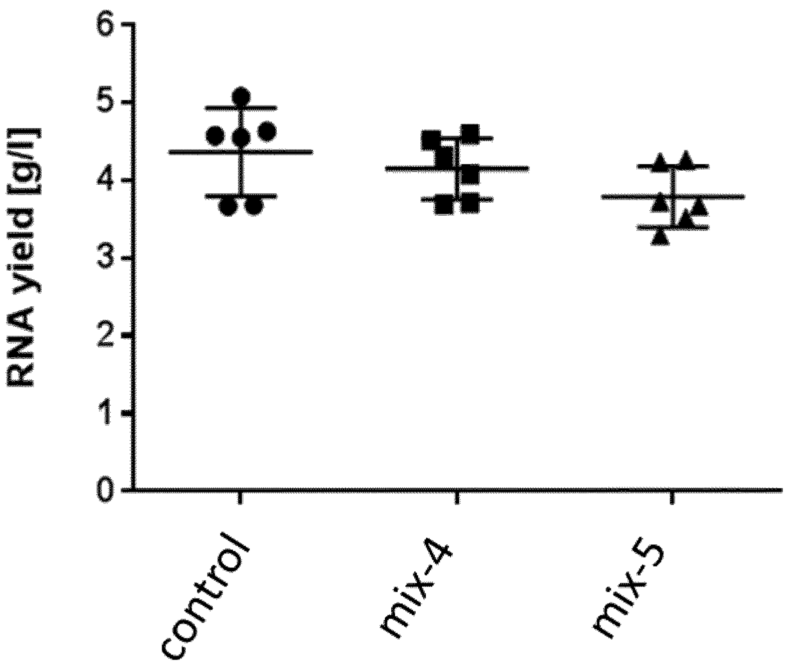
FIG. 6: Quantitative analysis of single RNA preparations, mix-4 preparations and mix-5 preparations. A detailed description of the experiment is provided in Example 9.

FIG. 6 shows that RNA in vitro transcription on a pDNA template mixture yields amounts of RNA comparable to those obtained from single RNA preparations. Moreover, the data shows that there is very little inter-sample variation in the mix-4 and mix-5 RNA preparations suggesting that the process works in a robust and reproducible way.

Summarizing the above, the data shows that RNA in vitro transcription on a pDNA mixture works in a robust and reproducible way. Moreover, the obtained RNA mixture displays the same quality attributes than single RNA preparations. Therefore, the inventive RNA in vitro transcription procedure streamlines and economize the production process of RNA mixture based therapeutics.

Example 10: Production of Template Cocktails Using Preparative PCR with Subsequent RNA In Vitro Transcription The aim of the experiment was to evaluate whether PCR on a DNA mixture is suitable to generate a DNA template mixture for RNA in vitro transcription.

Figure 9:
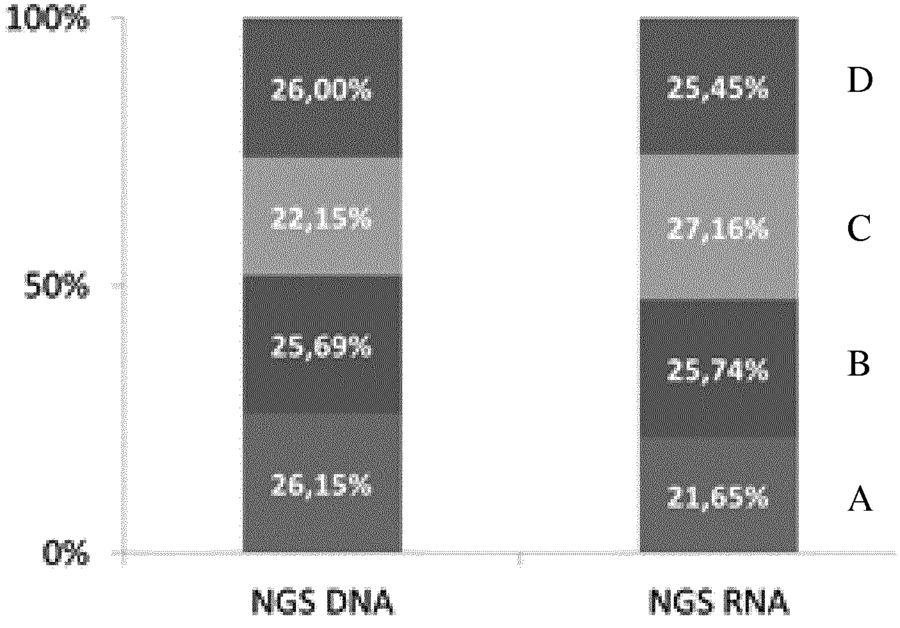
FIG. 9: NGS analysis of the PCR amplified DNA mixture and the RNA composition (4-mix) obtained using the PCR amplified DNA mixture as a template. A detailed description of the experiment is provided in Example 10.

10.1 Generation of PCR-Amplified DNA Template Mixtures:

As PCR template, the 4-mix pDNA mixture was used (see Example 9.1). The final concentrations of all components in WFI were 1×KAPA HiFi HotStart ReadyMix, 1 ng 4-mix DNA mixture, 1 M betaine, 0.3 μM T7 forward primer, and 0.3 μM reverse primer. The PCR was performed using a commercially available Thermocycler. The obtained PCR product mixture was purified using Agencourt® AMPure® XP-Kit (according to the manufacturer's instructions) and analyzed with restriction analysis on the 4-mix PCR product to reveal that each product was amplified to a similar extend (see FIG. 7). In addition, the PCR product was analyzed using NGS (FIG. 9).

Figure 8:
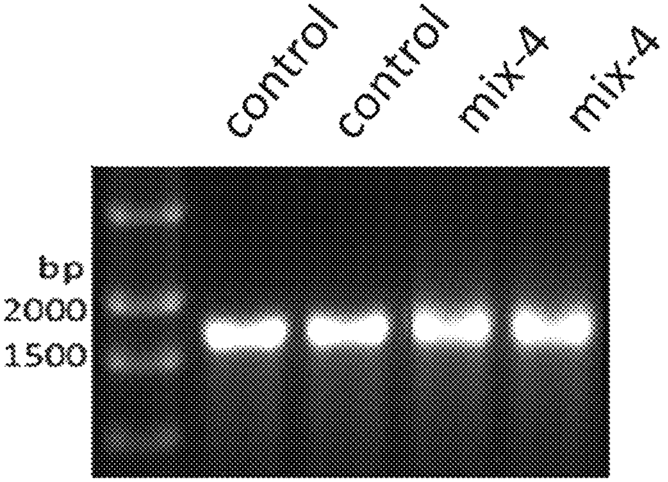
FIG. 8.

10.2 RNA In Vitro Transcription Using PCR-Amplified DNA Template Mixtures:

The obtained purified 4-mix PCR amplified DNA mixture was used in RNA in vitro transcription as described in Example 9.2. The composition of the produced RNA mixture was quantitatively and qualitatively analyzed using RNA agarose gelelectrophoresis (see FIG. 8) and NGS (see FIG. 9). Moreover the obtained RNA molecule composition is chracterized using qPCR. The obtained mRNA mixture may further be formulated according to Example 6.

Figure 7:
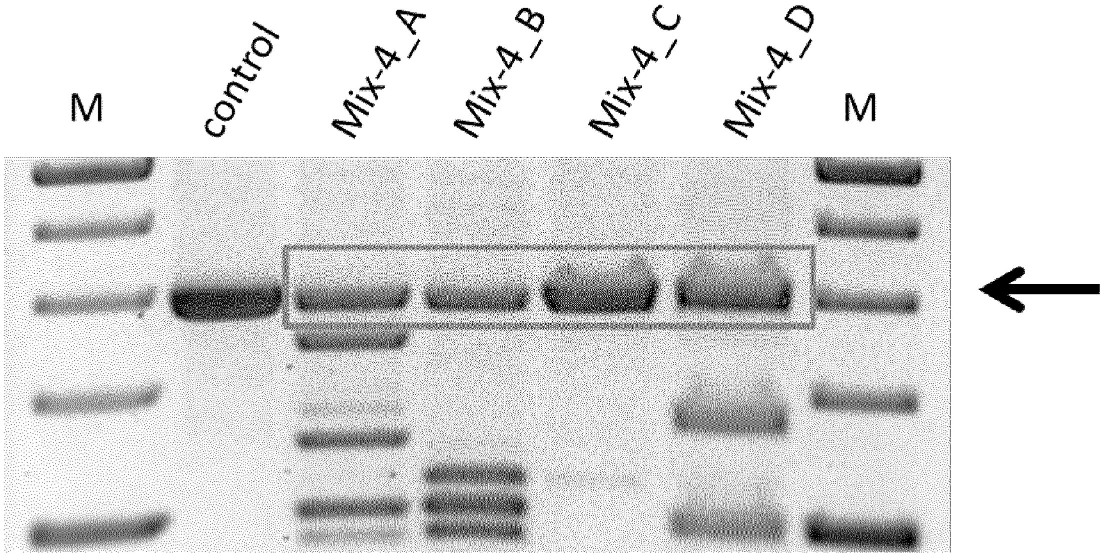
FIG. 7: Restriction analysis of a 4-mix PCR amplified DNA mixture. M: marker lane; control: irrelevant DNA; Mix-4_A: 4-mix PCR amplified DNA mixture treated with a combination of restriction enzymes that does not digest the A product; Mix-4_B: 4-mix PCR amplified DNA mixture treated with a combination of restriction enzymes that does not digest the B product; Mix-4_C: 4-mix PCR amplified DNA mixture treated with a combination of restriction enzymes that does not digest the C product; Mix-4_D: 4-mix PCR amplified DNA mixture treated with a combination of restriction enzymes that does not digest the D product; Arrow indicates the expected band indicating that all DNA species (A, B, C, D) were present in the PCR amplified DNA mixture.

10.3 Results:

FIG. 7 shows that PCR is suitable to amplify and generate a DNA mixture that can be used as a template for the production of an RNA mixture via RNA in vitro transcription. Each PCR product was present in the obtained 4-mix PCR amplified DNA mixture.

RNA AGE (see FIG. 8) showed that RNA was produced in comparable amounts for the control reaction (control RNA), and mix-4 reactions. Defined bands were visible for the control and the mix-4 in the expected size. Moreover, side-products could not be determined and no variation in band intensity in the respective duplicates could be observed. The data demonstrates that it is feasible to generate a RNA mixture via RNA in vitro transcription in one reaction using a PCR amplified DNA mixture as template. In addition, the data demonstrates that the RNA in vitro reaction yields the expected product in a robust, clean and reproducible manner.

Next generation sequencing (see FIG. 9) showed that simultaneous PCR amplification of a DNA template mixture yielded DNA in almost equal amounts. In addition, using the PCR-amplified DNA mixture as a template for simultaneous RNA in vitro transcription, a homogeneous RNA mixture (4-mix) was generated (25:27:25:22) that almost matched the theoretically expected ratio of 1:1:1:1. Notably, the NGS results also demonstrate the linearity of the process, meaning that the ratio of the PCR-generated mixture matched the ratio of the final RNA mixture.

Therefore, the results show that the inventive method is suitable to generate RNA mixtures also in other ratios, depending on the application or purpose.

Summarizing the above, the data shows that RNA in vitro transcription on a PCR amplified DNA mixture works in a robust and reproducible way. Moreover, the obtained RNA mixture displays the same quality attributes than single RNA preparations. Therefore, the inventive RNA in vitro transcription procedure streamlines and economize the production process of RNA mixture based therapeutics.

Example 11: Production of Template Cocktails Using On-Chip PCR with Subsequent RNA In Vitro Transcription A chip harboring a mixture of synthetic, immobilized DNA is used as a template for preparative PCR (DNA chip obtained from TWIST bioscience). The preparative PCR is performed essentially according to Example 10. The obtained PCR product is purified and used for RNA in vitro transcription to generate a mixture of RNA (essentially performed according to Example 10) and subjected to quantitative and qualitative measurements (e.g., RNA AGE, RT-qPCR, NGS, and Spectrometry). Following that, a purification step (e.g. PureMessenger®; WO2008077592) and, optionally, a formulation step is performed (e.g., protamine complexation, LNP encapsulation).

Example 12: Production of Template Cocktails Using dbDNA Templates with Subsequent RNA In Vitro Transcription An in vitro cell free process for amplifying a DNA template and converting the amplified DNA into closed linear "doggybone" DNAs (dbDNA) is carried out to generate a DNA mixture for subsequent RNA in vitro transcription. Rolling circle DNA template amplification and generation of dbDNA is performed according to WO 2010/086626. The obtained dbDNA templates are individually linearized using an appropriate restriction enzyme (e.g., EcoRI), purified, and mixed to generate a linearized template mixture (e.g., mix-4, mix-5; e.g. see Table 2). The linearized template mixture is used for RNA in vitro transcription (essentially performed according to Example 9) and subjected to quantitative and qualitative measurements (e.g., RNA AGE, RT-qPCR, NGS, and Spectrometry). Following that, a purification step (e.g. PureMessenger®; WO2008077592) and, optionally, a formulation step is performed (e.g., protamine complexation, LNP encapsulation).

The invention claimed is:

1. A method for producing a ribonucleic acid (RNA) pharmaceutical composition comprising at least two different RNA molecule species, the method comprising the following steps:

I) performing simultaneous RNA in vitro transcription of a mixture of at least two different deoxyribonucleic acid (DNA) molecule species in a single reaction vessel, wherein each of the at least two different DNA molecule species encode the at least two different RNA molecule species thereby generating the at least two different RNA molecule species;

II) obtaining an RNA molecule composition comprising the at least two different RNA molecule species generated in step I);

III) purifying the RNA from the RNA molecule composition; and

IV) formulating the at least two different RNA molecule species in a pharmaceutical formulation to produce the RNA pharmaceutical composition, wherein the at least two different RNA molecules vary in length from each other by no more than 100 nucleotides and wherein the amounts of each of the at least two different RNA molecules are not more than 20% different from each other in the RNA molecule composition.

2. The method according to claim 1, further comprising prior to step a step of:

1) generating the mixture of at least two different DNA molecule species using bacterial amplification, 2) generating the mixture of at least two different DNA molecule species using polymerase chain reaction (PCR), and/or 3) generating the mixture of at least two different DNA molecule species using enzymatic amplification.

3. The method according to claim 2, wherein step 1) comprises a step of:

i) transforming a bacterial cell culture with at least one single DNA plasmid species of the mixture of at least two different DNA plasmid species, wherein each DNA plasmid species encodes one of the at least two different RNA molecule species.

4. The method according to claim 2, wherein step 1) comprises a step of:

i)transforming at least two single bacterial cell cultures each with a single DNA plasmid species of the at least two different DNA plasmid species, wherein the single DNA plasmid species encodes one of the at least two different RNA molecule species.

5. The method according to claim 3, further comprising a step of:

ii) isolating at least one single bacterial cell clone for each DNA plasmid species of the mixture of at least two different DNA plasmid species, and iii) MHO growing each of the at least one single bacterial cell clone isolated in step ii) in a separate bacterial cell clone culture.

6. The method according to claim 4, further comprising after step i) the following steps:

ii) isolating at least one single bacterial cell clone of each of the at least two single bacterial cell cultures transformed in step i), iii) growing each of the single bacterial cell clones isolated in step ii) in a separate bacterial cell culture, and iv) selecting at least one bacterial cell clone culture for each of the at least two different DNA plasmid species.

7. The method according to claim 5, further comprising:
iv) determining at least one parameter of growth kinetics and/or amount of plasmid DNA of the at least one single bacterial cell clone culture, and
v) selecting one bacterial cell clone culture for each of the at least two different DNA plasmid species depending on the parameter determined in step iv).

8. The method according to claim 7, wherein step iv) comprises a step of:
determining a parameter of growth kinetics by measuring the optical density of the bacterial cell clone culture after a time interval, and/or
determining the amount of plasmid produced per volume and time of bacterial cell culture.

9. The method according to claim 7, wherein the selected bacterial cell clone culture for each of the at least two different DNA plasmid species exhibits similar or identical growth kinetics and/or similar or identical DNA production levels.

10. The method according to claim 7, wherein step 1) further comprises a step of:
inoculating and growing an amount of at least one of the one or more bacterial cell clone cultures selected for each of the at least two different DNA plasmid species in a single reaction vessel, or
inoculating and growing an amount of at least one of the one or more bacterial cell clone cultures selected for each of the at least two different DNA plasmid species in one or more separate reaction vessels for each of the at least two different DNA plasmid species.

11. The method according to claim 10, wherein equal amounts of each bacterial cell clone culture are inoculated.

12. The method according to claim 10, wherein the amount of each bacterial cell clone culture used for inoculating is selected so that equal or similar amounts of each of the at least two different DNA plasmid species are obtained.

13. The method according to claim 1, wherein the amount of each of the at least two different RNA molecule species in the RNA molecule composition is proportional or at least 90% proportional to the amount of the corresponding DNA molecule species in the mixture of at least two different DNA molecule species.

14. The method according to claim 1, wherein the DNA sequences of the at least two different deoxyribonucleic acid (DNA) molecule species are at least 90% identical to each other.

15. The method according to claim 1, wherein the RNA sequences of the at least two different RNA molecule species are at least 90% identical to each other.

16. The method according to claim 1, wherein each of the at least two different DNA molecule species encodes for different RNA molecule species, wherein each of the at least two different RNA molecule species encodes for an antigen of different serotypes or strains of a same pathogen.

17. The method according to claim 16, wherein each of the at least two different RNA molecule species encodes for an influenza antigen.

18. The method of claim 1, wherein the at least two different RNA molecule species encode different variants of the same target peptide or protein, wherein said composition comprises the at least two different RNA molecule species in identical amounts.

19. The method according to claim 2, wherein step 1) comprises a step of:
i)transforming a single bacterial cell culture with a mixture of at least two different DNA plasmid species, wherein each DNA plasmid species encodes one of the at least two different RNA molecule species.

20. The method according to claim 19, further comprising after step i) the following steps:
ii) isolating at least at least two single bacterial cell clones, and
iii) growing each of the at least two single bacterial cell clones isolated in step ii) in a separate bacterial cell clone culture,
iv) determining the identity of the DNA plasmid species of each of the at least at least two single bacterial cell clone cultures grown in step iii), and
v) selecting at least one single bacterial cell clone culture for each of the at least two different DNA plasmid species.

21. The method of claim 1, further comprising producing a RNA molecule composition comprising at least three different RNA molecule species.

22. The method of claim 21, further comprising producing a RNA molecule composition comprising at least four different RNA molecule species.

23. The method according to claim 1, wherein each of the at least two different RNA molecule species encodes for tumor antigen.

24. The method of claim 1, wherein the at least two different DNA molecule species comprise at least two different DNA plasmid species.

25. The method according to claim 24, wherein the DNA plasmid species have the same plasmid backbone.

* * * * *

UNITED STATES PATENT AND TRADEMARK OFFICE
CERTIFICATE OF CORRECTION

PATENT NO. : 11,684,665 B2
APPLICATION NO. : 16/063999
DATED : June 27, 2023
INVENTOR(S) : Tilmann Roos et al.

It is certified that error appears in the above-identified patent and that said Letters Patent is hereby corrected as shown below:

In the Claims

In Claim 5, Column 188, Line 55, delete "MHO".

Signed and Sealed this
Fifteenth Day of August, 2023

Katherine Kelly Vidal
*Director of the United States Patent and Trademark Office*